United States Patent
Ronai et al.

(10) Patent No.: US 10,577,349 B2
(45) Date of Patent: Mar. 3, 2020

(54) QUINOLINONES AS INHIBITORS OF TRANSLATION INITIATION COMPLEX

(71) Applicants: Sanford Burnham Prebys Medical Discovery Institute, La Jolla, CA (US); The Royal Institution for the Advancement of Learning / McGill University, Montreal (CA); The Government of the United States of America as Represented by the Secretary of the Department of Health and Human Services, Rockville, MD (US)

(72) Inventors: Ze'ev Ronai, La Jolla, CA (US); Anthony B. Pinkerton, La Jolla, CA (US); Yongmei Feng, La Jolla, CA (US); Ivan Topisirovic, Quebec (CA); Kevin Brown, Bethesda, MD (US); Christian A. Hassig, La Jolla, CA (US)

(73) Assignees: SANFORD BURNHAM PREBYS MEDICAL DISCOVERY INSTITUTE, La Jolla, CA (US); THE ROYAL INSTITUTION FOR THE ADVANCEMENT OF LEARNING/MCGILL UNIVERSITY, Montreal, Quebec (CA); THE UNITED STATES OF AMERICA, AS REPRESENTED BY THE SECRETARY, DEPARTMENT OF HEALTH AND HUMAN SERVICES, Bethesda, MD (US)

( * ) Notice: Subject to any disclaimer, the term of this patent is extended or adjusted under 35 U.S.C. 154(b) by 78 days.

(21) Appl. No.: 15/554,419

(22) PCT Filed: Mar. 1, 2016

(86) PCT No.: PCT/US2016/020273
§ 371 (c)(1),
(2) Date: Mar. 9, 2018

(87) PCT Pub. No.: WO2016/140973
PCT Pub. Date: Sep. 9, 2016

(65) Prior Publication Data
US 2018/0044324 A1    Feb. 15, 2018

Related U.S. Application Data

(60) Provisional application No. 62/126,715, filed on Mar. 2, 2015.

(51) Int. Cl.
*C07D 401/14* (2006.01)
*C07D 401/06* (2006.01)

(52) U.S. Cl.
CPC ......... *C07D 401/14* (2013.01); *C07D 401/06* (2013.01)

(58) Field of Classification Search
None
See application file for complete search history.

(56) References Cited

U.S. PATENT DOCUMENTS 7,326,788 B2 * 2/2008 Wall ................ C07D 215/227
546/153
2012/0190707 A1    7/2012 Ronai et al.

FOREIGN PATENT DOCUMENTS

| JP | 2002371078 A | 12/2002 |
| WO | WO-2010075443 A1 | 7/2010 |
| WO | WO-2014159837 A1 | 10/2014 |
| WO | WO-2016140973 A1 | 9/2016 |

OTHER PUBLICATIONS

Barile et al. Synthesis and SAR studies of dual AKT/NF-κB inhibitors against melanoma. Chem Biol Drug Des 82(5):520-533 (2013).
Feng et al. SBI-0640756 Attenuates the Growth of Clinically Unresponsive Melanomas by Disrupting the eIF4F Translation Initiation Complex. Cancer Res 75:5211-5218 (2015).
Forino et al. Virtual docking approaches to protein kinase B inhibition. J Med Chem 48:2278- 2281 (2005).
Ghouse et al. Green chemical approach: microwave assisted, titanium dioxide nanoparticles catalyzed, convenient and efficient C—C bond formation in the synthesis of highly functionalized quinolines and quinolinones. RSC Advances 4(84):44408-44417 (2014).
PCT/US2016/020273 International Search Report and Written Opinion dated Aug. 18, 2016.
STN express RN 337932-50-0 (1 pg.) (Entered STN: May 24, 2001).
STN RN 1321827-45-5 (1 pg.) (Entered STN: Aug. 23, 2011).
STN RN 337932-53-3 (2 pgs.) (Entered STN: May 24, 2001).
Barile et al. Synthesis and SAR studies of dual AKT/NF-κB inhibitors against melanoma. Chem Biol Drug Des 82(5):520-533 (2013) (Includes Supporting Information).

* cited by examiner

*Primary Examiner* — Heidi Reese
(74) *Attorney, Agent, or Firm* — Wilson Sonsini Goodrich & Rosati

(57) ABSTRACT

Provided herein are compounds and pharmaceutical compositions comprising quinolinones. The quinolinones and compositions thereof are useful as eukaryotic translation initiation factor 4F (eIF4F) complex modulators.

11 Claims, 29 Drawing Sheets

Lu1205

WM1346

A375

UACC903

WM3629

SBI-756

QUINOLINONES AS INHIBITORS OF TRANSLATION INITIATION COMPLEX

CROSS REFERENCE

This application is filed pursuant to 35 U.S.C. § 371 as a United States National Phase Application of International Application No. PCT/US 16/20273 filed Mar. 1, 2016; which claims the benefit of U.S. Provisional Patent Application No. 62/126,715, filed on Mar. 2, 2015, all of which are incorporated herein by reference in their entirety.

STATEMENT AS TO FEDERALLY SPONSERED RESEARCH

This invention was made with government support under ZIA CP010201 awarded by the National Institutes of Health. The government has certain rights in the invention.

BACKGROUND

Deregulation of cap-dependent translation is associated with cancer initiation and progression. The rate-limiting step of protein synthesis is the loading of ribosomes onto mRNA templates stimulated by the heterotrimeric complex, eukaryotic initiation factor eIF4F. This step represents an attractive target for anticancer drug discovery because it resides at the nexus of the TOR signaling pathway. Disrupting the eukaryotic translation initiation factor 4F (eIF4F) complex offers an appealing strategy to potentiate the effectiveness of existing cancer therapies and to overcome resistance to drugs such as BRAF or MEK inhibitors.

BRIEF SUMMARY OF THE INVENTION

This disclosure provides, for example, compounds and compositions which are eukaryotic translation initiation factor 4F (eIF4F) complex modulators, and their use as medicinal agents, processes for their preparation, and pharmaceutical compositions that include disclosed compounds as at least one active ingredient. The disclosure also provides for the use of disclosed compounds for the treatment of conditions that are mediated by altered translation initiation via targeting of eIF4G. The disclosure also provides for the use of disclosed compounds in combination with a BRAF or a MEK inhibitor.

One aspect provides a compound of Formula (Ia-1), or a pharmaceutically acceptable salt, solvate, tautomer, or N-oxide thereof:

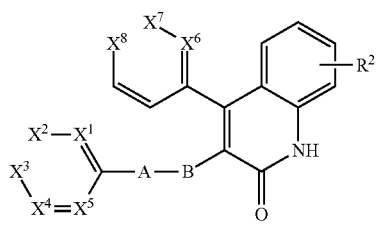

Formula (Ia-1)

wherein
A and B are independently a bond, $-CH_2-$, $-CH_2CH_2-$, $-C(=O)-$, $-CH=CH-$, or $-C(=O)NH-$;
$X^1$-$X^5$ are independently N or $CR^1$; wherein at least one of $X^1$-$X^5$ is N;
$X^6$-$X^8$ are independently N or $CR^1$;
each $R^1$ are independently hydrogen, halogen, hydroxyl, alkoxy, cyano, $-NR^aR^b$, $-C(=O)OR^c$, alkyl, cycloalkyl, or aryl; wherein the alkyl, alkoxy, cycloalkyl, and aryl are optionally substituted with one or more $R^d$;
$R^2$ is halogen, hydroxyl, alkoxy, alkyl, or cycloalkyl; wherein the alkyl and cycloalkyl are optionally substituted with one or more $R^d$;
$R^a$ and $R^b$ are independently hydrogen or alkyl; or $R^a$ and $R^b$ taken together with the nitrogen to which they are attached form a heterocycloalkyl optionally substituted with alkyl;
$R^c$ is hydrogen or alkyl; and
each $R^d$ is independently alkyl, halogen, hydroxyl, alkoxy, cyano, or $-NR^aR^b$.

In some embodiments of a compound of Formula (Ia-1), or a pharmaceutically acceptable salt, solvate, tautomer, or N-oxide thereof, at least one of $X^6$-$X^8$ is N.

In some embodiments of a compound of Formula (Ia-1), or a pharmaceutically acceptable salt, solvate, tautomer, or N-oxide thereof, $X^6$-$X^8$ are $CR^1$.

In some embodiments of a compound of Formula (Ia-1), or a pharmaceutically acceptable salt, solvate, tautomer, or N-oxide thereof, the compound of Formula (Ia-1) is of Formula (Ia-1'):

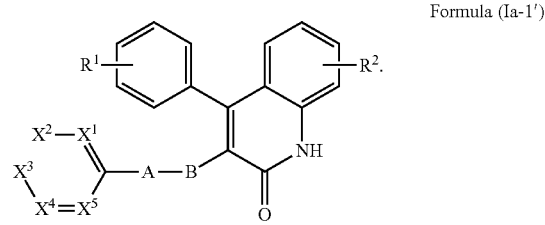

Formula (Ia-1')

In some embodiments of a compound of Formula (Ia-1), or a pharmaceutically acceptable salt, solvate, tautomer, or N-oxide thereof, the compound of Formula (Ia-1) is of Formula (Ia-1''):

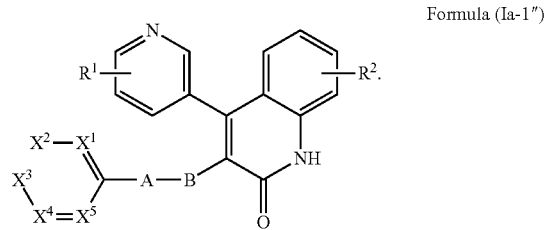

Formula (Ia-1'')

In some embodiments of a compound of Formula (Ia-1), (Ia-1'), or (Ia-1''), or a pharmaceutically acceptable salt, solvate, tautomer, or N-oxide thereof, one of $X^1$-$X^5$ is N.

In some embodiments of a compound of Formula (Ia-1), (Ia-1'), or (Ia-1''), or a pharmaceutically acceptable salt, solvate, tautomer, or N-oxide thereof, two of $X^1$-$X^5$ is N.

In some embodiments of a compound of Formula (Ia-1), (Ia-1'), or (Ia-1''), or a pharmaceutically acceptable salt, solvate, tautomer, or N-oxide thereof, $X^1$ is N and $X^2$-$X^5$ are $CR^1$.

In some embodiments of a compound of Formula (Ia-1), (Ia-1'), or (Ia-1''), or a pharmaceutically acceptable salt, solvate, tautomer, or N-oxide thereof, $X^2$ is N and $X^1$, $X^3$-$X^5$ are $CR^1$.

In some embodiments of a compound of Formula (Ia-1), (Ia-1'), or (Ia-1"), or a pharmaceutically acceptable salt, solvate, tautomer, or N-oxide thereof, $X^3$ is N and $X^1$-$X^2$ and $X^4$-$X^5$ are $CR^1$.

In some embodiments of a compound of Formula (Ia-1), (Ia-1'), or (Ia-1"), or a pharmaceutically acceptable salt, solvate, tautomer, or N-oxide thereof, $X^2$ and $X^4$ are N and $X^1$, $X^3$ and $X^5$ are $CR^1$.

In some embodiments of a compound of Formula (Ia-1), (Ia-1'), or (Ia-1"), or a pharmaceutically acceptable salt, solvate, tautomer, or N-oxide thereof, wherein $X^2$ and $X^5$ are N and $X^1$, $X^3$ and $X^4$ are $CR^1$.

In some embodiments of a compound of Formula (Ia-1), (Ia-1'), or (Ia-1"), or a pharmaceutically acceptable salt, solvate, tautomer, or N-oxide thereof, B is —C(=O)—.

In some embodiments of a compound of Formula (Ia-1), (Ia-1'), or (Ia-1"), or a pharmaceutically acceptable salt, solvate, tautomer, or N-oxide thereof, A is —CH=CH—.

In some embodiments of a compound of Formula (Ia-1), (Ia-1'), or (Ia-1"), or a pharmaceutically acceptable salt, solvate, tautomer, or N-oxide thereof, each $R^1$ is independently hydrogen, halogen, alkyl, alkoxy, cyano, —$NR^aR^b$, or —$C(=O)OR^c$; wherein the alkyl and alkoxy are optionally substituted with one or more halogen or alkoxy.

In some embodiments of a compound of Formula (Ia-1), (Ia-1'), or (Ia-1"), or a pharmaceutically acceptable salt, solvate, tautomer, or N-oxide thereof, each $R^1$ is independently hydrogen, fluoro, chloro, bromo, methyl, —$CF_3$, —$OCF_3$, methoxy, cyano, —$NMe_2$, —C(=O)OEt, or —$CH_2OCH_3$.

In some embodiments of a compound of Formula (Ia-1), (Ia-1'), or (Ia-1"), or a pharmaceutically acceptable salt, solvate, tautomer, or N-oxide thereof, each $R^1$ is independently hydrogen or fluoro.

In some embodiments of a compound of Formula (Ia-1), (Ia-1'), or (Ia-1"), or a pharmaceutically acceptable salt, solvate, tautomer, or N-oxide thereof, $R^2$ is halogen.

In some embodiments of a compound of Formula (Ia-1), (Ia-1'), or (Ia-1"), or a pharmaceutically acceptable salt, solvate, tautomer, or N-oxide thereof, $R^2$ is chloro.

One aspect provides a pharmaceutical composition comprising a compound of Formula (Ia-1), (Ia-1'), or (Ia-1"), or a pharmaceutically acceptable salt, solvate, tautomer, or N-oxide thereof, and a pharmaceutically acceptable excipient.

Another aspect provides a method of treating a disease in a subject mediated by altered translation initiation via targeting of eIF4G, wherein the method comprises administering to the subject a compound of Formula (Ia-1), (Ia-1'), or (Ia-1"), or a pharmaceutically acceptable salt, solvate, tautomer, or N-oxide thereof; or a pharmaceutical composition comprising a compound of Formula (Ia-1), (Ia-1'), or (Ia-1"), or a pharmaceutically acceptable salt, solvate, tautomer, or N-oxide thereof. In some embodiments, the disease in a subject mediated by altered translation initiation via targeting of eIF4G is cancer. In some embodiments, the cancer is a resistant cancer. In some embodiments, the resistant cancer is resistant to one or more BRAF inhibitors or one or more MEK inhibitors. In some embodiments, the cancer is melanoma. In some embodiments, the cancer is prostate cancer, pancreatic cancer or colorectal cancer. In some embodiments, the prostate cancer, pancreatic cancer or colorectal cancer are driven by upregulated MAPK signaling.

Another aspect provides a method of treating cancer in a subject, wherein the method comprises administering to the subject a compound of Formula (Ia-1), (Ia-1'), or (Ia-1"), or a pharmaceutically acceptable salt, solvate, tautomer, or N-oxide thereof; or a pharmaceutical composition comprising a compound of Formula (Ia-1), (Ia-1'), or (Ia-1"), or a pharmaceutically acceptable salt, solvate, tautomer, or N-oxide thereof. In some embodiments, the cancer is a resistant cancer. In some embodiments, the resistant cancer is resistant to one or more BRAF inhibitors or one or more MEK inhibitors. In some embodiments, the cancer is melanoma. In some embodiments, the cancer is prostate cancer, pancreatic cancer or colorectal cancer. In some embodiments, the prostate cancer, pancreatic cancer or colorectal cancer are driven by upregulated MAPK signaling.

Another aspect provides a method of treating cancer in a subject mediated by inhibition of AKT, NFκB, or mTOR components, wherein the method comprises administering to the subject a compound of Formula (Ia-1), (Ia-1'), or (Ia-1"), or a pharmaceutically acceptable salt, solvate, tautomer, or N-oxide thereof; or a pharmaceutical composition comprising a compound of Formula (Ia-1), (Ia-1'), or (Ia-1"), or a pharmaceutically acceptable salt, solvate, tautomer, or N-oxide thereof. In some embodiments, the cancer is a resistant cancer. In some embodiments, the resistant cancer is resistant to one or more BRAF inhibitors or one or more MEK inhibitors. In some embodiments, the cancer is melanoma. In some embodiments, the cancer is prostate cancer, pancreatic cancer or colorectal cancer. In some embodiments, the prostate cancer, pancreatic cancer or colorectal cancer are driven by upregulated MAPK signaling.

Another aspect provides a method of treating cancer in a subject mediated by inhibition of DNA damage response and DNA repair activities, wherein the method comprises administering to the subject a compound of Formula (Ia-1), (Ia-1'), or (Ia-1"), or a pharmaceutically acceptable salt, solvate, tautomer, or N-oxide thereof; or a pharmaceutical composition comprising a compound of Formula (Ia-1), (Ia-1'), or (Ia-1"), or a pharmaceutically acceptable salt, solvate, tautomer, or N-oxide thereof. In some embodiments, the cancer is a resistant cancer. In some embodiments, the resistant cancer is resistant to one or more BRAF inhibitors or one or more MEK inhibitors. In some embodiments, the cancer is melanoma. In some embodiments, the cancer is prostate cancer, pancreatic cancer or colorectal cancer. In some embodiments, the prostate cancer, pancreatic cancer or colorectal cancer are driven by upregulated MAPK signaling.

Another aspect provides a method of treating cancer in a subject mediated by inhibition of cell growth and induction of cell death, wherein the method comprises administering to the subject a compound of Formula (Ia-1), (Ia-1'), or (Ia-1"), or a pharmaceutically acceptable salt, solvate, tautomer, or N-oxide thereof; or a pharmaceutical composition comprising a compound of Formula (Ia-1), (Ia-1'), or (Ia-1"), or a pharmaceutically acceptable salt, solvate, tautomer, or N-oxide thereof. In some embodiments, the cancer is a resistant cancer. In some embodiments, the resistant cancer is resistant to one or more BRAF inhibitors or one or more MEK inhibitors. In some embodiments, the cancer is melanoma. In some embodiments, the cancer is prostate cancer, pancreatic cancer or colorectal cancer. In some embodiments, the prostate cancer, pancreatic cancer or colorectal cancer are driven by upregulated MAPK signaling.

In some embodiments, the methods comprise administering to the subject a compound of Formula (Ia-1), (Ia-1'), or (Ia-1"), or a pharmaceutically acceptable salt, solvate, tautomer, or N-oxide thereof; or a pharmaceutically acceptable salt, solvate, tautomer, or N-oxide thereof; or a pharmaceutical composition comprising a compound of Formula (Ia-1), (Ia-1'), or (Ia-1"), or a pharmaceutically acceptable salt, solvate, tautomer, or N-oxide thereof; in combination with a MEK inhibitor, a BRAF inhibitor, or a combination thereof.

DETAILED DESCRIPTION OF THE INVENTION

Figure 1:
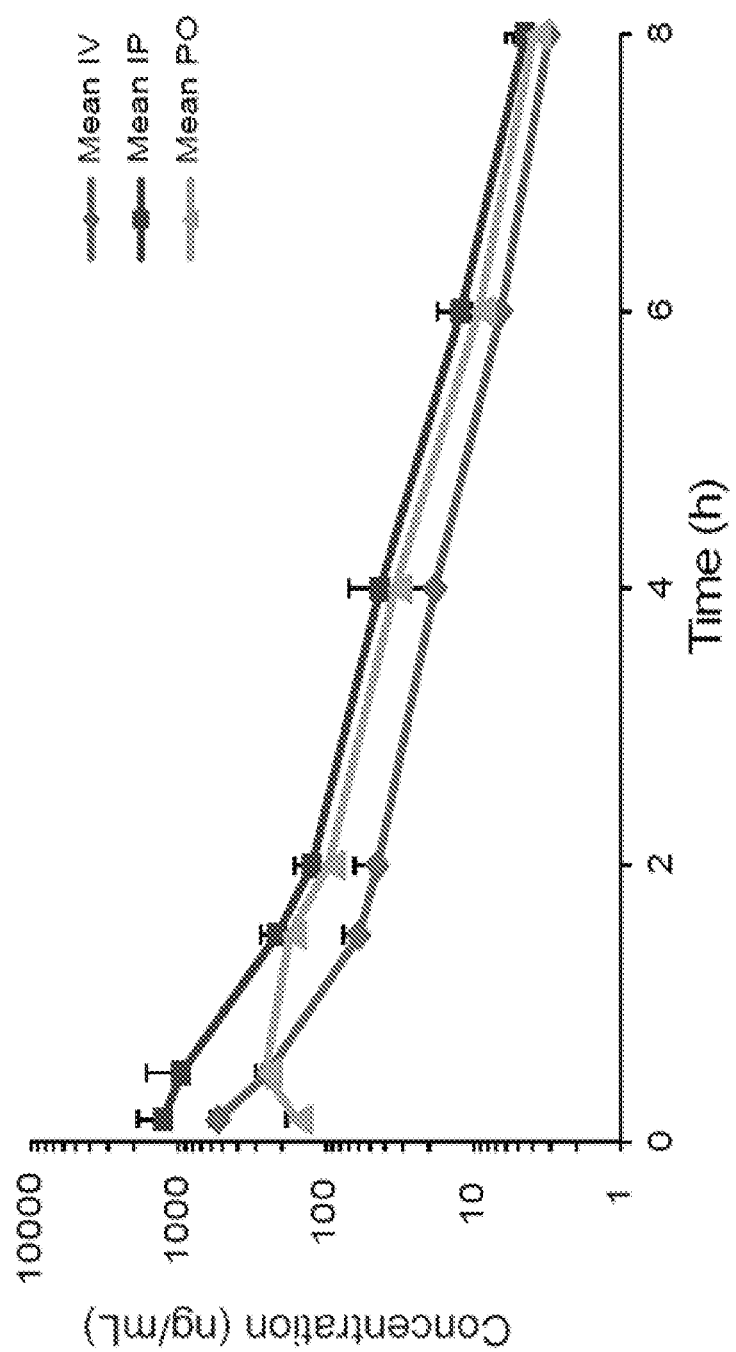
FIG. 1 shows the IV, IP, and PO PK curves for SBI-756 (Compound 38).
Figure 2A:
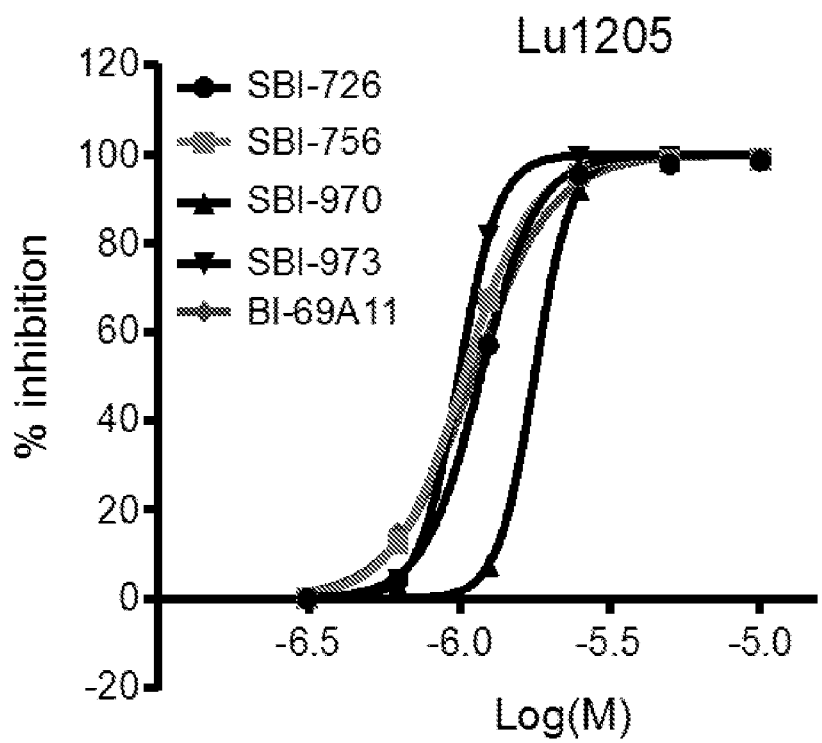
FIG. 2 shows the % inhibition of SBI-756 (Compound 38), SBI-726 (Compound 44), SBI-970 (Compound 12), SBI-973 (Compound 62), and BI-69A11 in Lu1205 cell line (FIG. 2A), WM793 cell line (FIG. 2B), WM1346 cell line (FIG. 2C), and WM1366 cell line (FIG. 2D).
Figure 2B:
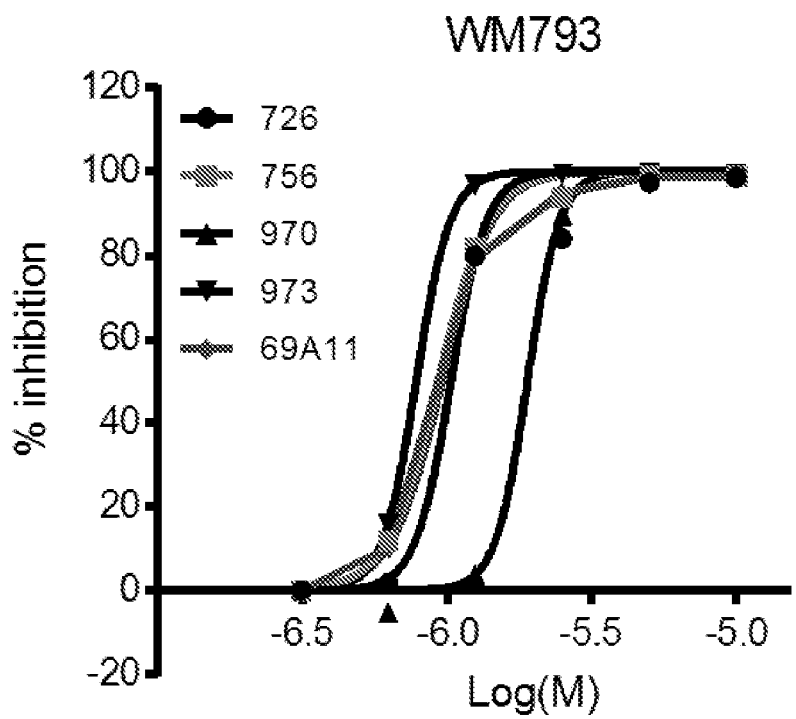
Figure 2C:
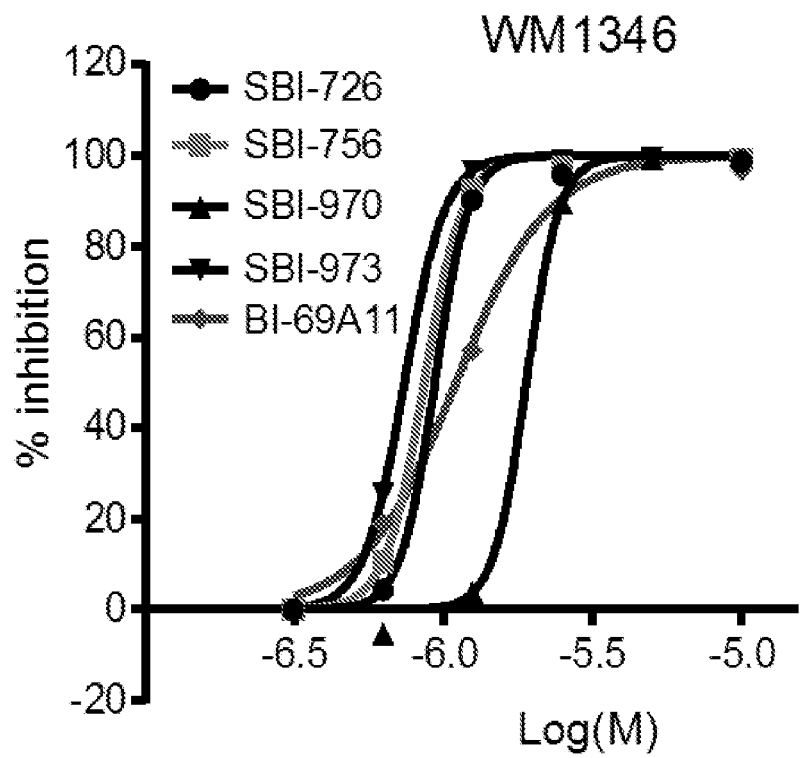
Figure 2D:
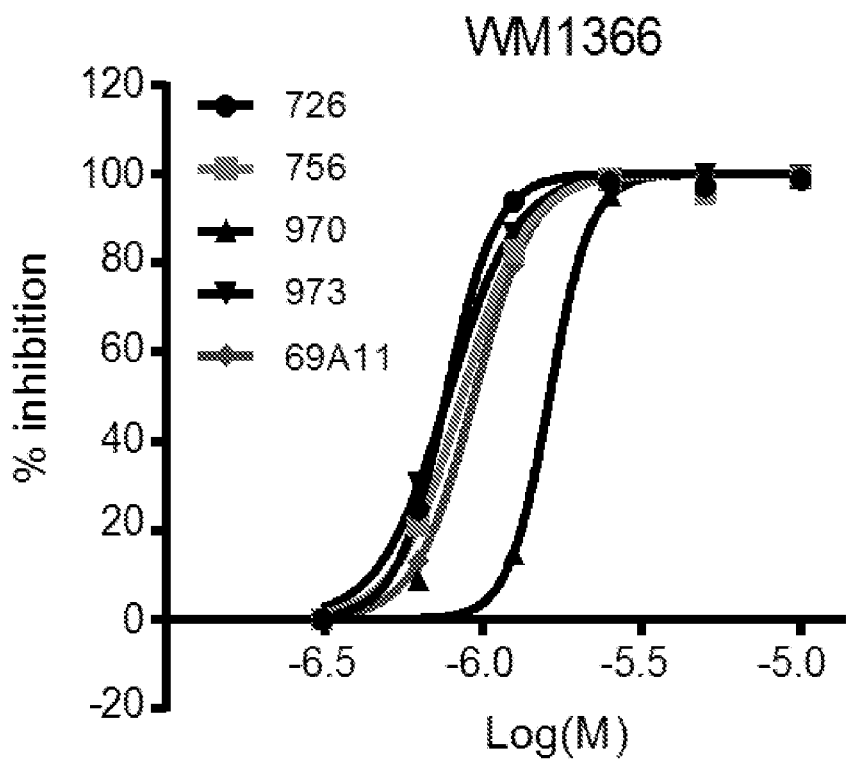

The emergence of effective inhibitors for BRAF-mutant melanoma has had major impact on the clinical management of melanoma. However, the initial success of such treatments has been limited due to the propensity of melanomas to develop resistance. In most cases, mechanisms underlying BRAF inhibitor (BRAFi) resistance include activation of genetic or epigenetic pathways that circumvent targeted BRAF and restore MAPK and related signaling to levels sufficient to fuel tumorigenesis. This outcome has led to development of combination therapies targeting both BRAF and associated pathways, such as MEK and PI3K, albeit, with limited success. Furthermore, 50% of melanomas, such as those harboring NRAS and NF1 mutations, lack BRAF mutations, and are thus not amenable to BRAFi therapy. Thus, tumor chemoresistance and the lack of therapies for BRAF wild-type (WT) tumors remains a major clinical challenge.

eIF4G1 is a large scaffolding protein that is a key component of the eukaryotic translation initiation factor 4F (eIF4F) complex. Small translational repressors, eIF4E-binding proteins (4E-BP), associate with eIF4E, and impair its binding to eIF4G and the eIF4F complex assembly. mTORC1-mediated phosphorylation of 4E-BPs leads to their dissociation form eIF4E, enabling eIF4E interaction with eIF4G and the formation of the eIF4F complex. Although required for cap-dependent translation of all nuclear-encoded mRNAs, increased eIF4F levels stimulate translation of mRNAs encoding cancer-promoting proteins while having only a marginal effect on translation of housekeeping mRNAs. Correspondingly, elevated eIF4F activity has been linked to resistance to BRAF- and MEK-targeted therapies. Thus, targeting the eIF4F complex and upstream signaling pathways that regulate its function addresses key unmet clinical needs.

This disclosure is directed to eukaryotic translation initiation factor 4F (eIF4F) complex modulators. This disclosure is also directed to the treatment of diseases mediated by altered translation initiation via targeting of eIF4G. This disclosure is additionally directed to the treatment of cancer with eukaryotic translation initiation factor 4F (eIF4F) complex modulators. In some embodiments the eukaryotic translation initiation factor 4F (eIF4F) complex modulator targets eIF4G. In some embodiments, the cancer is a resistant cancer. In some embodiments, the eukaryotic translation initiation factor 4F (eIF4F) complex modulator is used in combination with a BRAF or a MEK inhibitor.

Definitions

As used in the specification and appended claims, unless specified to the contrary, the following terms have the meaning indicated below.

"Amino" refers to the —$NH_2$ radical.
"Cyano" or "nitrile" refers to the —CN radical.
"Hydroxy" or "hydroxyl" refers to the —OH radical.
"Nitro" refers to the —$NO_2$ radical.
"Oxo" refers to the =O substituent.
"Oxime" refers to the =N—OH substituent.
"Thioxo" refers to the =S substituent.

"Alkyl" refers to a linear or branched hydrocarbon chain radical, which is fully saturated, has from one to thirty carbon atoms, and is attached to the rest of the molecule by a single bond. Alkyls comprising any number of carbon atoms from 1 to 30 are included. An alkyl comprising up to 30 carbon atoms is referred to as a $C_1$-$C_{30}$ alkyl, likewise, for example, an alkyl comprising up to 12 carbon atoms is a $C_1$-$C_{12}$ alkyl. Alkyls (and other moieties defined herein) comprising other numbers of carbon atoms are represented similarly. Alkyl groups include, but are not limited to, $C_1$-$C_{30}$ alkyl, $C_1$-$C_{20}$ alkyl, $C_1$-$C_{15}$ alkyl, $C_1$-$C_{10}$ alkyl, $C_1$-$C_8$ alkyl, $C_1$-$C_6$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl, $C_4$-$C_8$ alkyl, and $C_5$-$C_{12}$ alkyl. Representative alkyl groups include, but are not limited to, methyl, ethyl, n-propyl, 1-methylethyl (isopropyl), n-butyl, i-butyl, s-butyl, n-pentyl, 1,1-dimethylethyl (t-butyl), 2-ethylpropyl, and the like. Representative linear alkyl groups include, but are not limited to, methyl, ethyl, n-propyl, n-butyl, n-pentyl and the like. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)O$R^a$, —C(O)N($R^a)_2$, —N($R^a$)C(O)O$R^f$, —OC(O)—NR$^a$R$^f$, —N($R^a$)C(O)$R^f$, —N($R^a$)S(O)$_t$$R^f$ (where t is 1 or 2), —S(O)$_t$O$R^a$ (where t is 1 or 2), —S(O)$_t$$R^f$ (where t is 1 or 2) and —S(O)$_t$N($R^a)_2$ (where t is 1 or 2) where each $R^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, and each $R^f$ is independently alkyl, fluoroalkyl, cycloalkyl, cycloalkylalkyl, aryl, aralkyl, heterocycloalkyl, heterocycloalkylalkyl, heteroaryl or heteroarylalkyl.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In certain embodiments, an alkenyl comprises two to six carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)O$R^a$, —C(O)N($R^a)_2$, —N($R^a$)C(O)O$R^f$, —OC(O)—NR$^a$R$^f$, —N($R^a$)C(O)$R^f$, —N($R^a$)S(O)$_t$$R^f$ (where t is 1 or 2), —S(O)$_t$O$R^a$ (where t is 1 or 2), —S(O)$_t$$R^f$ (where t is 1 or 2) and —S(O)$_t$N($R^a)_2$ (where t is 1 or 2) where each $R^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, and each $R^f$ is independently alkyl, fluoroalkyl, cycloalkyl, cycloalkylalkyl, aryl, aralkyl, heterocycloalkyl, heterocycloalkylalkyl, heteroaryl or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In certain embodiments, an alkynyl comprises two to six carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)O$R^a$, —C(O)N($R^a)_2$, —N($R^a$)C(O) O$R^f$, —OC(O)—NR$^a$R$^f$, —N($R^a$)C(O)$R^f$, —N($R^a$)S(O)$_t$$R^f$ (where t is 1 or 2), —S(O)$_t$O$R^a$ (where t is 1 or 2), —S(O)$_t$$R^f$ (where t is 1 or 2) and —S(O)$_t$N($R^a)_2$ (where t is 1 or 2) where each $R^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, and each $R^f$ is independently alkyl, fluoroalkyl, cycloalkyl, cycloalkylalkyl, aryl, aralkyl, heterocycloalkyl, heterocycloalkylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —$OR^a$, —$SR^a$, —OC(O)—$R^a$, —N($R^a$)$_2$, —C(O)$R^a$, —C(O)O$R^a$, —C(O)N($R^a$)$_2$, —N($R^a$)C(O)O$R^f$, —OC(O)—N$R^a R^f$, —N($R^a$)C(O)$R^f$, —N($R^a$)S(O)$_t R^f$ (where t is 1 or 2), —S(O)$_t$O$R^f$ (where t is 1 or 2), —S(O)$_t R^f$ (where t is 1 or 2) and —S(O)$_t$N($R^a$)$_2$ (where t is 1 or 2) where each $R^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, and each $R^f$ is independently alkyl, fluoroalkyl, cycloalkyl, cycloalkylalkyl, aryl, aralkyl, heterocycloalkyl, heterocycloalkylalkyl, heteroaryl or heteroarylalkyl.

"Aminoalkyl" refers to a radical of the formula —$R^c$—N($R^a$)$_2$ or —$R^c$—N($R^a$)—$R^c$, where each $R^c$ is independently an alkylene chain as defined above, for example, methylene, ethylene, and the like; and each $R^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl.

"Alkoxy" refers to a radical of the formula —$OR^a$ where $R^a$ is an alkyl radical as defined. Unless stated otherwise specifically in the specification, an alkoxy group may be optionally substituted as described above for alkyl.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused (when fused with a cycloalkyl or heterocycloalkyl ring, the aryl is bonded through an aromatic ring atom) or bridged ring systems. Aryl radicals include, but are not limited to, aryl radicals derived from the hydrocarbon ring systems of aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl group is optionally substituted by one or more of the following substituents: alkyl, alkenyl, alkynyl, halo, fluoroalkyl, cyano, nitro, aryl, aralkyl, aralkenyl, aralkynyl, cycloalkyl, cycloalkylalkyl, heterocycloalkyl, heterocycloalkylalkyl, heteroaryl, heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t R^a$ (where t is 1 or 2), —$R^b$—S(O)$_t$O$R^a$ (where t is 1 or 2), —$R^b$—S(O)$_t R^a$ (where t is 1 or 2), and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl (optionally substituted with one or more halo groups), aralkyl, heterocycloalkyl (optionally substituted with one or more alkyl groups), heterocycloalkylalkyl, heteroaryl or heteroarylalkyl, or two $R^a$ attached to the same nitrogen atom are combined to form a heterocycloalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aryloxy" refers to a radical bonded through an oxygen atom of the formula —O-aryl, where aryl is as defined above.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Cycloalkyl" or "carbocycle" refers to a stable, non-aromatic, monocyclic or polycyclic carbocyclic ring, which may include fused (when fused with an aryl or a heteroaryl ring, the cycloalkyl is bonded through a non-aromatic ring atom) or bridged ring systems, which is saturated or unsaturated. Representative cycloalkyls or carbocycles include, but are not limited to, cycloalkyls having from three to fifteen carbon atoms, from three to ten carbon atoms, from three to eight carbon atoms, from three to six carbon atoms, from three to five carbon atoms, or three to four carbon atoms. Monocyclic cycloalkyls or carbocycles include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Unless otherwise stated specifically in the specification, the cycloalkyl is optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted heterocycloalkyl, optionally substituted heterocycloalkylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t$$R^a$ (where t is 1 or 2), —$R^b$—S(O)$_t$O$R^a$ (where t is 1 or 2), —$R^b$—S(O)$_t$$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Cycloalkylalkyl" refers to a radical of the formula —$R^c$-cycloalkyl where $R^c$ is an alkylene chain as defined above. The alkylene chain and the cycloalkyl radical are optionally substituted as defined above.

"Fused" refers to any ring structure described herein which is fused to an existing ring structure. When the fused ring is a heretocycloalkyl ring or a heteroaryl ring, any carbon atom on the existing ring structure which becomes part of the fused heretocycloalkyl ring or the fused heteroaryl ring may be replaced with a nitrogen atom.

"Heteroalkyl" refers to a straight or branched hydrocarbon chain alkyl radical containing no unsaturation, having from one to fifteen carbon atoms (e.g., $C_1$-$C_{15}$ alkyl) consisting of carbon and hydrogen atoms and one or two heteroatoms selected from O, N, and S, wherein the nitrogen or sulfur atoms may be optionally oxidized and the nitrogen atom may be quaternized. The heteroatom(s) may be placed at any position of the heteroalkyl group including between the rest of the heteroalkyl group and the fragment to which it is attached. The heteroalkyl is attached to the rest of the molecule by a single bond. Unless stated otherwise specifically in the specification, a heteroalkyl group is optionally substituted by one or more of the following substituents: halo, cyano, nitro, oxo, thioxo, imino, oximo, trimethylsilanyl, —O$R^a$, —S$R^a$, —OC(O)—$R^a$, —N($R^a$)$_2$, —C(O)$R^a$, —C(O)O$R^a$, —C(O)N($R^a$)$_2$, —N($R^a$)C(O) O$R^f$, —OC(O)—N$R^a$$R^f$, —N($R^a$)C(O)$R^f$, —N($R^a$)S(O)$_t$$R^f$ (where t is 1 or 2), —S(O)$_t$O$R^a$ (where t is 1 or 2), —S(O)$_t$$R^f$ (where t is 1 or 2) and —S(O)$_t$N($R^a$)$_2$ (where t is 1 or 2) where each $R^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, and each $R^f$ is independently alkyl, fluoroalkyl, cycloalkyl, cycloalkylalkyl, aryl, aralkyl, heterocycloalkyl, heterocycloalkylalkyl, heteroaryl or heteroarylalkyl.

"Halo" or "halogen" refers to bromo, chloro, fluoro or iodo. In some embodiments, halogen refers to chloro or fluoro.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Haloalkoxy" similarly refers to a radical of the formula —O$R^a$ where $R^a$ is a haloalkyl radical as defined. Unless stated otherwise specifically in the specification, a haloalkoxy group may be optionally substituted as described below.

"Heterocycloalkyl" or "heterocycle" refers to a stable 3- to 24-membered non-aromatic ring radical comprising 2 to 23 carbon atoms and from one to 8 heteroatoms selected from the group consisting of nitrogen, oxygen, phosphorous and sulfur. Unless stated otherwise specifically in the specification, the heterocycloalkyl radical may be a monocyclic, bicyclic, tricyclic or tetracyclic ring system, which may include fused (when fused with an aryl or a heteroaryl ring, the heterocycloalkyl is bonded through a non-aromatic ring atom) or bridged ring systems; and the nitrogen, carbon or sulfur atoms in the heterocycloalkyl radical may be optionally oxidized; the nitrogen atom may be optionally quaternized; and the heterocycloalkyl radical may be partially or fully saturated. Examples of such heterocycloalkyl radicals include, but are not limited to, aziridinyl, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, 2-oxo-1,3-dioxol-4-yl, 1,1-dioxidotetrahydro-2H-thiopyranyl, tetrahydro-2H-thiopyranyl, and tetrahydro-2H-pyranyl. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group is optionally substituted by one or more of the following substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted heterocycloalkyl, optionally substituted heterocycloalkylalkyl, optionally substituted heteroaryl, optionally substituted heteroarylalkyl, —$R^b$—O$R^a$, —$R^b$—OC(O)—$R^a$, —$R^b$—OC(O)—O$R^a$, —$R^b$—OC(O)—N($R^a$)$_2$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t$$R^a$ (where t is 1 or 2), —$R^b$—S(O)$_t$O$R^a$ (where t is 1 or 2), —$R^b$—S(O)$_t$$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Heterocycloalkyllalkyl" refers to a radical of the formula —$R^c$-heterocycloalkyl where $R^c$ is an alkylene chain as defined above. If the heterocycloalkyl is a nitrogen-containing heterocycloalkyl, the heterocycloalkyl is optionally attached to the alkyl radical at the nitrogen atom. The alkylene chain of the heterocycloalkylslkyl radical is optionally substituted as defined above for an alkylene chain. The heterocycloalkyl part of the heterocycloalkylalkyl radical is optionally substituted as defined above for a heterocycloalkyl group.

"heterocycloalkylalkoxy" refers to a radical bonded through an oxygen atom of the formula —O—$R^c$-heterocycloalkyl where $R^c$ is an alkylene chain as defined above. If the heterocycloalkyl is a nitrogen-containing heterocycloalkyl, the heterocycloalkyl is optionally attached to the alkyl radical at the nitrogen atom. The alkylene chain of the heterocycloalkylalkoxy radical is optionally substituted as defined above for an alkylene chain. The heterocycloalkyl part of the heterocycloalkylalkoxy radical is optionally substituted as defined above for a heterocycloalkyl group.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. In some embodiments, the heteroaryl is a 5-membered heteroaryl. In some embodiments, the heteroaryl is a 6-membered heteroaryl. For purposes of this invention, the heteroaryl radical may be a monocyclic, bicyclic, tricyclic or tetracyclic ring system, which may include fused (when fused with a cycloalkyl or heterocycloalkyl ring, the heteroaryl is bonded through an aromatic ring atom) or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group is optionally substituted by one or more of the following substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted heterocycloalkyl, optionally substituted heterocycloalkylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$R$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroaryloxy" refers to radical bonded through an oxygen atom of the formula —O— heteroaryl, where heteroaryl is as defined above.

"Heteroarylalkyl" refers to a radical of the formula —R$^c$-heteroaryl, where R$^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—R$^c$-heteroaryl, where R$^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

In some embodiments, the compounds disclosed herein contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. In certain embodiments, the compounds presented herein exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

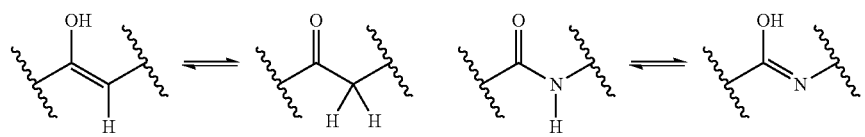

-continued

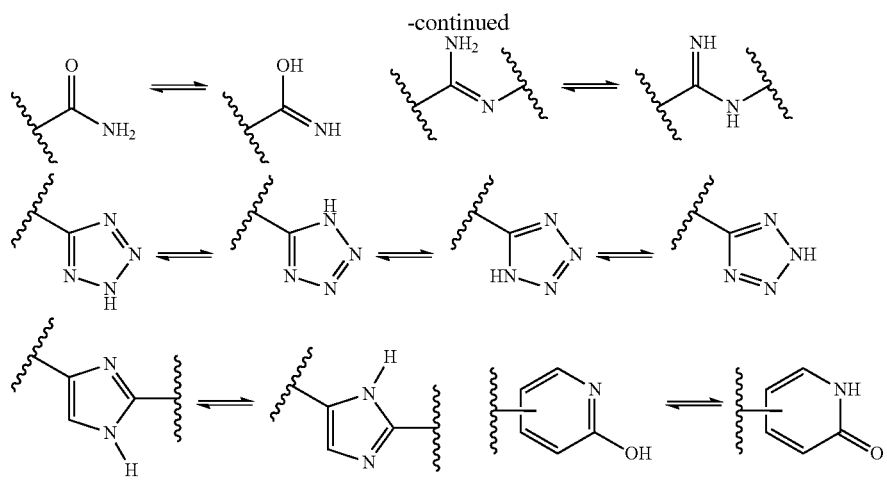

In some embodiments, the tautomeric equilibrium is:

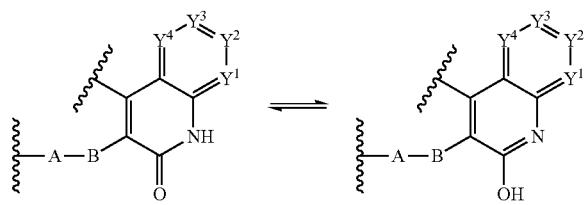

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution. "Optionally substituted" and "substituted or unsubstituted" and "unsubstituted or substituted" are used interchangeably herein.

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997)). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof.

When ranges are used herein for physical properties, such as molecular weight, or chemical properties, such as chemical formulae, all combinations and subcombinations of ranges and specific embodiments therein are intended to be included.

The term "about" when referring to a number or a numerical range means that the number or numerical range referred to is an approximation within experimental variability (or within statistical experimental error), and thus the number or numerical range varies between 1% and 15% of the stated number or numerical range.

The term "comprising" (and related terms such as "comprise" or "comprises" or "having" or "including") is not intended to exclude that which in other certain embodiments, for example, an embodiment of any composition of matter, composition, method, or process, or the like, described herein, "consist of" or "consist essentially of" the described features.

The term "subject" or "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The term "modulate," as used herein, means to interact with a target protein either directly or indirectly so as to alter the activity of the target protein, including, by way of example only, to inhibit the activity of the target, or to limit or reduce the activity of the target.

As used herein, the term "modulator" refers to a compound that alters an activity of a target. For example, a modulator can cause an increase or decrease in the magnitude of a certain activity of a target compared to the magnitude of the activity in the absence of the modulator. In certain embodiments, a modulator is an inhibitor, which decreases the magnitude of one or more activities of a target. In certain embodiments, an inhibitor completely prevents one or more activities of a target.

As used herein, "treatment" or "treating" or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has not been made.

Compounds

Compounds described herein are modulators of the eukaryotic translation initiation factor 4F (eIF4F) complex. These compounds, and compositions comprising these compounds, are useful for the treatment of cancer.

One aspect provides a compound of Formula (I), or a pharmaceutically acceptable salt, solvate, tautomer, or N-oxide thereof:

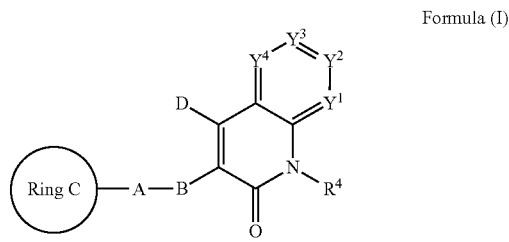

Formula (I)

wherein

Ring C is 6-membered aryl, 5-membered heteroaryl, or 6-membered heteroaryl; wherein the 6-membered aryl, 5-membered heteroaryl, and a 6-membered heteroaryl are optionally substituted with one or more $R^1$;

D is aryl, heteroaryl, alkyl, cycloalkyl, or heterocycloalkyl; wherein the aryl, heteroaryl, alkyl, cycloalkyl, and heterocycloalkyl are optionally substituted with one or more $R^1$;

A and B are independently a bond, —$CH_2$—, —$CH_2CH_2$—, —C(=O)—, —$CR^5$=$CR^6$—, ≡≡≡, —C(=O)$NR^a$—, or —$NR^aC$(=O)—;

$Y^1$-$Y^4$ are independently N or $CR^2$;

each $R^1$ are independently hydrogen, halogen, hydroxyl, alkoxy, cyano, —$NR^aR^b$, —C(=O)$OR^c$, alkyl, cycloalkyl, or aryl; wherein the alkyl, alkoxy, cycloalkyl, and aryl are optionally substituted with one or more $R^d$;

each $R^2$ are independently hydrogen, halogen, hydroxyl, nitro, alkoxy, —$NR^aR^b$, alkyl, or cycloalkyl; wherein the alkyl and cycloalkyl are optionally substituted with one or more $R^d$;

$R^4$ is hydrogen, alkyl, or aralkyl;

$R^5$ and $R^6$ are independently hydrogen, halogen, or alkyl;

each $R^a$ and $R^b$ are independently hydrogen or alkyl; or $R^a$ and $R^b$ taken together with the nitrogen to which they are attached form a heterocycloalkyl optionally substituted with alkyl;

$R^c$ is hydrogen or alkyl; and each $R^d$ is independently alkyl, halogen, hydroxyl, alkoxy, cyano, or —$NR^aR^b$;

provided that when ring C is unsubstituted phenyl, D is unsubstituted phenyl, $Y^1$, $Y^2$, $Y^4$ are CH, $R^4$ is H, B is —C(=O)—, A is —CH=CH—, then $Y^3$ is not C—Cl.

In some embodiments of a compound of Formula (I), or a pharmaceutically acceptable salt, solvate, tautomer, or N-oxide thereof, $R^4$ is hydrogen.

In some embodiments of a compound of Formula (I), or a pharmaceutically acceptable salt, solvate, tautomer, or N-oxide thereof, Ring C is a 5-membered heteroaryl optionally substituted with one or more $R^1$.

In some embodiments of a compound of Formula (I), or a pharmaceutically acceptable salt, solvate, tautomer, or N-oxide thereof, Ring C is pyrrolyl, imidazolyl, thiophenyl, or furanyl; wherein the pyrrolyl, imidazolyl, thiophenyl, and furanyl are optionally substituted with one or more $R^1$.

In some embodiments of a compound of Formula (I), or a pharmaceutically acceptable salt, solvate, tautomer, or N-oxide thereof, Ring C is a 6-membered aryl or a 6-membered heteroaryl of the general formula:

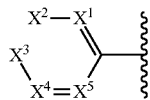

wherein $X^1$-$X^5$ are independently N or $CR^1$.

In some embodiments of a compound of Formula (I), or a pharmaceutically acceptable salt, solvate, tautomer, or N-oxide thereof, Ring C is a 6-membered aryl or a 6-membered heteroaryl of the general formula:

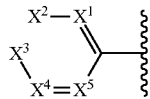

and at least one of $X^1$-$X^5$ is N.

In some embodiments of a compound of Formula (I), or a pharmaceutically acceptable salt, solvate, tautomer, or N-oxide thereof, Ring C is a 6-membered aryl or a 6-membered heteroaryl of the general formula:

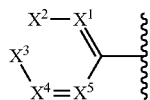

and one of $X^1$-$X^5$ is N.

In some embodiments of a compound of Formula (I), or a pharmaceutically acceptable salt, solvate, tautomer, or N-oxide thereof, Ring C is a 6-membered aryl or a 6-membered heteroaryl of the general formula:

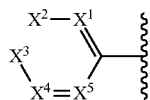

and two of $X^1$-$X^5$ is N.

In some embodiments of a compound of Formula (I), or a pharmaceutically acceptable salt, solvate, tautomer, or N-oxide thereof, Ring C is a 6-membered aryl or a 6-membered heteroaryl of the general formula:

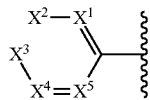

and $X^2$-$X^5$ are $CR^1$.

In some embodiments of a compound of Formula (I), or a pharmaceutically acceptable salt, solvate, tautomer, or N-oxide thereof, Ring C is a 6-membered aryl or a 6-membered heteroaryl of the general formula:

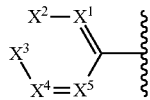

and $X^2$ is N and $X^1$, $X^3$-$X^5$ are $CR^1$.

In some embodiments of a compound of Formula (I), or a pharmaceutically acceptable salt, solvate, tautomer, or N-oxide thereof, Ring C is a 6-membered aryl or a 6-membered heteroaryl of the general formula:

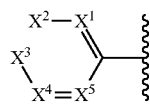

and $X^3$ is N and $X^1$-$X^2$ and $X^4$-$X^5$ are $CR^1$.

In some embodiments of a compound of Formula (I), or a pharmaceutically acceptable salt, solvate, tautomer, or N-oxide thereof, Ring C is a 6-membered aryl or a 6-membered heteroaryl of the general formula:

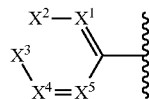

and $X^2$ and $X^4$ are N and $X^1$, $X^3$ and $X^5$ are $CR^1$.

In some embodiments of a compound of Formula (I), or a pharmaceutically acceptable salt, solvate, tautomer, or N-oxide thereof, Ring C is a 6-membered aryl or a 6-membered heteroaryl of the general formula:

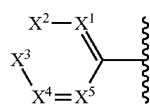

and $X^2$ and $X^5$ are N and $X^1$, $X^3$ and $X^4$ are $CR^1$.

In some embodiments of a compound of Formula (I), or a pharmaceutically acceptable salt, solvate, tautomer, or N-oxide thereof, Ring C is a 6-membered aryl or a 6-membered heteroaryl of the general formula:

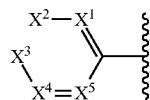

and $X^1$ and $X^5$ are N and $X^2$-$X^4$ are $CR^1$.

In some embodiments of a compound of Formula (I), or a pharmaceutically acceptable salt, solvate, tautomer, or N-oxide thereof, Ring C is a 6-membered aryl or a 6-membered heteroaryl of the general formula:

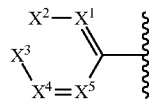

and $X^1$ and $X^3$ are N and $X^2$, $X^4$ and $X^5$ are $CR^1$.

In some embodiments of a compound of Formula (I), or a pharmaceutically acceptable salt, solvate, tautomer, or N-oxide thereof, Ring C is a 6-membered aryl or a 6-membered heteroaryl of the general formula:

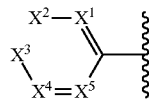

and $X^1$ and $X^2$ are N and $X^3$-$X^5$ are $CR^1$.

In some embodiments of a compound of Formula (I), or a pharmaceutically acceptable salt, solvate, tautomer, or N-oxide thereof, Ring C is a 6-membered aryl or a 6-membered heteroaryl of the general formula:

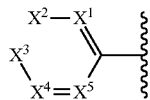

and $X^2$ and $X^3$ are N and $X^1$, $X^4$ and $X^5$ are $CR^1$.

In some embodiments of a compound of Formula (I), or a pharmaceutically acceptable salt, solvate, tautomer, or N-oxide thereof, D is cycloalkyl optionally substituted with one or more $R^1$.

In some embodiments of a compound of Formula (I), or a pharmaceutically acceptable salt, solvate, tautomer, or N-oxide thereof, D is cyclopropyl, cyclobutyl, cycopentyl, or cyclohexyl; wherein the cyclopropyl, cyclobutyl, cycopentyl, and cyclohexyl are optionally substituted with one or more $R^1$.

In some embodiments of a compound of Formula (I), or a pharmaceutically acceptable salt, solvate, tautomer, or N-oxide thereof, D is 5-membered heteroaryl optionally substituted with one or more $R^1$.

In some embodiments of a compound of Formula (I), or a pharmaceutically acceptable salt, solvate, tautomer, or N-oxide thereof, D is pyrrolyl, imidazolyl, thiophenyl, or furanyl; wherein the pyrrolyl, imidazolyl, thiophenyl, and furanyl are optionally substituted with one or more $R^1$.

In some embodiments of a compound of Formula (I), or a pharmaceutically acceptable salt, solvate, tautomer, or N-oxide thereof, D is aryl or heteroaryl of the general formula:

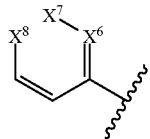

wherein $X^6$-$X^8$ are independently N or $CR^1$.

In some embodiments of a compound of Formula (I), or a pharmaceutically acceptable salt, solvate, tautomer, or N-oxide thereof, D is aryl or heteroaryl of the general formula:

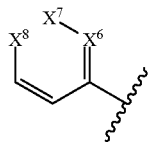

and at least one of $X^6$-$X^8$ is N.

In some embodiments of a compound of Formula (I), or a pharmaceutically acceptable salt, solvate, tautomer, or N-oxide thereof, D is aryl or heteroaryl of the general formula:

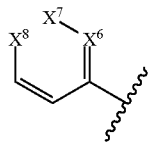

and one of $X^6$-$X^8$ is N.

In some embodiments of a compound of Formula (I), or a pharmaceutically acceptable salt, solvate, tautomer, or N-oxide thereof, D is aryl or heteroaryl of the general formula:

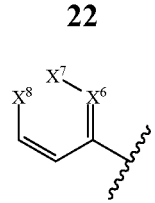

and $X^6$ is N; and $X^7$ and $X^8$ are $CR^1$.

In some embodiments of a compound of Formula (I), or a pharmaceutically acceptable salt, solvate, tautomer, or N-oxide thereof, D is aryl or heteroaryl of the general formula:

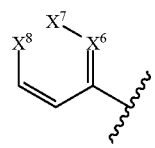

and $X^7$ is N; and $X^6$ and $X^8$ are $CR^1$.

In some embodiments of a compound of Formula (I), or a pharmaceutically acceptable salt, solvate, tautomer, or N-oxide thereof, D is aryl or heteroaryl of the general formula:

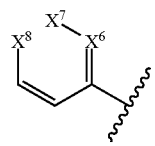

and $X^8$ is N; and $X^6$ and $X^7$ are $CR^1$.

In some embodiments of a compound of Formula (I), or a pharmaceutically acceptable salt, solvate, tautomer, or N-oxide thereof, D is aryl or heteroaryl of the general formula:

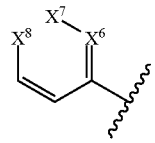

and $X^6$-$X^8$ are $CR^1$.

In some embodiments of a compound of Formula (I), or a pharmaceutically acceptable salt, solvate, tautomer, or N-oxide thereof, at least one of $Y^1$-$Y^4$ is N. In some embodiments of a compound of Formula (I), or a pharmaceutically acceptable salt, solvate, tautomer, or N-oxide thereof, $Y^1$ is N. In some embodiments of a compound of Formula (I), or a pharmaceutically acceptable salt, solvate, tautomer, or N-oxide thereof, $Y^2$ is N. In some embodiments of a compound of Formula (I), or a pharmaceutically acceptable salt, solvate, tautomer, or N-oxide thereof, $Y^3$ is N. In some embodiments of a compound of Formula (I), or a pharmaceutically acceptable salt, solvate, tautomer, or N-oxide thereof, $Y^4$ is N. In some embodiments of a compound of Formula (I), or a pharmaceutically acceptable salt, solvate, tautomer, or N-oxide thereof, $Y^1$-$Y^4$ are $CR^2$.

In some embodiments of a compound of Formula (I), or a pharmaceutically acceptable salt, solvate, tautomer, or N-oxide thereof, B is —C(=O)—. In some embodiments of a compound of Formula (I), or a pharmaceutically acceptable salt, solvate, tautomer, or N-oxide thereof, B is a bond.

In some embodiments of a compound of Formula (I), or a pharmaceutically acceptable salt, solvate, tautomer, or N-oxide thereof, A is —CH=CH—. In some embodiments of a compound of Formula (I), or a pharmaceutically acceptable salt, solvate, tautomer, or N-oxide thereof, A is —CH₂CH₂—.

In some embodiments of a compound of Formula (I), or a pharmaceutically acceptable salt, solvate, tautomer, or N-oxide thereof, B is —C(=O)— and A is —CH=CH—.

In some embodiments of a compound of Formula (I), or a pharmaceutically acceptable salt, solvate, tautomer, or N-oxide thereof, each $R^1$ is independently hydrogen, halogen, alkyl, alkoxy, cyano, —NR$^a$R$^b$, or —C(=O)OR$^c$; wherein the alkyl and alkoxy are optionally substituted with one or more halogen or alkoxy.

In some embodiments of a compound of Formula (I), or a pharmaceutically acceptable salt, solvate, tautomer, or N-oxide thereof, each $R^1$ is independently hydrogen, fluoro, chloro, bromo, methyl, —CF₃, —OCF₃, methoxy, cyano, —CH₂OCH₃, —N(Me)₂, or —C(=O)OEt.

In some embodiments of a compound of Formula (I), or a pharmaceutically acceptable salt, solvate, tautomer, or N-oxide thereof, each $R^1$ is independently hydrogen or fluoro.

In some embodiments of a compound of Formula (I), or a pharmaceutically acceptable salt, solvate, tautomer, or N-oxide thereof, each $R^2$ is independently hydrogen or halogen.

In some embodiments of a compound of Formula (I), or a pharmaceutically acceptable salt, solvate, tautomer, or N-oxide thereof, each $R^2$ is independently hydrogen or chloro.

A compound of Formula (I), or a pharmaceutically acceptable salt, solvate, tautomer, or N-oxide thereof, selected from:

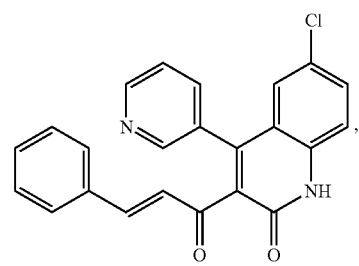

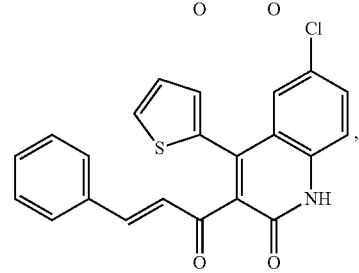

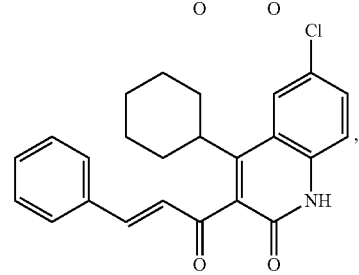

-continued

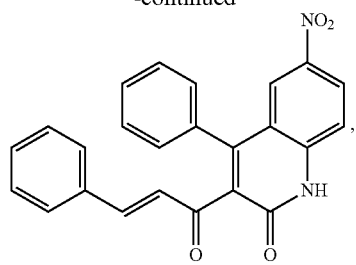

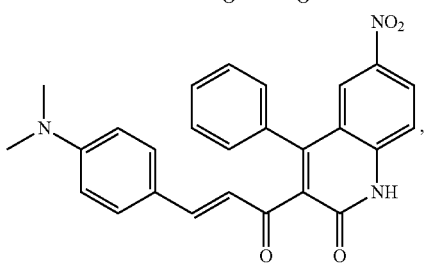

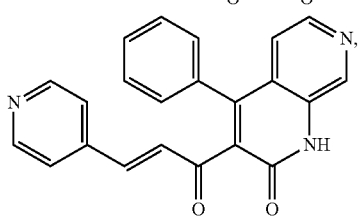

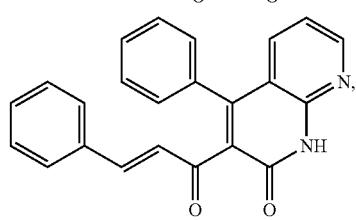

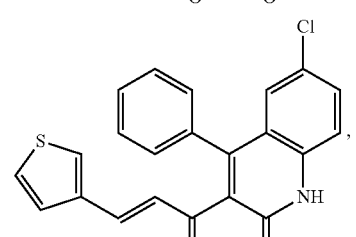

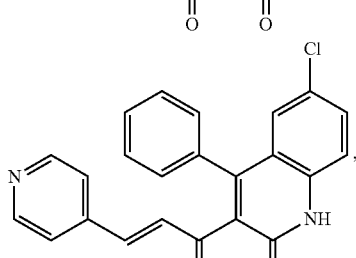

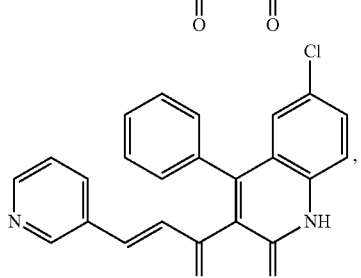

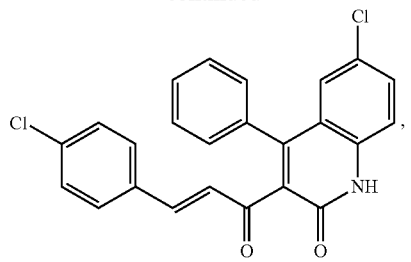,
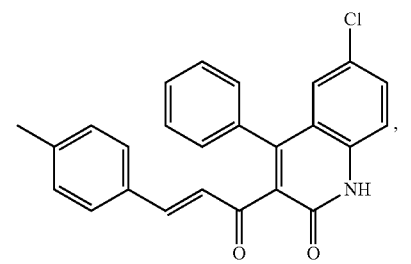,
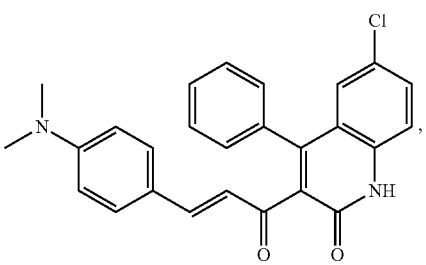,
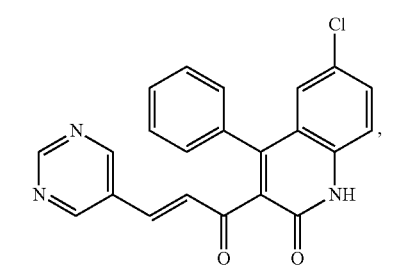,
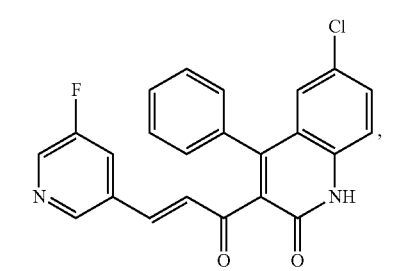,
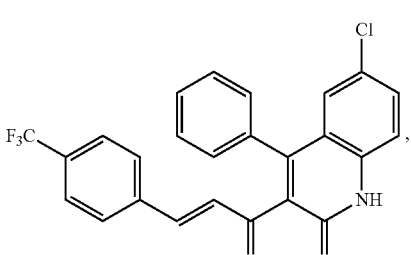,
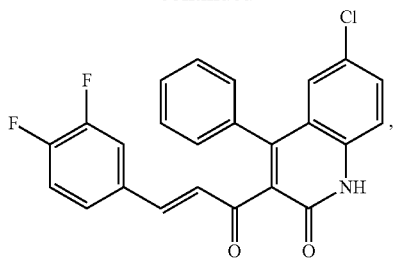,
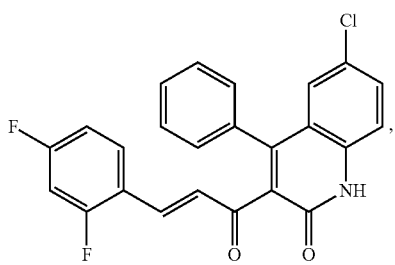,
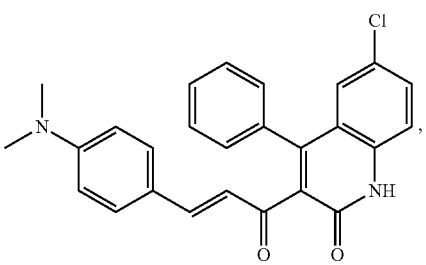,
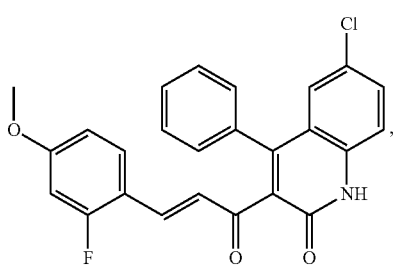,
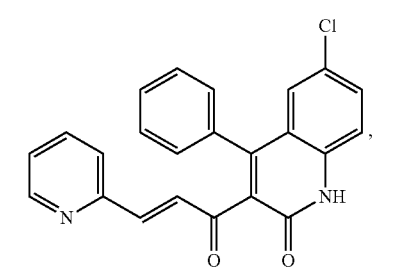,
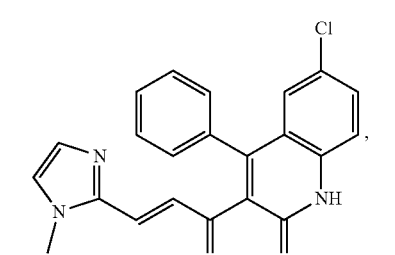, -continued
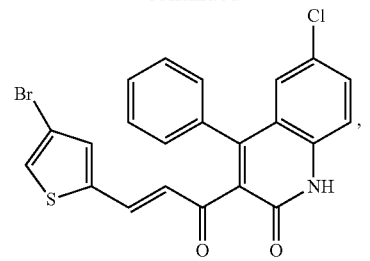
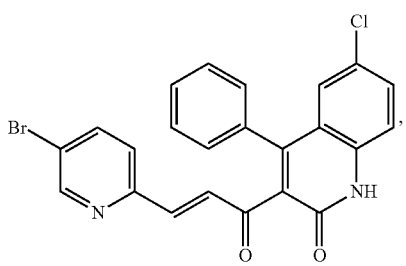
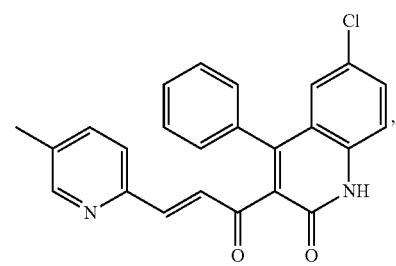
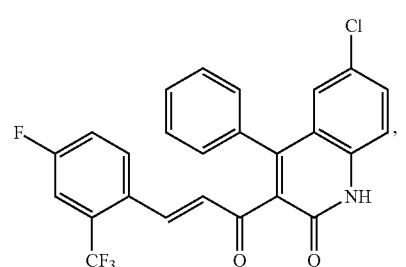
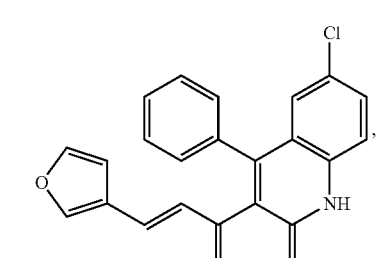
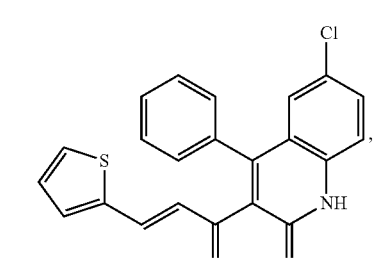
-continued
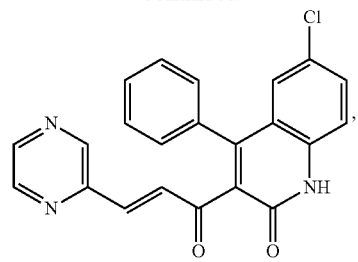
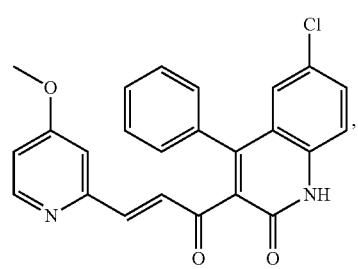
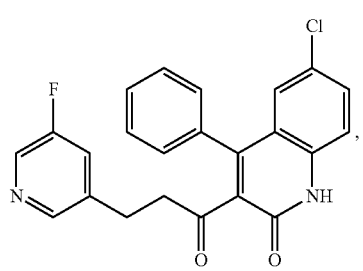
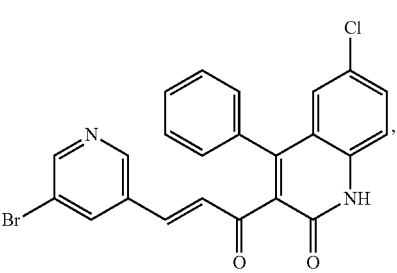
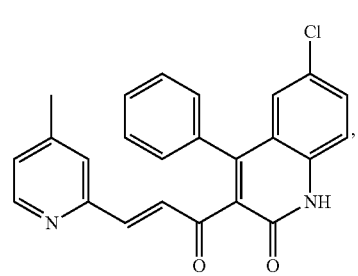
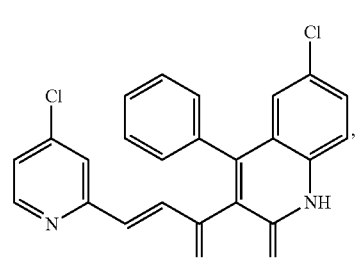

-continued
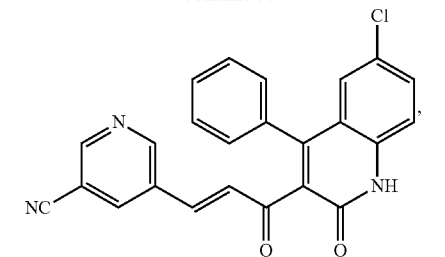
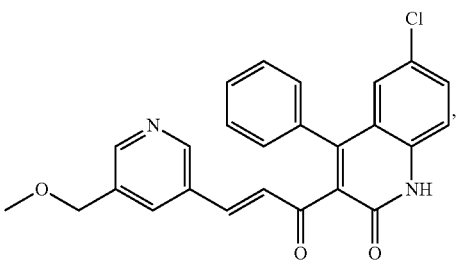
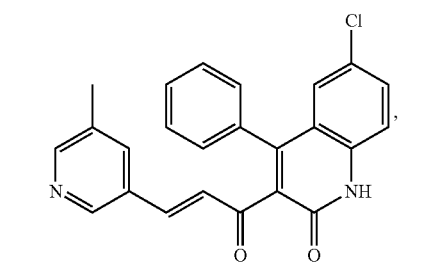
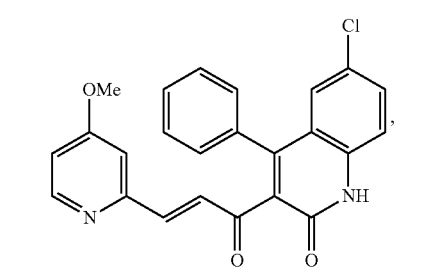
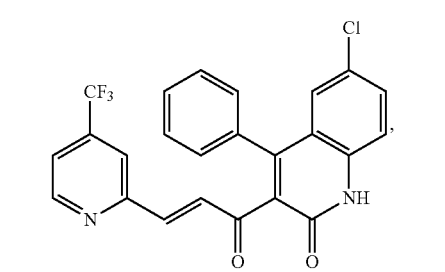
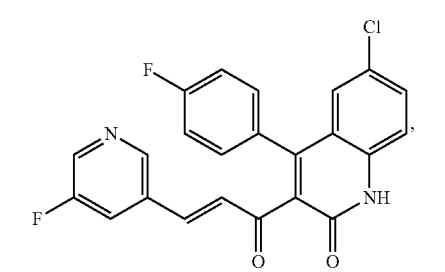
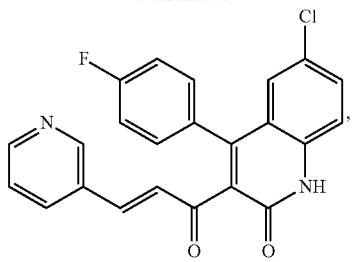
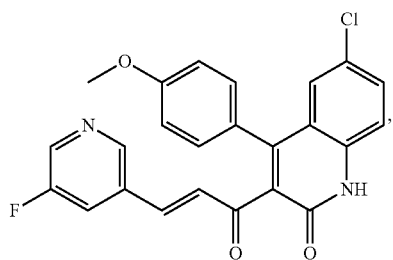
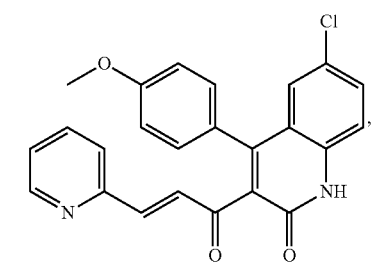
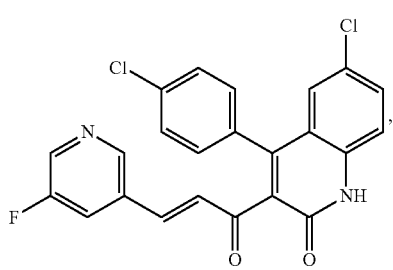
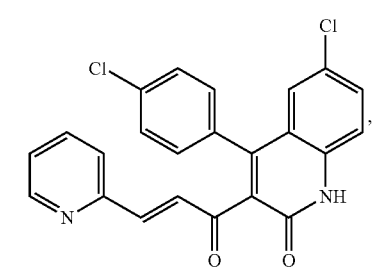
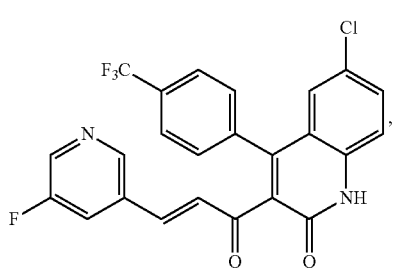

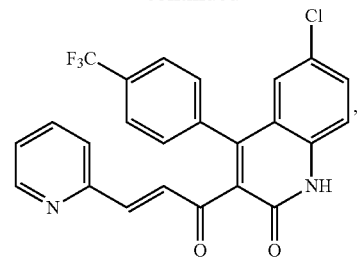
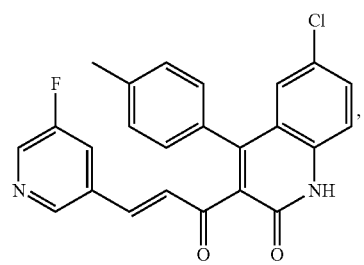
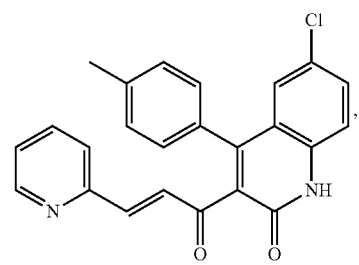
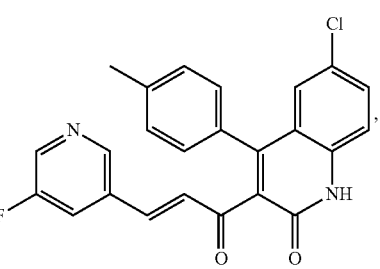
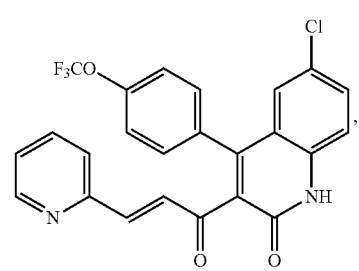
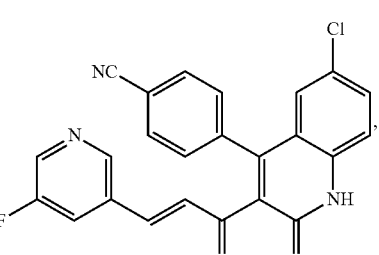
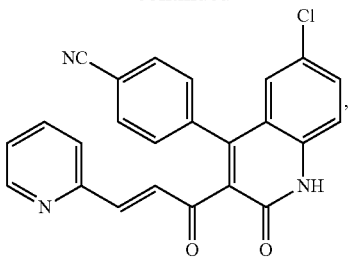
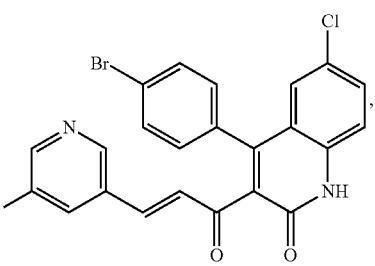
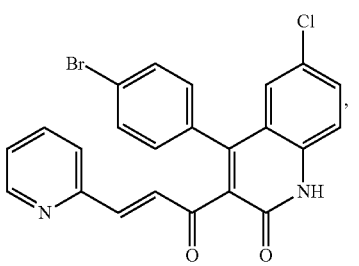
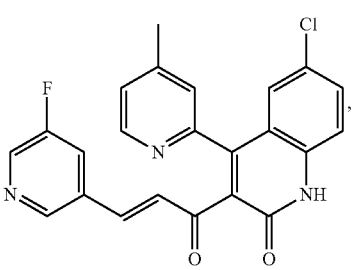
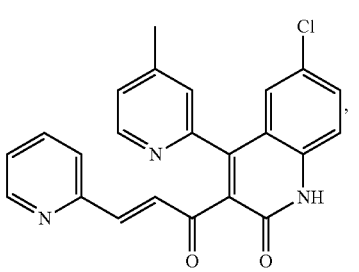
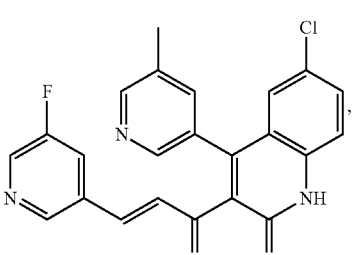

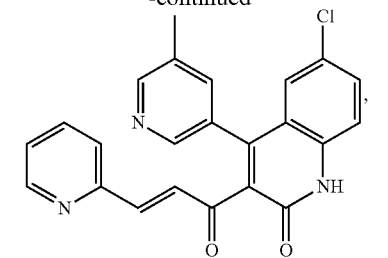
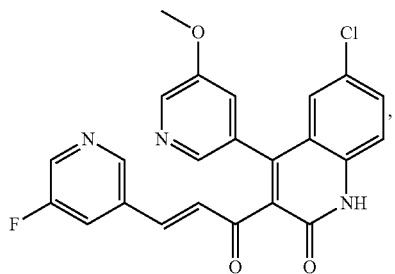
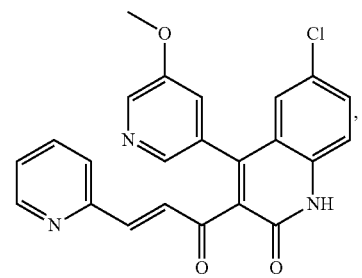
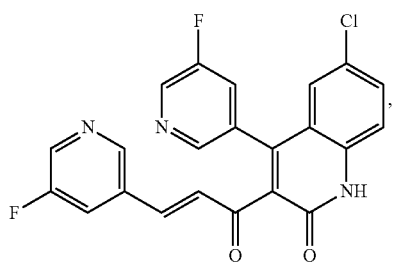
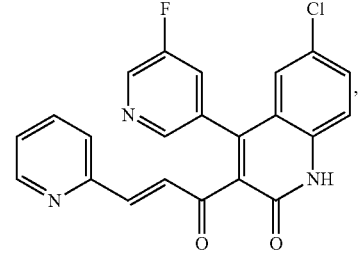
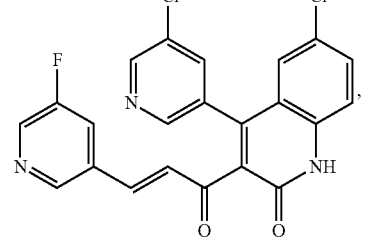
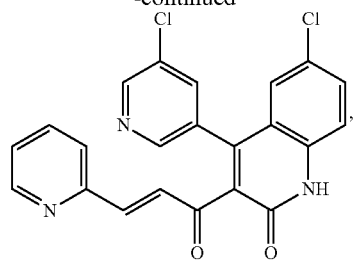
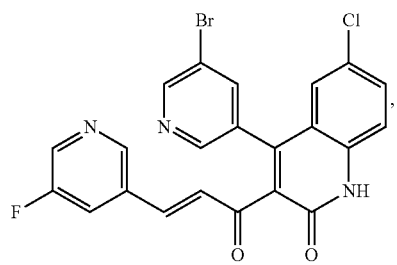
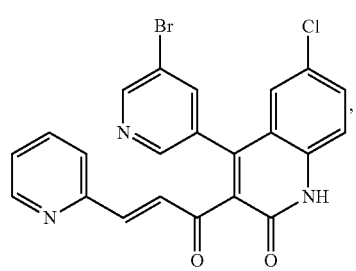
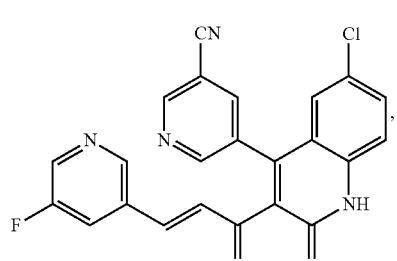
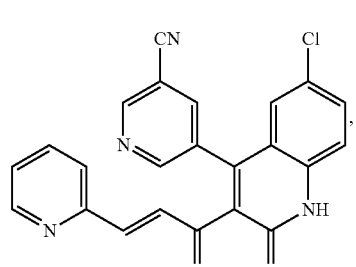
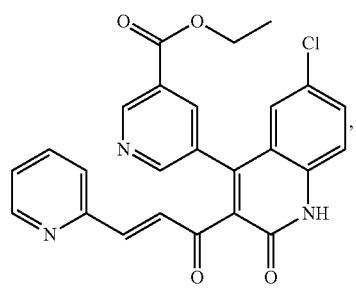

-continued

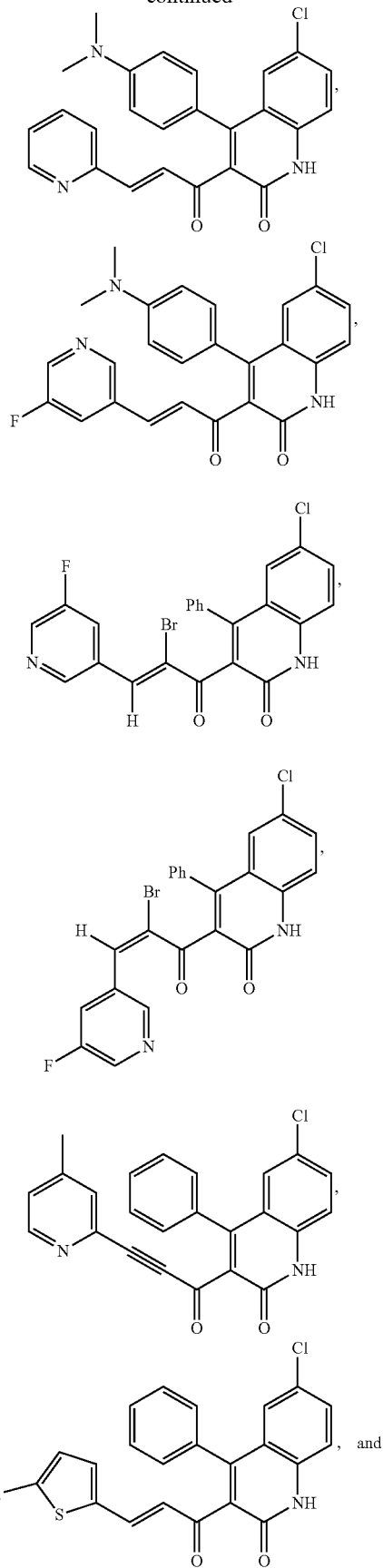

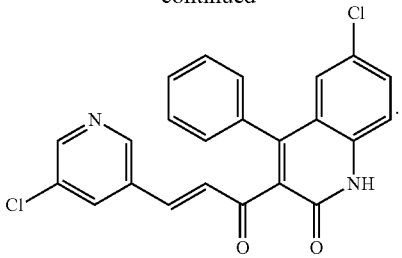

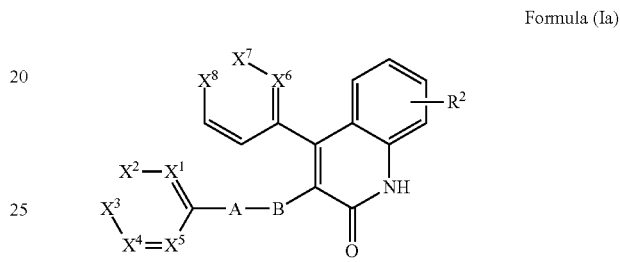

One aspect provides a compound of Formula (Ia), or a pharmaceutically acceptable salt, solvate, tautomer, or N-oxide thereof:

Formula (Ia)

wherein
A and B are independently a bond, —CH$_2$—, —CH$_2$CH$_2$—, —C(=O)—, —CH=CH—, or —C(=O)NH—;
X$^1$-X$^5$ are independently N or CR$^1$;
X$^6$-X$^8$ are independently N or CR$^1$;
each R$^1$ are independently hydrogen, halogen, hydroxyl, alkoxy, cyano, —NR$^a$R$^b$, —C(=O)OR$^c$, alkyl, cycloalkyl, or aryl; wherein the alkyl, alkoxy, cycloalkyl, and aryl are optionally substituted with one or more R$^d$;
R$^2$ is halogen, hydroxyl, alkoxy, alkyl, or cycloalkyl; wherein the alkyl and cycloalkyl are optionally substituted with one or more R$^d$;
R$^a$ and R$^b$ are independently hydrogen or alkyl; or R$^a$ and R$^b$ taken together with the nitrogen to which they are attached form a heterocycloalkyl optionally substituted with alkyl;
R$^c$ is hydrogen or alkyl; and
each R$^d$ is independently alkyl, halogen, hydroxyl, alkoxy, cyano, or —NR$^a$R$^b$;
provided that when ring C is unsubstituted phenyl, D is unsubstituted phenyl, Y$^1$, Y$^2$, Y$^4$ are CH, R$^4$ is H, B is —C(=O)—, A is —CH=CH—, then Y$^3$ is not C—Cl.

In some embodiments of a compound of Formula (Ia), or a pharmaceutically acceptable salt, solvate, tautomer, or N-oxide thereof, at least one of X$^1$-X$^5$ is N.

In some embodiments of a compound of Formula (Ia), or a pharmaceutically acceptable salt, solvate, tautomer, or N-oxide thereof, one of X$^1$-X$^5$ is N.

In some embodiments of a compound of Formula (Ia), or a pharmaceutically acceptable salt, solvate, tautomer, or N-oxide thereof, two of X$^1$-X$^5$ are N.

In some embodiments of a compound of Formula (Ia), or a pharmaceutically acceptable salt, solvate, tautomer, or N-oxide thereof, X$^1$-X$^5$ are CR$^1$.

A compound of Formula (Ia), or a pharmaceutically acceptable salt, solvate, tautomer, or N-oxide thereof, selected from:

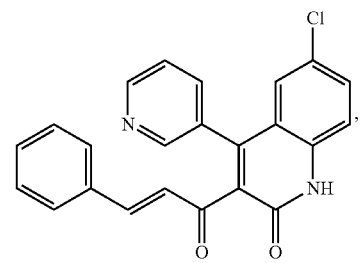
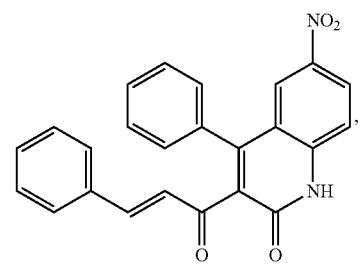
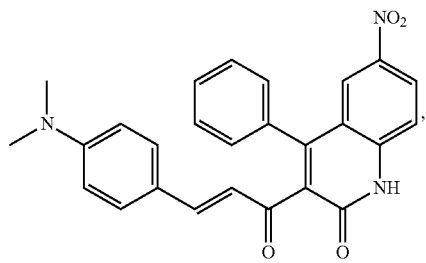
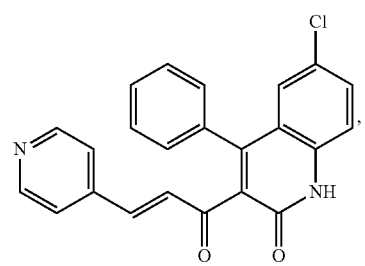
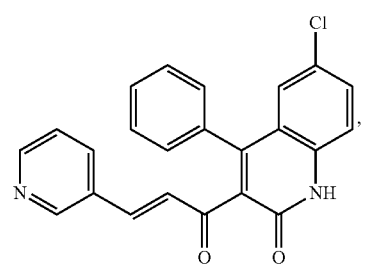
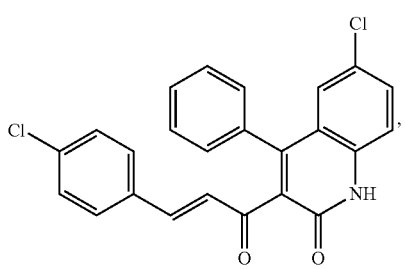
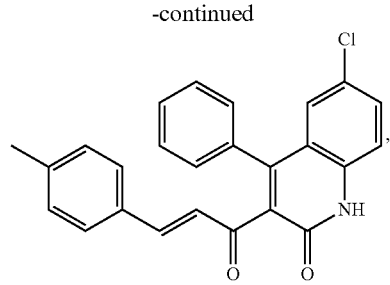
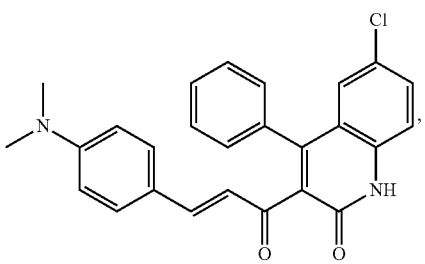
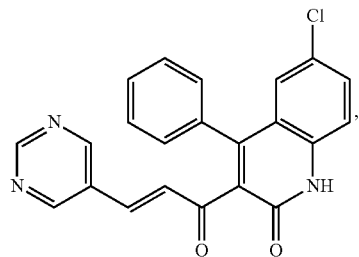
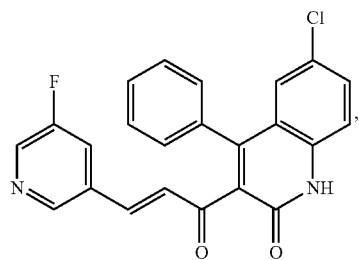
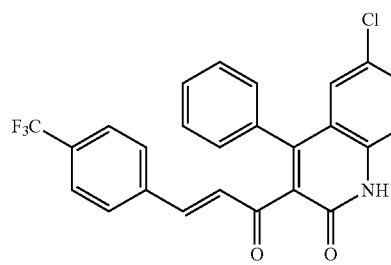
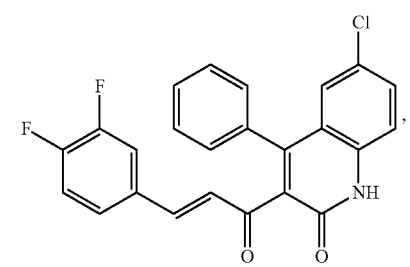

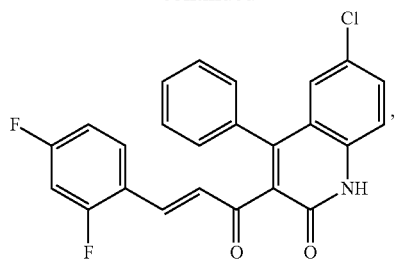
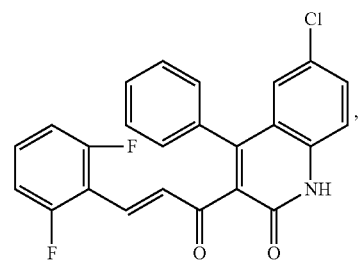
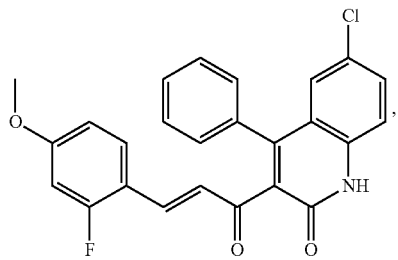
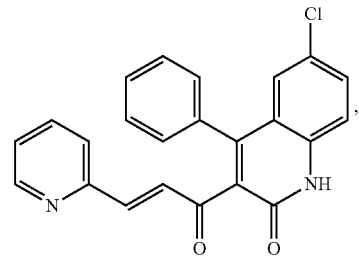
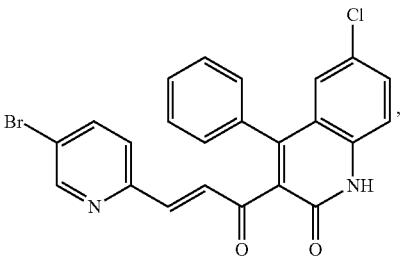
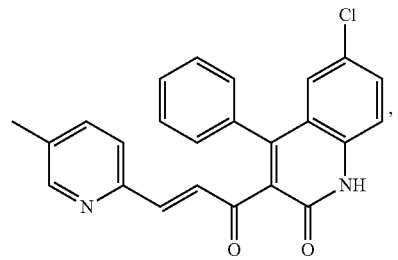
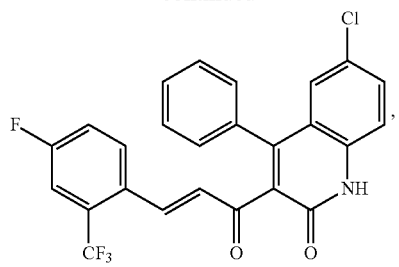
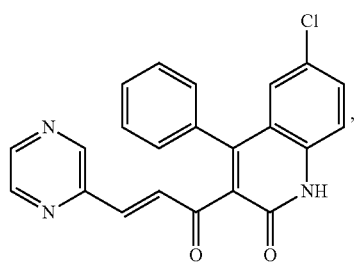
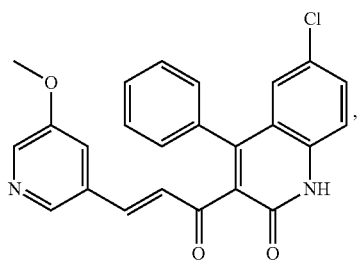
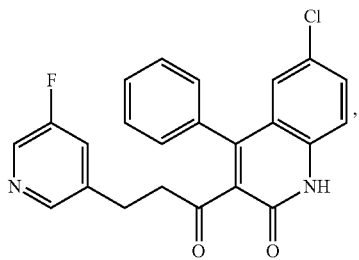
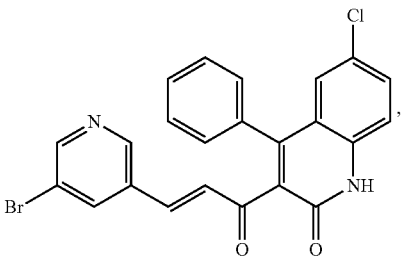
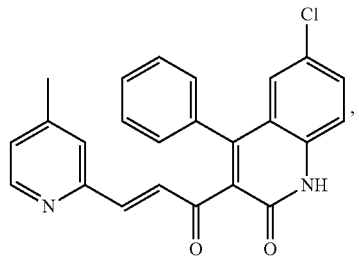

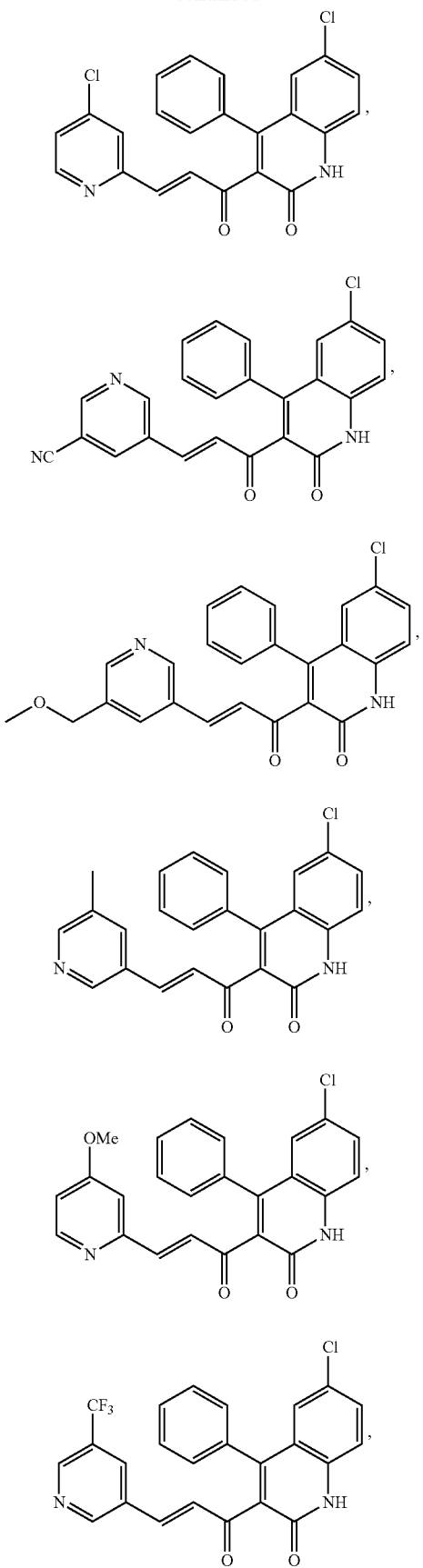
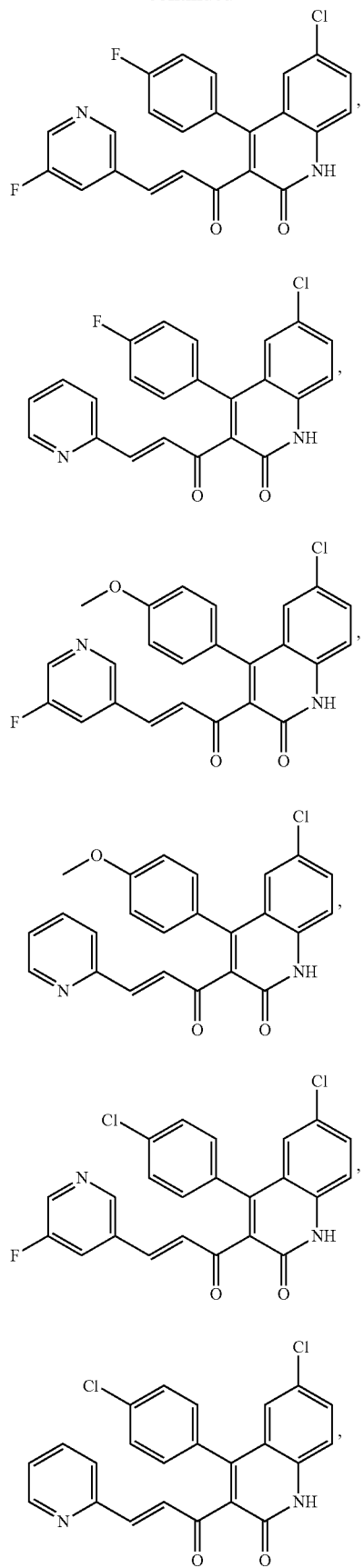

-continued
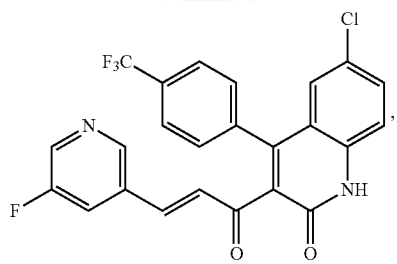
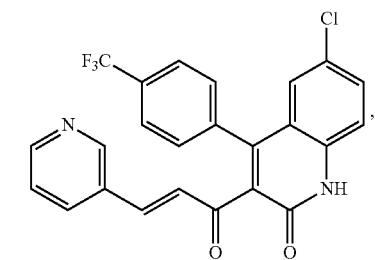
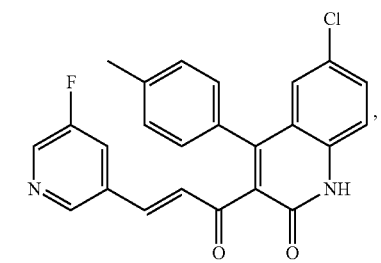
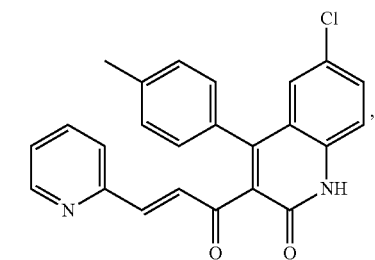
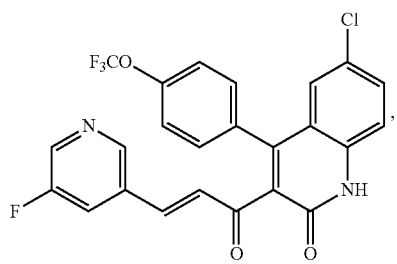
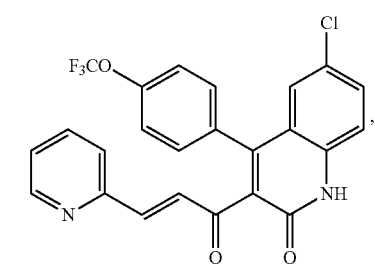
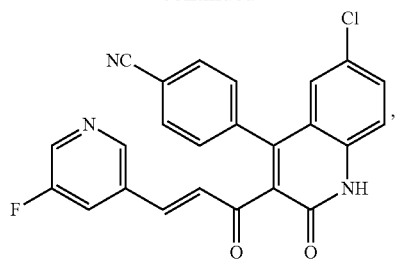
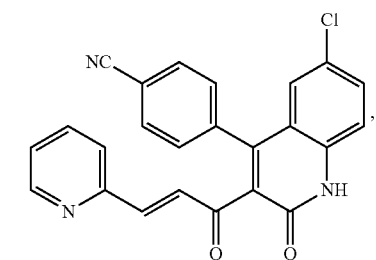
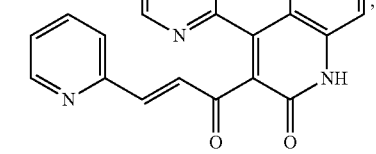
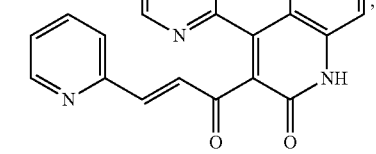
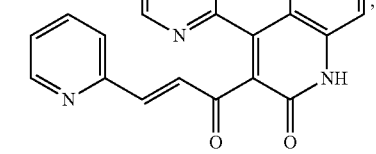
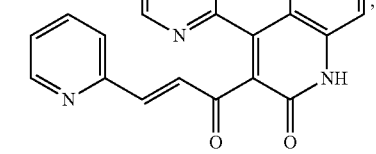

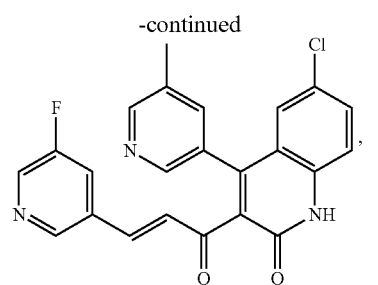,
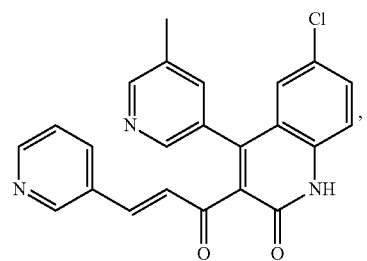,
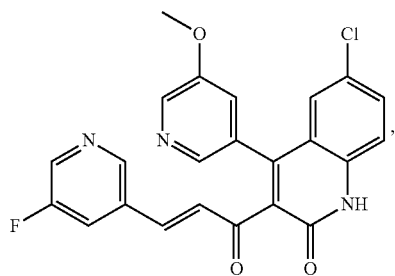,
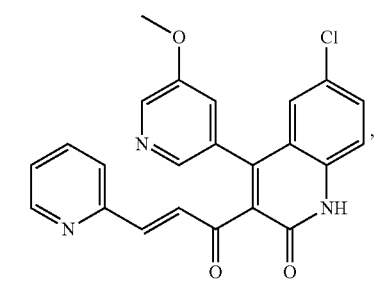,
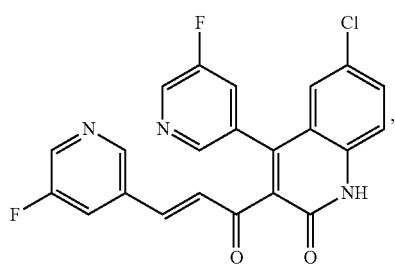,
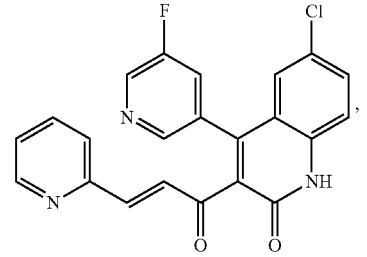,
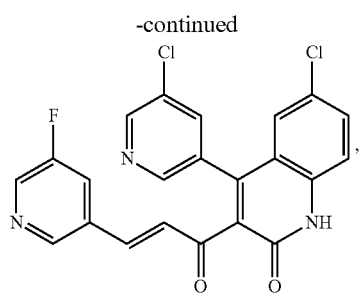,
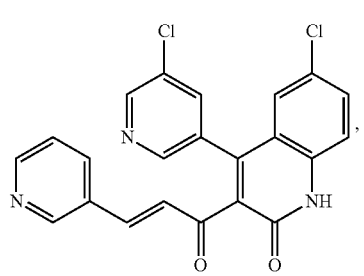,
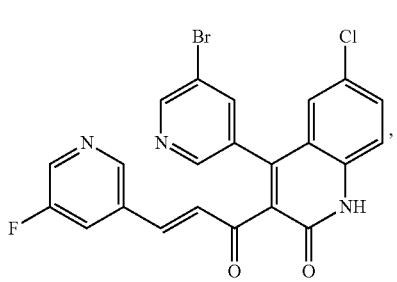,
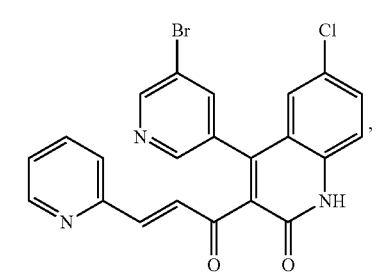,
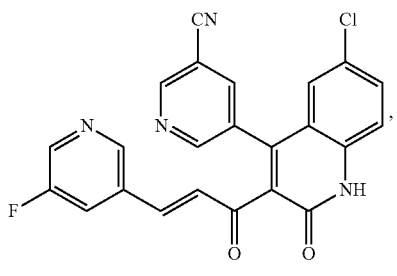,
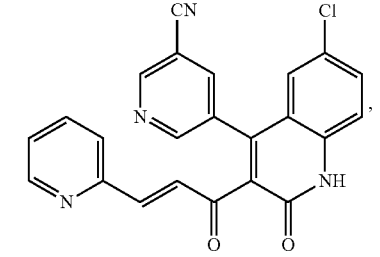,

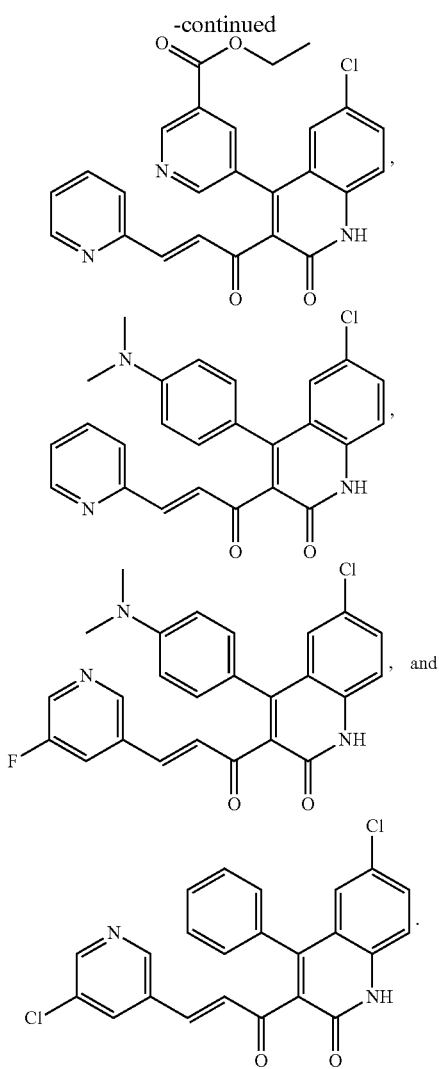

One aspect provides a compound of Formula (Ia-1), or a pharmaceutically acceptable salt, solvate, tautomer, or N-oxide thereof:

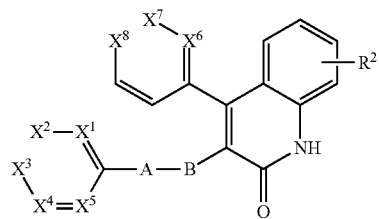

Formula (Ia-1)

wherein

A and B are independently a bond, —CH$_2$—, —CH$_2$CH$_2$—, —C(=O)—, —CH=CH—, or —C(=O)NH—;

X$^1$-X$^5$ are independently N or CR$^1$; wherein at least one of X$^1$-X$^5$ is N;

X$^6$-X$^8$ are independently N or CR$^1$;

each R$^1$ are independently hydrogen, halogen, hydroxyl, alkoxy, cyano, —NR$^a$R$^b$, —C(=O)OR$^c$, alkyl, cycloalkyl, or aryl; wherein the alkyl, alkoxy, cycloalkyl, and aryl are optionally substituted with one or more R$^d$;

R$^2$ is halogen, hydroxyl, alkoxy, alkyl, or cycloalkyl; wherein the alkyl and cycloalkyl are optionally substituted with one or more R$^d$;

R$^a$ and R$^b$ are independently hydrogen or alkyl; or R$^a$ and R$^b$ taken together with the nitrogen to which they are attached form a heterocycloalkyl optionally substituted with alkyl;

R$^c$ is hydrogen or alkyl; and each R$^d$ is independently alkyl, halogen, hydroxyl, alkoxy, cyano, or —NR$^a$R$^b$.

In some embodiments of a compound of Formula (Ia) or (Ia-1), or a pharmaceutically acceptable salt, solvate, tautomer, or N-oxide thereof, at least one of X$^6$-X$^8$ is N. In some embodiments of a compound of Formula (Ia) or (Ia-1), or a pharmaceutically acceptable salt, solvate, tautomer, or N-oxide thereof, one of X$^6$-X$^8$ is N. In some embodiments of a compound of Formula (Ia) or (Ia-1), or a pharmaceutically acceptable salt, solvate, tautomer, or N-oxide thereof, X$^6$ is N; and X$^7$ and X$^8$ are CR$^1$. In some embodiments of a compound of Formula (Ia) or (Ia-1), or a pharmaceutically acceptable salt, solvate, tautomer, or N-oxide thereof, X$^7$ is N; and X$^6$ and X$^8$ are CR$^1$. In some embodiments of a compound of Formula (Ia) or (Ia-1), or a pharmaceutically acceptable salt, solvate, tautomer, or N-oxide thereof, X$^8$ is N; and X$^6$ and X$^7$ are CR$^1$. In some embodiments of a compound of Formula (Ia-1), or a pharmaceutically acceptable salt, solvate, tautomer, or N-oxide thereof, X$^6$-X$^8$ are CR$^1$.

In some embodiments of a compound of Formula (Ia-1), or a pharmaceutically acceptable salt, solvate, tautomer, or N-oxide thereof, the compound of Formula (Ia-1) is of Formula (Ia-1'):

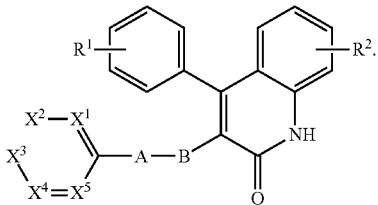

Formula (Ia-1')

In some embodiments of a compound of Formula (Ia-1), or a pharmaceutically acceptable salt, solvate, tautomer, or N-oxide thereof, the compound of Formula (Ia-1) is of Formula (Ia-1''):

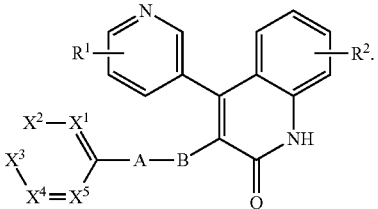

Formula (Ia-1'')

One aspect provides a compound of Formula (Ib), or a pharmaceutically acceptable salt, solvate, tautomer, or N-oxide thereof:

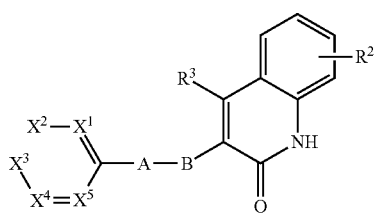

Formula (Ib)

wherein
A and B are independently a bond, —CH$_2$—, —CH$_2$CH$_2$—, —C(=O)—, —CH=CH—, or —C(=O)NH—;
X$^1$-X$^5$ are independently N or CR$^1$;
each R$^1$ are independently hydrogen, halogen, hydroxyl, alkoxy, cyano, —NR$^a$R$^b$, —C(=O)OR$^c$, alkyl, cycloalkyl, or aryl; wherein the alkyl, alkoxy, cycloalkyl, and aryl are optionally substituted with one or more R$^d$;
each R$^2$ are independently halogen, hydroxyl, alkoxy, alkyl, or cycloalkyl; wherein the alkyl and cycloalkyl are optionally substituted with one or more R$^d$;
R$^3$ is alkyl, cycloalkyl, or heterocycloalkyl; wherein the alkyl, cycloalkyl, and heterocycloalkyl are optionally substituted with one or more R$^1$;
R$^a$ and R$^b$ are independently hydrogen or alkyl; or R$^a$ and R$^b$ taken together with the nitrogen to which they are attached form a heterocycloalkyl optionally substituted with alkyl;
R$^c$ is hydrogen or alkyl; and
each R$^d$ is independently alkyl, halogen, hydroxyl, alkoxy, cyano, or —NR$^a$R$^b$.

In some embodiments of a compound of Formula (Ib), or a pharmaceutically acceptable salt, solvate, tautomer, or N-oxide thereof, R$^3$ is cycloalkyl optionally substituted with one or more R$^1$.

In some embodiments of a compound of Formula (Ib), or a pharmaceutically acceptable salt, solvate, tautomer, or N-oxide thereof, R$^3$ is cyclopropyl, cyclobutyl, cyclopentyl, or cyclohexyl; wherein the cyclopropyl, cyclobutyl, cyclopentyl, and cyclohexyl are optionally substituted with one or more R$^1$. In some embodiments of a compound of Formula (Ib), or a pharmaceutically acceptable salt, solvate, tautomer, or N-oxide thereof, R$^3$ is cyclohexyl optionally substituted with one or more R$^1$. In some embodiments of a compound of Formula (Ib), or a pharmaceutically acceptable salt, solvate, tautomer, or N-oxide thereof, R$^3$ is unsubstituted cyclohexyl.

In some embodiments of a compound of Formula (Ia), (Ia-1), (Ia-1'), (Ia-1") or (Ib), or a pharmaceutically acceptable salt, solvate, tautomer, or N-oxide thereof, X$^1$ is N and X$^2$-X$^5$ are CR$^1$.

In some embodiments of a compound of Formula (Ia), (Ia-1), (Ia-1'), (Ia-1") or (Ib), or a pharmaceutically acceptable salt, solvate, tautomer, or N-oxide thereof, X$^2$ is N and X$^1$, X$^3$-X$^5$ are CR$^1$. In some embodiments of a compound of Formula (Ia), (Ia-1), (Ia-1'), (Ia-1") or (Ib), or a pharmaceutically acceptable salt, solvate, tautomer, or N-oxide thereof, X$^3$ is N and X$^1$-X$^2$ and X$^4$-X$^5$ are CR$^1$. In some embodiments of a compound of Formula (Ia), (Ia-1), (Ia-1'), (Ia-1") or (Ib), or a pharmaceutically acceptable salt, solvate, tautomer, or N-oxide thereof, X$^2$ and X$^4$ are N and X$^1$, X$^3$ and X$^5$ are CR$^1$. In some embodiments of a compound of Formula (Ia), (Ia-1), (Ia-1'), (Ia-1") or (Ib), or a pharmaceutically acceptable salt, solvate, tautomer, or N-oxide thereof, X$^2$ and X$^5$ are N and X$^1$, X$^3$ and X$^4$ are CR$^1$. In some embodiments of a compound of Formula (Ia), (Ia-1), (Ia-1'), (Ia-1") or (Ib), or a pharmaceutically acceptable salt, solvate, tautomer, or N-oxide thereof, X$^1$ and X$^5$ are N and X$^2$-X$^4$ are CR$^1$. In some embodiments of a compound of Formula (Ia), (Ia-1), (Ia-1'), (Ia-1") or (Ib), or a pharmaceutically acceptable salt, solvate, tautomer, or N-oxide thereof, X$^1$ and X$^3$ are N and X$^2$, X$^4$ and X$^5$ are CR$^1$. In some embodiments of a compound of Formula (Ia), (Ia-1), (Ia-1'), (Ia-1") or (Ib), or a pharmaceutically acceptable salt, solvate, tautomer, or N-oxide thereof, X$^1$ and X$^2$ are N and X$^3$-X$^5$ are CR$^1$. In some embodiments of a compound of Formula (Ia), (Ia-1), (Ia-1'), (Ia-1") or (Ib), or a pharmaceutically acceptable salt, solvate, tautomer, or N-oxide thereof, X$^2$ and X$^3$ are N and X$^1$, X$^4$ and X$^5$ are CR$^1$.

In some embodiments of a compound of Formula (Ia), (Ia-1), (Ia-1'), (Ia-1") or (Ib), or a pharmaceutically acceptable salt, solvate, tautomer, or N-oxide thereof, B is —C(=O)—. In some embodiments of a compound of Formula (Ia), (Ia-1), (Ia-1'), (Ia-1") or (Ib), or a pharmaceutically acceptable salt, solvate, tautomer, or N-oxide thereof, B is a bond.

In some embodiments of a compound of Formula (Ia), (Ia-1), (Ia-1'), (Ia-1") or (Ib), or a pharmaceutically acceptable salt, solvate, tautomer, or N-oxide thereof, A is —CH=CH—. In some embodiments of a compound of Formula (Ia), (Ia-1), (Ia-1'), (Ia-1") or (Ib), or a pharmaceutically acceptable salt, solvate, tautomer, or N-oxide thereof, A is —CH$_2$CH$_2$—. In some embodiments of a compound of Formula (Ia), (Ia-1), (Ia-1'), (Ia-1") or (Ib), or a pharmaceutically acceptable salt, solvate, tautomer, or N-oxide thereof, B is —C(=O)— and A is —CH=CH—.

In some embodiments of a compound of Formula (Ia), (Ia-1), (Ia-1'), (Ia-1") or (Ib), or a pharmaceutically acceptable salt, solvate, tautomer, or N-oxide thereof, each R$^1$ are independently hydrogen, halogen, hydroxyl, alkoxy, cyano, —NR$^a$R$^b$, —C(=O)OR$^c$, or alkyl; wherein the alkyl and alkoxy are optionally substituted with one or more R$^d$.

In some embodiments of a compound of Formula (Ia), (Ia-1), (Ia-1'), (Ia-1") or (Ib), or a pharmaceutically acceptable salt, solvate, tautomer, or N-oxide thereof, each R$^1$ are independently hydrogen, halogen, hydroxyl, alkoxy, cyano, alkyl, cycloalkyl, or aryl; wherein the alkyl, cycloalkyl, and aryl are optionally substituted with one or more R$^d$.

In some embodiments of a compound of Formula (Ia), (Ia-1), (Ia-1'), (Ia-1") or (Ib), or a pharmaceutically acceptable salt, solvate, tautomer, or N-oxide thereof, each R$^1$ are independently hydrogen, halogen, hydroxyl, alkoxy, cyano, or alkyl; wherein the alkyl is optionally substituted with one or more R$^d$.

In some embodiments of a compound of Formula (Ia), (Ia-1), (Ia-1'), (Ia-1") or (Ib), or a pharmaceutically acceptable salt, solvate, tautomer, or N-oxide thereof, each R$^1$ is independently hydrogen, fluoro, chloro, bromo, methyl, —CF$_3$, —OCF$_3$, methoxy, cyano, —NMe$_2$, —C(=O)OEt, or —CH$_2$OCH$_3$.

In some embodiments of a compound of Formula (Ia), (Ia-1), (Ia-1'), (Ia-1") or (Ib), or a pharmaceutically acceptable salt, solvate, tautomer, or N-oxide thereof, each R$^1$ is independently hydrogen, fluoro, chloro, bromo, methyl, —CF$_3$, methoxy, cyano, or —CH$_2$OCH$_3$.

In some embodiments of a compound of Formula (Ia), (Ia-1), (Ia-1'), (Ia-1") or (Ib), or a pharmaceutically acceptable salt, solvate, tautomer, or N-oxide thereof, each R$^1$ is independently hydrogen or fluoro.

In some embodiments of a compound of Formula (Ia), (Ia-1), (Ia-1'), (Ia-1") or (Ib), or a pharmaceutically acceptable salt, solvate, tautomer, or N-oxide thereof, $R^1$ is not nitro.

In some embodiments of a compound of Formula (Ia), (Ia-1), (Ia-1'), (Ia-1") or (Ib), or a pharmaceutically acceptable salt, solvate, tautomer, or N-oxide thereof, $R^2$ is halogen.

In some embodiments of a compound of Formula (Ia), (Ia-1), (Ia-1'), (Ia-1") or (Ib), or a pharmaceutically acceptable salt, solvate, tautomer, or N-oxide thereof, $R^2$ is chloro. In some embodiments of a compound of Formula (Ia), (Ia-1), (Ia-1'), (Ia-1") or (Ib), or a pharmaceutically acceptable salt, solvate, tautomer, or N-oxide thereof, $R^2$ is 6-chloro.

A compound of Formula (Ia-1), or a pharmaceutically acceptable salt, solvate, tautomer, or N-oxide thereof, selected from:

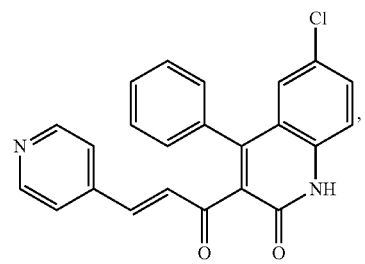

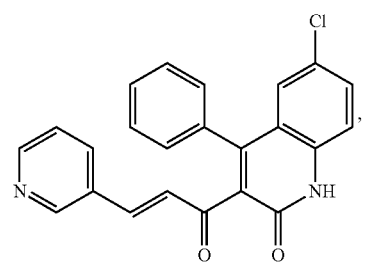

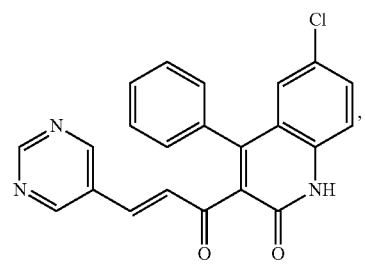

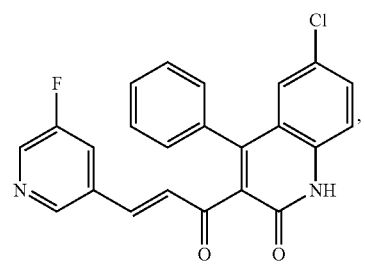

-continued

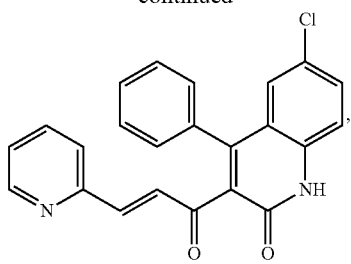

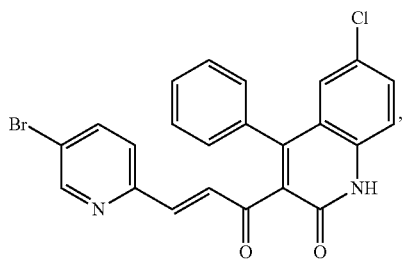

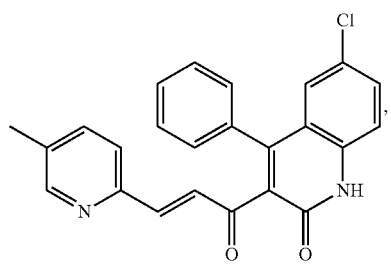

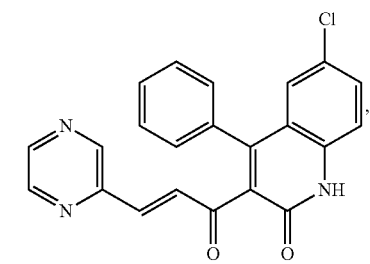

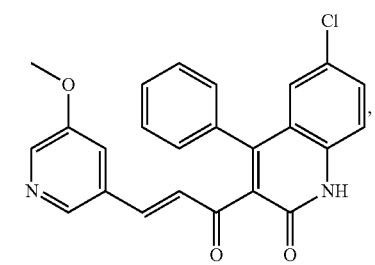

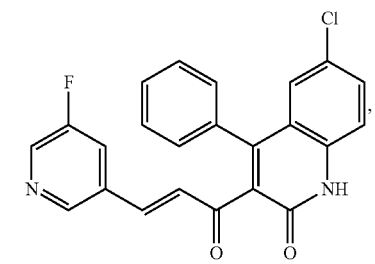

53
-continued
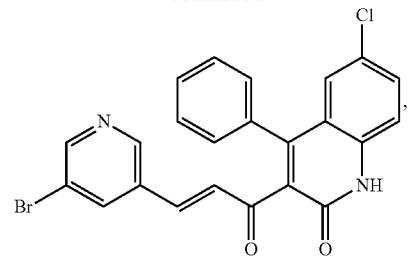
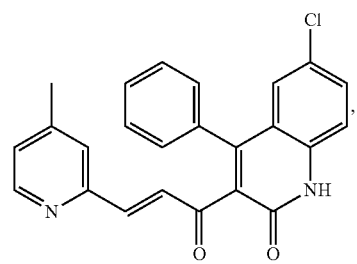
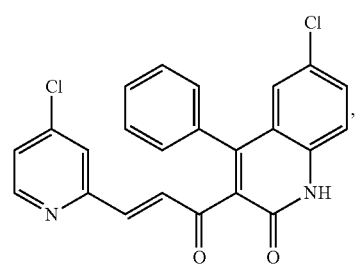
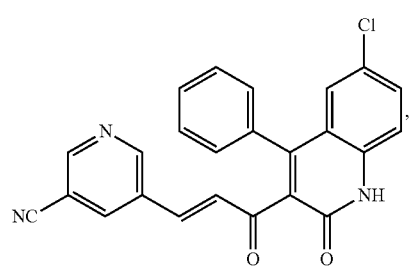
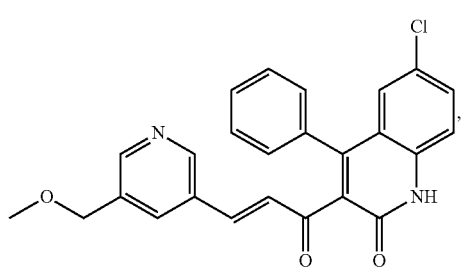
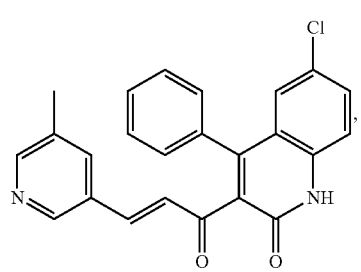
54
-continued
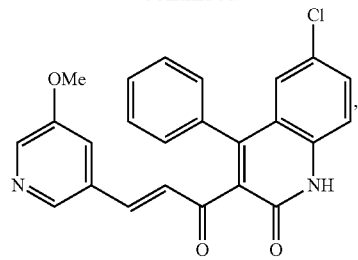
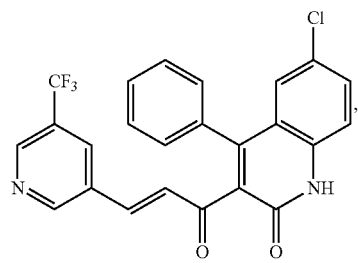
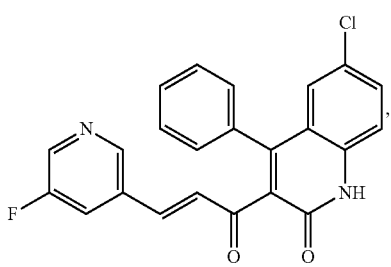
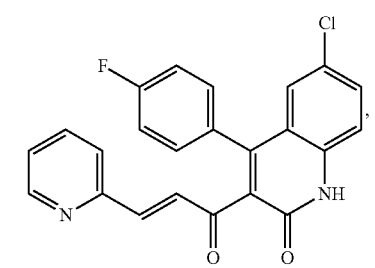
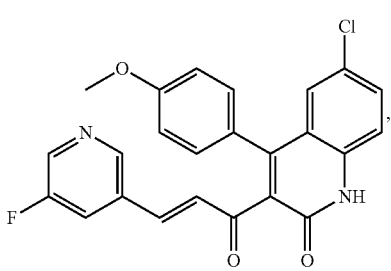
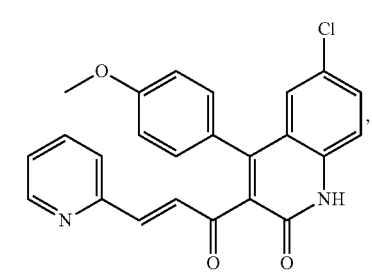

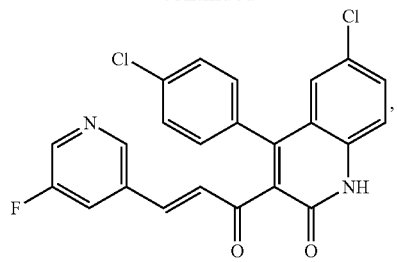
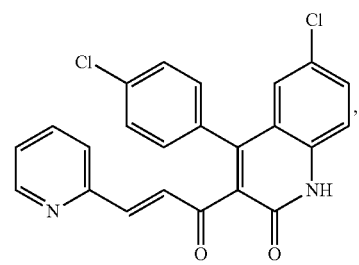
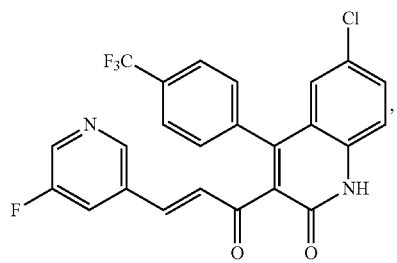
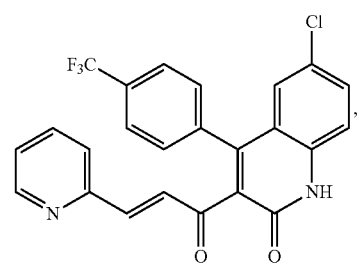
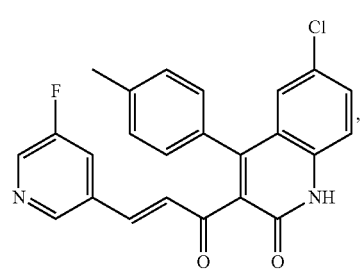
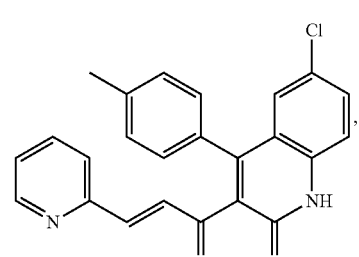
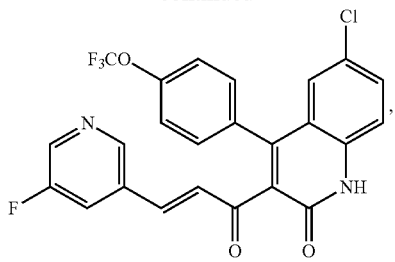
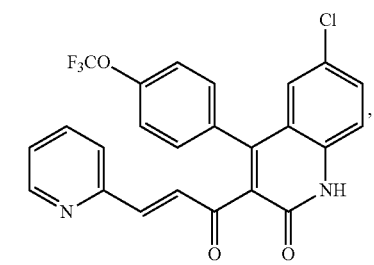
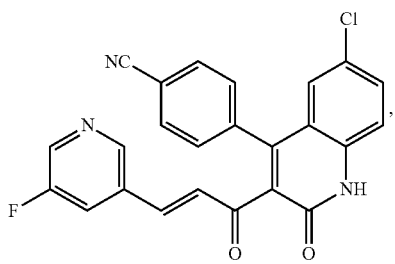
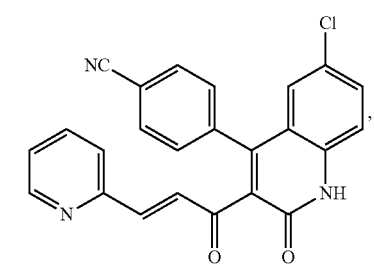
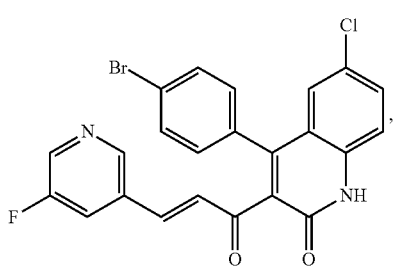
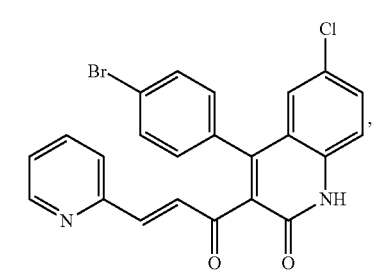

57
-continued
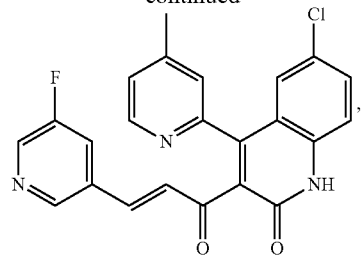
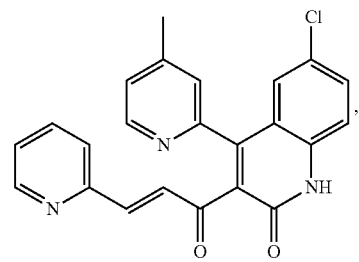
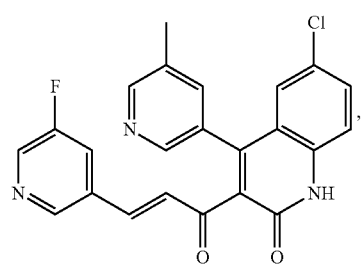
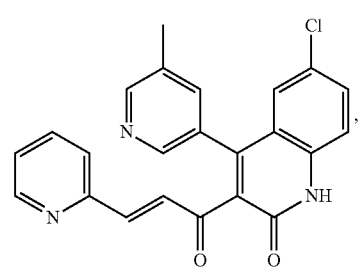
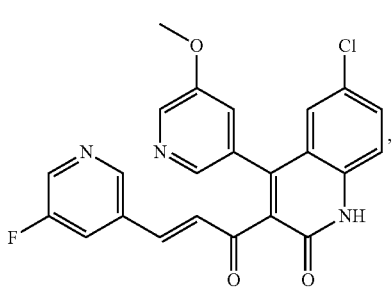
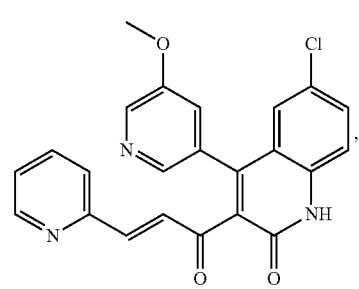
58
-continued
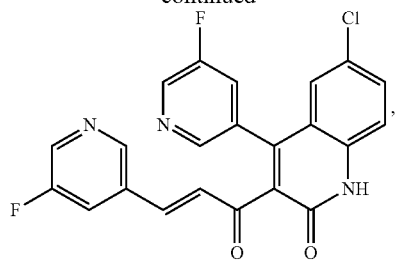
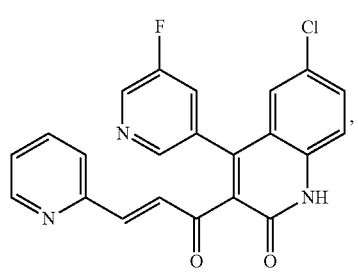
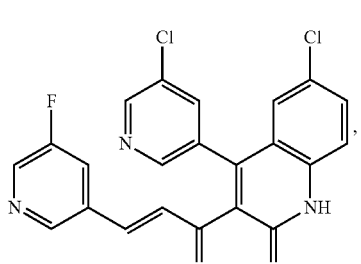
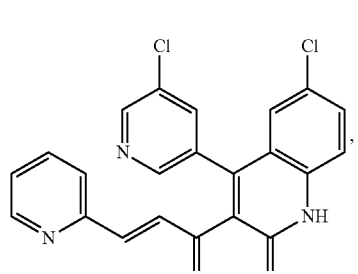
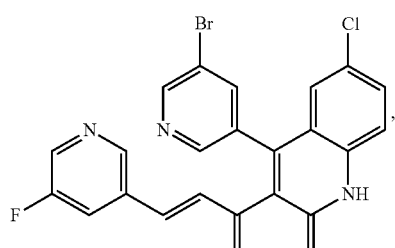
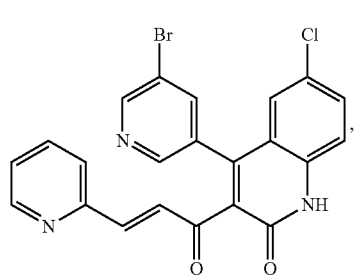

-continued

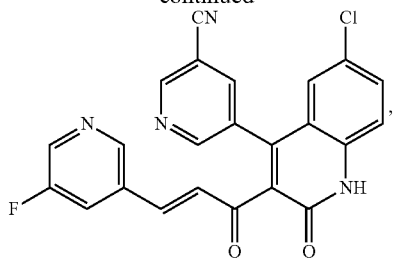

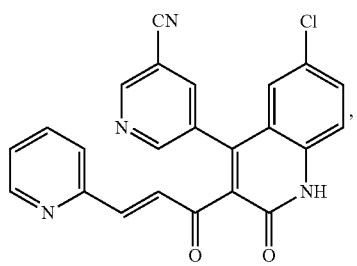

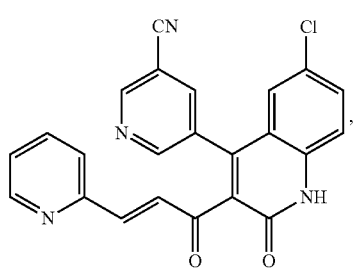

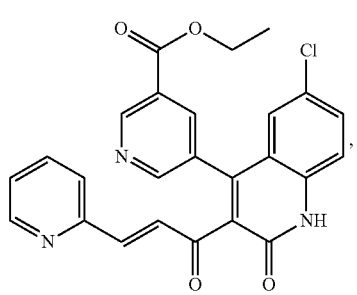

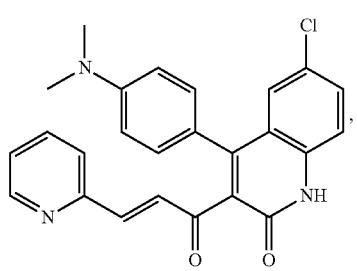

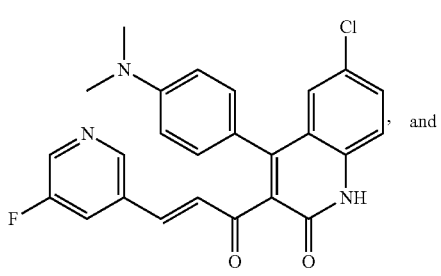
and

-continued

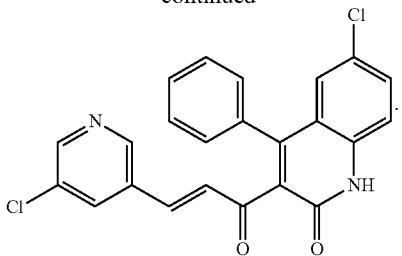

One aspect provides a compound of Formula (II), or a pharmaceutically acceptable salt, solvate, tautomer, or N-oxide thereof:

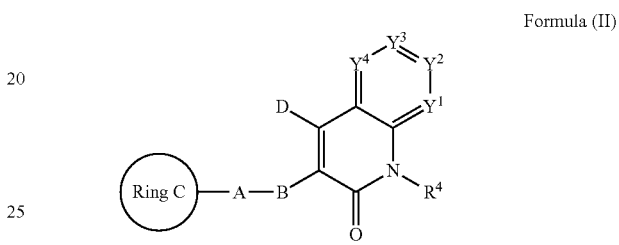

Formula (II)

wherein
Ring C is imidazolyl, thiophenyl, furanyl,

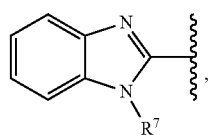

indolyl, benzothiophenyl, or benzofuranyl; wherein the imidazolyl, thiophenyl, furanyl,

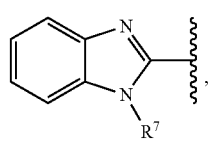

indolyl, benzothiophenyl, and benzofuranyl are optionally substituted with one or more $R^1$;
D is aryl, heteroaryl, alkyl, cycloalkyl, or heterocycloalkyl; wherein the aryl, heteroaryl, alkyl, cycloalkyl, and heterocycloalkyl are optionally substituted with one or more $R^1$;
A and B are independently a bond, —$CH_2$—, —$CH_2CH_2$—, —C(=O)—, —$CR^5$=$CR^6$—, ≡, —C(=O)$NR^a$—, or —$NR^a$C(=O)—;
$Y^1$-$Y^4$ are independently N or $CR^2$;
each $R^1$ are independently hydrogen, halogen, hydroxyl, alkoxy, cyano, —$NR^aR^b$, —C(=O)$OR^c$, alkyl, cycloalkyl, or aryl; wherein the alkyl, alkoxy, cycloalkyl, and aryl are optionally substituted with one or more $R^d$;
each $R^2$ are independently hydrogen, halogen, hydroxyl, nitro, alkoxy, —$NR^aR^b$, alkyl, or cycloalkyl; wherein the alkyl and cycloalkyl are optionally substituted with one or more $R^d$;

R⁴ is hydrogen, alkyl, or aralkyl;

R⁵ and R⁶ are independently hydrogen, halogen, or alkyl;

R⁷ is alkyl or aralkyl; wherein the alkyl and aralkyl are optionally substituted with one or more alkyl, halogen, or alkoxy;

each $R^a$ and $R^b$ are independently hydrogen or alkyl; or $R^a$ and $R^b$ taken together with the nitrogen to which they are attached form a heterocycloalkyl optionally substituted with alkyl;

$R^c$ is hydrogen or alkyl; and each $R^d$ is independently alkyl, halogen, hydroxyl, alkoxy, cyano, or —$NR^aR^b$;

provided that when ring C is

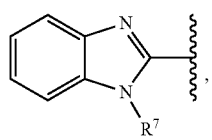

D is unsubstituted phenyl, Y¹, Y², Y⁴ are CH, Y³ is C—Cl, R⁴ is H, B is —C(=O)—, A is —CH=CH—, then R⁷ is not methyl.

In some embodiments of a compound of Formula (II), or a pharmaceutically acceptable salt, solvate, tautomer, or N-oxide thereof, R⁴ is hydrogen.

In some embodiments of a compound of Formula (II), or a pharmaceutically acceptable salt, solvate, tautomer, or N-oxide thereof, B is —C(=O)—

In some embodiments of a compound of Formula (II), or a pharmaceutically acceptable salt, solvate, tautomer, or N-oxide thereof, A is —CH=CH—.

In some embodiments of a compound of Formula (II), or a pharmaceutically acceptable salt, solvate, tautomer, or N-oxide thereof, Y¹-Y⁴ are independently CR². In some embodiments of a compound of Formula (II), or a pharmaceutically acceptable salt, solvate, tautomer, or N-oxide thereof, each R² is independently hydrogen or halogen. In some embodiments of a compound of Formula (II), or a pharmaceutically acceptable salt, solvate, tautomer, or N-oxide thereof, at least one of Y¹-Y⁴ is N.

In some embodiments of a compound of Formula (II), or a pharmaceutically acceptable salt, solvate, tautomer, or N-oxide thereof, D is aryl or heteroaryl of the general formula:

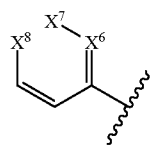

wherein X⁶-X⁸ are independently N or CR¹.

In some embodiments of a compound of Formula (II), or a pharmaceutically acceptable salt, solvate, tautomer, or N-oxide thereof, D is aryl or heteroaryl of the general formula:

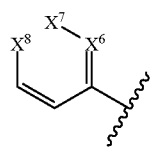

wherein X⁶-X⁸ are CR¹. In some embodiments of a compound of Formula (II), or a pharmaceutically acceptable salt, solvate, tautomer, or N-oxide thereof, X⁶-X⁸ are CR¹ and R¹ are hydrogen.

In some embodiments of a compound of Formula (II), or a pharmaceutically acceptable salt, solvate, tautomer, or N-oxide thereof, each R¹ are independently hydrogen, halogen, alkoxy, cyano, —$NR^aR^b$, —$C(=O)OR^c$, or alkyl; wherein the alkyl and alkoxy are optionally substituted with one or more $R^d$.

In some embodiments of a compound of Formula (II), or a pharmaceutically acceptable salt, solvate, tautomer, or N-oxide thereof, each R¹ is independently hydrogen, fluoro, chloro, bromo, methyl, —CF₃, —OCF₃, methoxy, cyano, —NMe₂, —C(=O)OEt, or —CH₂OCH₃.

In some embodiments of a compound of Formula (II), or a pharmaceutically acceptable salt, solvate, tautomer, or N-oxide thereof, R⁷ is methyl, ethyl, or benzyl.

A compound of Formula (II), or a pharmaceutically acceptable salt, solvate, tautomer, or N-oxide thereof, selected from:

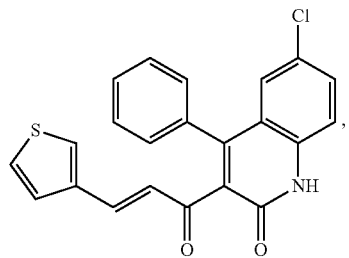

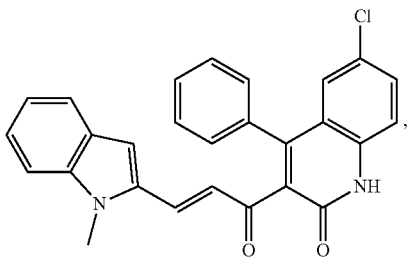

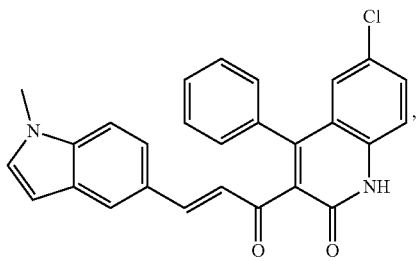

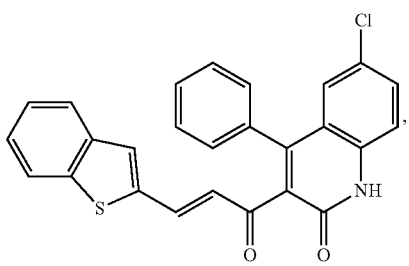

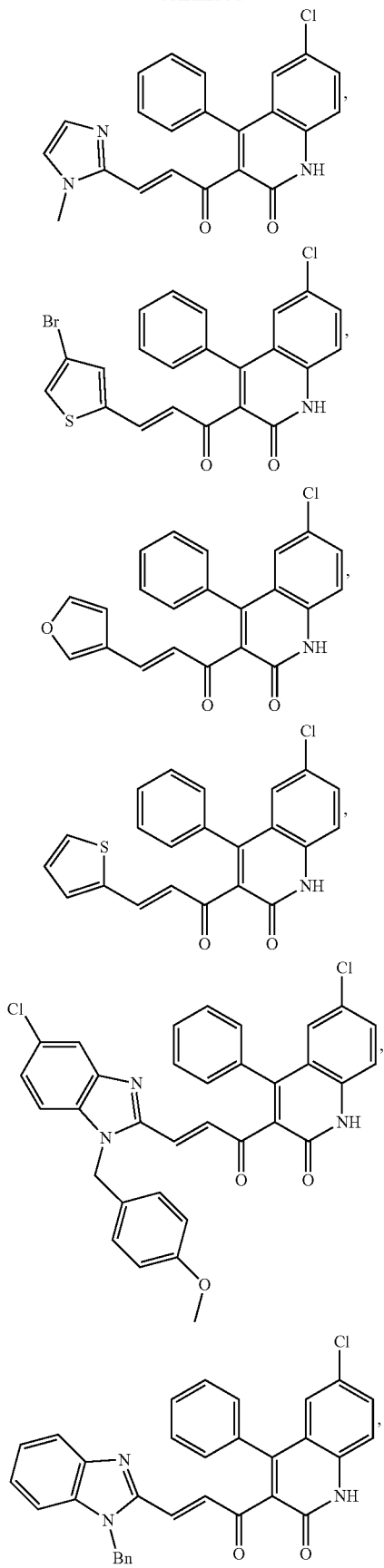
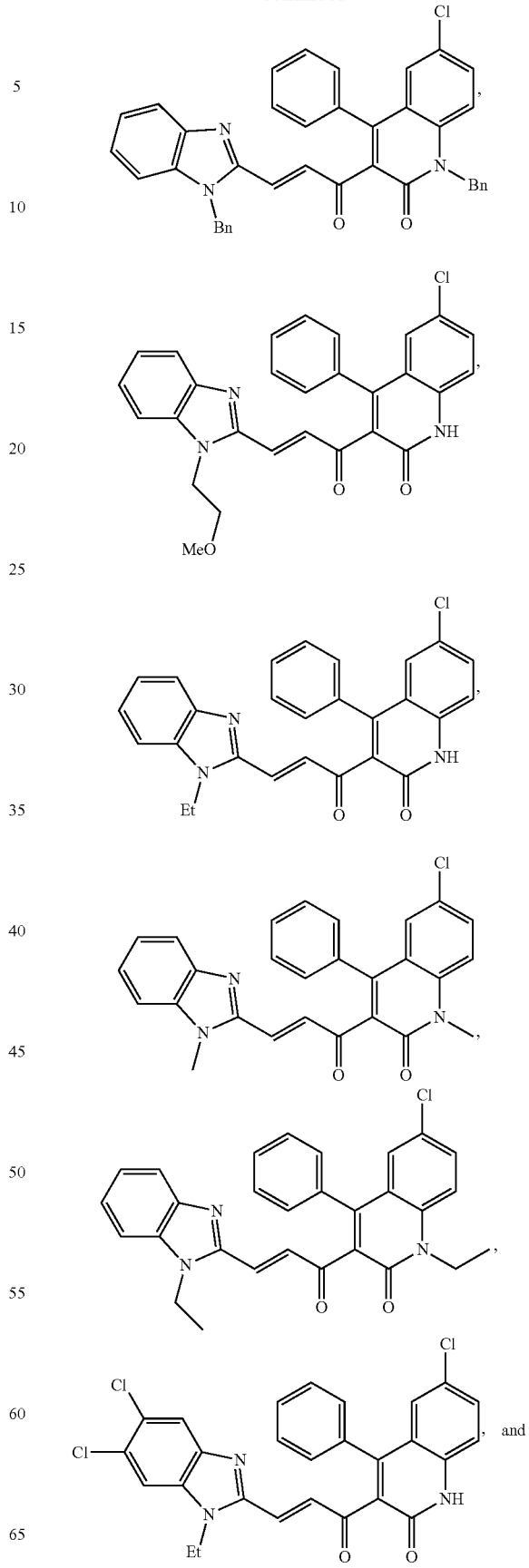

-continued

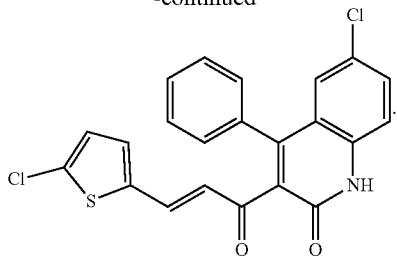

One aspect provides a compound of Formula (III), or a pharmaceutically acceptable salt, solvate, tautomer, or N-oxide thereof:

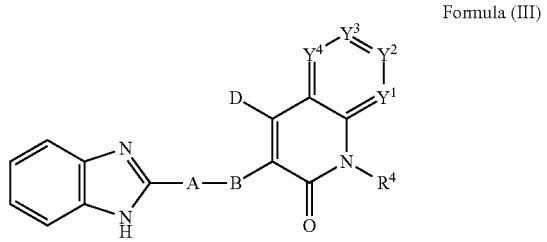

Formula (III)

wherein
D is 6-membered aryl substituted with one or more $R^1$, 5-membered heteroaryl, 6-membered heteroaryl, alkyl, cycloalkyl, or heterocycloalkyl; wherein the 5-membered heteroaryl, 6-membered heteroaryl, alkyl, cycloalkyl, and heterocycloalkyl are optionally substituted with one or more $R^1$;
A and B are independently a bond, —CH$_2$—, —CH$_2$CH$_2$—, —C(=O)—, —CR$^5$=CR$^6$—, ≡, —C(=O)NR$^a$—, or —NR$^a$C(=O)—;
$Y^1$-$Y^4$ are independently N or CR$^2$;
each $R^1$ are independently hydrogen, halogen, hydroxyl, alkoxy, cyano, —NR$^a$R$^b$, —C(=O)OR$^c$, alkyl, alkoxy, cycloalkyl, or aryl; wherein the alkyl, alkoxy, cycloalkyl, and aryl are optionally substituted with one or more $R^d$;
each $R^2$ are independently hydrogen, halogen, hydroxyl, nitro, alkoxy, —NR$^a$R$^b$, alkyl, or cycloalkyl; wherein the alkyl and cycloalkyl are optionally substituted with one or more $R^d$;
$R^4$ is hydrogen, alkyl, or aralkyl;
$R^5$ and $R^6$ are independently hydrogen, halogen, or alkyl;
each $R^a$ and $R^b$ are independently hydrogen or alkyl; or $R^a$ and $R^b$ taken together with the nitrogen to which they are attached form a heterocycloalkyl optionally substituted with alkyl;
$R^c$ is hydrogen or alkyl; and
each $R^d$ is independently alkyl, halogen, hydroxyl, alkoxy, cyano, or —NR$^a$R$^b$.

In some embodiments of a compound of Formula (III), or a pharmaceutically acceptable salt, solvate, tautomer, or N-oxide thereof, $R^4$ is hydrogen.

In some embodiments of a compound of Formula (III), or a pharmaceutically acceptable salt, solvate, tautomer, or N-oxide thereof, B is —C(=O)—

In some embodiments of a compound of Formula (III), or a pharmaceutically acceptable salt, solvate, tautomer, or N-oxide thereof, A is —CH=CH—.

In some embodiments of a compound of Formula (III), or a pharmaceutically acceptable salt, solvate, tautomer, or N-oxide thereof, $Y^1$-$Y^4$ are independently CR$^2$. In some embodiments of a compound of Formula (III), or a pharmaceutically acceptable salt, solvate, tautomer, or N-oxide thereof, each $R^2$ is independently hydrogen or halogen. In some embodiments of a compound of Formula (III), or a pharmaceutically acceptable salt, solvate, tautomer, or N-oxide thereof, at least one of $Y^1$-$Y^4$ is N.

In some embodiments of a compound of Formula (III), or a pharmaceutically acceptable salt, solvate, tautomer, or N-oxide thereof, D is 6-membered aryl substituted with one or more $R^1$.

In some embodiments of a compound of Formula (III), or a pharmaceutically acceptable salt, solvate, tautomer, or N-oxide thereof, D is 6-membered aryl substituted with one or more halogen, alkyl, or alkoxy; wherein the alkyl and alkoxy are optionally substituted with halogen.

In some embodiments of a compound of Formula (III), or a pharmaceutically acceptable salt, solvate, tautomer, or N-oxide thereof, D is 5-membered heteroaryl optionally substituted with one or more $R^1$.

In some embodiments of a compound of Formula (III), or a pharmaceutically acceptable salt, solvate, tautomer, or N-oxide thereof, D is 6-membered heteroaryl optionally substituted with one or more $R^1$.

In some embodiments of a compound of Formula (III), or a pharmaceutically acceptable salt, solvate, tautomer, or N-oxide thereof, each $R^1$ are independently hydrogen, halogen, alkoxy, cyano, —NR$^a$R$^b$, —C(=O)OR$^c$, or alkyl; wherein the alkyl and alkoxy are optionally substituted with one or more $R^d$.

In some embodiments of a compound of Formula (III), or a pharmaceutically acceptable salt, solvate, tautomer, or N-oxide thereof, each $R^1$ is independently hydrogen, fluoro, chloro, bromo, methyl, —CF$_3$, —OCF$_3$, methoxy, cyano, —NMe$_2$, —C(=O)OEt, or —CH$_2$OCH$_3$.

A compound of Formula (III), or a pharmaceutically acceptable salt, solvate, tautomer, or N-oxide thereof, selected from:

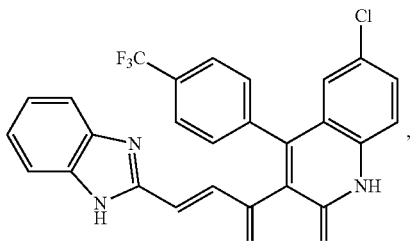

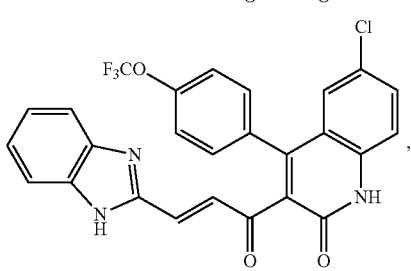

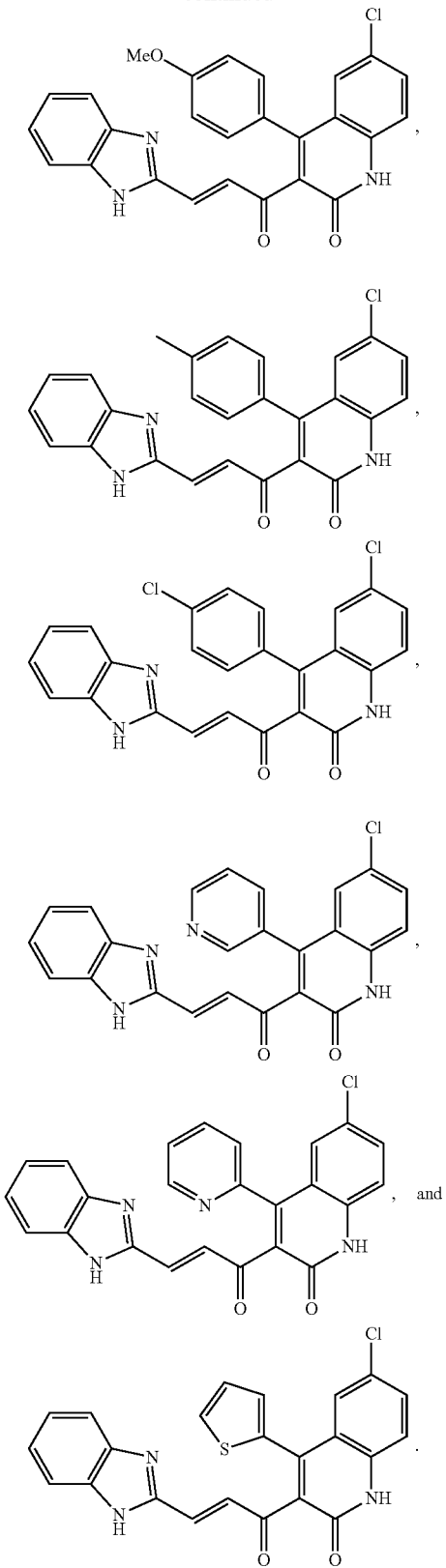

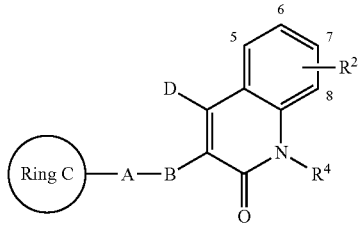

Formula (IV)

wherein
Ring C is aryl or heteroaryl; wherein the aryl and heteroaryl are optionally substituted with one or more $R^1$;
D is aryl, heteroaryl, alkyl, cycloalkyl, or heterocycloalkyl; wherein the aryl, heteroaryl, alkyl, cycloalkyl, and heterocycloalkyl are optionally substituted with one or more $R^1$;
A and B are independently a bond, —$CH_2$—, —$CH_2CH_2$—, —C(=O)—, —$CR^5$=$CR^6$—, ≡≡≡ , —C(=O)$NR^a$—, or —$NR^a$C(=O)—;
each $R^1$ are independently hydrogen, halogen, hydroxyl, alkoxy, cyano, —$NR^aR^b$, —C(=O)$OR^c$, alkyl, cycloalkyl, or aryl; wherein the alkyl, alkoxy, cycloalkyl, and aryl are optionally substituted with one or more $R^d$;
$R^2$ is halogen, hydroxyl, nitro, alkoxy, —$NR^aR^b$, alkyl, or cycloalkyl; wherein the alkyl and cycloalkyl are optionally substituted with one or more $R^d$; provided that $R^2$ is not 6-halogen or 6-$CH_3$;
$R^4$ is hydrogen, alkyl, or aralkyl;
$R^5$ and $R^6$ are independently hydrogen, halogen, or alkyl;
each $R^a$ and $R^b$ are independently hydrogen or alkyl; or $R^a$ and $R^b$ taken together with the nitrogen to which they are attached form a heterocycloalkyl optionally substituted with alkyl;
$R^c$ is hydrogen or alkyl; and
each $R^d$ is independently alkyl, halogen, hydroxyl, alkoxy, cyano, or —$NR^aR^b$.

In some embodiments of a compound of Formula (IV), or a pharmaceutically acceptable salt, solvate, tautomer, or N-oxide thereof, $R^4$ is hydrogen.

In some embodiments of a compound of Formula (IV), or a pharmaceutically acceptable salt, solvate, tautomer, or N-oxide thereof, B is —C(=O)—

In some embodiments of a compound of Formula (IV), or a pharmaceutically acceptable salt, solvate, tautomer, or N-oxide thereof, A is —CH=CH—.

In some embodiments of a compound of Formula (IV), or a pharmaceutically acceptable salt, solvate, tautomer, or N-oxide thereof, D is aryl or heteroaryl of the general formula:

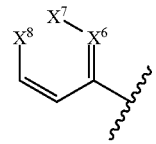

wherein $X^6$-$X^8$ are independently N or $CR^1$.

In some embodiments of a compound of Formula (IV), or a pharmaceutically acceptable salt, solvate, tautomer, or N-oxide thereof, D is aryl or heteroaryl of the general formula:

One aspect provides a compound of Formula (IV), or a pharmaceutically acceptable salt, solvate, tautomer, or N-oxide thereof:

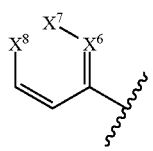

wherein $X^6$-$X^8$ are independently $CR^1$. In some embodiments of a compound of Formula (IV), or a pharmaceutically acceptable salt, solvate, tautomer, or N-oxide thereof, $X^6$-$X^8$ are $CR^1$ and $R^1$ are hydrogen.

In some embodiments of a compound of Formula (IV), or a pharmaceutically acceptable salt, solvate, tautomer, or N-oxide thereof, Ring C is benzimidazolyl optionally substituted with one or more $R^1$.

In some embodiments of a compound of Formula (IV), or a pharmaceutically acceptable salt, solvate, tautomer, or N-oxide thereof, Ring C is phenyl optionally substituted with one or more $R^1$.

In some embodiments of a compound of Formula (IV), or a pharmaceutically acceptable salt, solvate, tautomer, or N-oxide thereof, each $R^1$ are independently hydrogen, halogen, alkoxy, cyano, —$NR^aR^b$, —C(=O)$OR^c$, or alkyl; wherein the alkyl and alkoxy are optionally substituted with one or more $R^d$.

In some embodiments of a compound of Formula (IV), or a pharmaceutically acceptable salt, solvate, tautomer, or N-oxide thereof, each $R^1$ is independently hydrogen, fluoro, chloro, bromo, methyl, —$CF_3$, —$OCF_3$, methoxy, cyano, —$NMe_2$, —C(=O)OEt, or —$CH_2OCH_3$.

In some embodiments of a compound of Formula (IV), or a pharmaceutically acceptable salt, solvate, tautomer, or N-oxide thereof, $R^2$ is 6-nitro, 6-amino, 6-methoxy, 6-$CF_3$, or 6-$OCF_3$.

A compound of Formula (IV), or a pharmaceutically acceptable salt, solvate, tautomer, or N-oxide thereof, selected from:

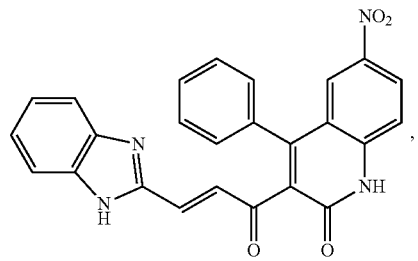

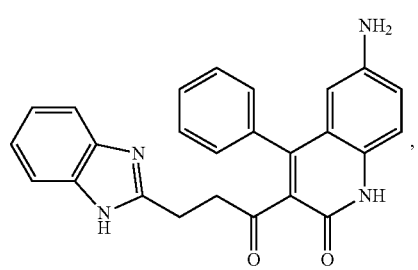

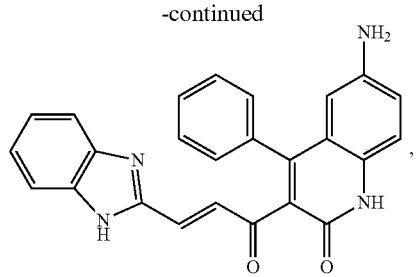

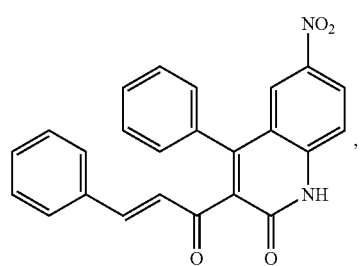

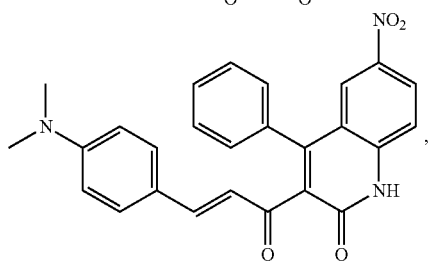

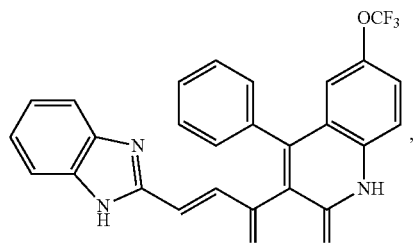

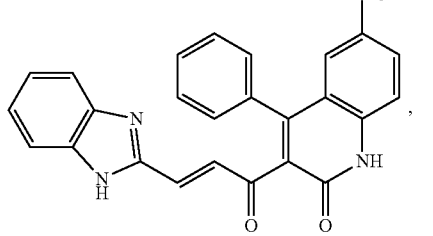

, and

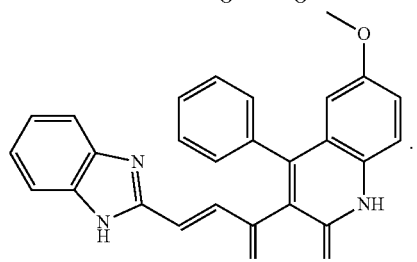

One aspect provides a compound of Formula (V), or a pharmaceutically acceptable salt, solvate, tautomer, or N-oxide thereof:

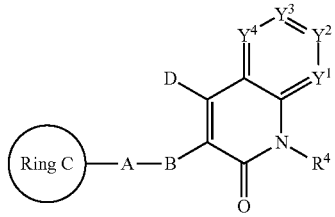

Formula (V)

wherein
Ring C aryl or heteroaryl; wherein the aryl and heteroaryl are optionally substituted with one or more $R^1$;
D is aryl, heteroaryl, alkyl, cycloalkyl, or heterocycloalkyl; wherein the aryl, heteroaryl, alkyl, cycloalkyl, and heterocycloalkyl are optionally substituted with one or more $R^1$;
A and B are independently a bond, —$CH_2$—, —$CH_2CH_2$—, —C(=O)—, —$CR^5$=$CR^6$—, ≡, C(=O)$NR^a$—, or —$NR^aC$(=O)—;
$Y^1$-$Y^4$ are independently N or $CR^2$; provided that at least one of $Y^1$-$Y^4$ is N;
each $R^1$ are independently hydrogen, halogen, hydroxyl, alkoxy, cyano, —$NR^aR^b$, —C(=O)$OR^c$, alkyl, cycloalkyl, or aryl; wherein the alkyl, alkoxy, cycloalkyl, and aryl are optionally substituted with one or more $R^d$;
$R^2$ is independently hydrogen, halogen, hydroxyl, nitro, alkoxy, —$NR^aR^b$, alkyl, or cycloalkyl; wherein the alkyl and cycloalkyl are optionally substituted with one or more $R^d$;
$R^4$ is hydrogen, alkyl, or aralkyl;
$R^5$ and $R^6$ are independently hydrogen, halogen, or alkyl;
each $R^a$ and $R^b$ are independently hydrogen or alkyl; or $R^a$ and $R^b$ taken together with the nitrogen to which they are attached form a heterocycloalkyl optionally substituted with alkyl;
$R^c$ is hydrogen or alkyl; and
each $R^d$ is independently alkyl, halogen, hydroxyl, alkoxy, cyano, or —$NR^aR^b$.

In some embodiments of a compound of Formula (V), or a pharmaceutically acceptable salt, solvate, tautomer, or N-oxide thereof, $R^4$ is hydrogen.

In some embodiments of a compound of Formula (V), or a pharmaceutically acceptable salt, solvate, tautomer, or N-oxide thereof, B is —C(=O)—

In some embodiments of a compound of Formula (V), or a pharmaceutically acceptable salt, solvate, tautomer, or N-oxide thereof, A is —CH=CH—.

In some embodiments of a compound of Formula (V), or a pharmaceutically acceptable salt, solvate, tautomer, or N-oxide thereof, $Y^1$ is N. In some embodiments of a compound of Formula (V), or a pharmaceutically acceptable salt, solvate, tautomer, or N-oxide thereof, $Y^2$ is N. In some embodiments of a compound of Formula (V), or a pharmaceutically acceptable salt, solvate, tautomer, or N-oxide thereof, $Y^3$ is N. In some embodiments of a compound of Formula (V), or a pharmaceutically acceptable salt, solvate, tautomer, or N-oxide thereof, $Y^4$ is N.

In some embodiments of a compound of Formula (V), or a pharmaceutically acceptable salt, solvate, tautomer, or N-oxide thereof, each $R^2$ is independently hydrogen or halogen.

In some embodiments of a compound of Formula (V), or a pharmaceutically acceptable salt, solvate, tautomer, or N-oxide thereof, D is aryl or heteroaryl of the general formula:

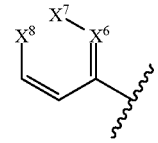

wherein $X^6$-$X^8$ are independently N or $CR^1$.

In some embodiments of a compound of Formula (V), or a pharmaceutically acceptable salt, solvate, tautomer, or N-oxide thereof, D is aryl or heteroaryl of the general formula:

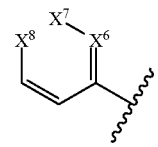

wherein $X^6$-$X^8$ are independently $CR^1$. In some embodiments of a compound of Formula (V), or a pharmaceutically acceptable salt, solvate, tautomer, or N-oxide thereof, $X^6$-$X^8$ are $CR^1$ and $R^1$ are hydrogen.

In some embodiments of a compound of Formula (V), or a pharmaceutically acceptable salt, solvate, tautomer, or N-oxide thereof, Ring C is benzimidazolyl optionally substituted with one or more $R^1$.

In some embodiments of a compound of Formula (V), or a pharmaceutically acceptable salt, solvate, tautomer, or N-oxide thereof, Ring C is pyridyl optionally substituted with one or more $R^1$.

In some embodiments of a compound of Formula (V), or a pharmaceutically acceptable salt, solvate, tautomer, or N-oxide thereof, Ring C is phenyl optionally substituted with one or more $R^1$.

In some embodiments of a compound of Formula (V), or a pharmaceutically acceptable salt, solvate, tautomer, or N-oxide thereof, each $R^1$ are independently hydrogen, halogen, alkoxy, cyano, —$NR^aR^b$, —C(=O)$OR^c$, or alkyl; wherein the alkyl and alkoxy are optionally substituted with one or more $R^d$.

In some embodiments of a compound of Formula (V), or a pharmaceutically acceptable salt, solvate, tautomer, or N-oxide thereof, each $R^1$ is independently hydrogen, fluoro, chloro, bromo, methyl, —$CF_3$, —$OCF_3$, methoxy, cyano, —$NMe_2$, —C(=O)OEt, or —$CH_2OCH_3$.

A compound of Formula (V), or a pharmaceutically acceptable salt, solvate, tautomer, or N-oxide thereof, selected from:

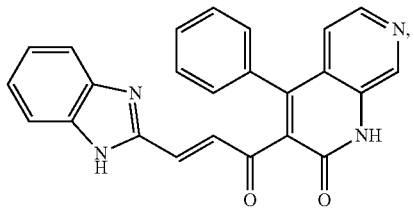

-continued

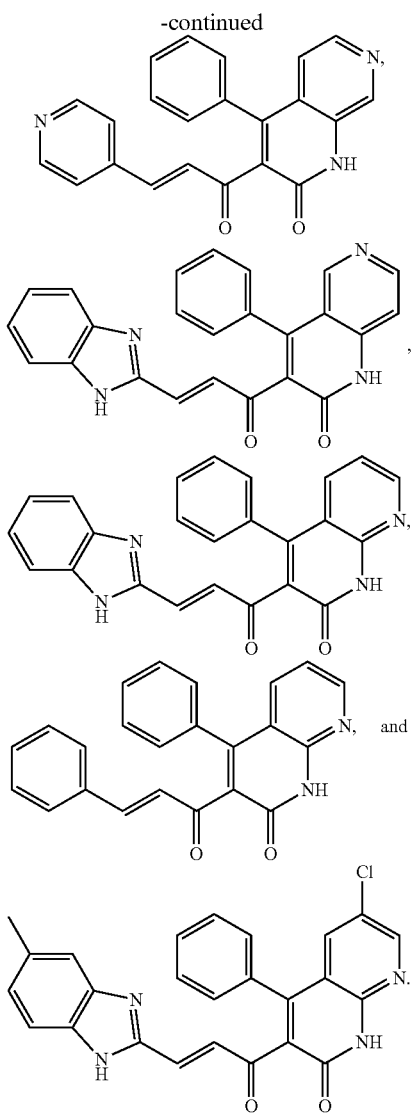

One aspect provides a compound of Formula (VI), or a pharmaceutically acceptable salt, solvate, tautomer, or N-oxide thereof:

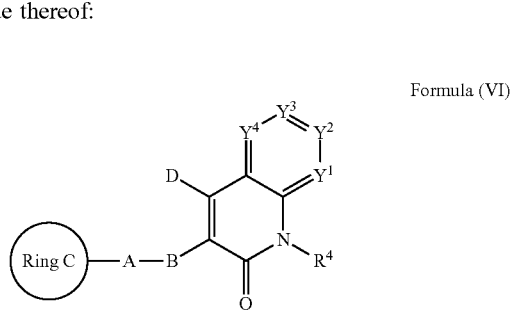

Formula (VI)

wherein
Ring C is aryl or heteroaryl; wherein the aryl and heteroaryl are optionally substituted with one or more $R^1$;
D is aryl, heteroaryl, alkyl, cycloalkyl, or heterocycloalkyl; wherein the aryl, heteroaryl, alkyl, cycloalkyl, and heterocycloalkyl are optionally substituted with one or more $R^1$;
A and B are independently a bond, —$CH_2$—, —$CH_2CH_2$—, —C(=O)—, —$CR^5$=$CR^6$—, ≡, —C(=O)$NR^a$—, or —$NR^a$C(=O)—;

$Y^1$-$Y^4$ are independently N or $CR^2$;
each $R^1$ are independently hydrogen, halogen, hydroxyl, alkoxy, cyano, —$NR^aR^b$, —C(=O)$OR^c$, alkyl, cycloalkyl, or aryl; wherein the alkyl, alkoxy, cycloalkyl, and aryl are optionally substituted with one or more $R^d$;
each $R^2$ are independently hydrogen, halogen, hydroxyl, nitro, alkoxy, —$NR^aR^b$, alkyl, or cycloalkyl; wherein the alkyl and cycloalkyl are optionally substituted with one or more $R^d$;
$R^4$ is alkyl or aralkyl;
$R^5$ and $R^6$ are independently hydrogen, halogen, or alkyl;
each $R^a$ and $R^b$ are independently hydrogen or alkyl; or $R^a$ and $R^b$ taken together with the nitrogen to which they are attached form a heterocycloalkyl optionally substituted with alkyl;
$R^c$ is hydrogen or alkyl; and
each $R^d$ is independently alkyl, halogen, hydroxyl, alkoxy, cyano, or —$NR^aR^b$;
provided that when ring C is

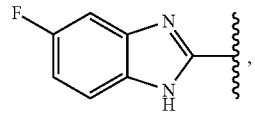

D is unsubstituted phenyl, $Y^1$, $Y^2$, $Y^4$ are CH, $Y^3$ is C—Cl, B is —C(=O)—, A is —CH=CH—, then $R^4$ is not methyl.

In some embodiments of a compound of Formula (VI), or a pharmaceutically acceptable salt, solvate, tautomer, or N-oxide thereof, $R^4$ is methyl, ethyl or benzyl.

In some embodiments of a compound of Formula (VI), or a pharmaceutically acceptable salt, solvate, tautomer, or N-oxide thereof, B is —C(=O)—

In some embodiments of a compound of Formula (VI), or a pharmaceutically acceptable salt, solvate, tautomer, or N-oxide thereof, A is —CH=CH—.

In some embodiments of a compound of Formula (VI), or a pharmaceutically acceptable salt, solvate, tautomer, or N-oxide thereof, $Y^1$-$Y^4$ are independently $CR^2$. In some embodiments of a compound of Formula (VI), or a pharmaceutically acceptable salt, solvate, tautomer, or N-oxide thereof, each $R^2$ is independently hydrogen or halogen. In some embodiments of a compound of Formula (VI), or a pharmaceutically acceptable salt, solvate, tautomer, or N-oxide thereof, at least one of $Y^1$-$Y^4$ is N.

In some embodiments of a compound of Formula (VI), or a pharmaceutically acceptable salt, solvate, tautomer, or N-oxide thereof, D is aryl or heteroaryl of the general formula:

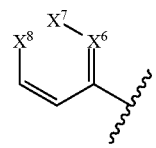

wherein $X^6$-$X^8$ are independently N or $CR^1$.

In some embodiments of a compound of Formula (VI), or a pharmaceutically acceptable salt, solvate, tautomer, or N-oxide thereof, D is aryl or heteroaryl of the general formula:

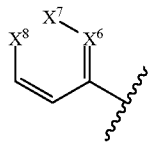

wherein $X^6$-$X^8$ are independently $CR^1$. In some embodiments of a compound of Formula (VI), or a pharmaceutically acceptable salt, solvate, tautomer, or N-oxide thereof, $X^6$-$X^8$ are $CR^1$ and $R^1$ are hydrogen.

In some embodiments of a compound of Formula (VI), or a pharmaceutically acceptable salt, solvate, tautomer, or N-oxide thereof, Ring C is benzimidazolyl optionally substituted with one or more $R^1$.

In some embodiments of a compound of Formula (VI), or a pharmaceutically acceptable salt, solvate, tautomer, or N-oxide thereof, Ring C is phenyl optionally substituted with one or more $R^1$.

In some embodiments of a compound of Formula (VI), or a pharmaceutically acceptable salt, solvate, tautomer, or N-oxide thereof, each $R^1$ are independently hydrogen, halogen, alkoxy, cyano, —$NR^aR^b$, —C(=O)$OR^c$, or alkyl; wherein the alkyl and alkoxy are optionally substituted with one or more $R^d$.

In some embodiments of a compound of Formula (VI), or a pharmaceutically acceptable salt, solvate, tautomer, or N-oxide thereof, each $R^1$ is independently hydrogen, fluoro, chloro, bromo, methyl, —$CF_3$, —$OCF_3$, methoxy, cyano, —$NMe_2$, —C(=O)OEt, or —$CH_2OCH_3$.

A compound of Formula (VI), or a pharmaceutically acceptable salt, solvate, tautomer, or N-oxide thereof, selected from:

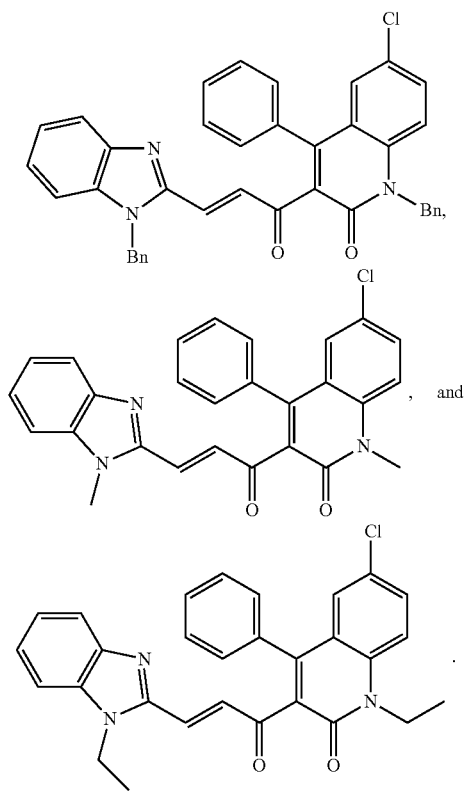

One aspect provides a compound of Formula (VII), or a pharmaceutically acceptable salt, solvate, tautomer, or N-oxide thereof:

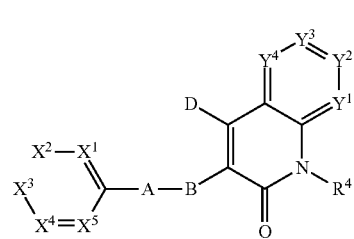

Formula (VII)

wherein

D is aryl, heteroaryl, alkyl, cycloalkyl, or heterocycloalkyl; wherein the aryl, heteroaryl, alkyl, cycloalkyl, and heterocycloalkyl are optionally substituted with one or more $R^1$;

A and B are independently a bond, —$CH_2$—, —$CH_2CH_2$—, —C(=O)—, —$CR^5$=$CR^6$—, ≡, —C(=O)$NR^a$—, or —$NR^aC$(=O)—;

$X^1$-$X^5$ are independently N or $CR^1$; wherein at least one of $X^1$-$X^5$ is N;

$Y^1$-$Y^4$ are independently N or $CR^2$;

each $R^1$ are independently hydrogen, halogen, hydroxyl, alkoxy, cyano, —$NR^aR^b$, —C(=O)$OR^c$, alkyl, cycloalkyl, or aryl; wherein the alkyl, alkoxy, cycloalkyl, and aryl are optionally substituted with one or more $R^d$;

each $R^2$ are independently hydrogen, halogen, hydroxyl, nitro, alkoxy, —$NR^aR^b$, alkyl, or cycloalkyl; wherein the alkyl and cycloalkyl are optionally substituted with one or more $R^d$;

$R^4$ is hydrogen, alkyl, or aralkyl;

$R^5$ and $R^6$ are independently hydrogen, halogen, or alkyl;

each $R^a$ and $R^b$ are independently hydrogen or alkyl; or $R^a$ and $R^b$ taken together with the nitrogen to which they are attached form a heterocycloalkyl optionally substituted with alkyl;

$R^c$ is hydrogen or alkyl; and each $R^d$ is independently alkyl, halogen, hydroxyl, alkoxy, cyano, or —$NR^aR^b$.

In some embodiments of a compound of Formula (VII), or a pharmaceutically acceptable salt, solvate, tautomer, or N-oxide thereof, $R^4$ is hydrogen.

In some embodiments of a compound of Formula (VII), or a pharmaceutically acceptable salt, solvate, tautomer, or N-oxide thereof, B is —C(=O)—

In some embodiments of a compound of Formula (VII), or a pharmaceutically acceptable salt, solvate, tautomer, or N-oxide thereof, A is —CH=CH—.

In some embodiments of a compound of Formula (VII), or a pharmaceutically acceptable salt, solvate, tautomer, or N-oxide thereof, $Y^1$-$Y^4$ are independently $CR^2$. In some embodiments of a compound of Formula (VII), or a pharmaceutically acceptable salt, solvate, tautomer, or N-oxide thereof, each $R^2$ is independently hydrogen or halogen. In some embodiments of a compound of Formula (VII), or a pharmaceutically acceptable salt, solvate, tautomer, or N-oxide thereof, at least one of $Y^1$-$Y^4$ is N.

In some embodiments of a compound of Formula (VII), or a pharmaceutically acceptable salt, solvate, tautomer, or N-oxide thereof, D is aryl or heteroaryl of the general formula:

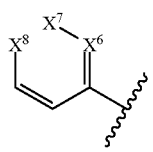

wherein $X^6$-$X^8$ are independently N or $CR^1$.

In some embodiments of a compound of Formula (VII), or a pharmaceutically acceptable salt, solvate, tautomer, or N-oxide thereof, D is aryl or heteroaryl of the general formula:

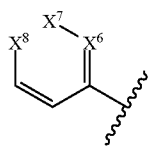

wherein $X^6$-$X^8$ are independently $CR^1$. In some embodiments of a compound of Formula (VII), or a pharmaceutically acceptable salt, solvate, tautomer, or N-oxide thereof, $X^6$-$X^8$ are $CR^1$ and $R^1$ are hydrogen.

In some embodiments of a compound of Formula (VII), $X^1$ is N and $X^2$-$X^5$ are $CR^1$. In some embodiments of a compound of Formula (VII), or a pharmaceutically acceptable salt, solvate, tautomer, or N-oxide thereof, $X^2$ is N and $X^1$, $X^3$-$X^5$ are $CR^1$. In some embodiments of a compound of Formula (VII), or a pharmaceutically acceptable salt, solvate, tautomer, or N-oxide thereof, $X^3$ is N and $X^1$-$X^2$ and $X^4$-$X^5$ are $CR^1$. In some embodiments of a compound of Formula (VII), or a pharmaceutically acceptable salt, solvate, tautomer, or N-oxide thereof, $X^2$ and $X^4$ are N and $X^1$, $X^3$ and $X^5$ are $CR^1$. In some embodiments of a compound of Formula (VII), or a pharmaceutically acceptable salt, solvate, tautomer, or N-oxide thereof, $X^2$ and $X^5$ are N and $X^1$, $X^3$ and $X^4$ are $CR^1$.

In some embodiments of a compound of Formula (VII), or a pharmaceutically acceptable salt, solvate, tautomer, or N-oxide thereof, each $R^1$ are independently hydrogen, halogen, alkoxy, cyano, —$NR^aR^b$, —$C(=O)OR^c$, or alkyl; wherein the alkyl and alkoxy are optionally substituted with one or more $R^d$.

In some embodiments of a compound of Formula (VII), or a pharmaceutically acceptable salt, solvate, tautomer, or N-oxide thereof, each $R^1$ is independently hydrogen, fluoro, chloro, bromo, methyl, —$CF_3$, —$OCF_3$, methoxy, cyano, —$NMe_2$, —$C(=O)OEt$, or —$CH_2OCH_3$.

A compound of Formula (VII), or a pharmaceutically acceptable salt, solvate, tautomer, or N-oxide thereof, selected from:

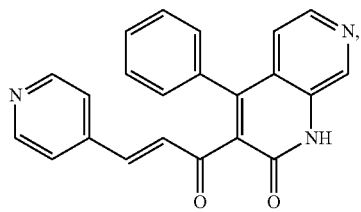

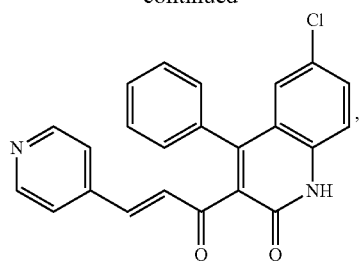

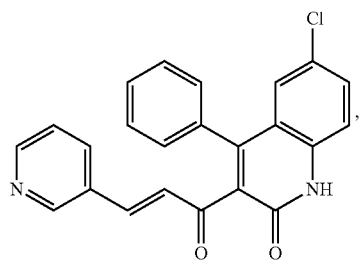

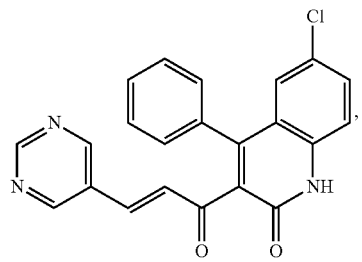

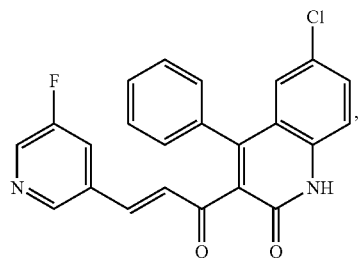

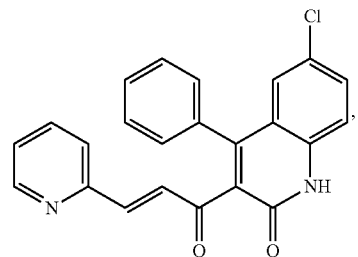

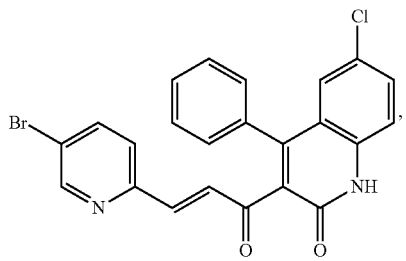

-continued
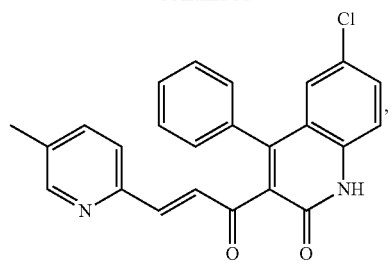
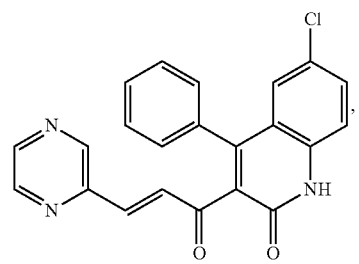
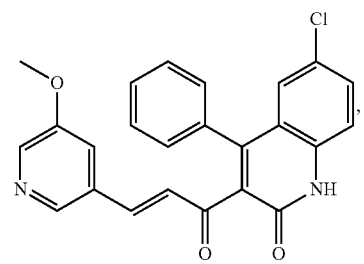
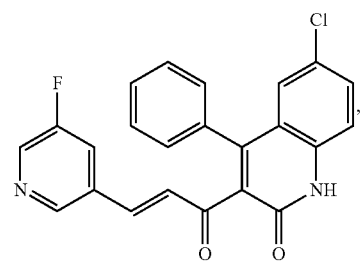
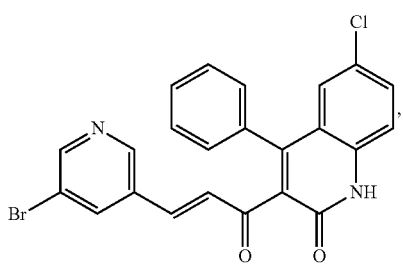
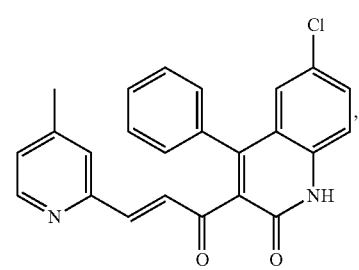
-continued
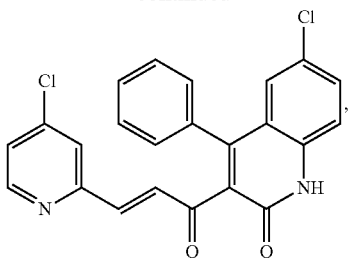
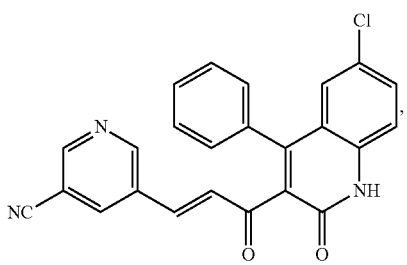
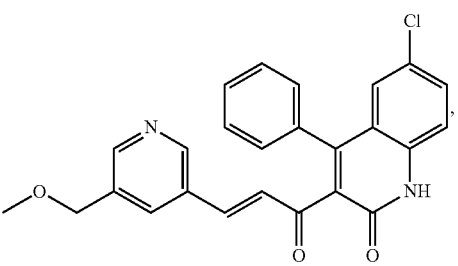
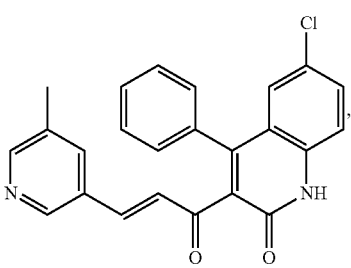
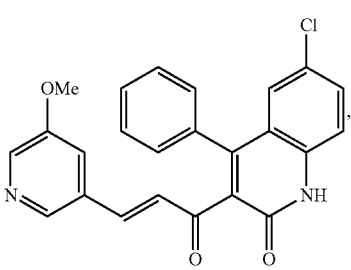

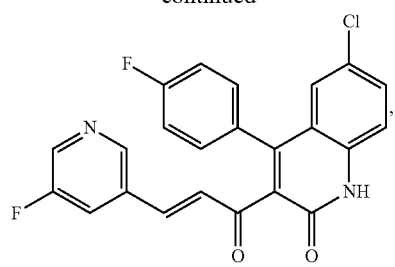
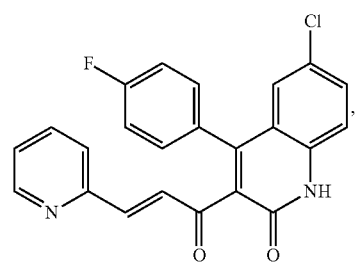
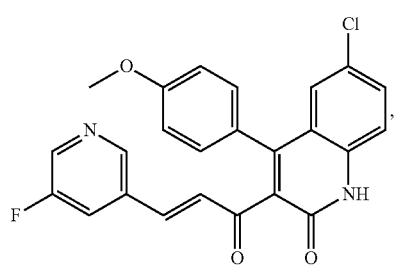
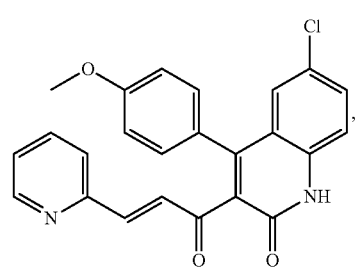
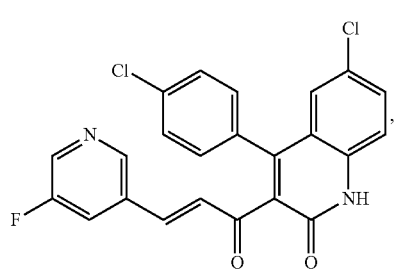
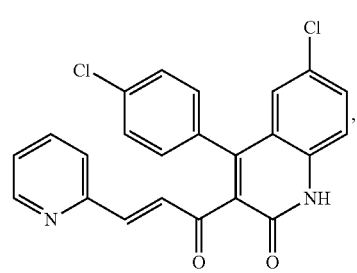
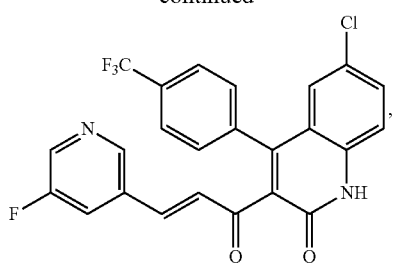
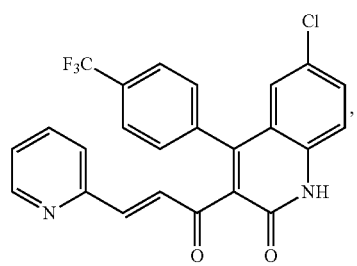
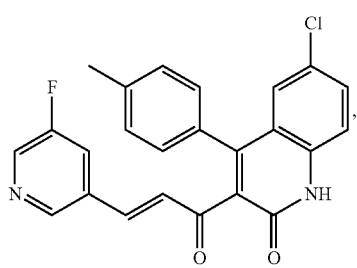
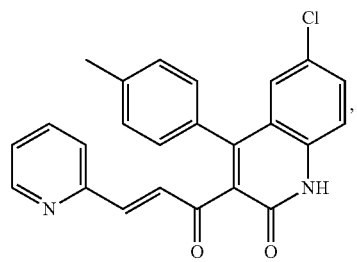
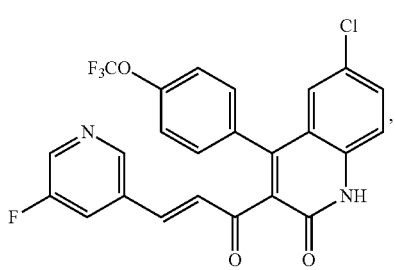
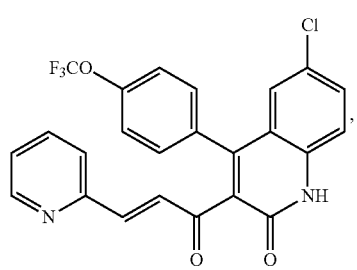

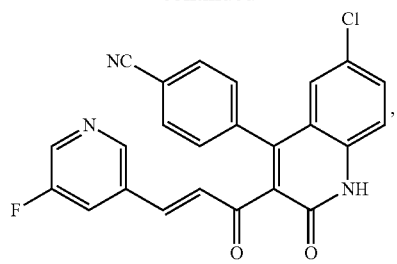,
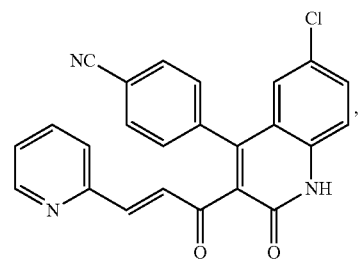,
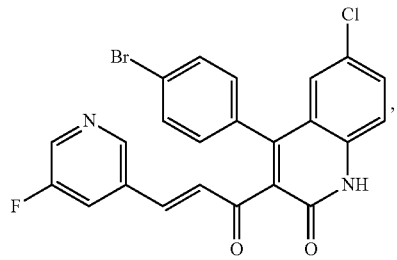,
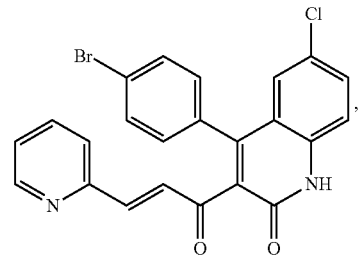,
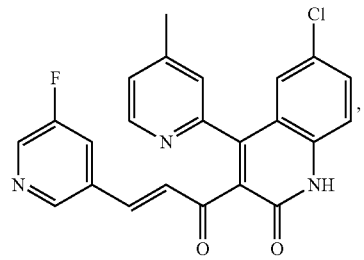,
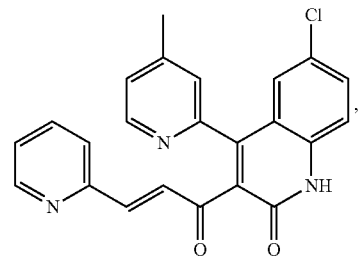,
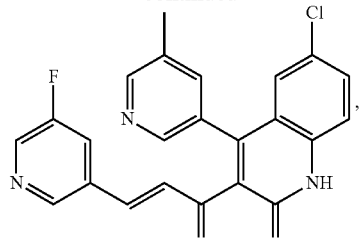,
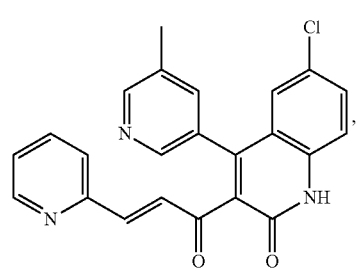,
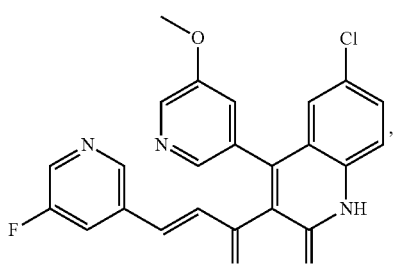,
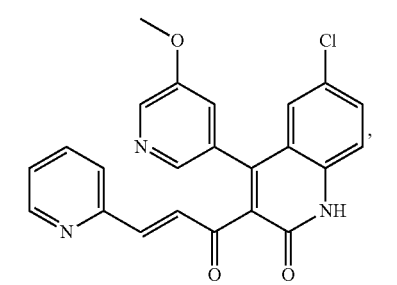,
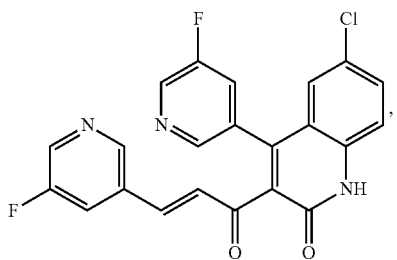,
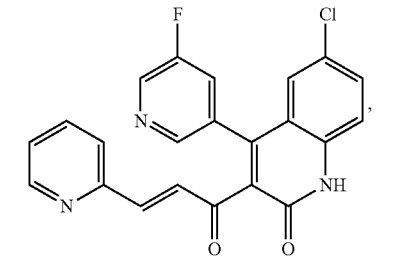,

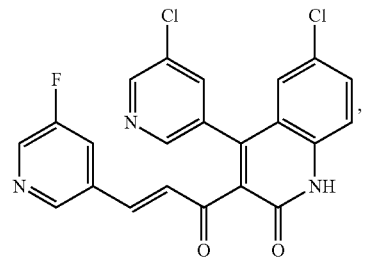
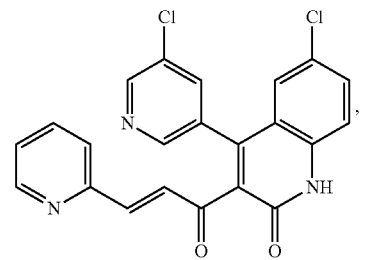
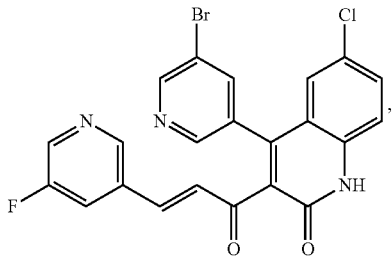
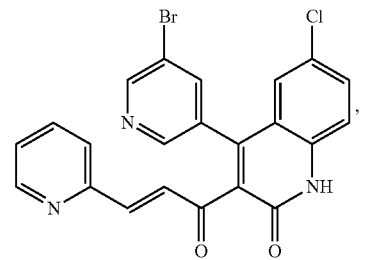
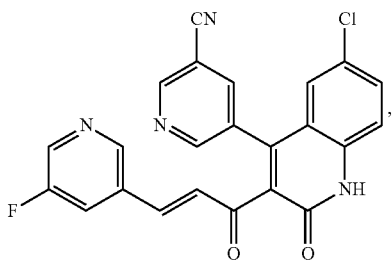
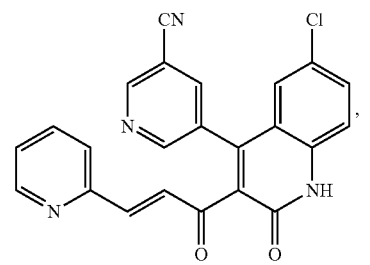
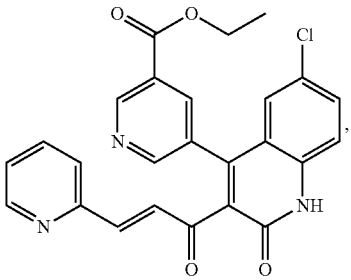
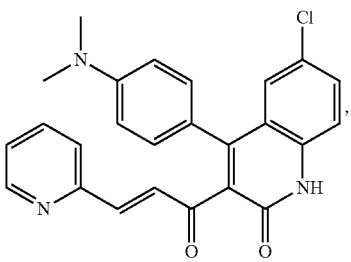
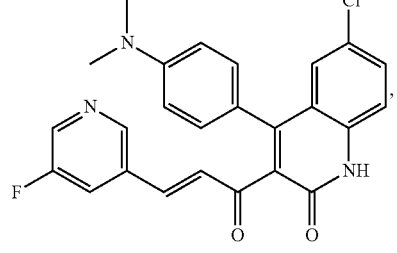
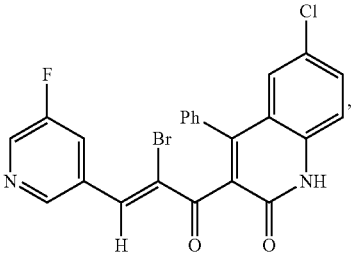
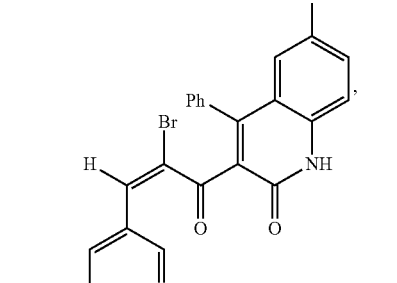
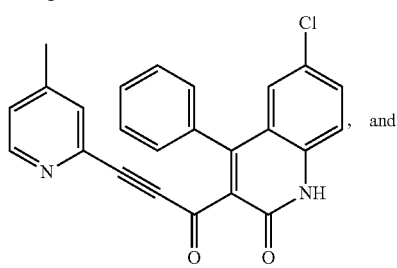

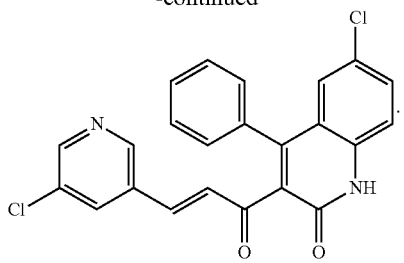

One aspect provides a compound of Formula (VIII), or a pharmaceutically acceptable salt, solvate, tautomer, or N-oxide thereof.

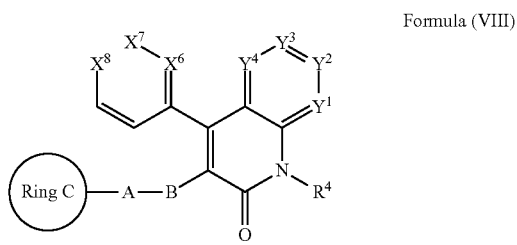

Formula (VIII)

wherein
Ring C is aryl or heteroaryl; wherein the aryl and heteroaryl are optionally substituted with one or more $R^1$;
A and B are independently a bond, —$CH_2$—, —$CH_2CH_2$—, —C(=O)—, —$CR^5$=$CR^6$—, ≡, —C(=O)$NR^a$—, or —$NR^a$C(=O)—;
$X^6$-$X^8$ are independently N or $CR^1$; wherein at least one of $X^6$-$X^8$ is N;
$Y^1$-$Y^4$ are independently N or $CR^2$;
each $R^1$ are independently hydrogen, halogen, hydroxyl, alkoxy, cyano, —$NR^aR^b$, —C(=O)$OR^c$, alkyl, cycloalkyl, or aryl; wherein the alkyl, alkoxy, cycloalkyl, and aryl are optionally substituted with one or more $R^d$;
each $R^2$ are independently hydrogen, halogen, hydroxyl, nitro, alkoxy, —$NR^aR^b$, alkyl, or cycloalkyl; wherein the alkyl and cycloalkyl are optionally substituted with one or more $R^d$;
$R^4$ is hydrogen, alkyl, or aralkyl;
$R^5$ and $R^6$ are independently hydrogen, halogen, or alkyl;
each $R^a$ and $R^b$ are independently hydrogen or alkyl; or $R^a$ and $R^b$ taken together with the nitrogen to which they are attached form a heterocycloalkyl optionally substituted with alkyl;
$R^c$ is hydrogen or alkyl; and
each $R^d$ is independently alkyl, halogen, hydroxyl, alkoxy, cyano, or —$NR^aR^b$.

In some embodiments of a compound of Formula (VIII), or a pharmaceutically acceptable salt, solvate, tautomer, or N-oxide thereof, $R^4$ is hydrogen.

In some embodiments of a compound of Formula (VIII), or a pharmaceutically acceptable salt, solvate, tautomer, or N-oxide thereof, B is —C(=O)—

In some embodiments of a compound of Formula (VIII), or a pharmaceutically acceptable salt, solvate, tautomer, or N-oxide thereof, A is —CH=CH—.

In some embodiments of a compound of Formula (VIII), or a pharmaceutically acceptable salt, solvate, tautomer, or N-oxide thereof, $Y^1$-$Y^4$ are independently $CR^2$. In some embodiments of a compound of Formula (VIII), or a pharmaceutically acceptable salt, solvate, tautomer, or N-oxide thereof, each $R^2$ is independently hydrogen or halogen. In some embodiments of a compound of Formula (VIII), or a pharmaceutically acceptable salt, solvate, tautomer, or N-oxide thereof, at least one of $Y^1$-$Y^4$ is N.

In some embodiments of a compound of Formula (VIII), or a pharmaceutically acceptable salt, solvate, tautomer, or N-oxide thereof, Ring C is benzimidazolyl optionally substituted with one or more $R^1$.

In some embodiments of a compound of Formula (VIII), or a pharmaceutically acceptable salt, solvate, tautomer, or N-oxide thereof, Ring C is phenyl optionally substituted with one or more $R^1$.

In some embodiments of a compound of Formula (VIII), or a pharmaceutically acceptable salt, solvate, tautomer, or N-oxide thereof, $X^6$ is N; and $X^7$ and $X^8$ are $CR^1$. In some embodiments of a compound of Formula (VIII), or a pharmaceutically acceptable salt, solvate, tautomer, or N-oxide thereof, $X^7$ is N; and $X^6$ and $X^8$ are $CR^1$. In some embodiments of a compound of Formula (VIII), or a pharmaceutically acceptable salt, solvate, tautomer, or N-oxide thereof, $X^8$ is N; and $X^6$ and $X^7$ are $CR^1$.

In some embodiments of a compound of Formula (VIII), or a pharmaceutically acceptable salt, solvate, tautomer, or N-oxide thereof, each $R^1$ are independently hydrogen, halogen, alkoxy, cyano, —$NR^aR^b$, —C(=O)$OR^c$, or alkyl; wherein the alkyl and alkoxy are optionally substituted with one or more $R^d$.

In some embodiments of a compound of Formula (VIII), or a pharmaceutically acceptable salt, solvate, tautomer, or N-oxide thereof, each $R^1$ is independently hydrogen, fluoro, chloro, bromo, methyl, —$CF_3$, —$OCF_3$, methoxy, cyano, —$NMe_2$, —C(=O)OEt, or —$CH_2OCH_3$.

A compound of Formula (VIII), or a pharmaceutically acceptable salt, solvate, tautomer, or N-oxide thereof, selected from:

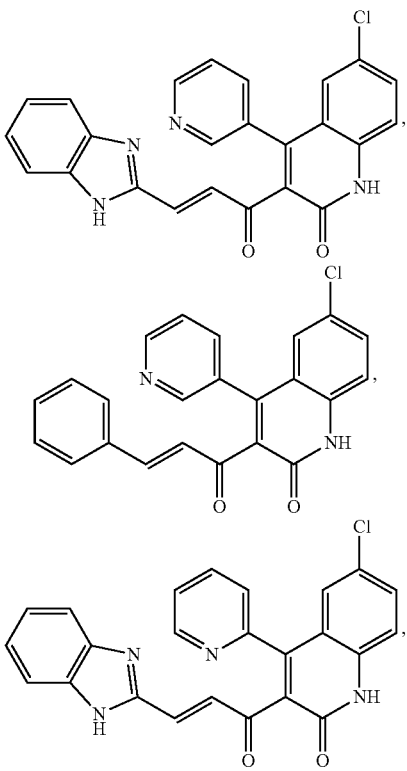

-continued
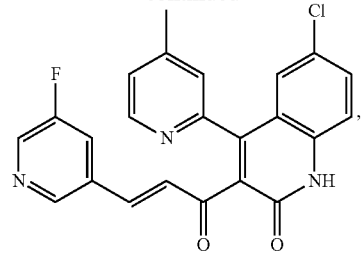
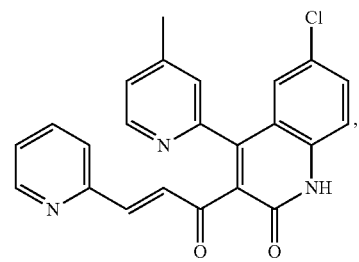
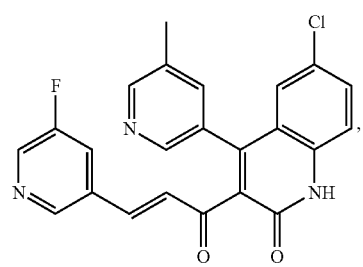
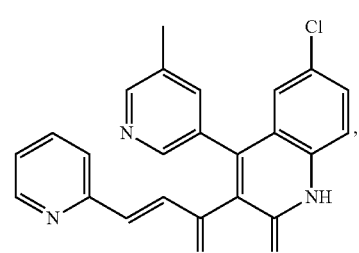
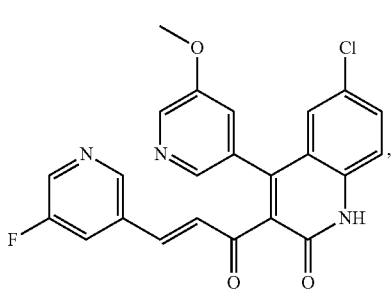
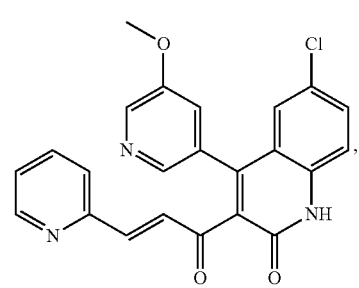
-continued
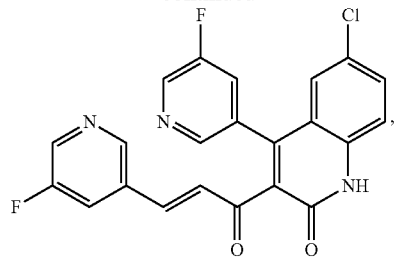
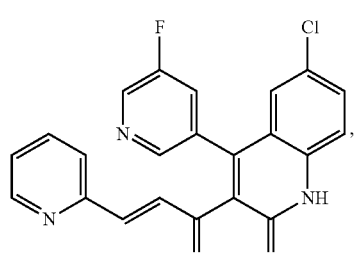
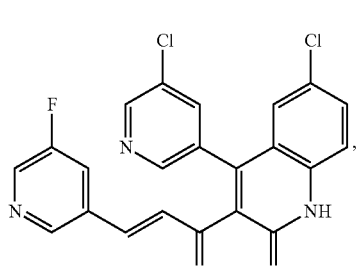
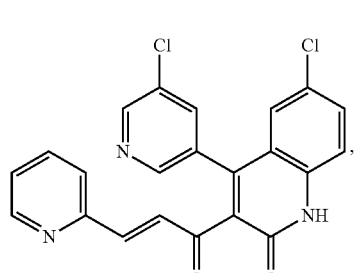
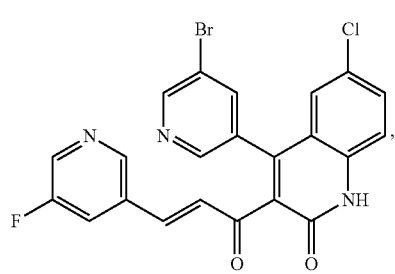
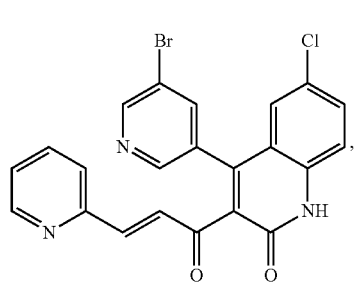

-continued

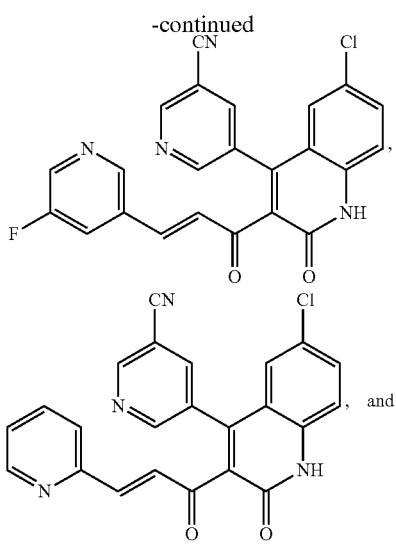

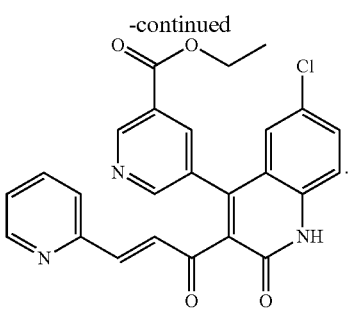

Further embodiments provided herein include combinations of one or more of the particular embodiments set forth above.

In some embodiments, the compound disclosed herein has the structure provided in Table 1.

TABLE 1

| Ex. | Name | Structure |
|---|---|---|
| BI-69A11 | (E)-3-(3-(1H-benzo[d]imidazol-2-yl)acryloyl)-6-chloro-4-phenylquinolin-2(1H)-one | 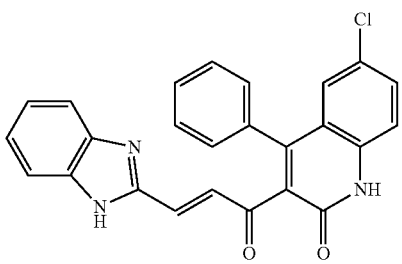 [SMILES: O=C(/C=C/c1nc2ccccc2[nH]1)c1c(-c2ccccc2)c2cc(Cl)ccc2[nH]c1=O] |
| 1 | 3-(3-1H-Benzoimidazol-2-yl-acryloyl)-6-chloro-4-(4-trifluoromethyl-phenyl)-1H-quinolin-2-one | 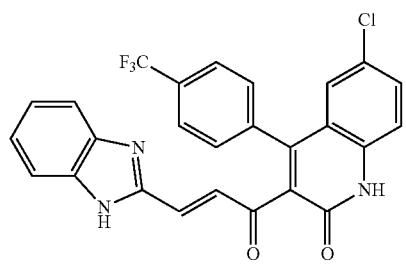 [SMILES: O=C(/C=C/c1nc2ccccc2[nH]1)c1c(-c2ccc(C(F)(F)F)cc2)c2cc(Cl)ccc2[nH]c1=O] |
| 2 | 3-(3-1H-Benzoimidazol-2-yl-acryloyl)-6-chloro-4-(4-trifluoromethoxy-phenyl)-1H-quinolin-2-one | 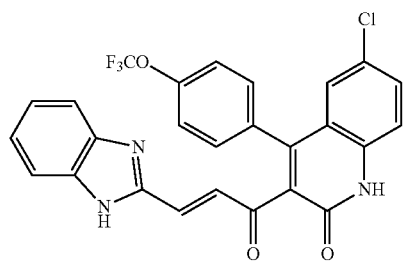 [SMILES: O=C(/C=C/c1nc2ccccc2[nH]1)c1c(-c2ccc(OC(F)(F)F)cc2)c2cc(Cl)ccc2[nH]c1=O] |

TABLE 1-continued

| Ex. | Name | Structure |
|---|---|---|
| 3 | 3-(3-1H-Benzoimidazol-2-yl-acryloyl)-6-chloro-4-(4-methoxy-phenyl)-1H-quinolin-2-one | 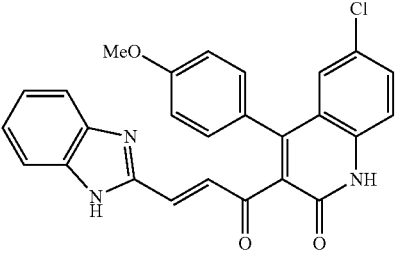 [SMILES: COc1ccc(-c2c(C(=O)/C=C/c3nc4ccccc4[nH]3)c(=O)[nH]c3ccc(Cl)cc23)cc1] |
| 4 | 3-(3-1H-Benzoimidazol-2-yl-acryloyl)-6-chloro-4-p-tolyl-1H-quinolin-2-one | 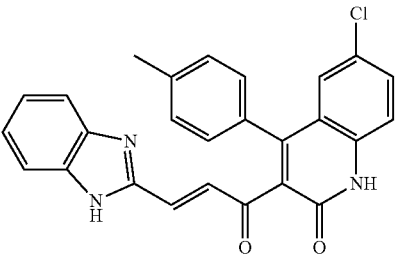 [SMILES: Cc1ccc(-c2c(C(=O)/C=C/c3nc4ccccc4[nH]3)c(=O)[nH]c3ccc(Cl)cc23)cc1] |
| 5 | 3-(3-1H-Benzoimidazol-2-yl-acryloyl)-6-chloro-4-(4-chloro-phenyl)-1H-quinolin-2-one | 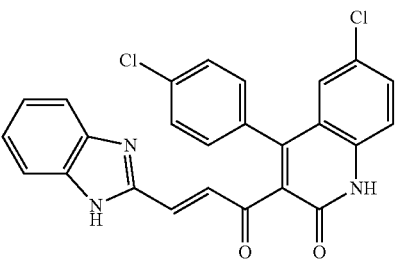 [SMILES: O=C(/C=C/c1nc2ccccc2[nH]1)c1c(-c2ccc(Cl)cc2)c2cc(Cl)ccc2[nH]c1=O] |
| 6 | 3-(3-1H-Benzoimidazol-2-yl-acryloyl)-6-chloro-4-pyridin-3-yl-1H-quinolin-2-one | 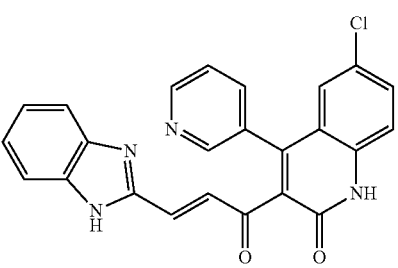 |
| 7 | 6-Chloro-3-(3-phenyl-acryloyl)-4-pyridin-3-yl-1H-quinolin-2-one | 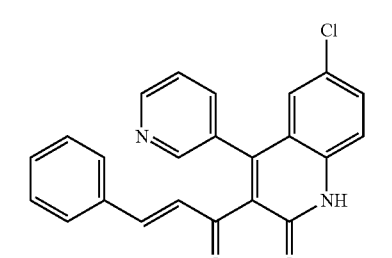 |
| 8 | 3-(3-1H-Benzoimidazol-2-yl-acryloyl)-6-chloro-4-pyridin-2-yl-1H-quinolin-2-one | 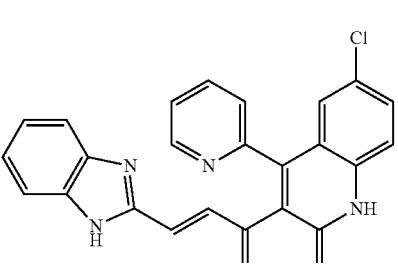 |

TABLE 1-continued

| Ex. | Name | Structure |
|---|---|---|
| 9 | 3-(3-1H-Benzoimidazol-2-yl-acryloyl)-6-chloro-4-thiophen-2-yl-1H-quinolin-2-one | 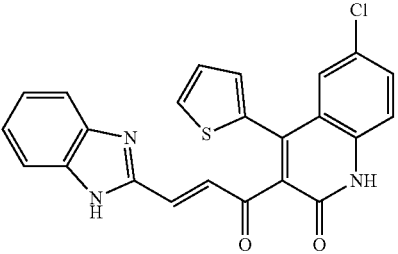 [SMILES: O=C(/C=C/c1nc2ccccc2[nH]1)c1c(-c2cccs2)c2cc(Cl)ccc2[nH]c1=O] |
| 10 | 3-(3-1H-Benzoimidazol-2-yl-acryloyl)-6-chloro-4-thiophen-2-yl-1H-quinolin-2-one | 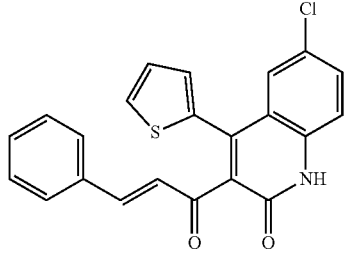 [SMILES: O=C(/C=C/c1ccccc1)c1c(-c2cccs2)c2cc(Cl)ccc2[nH]c1=O] |
| 11 | (E)-3-(3-(1H-benzo[d]imidazol-2-yl)acryloyl)-6-chloro-4-cyclohexylquinolin-2(1H)-one | 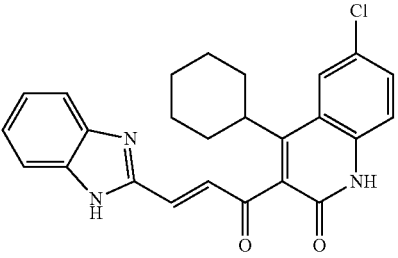 [SMILES: O=C(/C=C/c1nc2ccccc2[nH]1)c1c(C2CCCCC2)c2cc(Cl)ccc2[nH]c1=O] |
| 12 | 6-chloro-3-cinnamoyl-4-cyclohexylquinolin-2(1H)-one SBI-970 | 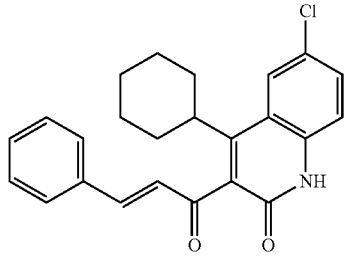 [SMILES: O=C(/C=C/c1ccccc1)c1c(C2CCCCC2)c2cc(Cl)ccc2[nH]c1=O] |
| 13 | 3-(3-1H-Benzoimidazol-2-yl-acryloyl)-6-nitro-4-phenyl-1H-quinolin-2-one | 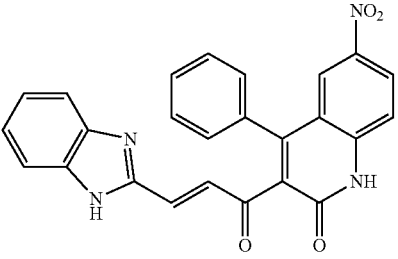 [SMILES: O=C(/C=C/c1nc2ccccc2[nH]1)c1c(-c2ccccc2)c2cc([N+](=O)[O-])ccc2[nH]c1=O] |
| 14 | 6-Amino-3-(3-1H-benzoimidazol-2-yl-propionyl)-4-phenyl-1H-quinolin-2-one | 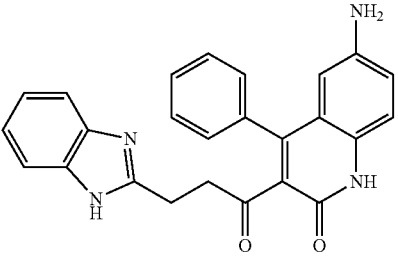 [SMILES: Nc1ccc2[nH]c(=O)c(C(=O)CCc3nc4ccccc4[nH]3)c(-c3ccccc3)c2c1] |

TABLE 1-continued

| Ex. | Name | Structure |
|---|---|---|
| 15 | 6-Amino-3-(3-1H-benzoimidazol-2-yl-acryloyl)-4-phenyl-1H-quinolin-2-one | 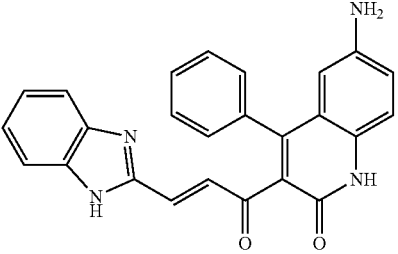 |
| 16 | 6-Nitro-4-phenyl-3-(3-phenyl-acryloyl)-1H-quinolin-2-one | 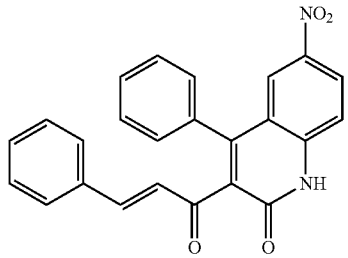 [SMILES: O=C(/C=C/c1ccccc1)c1c(-c2ccccc2)c2cc([N+](=O)[O-])ccc2[nH]c1=O] |
| 17 | 3-[3-(4-Dimethylamino-phenyl)-acryloyl]-6-nitro-4-phenyl-1H-quinolin-2-one | 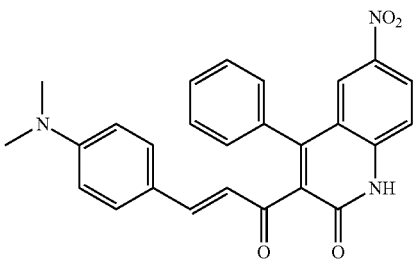 [SMILES: CN(C)c1ccc(/C=C/C(=O)c2c(-c3ccccc3)c3cc([N+](=O)[O-])ccc3[nH]c2=O)cc1] |
| 18 | 3-[3-(4-Dimethylamino-phenyl)-acryloyl]-6-nitro-4-phenyl-1H-quinolin-2-one | 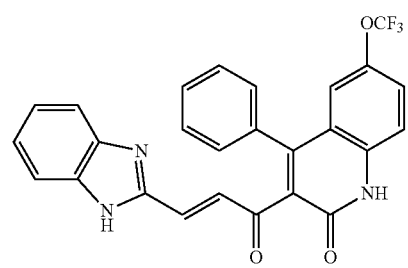 [SMILES: O=C(/C=C/c1nc2ccccc2[nH]1)c1c(-c2ccccc2)c2cc(OC(F)(F)F)ccc2[nH]c1=O] |
| 19 | 3-(3-1H-Benzoimidazol-2-yl-acryloyl)-4-phenyl-6-trifluoromethyl-1H-quinolin-2-one | 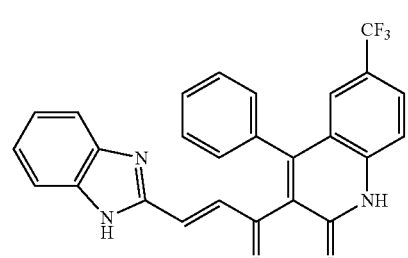 |
| 20 | 3-(3-1H-Benzoimidazol-2-yl-acryoyl)-6-fluoro-4-phenyl-1H-quinolin-2-one | 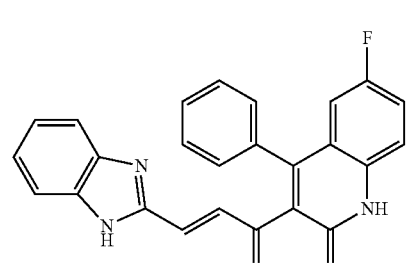 |

TABLE 1-continued

| Ex. | Name |
|---|---|
| 21 | 3-(3-1H-Benzoimidazol-2-yl-acryloyl)-6-methoxy-4-phenyl-1H-quinolin-2-one |
| 22 | 3-(3-1H-Benzoimidazol-2-yl-acryloyl)-4-phenyl-1H-[1,7]naphthyridin-2-one |
| 23 | 4-Phenyl-3-(3-pyridin-4-yl-acryloyl)-1H-[1,7]naphthyridin-2-one |
| 24 | 3-(3-1H-Benzoimidazol-2-yl-acryloyl)-4-phenyl-1H-[1,6]naphthyridin-2-one |
| 25 | 3-(3-1H-Benzoimidazol-2-yl-acryloyl)-4-phenyl-1H-[1,8]naphthyridin-2-one |
| 26 | 4-Phenyl-3-(3-phenyl-acryloyl)-1H-[1,7]naphthyridin-2-one |

TABLE 1-continued

| Ex. | Name | Structure |
|-----|------|-----------|
| 27 | 6-Chloro-4-phenyl-3-(3-thiophen-3-yl-acryloyl)-1H-quinolin-2-one | 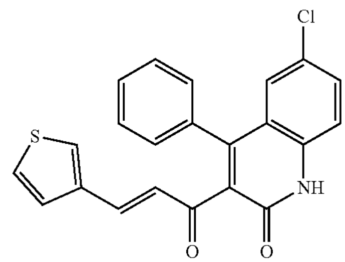 [SMILES: O=C(/C=C/c1ccsc1)c1c(-c2ccccc2)c2cc(Cl)ccc2[nH]c1=O] |
| 28 | 6-Chloro-4-phenyl-3-(3-pyridin-4-yl-acryloyl)-1H-quinolin-2-one | 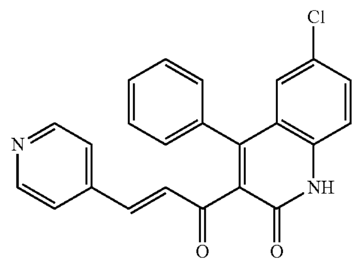 |
| 29 | 6-Chloro-3-[3-(1-methyl-1H-indol-2-yl)-acryloyl]-4-phenyl-1H-quinolin-2-one | 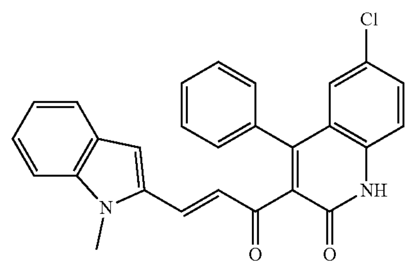 [SMILES: Cn1c(/C=C/C(=O)c2c(-c3ccccc3)c3cc(Cl)ccc3[nH]c2=O)cc2ccccc21] |
| 30 | 6-Chloro-3-[3-(1-methyl-1H-indol-5-yl)-acryloyl]-4-phenyl-1H-quinolin-2-one | 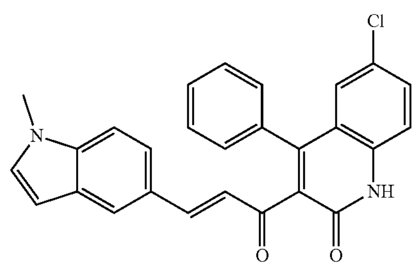 [SMILES: Cn1ccc2cc(/C=C/C(=O)c3c(-c4ccccc4)c4cc(Cl)ccc4[nH]c3=O)ccc21] |
| 31 | 6-Chloro-4-phenyl-3-(3-phenyl-acryloyl)-1H-quinolin-2-one | 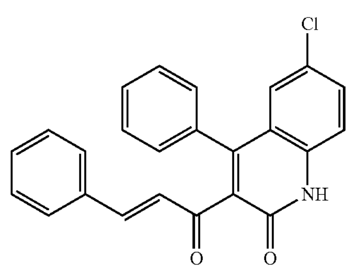 [SMILES: O=C(/C=C/c1ccccc1)c1c(-c2ccccc2)c2cc(Cl)ccc2[nH]c1=O] |
| 32 | 6-Chloro-4-phenyl-3-(3-pyridin-3-yl-acryloyl)-1H-quinolin-2-one | 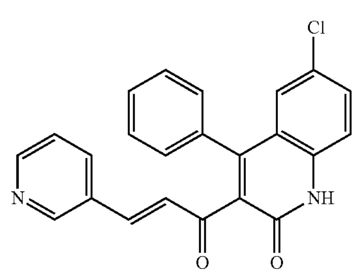 |

TABLE 1-continued

| Ex. | Name | Structure |
|---|---|---|
| 33 | 6-Chloro-3-[3-(4-chloro-phenyl)-acryloyl]-4-phenyl-1H-quinolin-2-one | 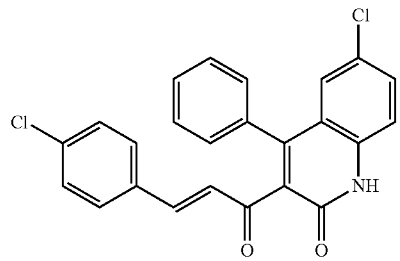 [SMILES: O=C(/C=C/c1ccc(Cl)cc1)c1c(-c2ccccc2)c2cc(Cl)ccc2[nH]c1=O] |
| 34 | 6-Chloro-4-phenyl-3-(3-p-tolyl-acryloyl)-1H-quinolin-2-one | 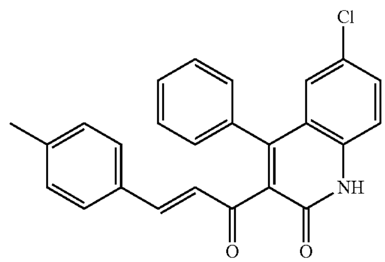 |
| 35 | 6-Chloro-3-[3-(4-dimethylamino-phenyl)-acryloyl]-4-phenyl-1H-quinolin-2-one | 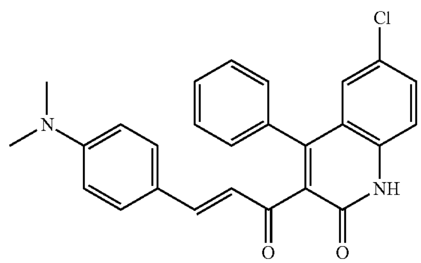 [SMILES: CN(C)c1ccc(/C=C/C(=O)c2c(-c3ccccc3)c3cc(Cl)ccc3[nH]c2=O)cc1] |
| 36 | 3-(3-Benzo[b]thiophen-2-yl-acryloyl)-6-chloro-4-phenyl-1H-quinolin-2-one | 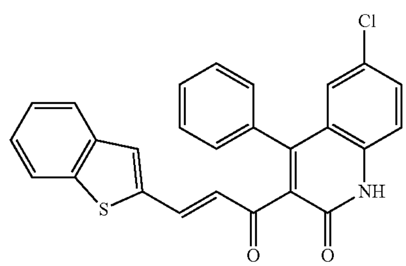 [SMILES: O=C(/C=C/c1cc2ccccc2s1)c1c(-c2ccccc2)c2cc(Cl)ccc2[nH]c1=O] |
| 37 | 6-Chloro-4-phenyl-3-(3-pyrimidin-5-yl-acryloyl)-1H-quinolin-2-one | 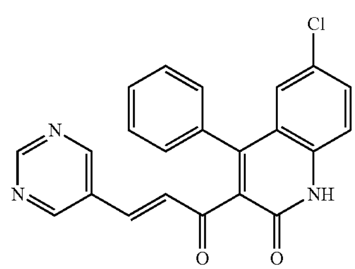 |
| 38 | 6-Chloro-3-[3-(5-fluoro-pyridin-3-yl)-acryloyl]-4-phenyl-1H-quinolin-2-one SBI-756 SBI-0640756 | 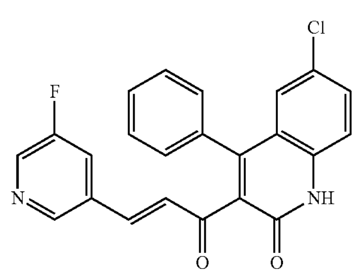 |

TABLE 1-continued

| Ex. | Name | Structure |
|---|---|---|
| 39 | 6-Chloro-4-phenyl-3-[3-(4-trifluoromethyl-phenyl)-acryloyl]-1H-quinolin-2-one | 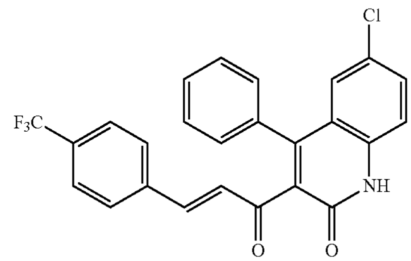 [SMILES: O=C(/C=C/c1ccc(C(F)(F)F)cc1)c1c(-c2ccccc2)c2cc(Cl)ccc2[nH]c1=O] |
| 40 | 6-Chloro-3-[3-(3,4-difluoro-phenyl)-acryloyl]-4-phenyl-1H-quinolin-2-one | 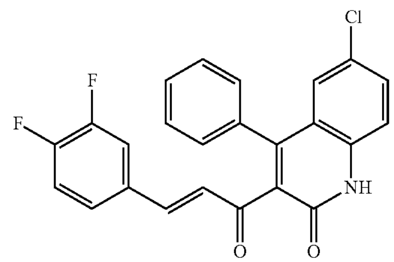 [SMILES: O=C(/C=C/c1ccc(F)c(F)c1)c1c(-c2ccccc2)c2cc(Cl)ccc2[nH]c1=O] |
| 41 | 6-Chloro-3-[3-(2,4-difluoro-phenyl)-acryloyl]-4-phenyl-1H-quinolin-2-one | 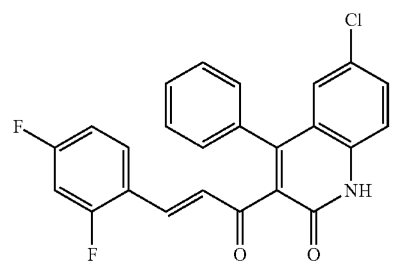 [SMILES: O=C(/C=C/c1ccc(F)cc1F)c1c(-c2ccccc2)c2cc(Cl)ccc2[nH]c1=O] |
| 42 | 6-Chloro-3-[3-(2,6-difluoro-phenyl)-acryloyl]-4-phenyl-1H-quinolin-2-one | 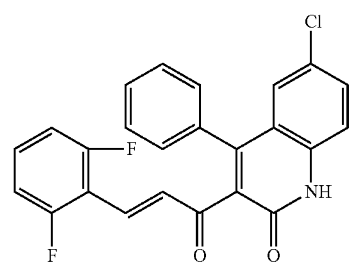 [SMILES: O=C(/C=C/c1c(F)cccc1F)c1c(-c2ccccc2)c2cc(Cl)ccc2[nH]c1=O] |
| 43 | 6-Chloro-3-[3-(2-fluoro-4-methoxy-phenyl)-acryloyl]-4-phenyl-1H-quinolin-2-one | 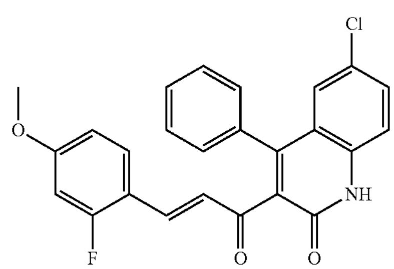 [SMILES: COc1ccc(/C=C/C(=O)c2c(-c3ccccc3)c3cc(Cl)ccc3[nH]c2=O)c(F)c1] |
| 44 | 6-Chloro-4-phenyl-3-(3-pyridin-3-yl-acryloyl)-1H-quinolin-2-one<br>SBI-726 | 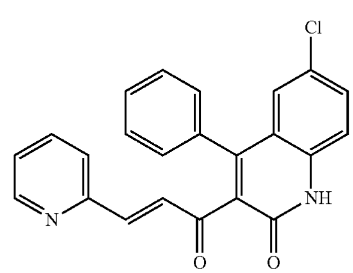 [SMILES: O=C(/C=C/c1ccccn1)c1c(-c2ccccc2)c2cc(Cl)ccc2[nH]c1=O] |

TABLE 1-continued

| Ex. | Name | Structure |
|---|---|---|
| 45 | 6-Chloro-3-[3-(1-methyl-1H-imidazol-2-yl)-acryloyl]-4-phenyl-1H-quinolin-2-one | 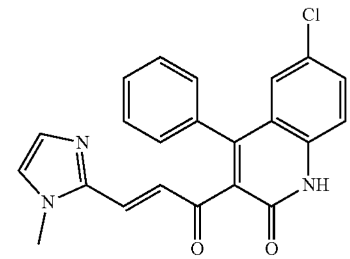 [SMILES: Cn1ccnc1/C=C/C(=O)c1c(-c2ccccc2)c2cc(Cl)ccc2[nH]c1=O] |
| 46 | 3-[3-(4-Bromo-thiophen-2-yl)-acryloyl]-6-chloro-4-phenyl-1H-quinolin-2-one | 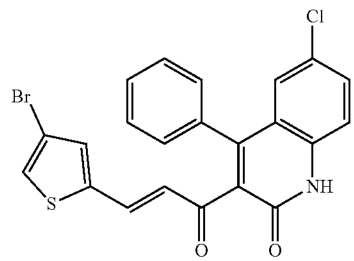 [SMILES: O=C(/C=C/c1cc(Br)cs1)c1c(-c2ccccc2)c2cc(Cl)ccc2[nH]c1=O] |
| 47 | 3-[3-(5-Bromo-pyridin-2-yl)-acryloyl]-6-chloro-4-phenyl-1H-quinolin-2-one | 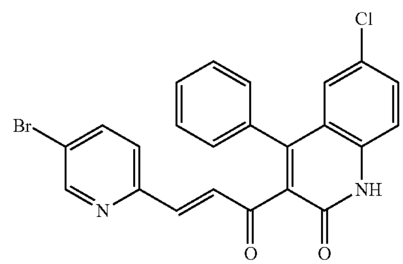 [SMILES: O=C(/C=C/c1ccc(Br)cn1)c1c(-c2ccccc2)c2cc(Cl)ccc2[nH]c1=O] |
| 48 | 6-Chloro-3-[3-(5-methyl-pyridin-2-yl)-acryloyl]-4-phenyl-1H-quinolin-2-one | 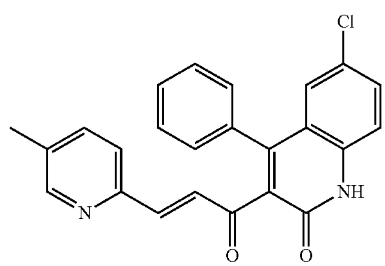 [SMILES: Cc1ccc(/C=C/C(=O)c2c(-c3ccccc3)c3cc(Cl)ccc3[nH]c2=O)nc1] |
| 49 | 6-Chloro-3-[3-(4-fluoro-2-trifluoromethyl-phenyl)-acryloyl]-4-phenyl-1H-quinolin-2-one | 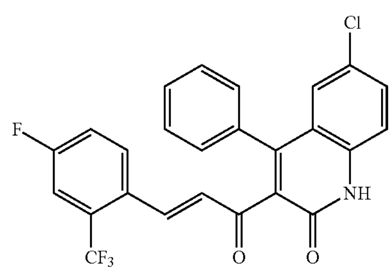 [SMILES: O=C(/C=C/c1ccc(F)cc1C(F)(F)F)c1c(-c2ccccc2)c2cc(Cl)ccc2[nH]c1=O] |
| 50 | 6-Chloro-3-(3-furan-3-yl-acryloyl)-4-phenyl-1H-quinolin-2-one | 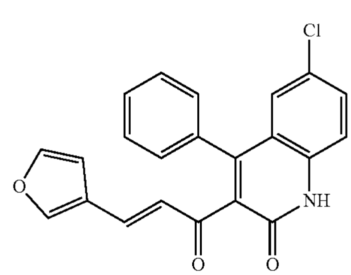 [SMILES: O=C(/C=C/c1ccoc1)c1c(-c2ccccc2)c2cc(Cl)ccc2[nH]c1=O] |

TABLE 1-continued

| Ex. | Name | Structure |
|---|---|---|
| 51 | 6-Chloro-4-phenyl-3-(3-thiophen-2-yl-acryloyl)-1H-quinolin-2-one | 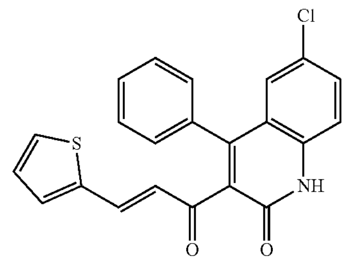 [SMILES: O=C(/C=C/c1cccs1)c1c(-c2ccccc2)c2cc(Cl)ccc2[nH]c1=O] |
| 52 | 6-Chloro-4-phenyl-3-(3-pyrazin-2-yl-acryloyl)-1H-quinolin-2-one | 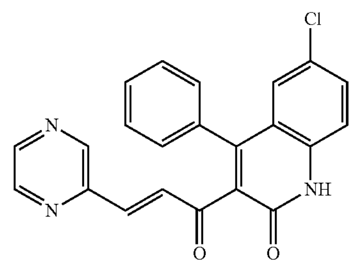 [SMILES: O=C(/C=C/c1cnccn1)c1c(-c2ccccc2)c2cc(Cl)ccc2[nH]c1=O] |
| 53 | 6-Chloro-3-[3-(1-methyl-1H-benzoimidazol-2-yl)-acryloyl]-4-phenyl-1H-quinolin-2-one | 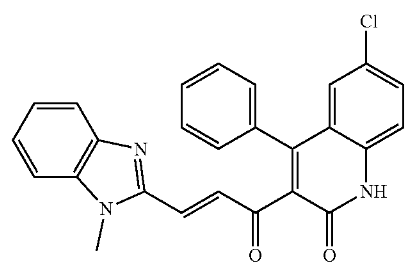 [SMILES: Cn1c(/C=C/C(=O)c2c(-c3ccccc3)c3cc(Cl)ccc3[nH]c2=O)nc2ccccc21] |
| 54 | (E)-6-chloro-3-(3-(5-chloro-1-(4-methoxybenzyl)-1H-benzo[d]imidazol-2-yl)acryloyl)-4-phenylquinolin-2(1H)-one | 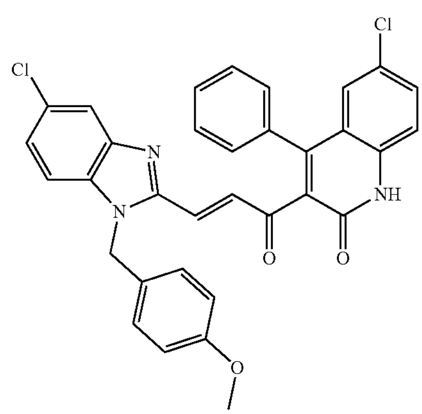 [SMILES: COc1ccc(Cn2c(/C=C/C(=O)c3c(-c4ccccc4)c4cc(Cl)ccc4[nH]c3=O)nc3cc(Cl)ccc32)cc1] |
| 55 | 3-[3-(1-Benzyl-1H-benzoimidazol-2-yl)-acryloyl]-6-chloro-4-phenyl-1H-quinolin-2-one | 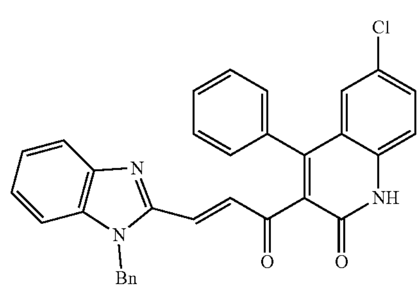 [SMILES: O=C(/C=C/c1nc2ccccc2n1Cc1ccccc1)c1c(-c2ccccc2)c2cc(Cl)ccc2[nH]c1=O] |

TABLE 1-continued

| Ex. | Name | Structure |
|---|---|---|
| 56 | 1-benzyl-3-[3-(1-benzyl-1H-benzoimidazol-2-yl)-acryloyl]-6-chloro-4-phenyl-1H-quinolin-2-one | 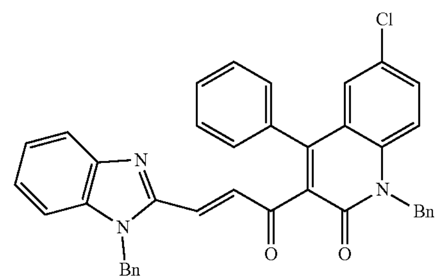 [SMILES: O=C(/C=C/c1nc2ccccc2n1Cc1ccccc1)c1c(-c2ccccc2)c2cc(Cl)ccc2n(Cc2ccccc2)c1=O] |
| 57 | 6-Chloro-3-{3-[1-(2-methoxy-ethyl)-1H-benzoimidazol-2-yl]-acryloyl}-4-phenyl-1H-quinolin-2-one | 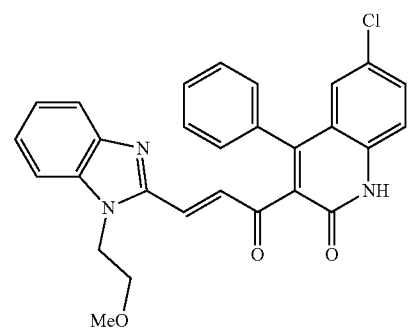 [SMILES: COCCn1c(/C=C/C(=O)c2c(-c3ccccc3)c3cc(Cl)ccc3[nH]c2=O)nc2ccccc21] |
| 58 | 6-Chloro-3-[3-(1-ethyl-1H-benzoimidazol-2-yl)-acryloyl]-4-phenyl-1H-quinolin-2-one | 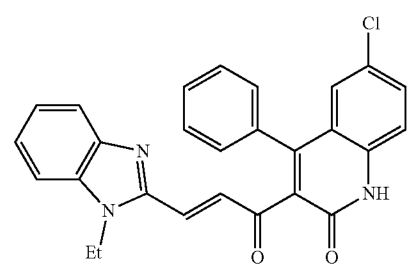 [SMILES: CCn1c(/C=C/C(=O)c2c(-c3ccccc3)c3cc(Cl)ccc3[nH]c2=O)nc2ccccc21] |
| 59 | 6-Chloro-1-methyl-3-[3-(1-methyl-1H-benzoimidazol-2-yl)-acryloyl]-4-phenyl-1H-quinolin-2-one | 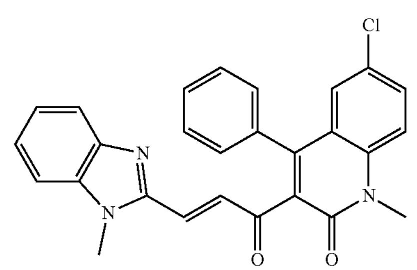 [SMILES: Cn1c(/C=C/C(=O)c2c(-c3ccccc3)c3cc(Cl)ccc3n(C)c2=O)nc2ccccc21] |
| 60 | (E)-6-chloro-1-ethyl-3-(3-(1-ethyl-1H-benzo[d]imidazol-2-yl)acryloyl)-4-phenylquinolin-2(1H)-one | 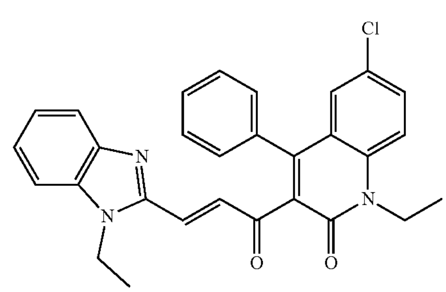 [SMILES: CCn1c(/C=C/C(=O)c2c(-c3ccccc3)c3cc(Cl)ccc3n(CC)c2=O)nc2ccccc21] |

US 10,577,349 B2

TABLE 1-continued

| Ex. | Name | Structure |
|---|---|---|
| 61 | 6-Chloro-3-[3-(5-methyl-1H-benzoimidazol-2-yl)-acryloyl]-4-phenyl-1H-quinolin-2-one | 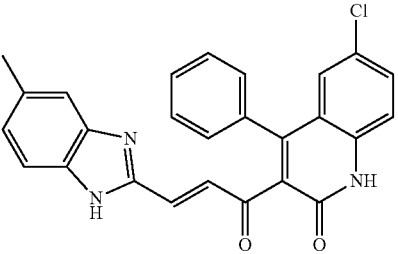 [SMILES: Cc1ccc2[nH]c(/C=C/C(=O)c3c(-c4ccccc4)c4cc(Cl)ccc4[nH]c3=O)nc2c1] |
| 62 | 6-Chloro-3-[3-(5-chloro-1H-benzoimidazol-2-yl)-acryloyl]-4-phenyl-1H-quinolin-2-one SBI-973 | 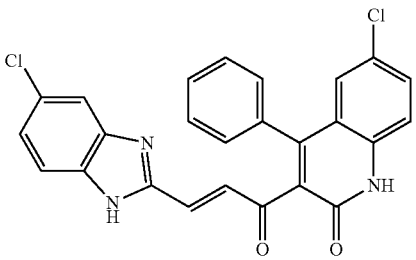 [SMILES: O=C(/C=C/c1nc2cc(Cl)ccc2[nH]1)c1c(-c2ccccc2)c2cc(Cl)ccc2[nH]c1=O] |
| 63 | 6-Chloro-3-[3-(5,6-dichloro-1H-benzoimidazol-2-yl)-acryloyl]-4-phenyl-1H-quinolin-2-one | 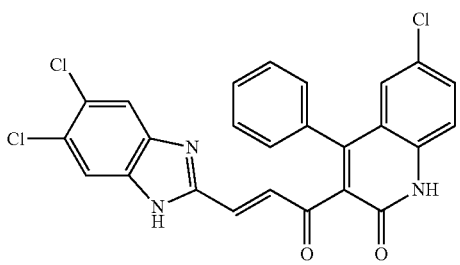 [SMILES: O=C(/C=C/c1nc2cc(Cl)c(Cl)cc2[nH]1)c1c(-c2ccccc2)c2cc(Cl)ccc2[nH]c1=O] |
| 64 | 6-Chloro-3-[3-(5,6-dichloro-1-ethyl-1H-benzoimidazol-2-yl)-acryloyl]-4-phenyl-1H-quinolin-2-one | 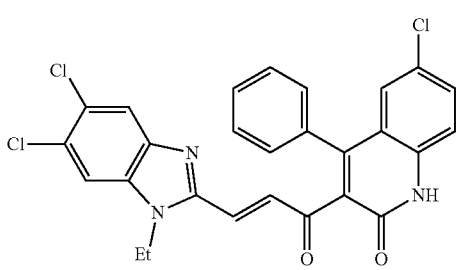 [SMILES: CCn1c(/C=C/C(=O)c2c(-c3ccccc3)c3cc(Cl)ccc3[nH]c2=O)nc2cc(Cl)c(Cl)cc21] |
| 65 | 6-Chloro-3-[3-(5-methoxy-1H-benzoimidazol-2-yl)-acryloyl]-4-phenyl-1H-quinolin-2-one | 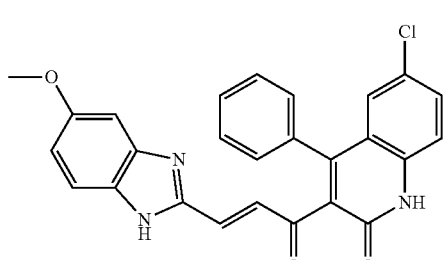 |
| 66 | 3-[(2E)-3-(5-methoxy(3-pyridyl))prop-2-enoyl]-6-chloro-4-phenylhydroquinolin-2-one | 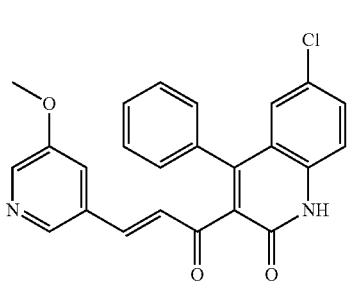 [SMILES: COc1cncc(/C=C/C(=O)c2c(-c3ccccc3)c3cc(Cl)ccc3[nH]c2=O)c1] |

TABLE 1-continued

| Ex. | Name |
|---|---|
| 67 | 6-Chloro-3-[3-(5-fluoro(3-pyridyl))propanoyl]-4-phenylhydroquinolin-2-one |
| 68 | 3-(3-1H-Benzoimidazol-2-yl-propionyl)-6-chloro-4-phenyl-1H-quinolin-2-one |
| 69 | 3-[(2E)-3-(5-bromo(3-pyridyl))prop-2-enoyl]-6-chloro-4-phenylhydroquinolin-2-one |
| 70 | 3-[(2E)-3-(4-methyl(2-pyridyl))prop-2-enoyl]-6-chloro-4-phenylhydroquinolin-2-one |
| 71 | 3-[(2E)-3-(4-chloro(2-pyridyl))prop-2-enoyl]-6-chloro-4-phenylhydroquinolin-2-one |
| 72 | 5-[(1E)-3-(6-chloro-2-oxo-4-phenyl(3-hydroquinolyl))-3-oxoprop-1-enyl]pyridine-3-carbonitrile |

TABLE 1-continued

| Ex. | Name | Structure |
|---|---|---|
| 73 | 3-{(2E)-3-[5-(methoxymethyl)(3-pyridyl)]prop-2-enoyl}-6-chloro-4-phenylhydroquinolin-2-one | 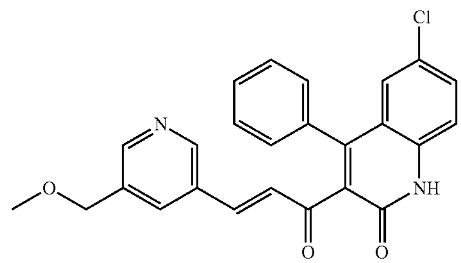 [SMILES: COCc1cncc(/C=C/C(=O)c2c(-c3ccccc3)c3cc(Cl)ccc3[nH]c2=O)c1] |
| 74 | 3-[(2E)-3-(5-methyl(3-pyridyl))prop-2-enoyl]-6-chloro-4-phenylhydroquinolin-2-one | 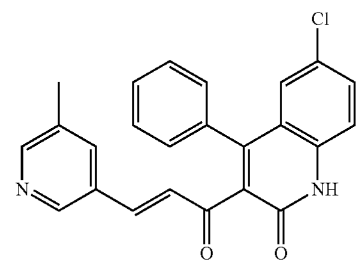 |
| 75 | 3-[(2E)-3-(4-methoxy(2-pyridyl))prop-2-enoyl]-6-chloro-4-phenylhydroquinolin-2-one | 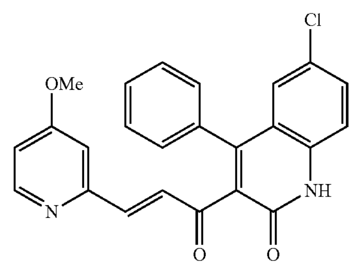 [SMILES: COc1ccnc(/C=C/C(=O)c2c(-c3ccccc3)c3cc(Cl)ccc3[nH]c2=O)c1] |
| 76 | 3-{(2E)-3-[5-(trifluoromethyl)(3-pyridyl)]prop-2-enoyl}-6-chloro-4-phenylhydroquinolin-2-one | 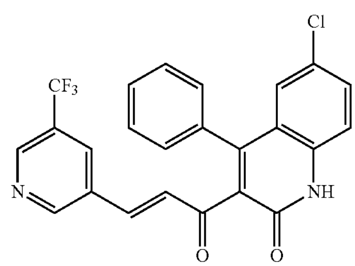 |
| 77 | 3-[(2E)-3-(5-fluoro(3-pyridyl))prop-2-enoyl]-6-chloro-4-(4-fluorophenyl)hydroquinolin-2-one | 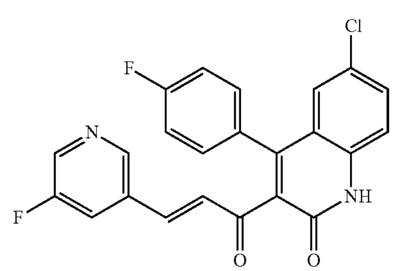 [SMILES: O=C(/C=C/c1cncc(F)c1)c1c(-c2ccc(F)cc2)c2cc(Cl)ccc2[nH]c1=O] |
| 78 | (E)-6-Chloro-4-(4-fluorophenyl)-3-(3-pyridin-2-yl-acryloyl)-1H-quinolin-2-one | 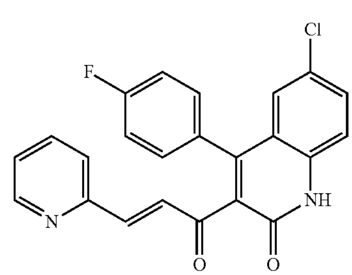 [SMILES: O=C(/C=C/c1ccccn1)c1c(-c2ccc(F)cc2)c2cc(Cl)ccc2[nH]c1=O] |

TABLE 1-continued

| Ex. | Name | Structure |
|---|---|---|
| 79 | 3-[(2E)-3-(5-fluoro(3-pyridyl))prop-2-enoyl]-6-chloro-4-(4-methoxyphenyl)hydroquinolin-2-one | 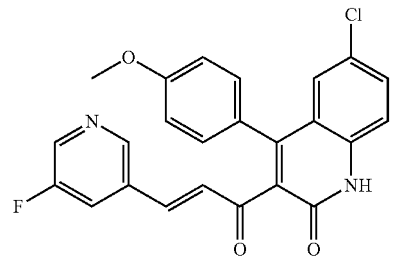 [SMILES: COc1ccc(-c2c(C(=O)/C=C/c3cncc(F)c3)c(=O)[nH]c3ccc(Cl)cc23)cc1] |
| 80 | 3-((2E)-3-(2-pyridyl)prop-2-enoyl)-6-chloro-4-(4-methoxyphenyl)hydroquinolin-2-one | 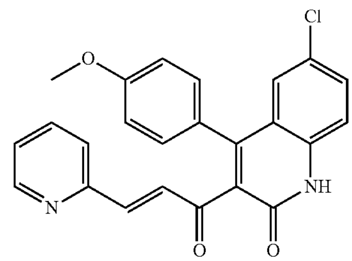 [SMILES: COc1ccc(-c2c(C(=O)/C=C/c3ccccn3)c(=O)[nH]c3ccc(Cl)cc23)cc1] |
| 81 | 3-[(2E)-3-(5-fluoro(3-pyridyl))prop-2-enoyl]-6-chloro-4-(4-chlorophenyl)hydroquinolin-2-one | 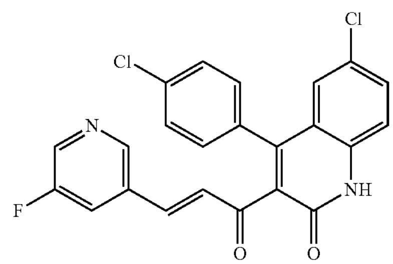 [SMILES: O=C(/C=C/c1cncc(F)c1)c1c(-c2ccc(Cl)cc2)c2cc(Cl)ccc2[nH]c1=O] |
| 82 | 3-((2E)-3-(2-pyridyl)prop-2-enoyl)-6-chloro-4-(4-chlorophenyl)hydroquinolin-2-one | 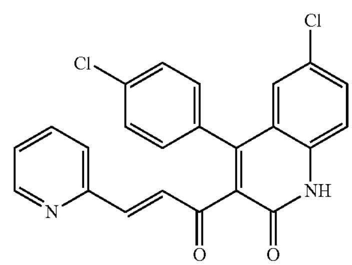 [SMILES: O=C(/C=C/c1ccccn1)c1c(-c2ccc(Cl)cc2)c2cc(Cl)ccc2[nH]c1=O] |
| 83 | 3-[(2E)-3-(5-fluoro(3-pyridyl))prop-2-enoyl]-6-chloro-4-[4-(trifluoromethyl)phenyl]hydroquinolin-2-one | 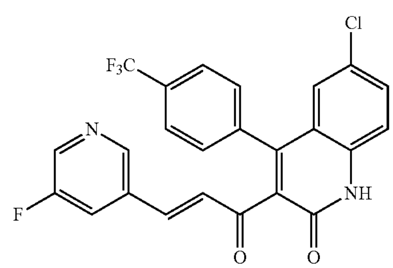 [SMILES: O=C(/C=C/c1cncc(F)c1)c1c(-c2ccc(C(F)(F)F)cc2)c2cc(Cl)ccc2[nH]c1=O] |
| 84 | 3-((2E)-3-(2-pyridyl)prop-2-enoyl)-6-chloro-4-[4-(trifluoromethyl)phenyl]hydroquinolin-2-one | 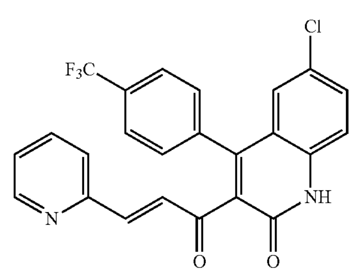 [SMILES: O=C(/C=C/c1ccccn1)c1c(-c2ccc(C(F)(F)F)cc2)c2cc(Cl)ccc2[nH]c1=O] |

TABLE 1-continued

| Ex. | Name | Structure |
|---|---|---|
| 85 | 3-[(2E)-3-(5-fluoro(3-pyridyl))prop-2-enoyl]-6-chloro-4-(4-methylphenyl)hydroquinolin-2-one | 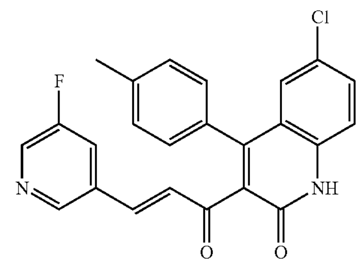 [SMILES: Cc1ccc(-c2c(C(=O)/C=C/c3cncc(F)c3)c(=O)[nH]c3ccc(Cl)cc23)cc1] |
| 86 | 3-((2E)-3-(2-pyridyl)prop-2-enoyl)-6-chloro-4-(4-methylphenyl)hydroquinolin-2-one | 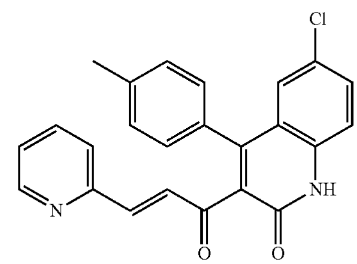 [SMILES: Cc1ccc(-c2c(C(=O)/C=C/c3ccccn3)c(=O)[nH]c3ccc(Cl)cc23)cc1] |
| 87 | 3-[(2E)-3-(5-fluoro(3-pyridyl))prop-2-enoyl]-6-chloro-4-[4-(trifluoromethoxy)phenyl]hydroquinolin-2-one | 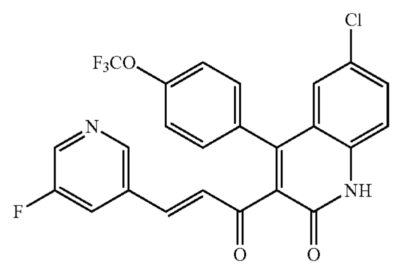 [SMILES: O=C(/C=C/c1cncc(F)c1)c1c(-c2ccc(OC(F)(F)F)cc2)c2cc(Cl)ccc2[nH]c1=O] |
| 88 | 3-((2E)-3-(2-pyridyl)prop-2-enoyl)-6-chloro-4-[4-(trifluoromethoxy)phenyl]hydroquinolin-2-one | 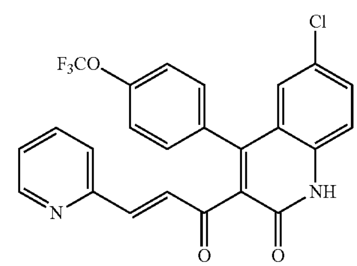 [SMILES: O=C(/C=C/c1ccccn1)c1c(-c2ccc(OC(F)(F)F)cc2)c2cc(Cl)ccc2[nH]c1=O] |
| 89 | 4-[3-((2E)-3-(2-pyridyl)prop-2-enoyl)-6-chloro-2-oxo-4-hydroquinolyl]benzenecarbonitrile | 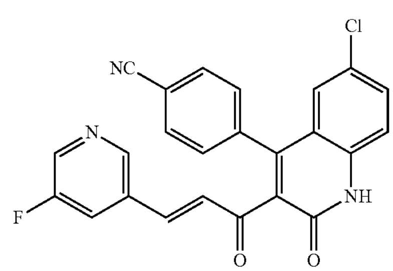 [SMILES: N#Cc1ccc(-c2c(C(=O)/C=C/c3cncc(F)c3)c(=O)[nH]c3ccc(Cl)cc23)cc1] |
| 90 | 4-[3-((2E)-3-(2-pyridyl)prop-2-enoyl)-6-chloro-2-oxo-4-hydroquinolyl]benzenecarbonitrile | 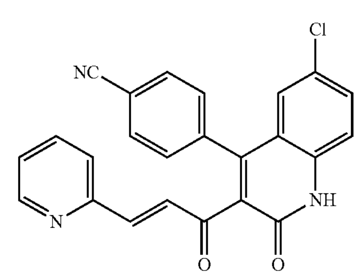 [SMILES: N#Cc1ccc(-c2c(C(=O)/C=C/c3ccccn3)c(=O)[nH]c3ccc(Cl)cc23)cc1] |

TABLE 1-continued

| Ex. | Name | Structure |
|---|---|---|
| 91 | 3-[(2E)-3-(5-fluoro(3-pyridyl))prop-2-enoyl]-4-(4-bromophenyl)-6-chlorohydroquinolin-2-one | 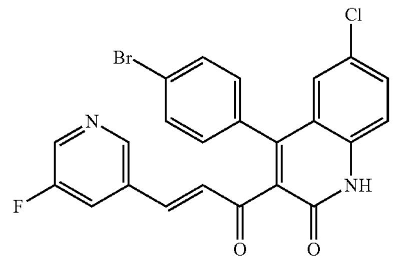 [SMILES: O=C(/C=C/c1cncc(F)c1)c1c(-c2ccc(Br)cc2)c2cc(Cl)ccc2[nH]c1=O] |
| 92 | 3-((2E)-3-(2-pyridyl)prop-2-enoyl)-4-(4-bromophenyl)-6-chlorohydroquinolin-2-one | 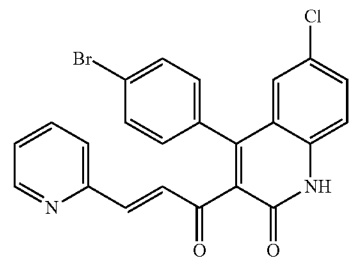 [SMILES: O=C(/C=C/c1ccccn1)c1c(-c2ccc(Br)cc2)c2cc(Cl)ccc2[nH]c1=O] |
| 93 | 3-[(2E)-3-(5-fluoro(3-pyridyl))prop-2-enoyl]-6-chloro-4-(4-methyl(2-pyridyl))hydroquinolin-2-one | 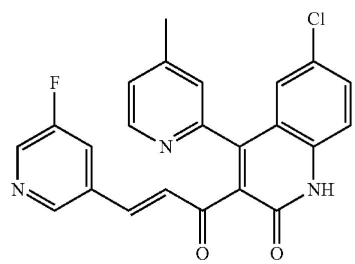 |
| 94 | 3-((2E)-3-(2-pyridyl)prop-2-enoyl)-6-chloro-4-(4-methyl(2-pyridyl))hydroquinolin-2-one | 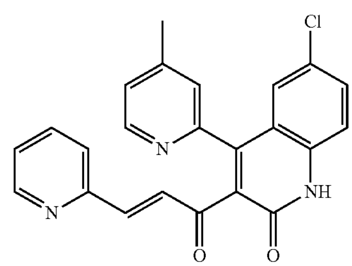 [SMILES: Cc1ccnc(-c2c(C(=O)/C=C/c3ccccn3)c(=O)[nH]c3ccc(Cl)cc23)c1] |
| 95 | 3-[(2E)-3-(5-fluoro(3-pyridyl))prop-2-enoyl]-6-chloro-4-(5-methyl(3-pyridyl))hydroquinolin-2-one | 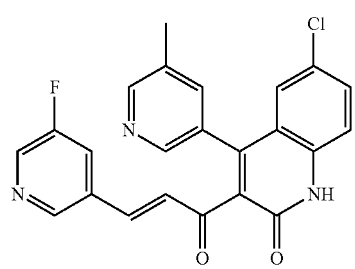 |
| 96 | 3-((2E)-3-(2-pyridyl)prop-2-enoyl)-6-chloro-4-(5-methyl(3-pyridyl))hydroquinolin-2-one | 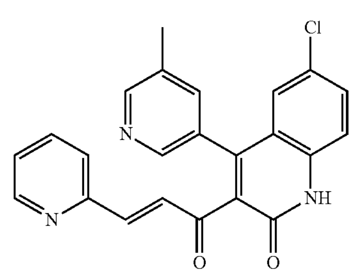 [SMILES: Cc1cncc(-c2c(C(=O)/C=C/c3ccccn3)c(=O)[nH]c3ccc(Cl)cc23)c1] |

TABLE 1-continued

| Ex. | Name | Structure |
|---|---|---|
| 97 | 3-[(2E)-3-(5-fluoro(3-pyridyl))prop-2-enoyl]-6-chloro-4-(5-methoxy(3-pyridyl))hydroquinolin-2-one | 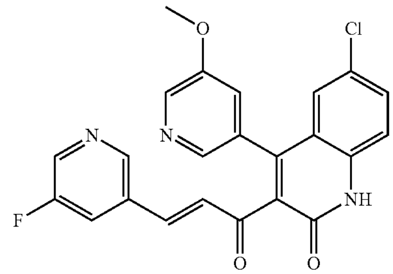 [SMILES: COc1cncc(-c2c(C(=O)/C=C/c3cncc(F)c3)c(=O)[nH]c3ccc(Cl)cc23)c1] |
| 98 | 3-((2E)-3-(2-pyridyl)prop-2-enoyl)-6-chloro-4-(5-methoxy(3-pyridyl))hydroquinolin-2-one | 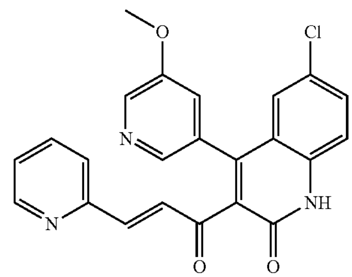 [SMILES: COc1cncc(-c2c(C(=O)/C=C/c3ccccn3)c(=O)[nH]c3ccc(Cl)cc23)c1] |
| 99 | 3-[(2E)-3-(5-fluoro(3-pyridyl))prop-2-enoyl]-6-chloro-4-(5-fluoro(3-pyridyl))hydroquinolin-2-one | 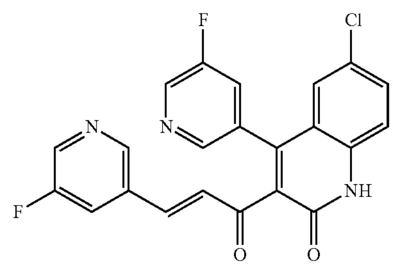 [SMILES: O=C(/C=C/c1cncc(F)c1)c1c(-c2cncc(F)c2)c2cc(Cl)ccc2[nH]c1=O] |
| 100 | 3-((2E)-3-(2-pyridyl)prop-2-enoyl)-6-chloro-4-(5-fluoro(3-pyridyl))hydroquinolin-2-one | 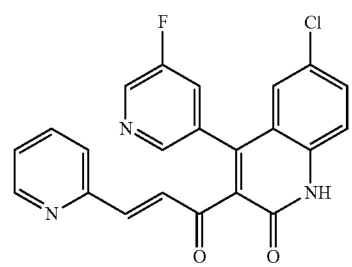 [SMILES: O=C(/C=C/c1ccccn1)c1c(-c2cncc(F)c2)c2cc(Cl)ccc2[nH]c1=O] |
| 101 | 3-[(2E)-3-(5-fluoro(3-pyridyl))prop-2-enoyl]-6-chloro-4-(5-chloro(3-pyridyl))hydroquinolin-2-one | 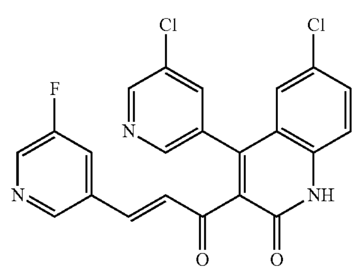 |

TABLE 1-continued

| Ex. | Name | Structure |
|---|---|---|
| 102 | 3-((2E)-3-(2-pyridyl)prop-2-enoyl)-6-chloro-4-(5-chloro(3-pyridyl))hydroquinolin-2-one | 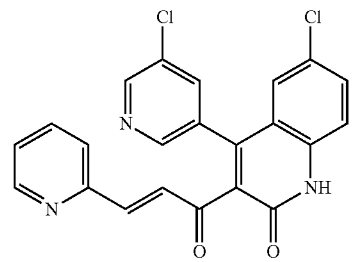 [SMILES: O=C(/C=C/c1ccccn1)c1c(-c2cncc(Cl)c2)c2cc(Cl)ccc2[nH]c1=O] |
| 103 | (E)-4-(5-Bromo-pyridin-3-yl)-6-chloro-3-[3-(5-fluoro-pyridin-3-yl)-acryloyl]-1H-quinolin-2-one | 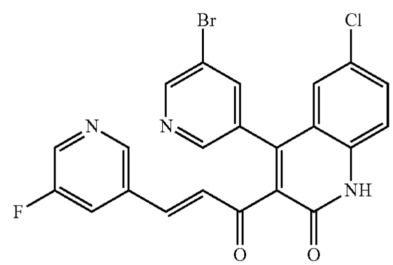 [SMILES: O=C(/C=C/c1cncc(F)c1)c1c(-c2cncc(Br)c2)c2cc(Cl)ccc2[nH]c1=O] |
| 104 | 3-((2E)-3-(2-pyridyl)prop-2-enoyl)-4-(5-bromo(3-pyridyl))-6-chlorohydroquinolin-2-one | 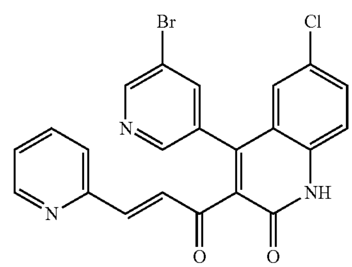 [SMILES: O=C(/C=C/c1ccccn1)c1c(-c2cncc(Br)c2)c2cc(Cl)ccc2[nH]c1=O] |
| 105 | 5-{3-[(2E)-3-(5-fluoro(3-pyridyl))prop-2-enoyl]-6-chloro-2-oxo-4-hydroquinolyl}pyridine-3-carbonitrile | 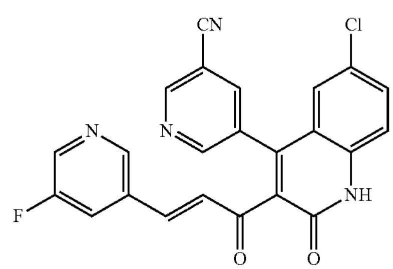 [SMILES: N#Cc1cncc(-c2c(C(=O)/C=C/c3cncc(F)c3)c(=O)[nH]c3ccc(Cl)cc23)c1] |
| 106 | 5-[3-((2E)-3-(2-pyridyl)prop-2-enoyl)-6-chloro-2-oxo-4-hydroquinolyl]pyridine-3-carbonitrile | 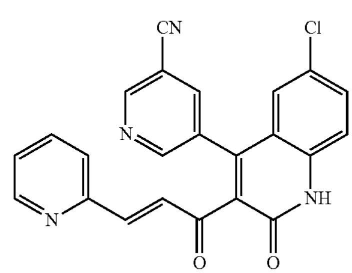 [SMILES: N#Cc1cncc(-c2c(C(=O)/C=C/c3ccccn3)c(=O)[nH]c3ccc(Cl)cc23)c1] |
| 107 | Ethyl 5-[3-((2E)-3-(2-pyridyl)prop-2-enoyl)-6-chloro-2-oxo-4-hydroquinolyl]pyridine-3-carboxylate | 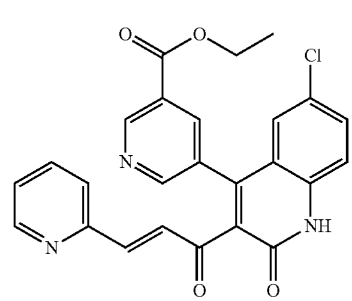 [SMILES: CCOC(=O)c1cncc(-c2c(C(=O)/C=C/c3ccccn3)c(=O)[nH]c3ccc(Cl)cc23)c1] |

TABLE 1-continued

| Ex. | Name |
|---|---|
| 108 | 3-((2E)-3-(2-pyridyl)prop-2-enoyl)-4-[4-(dimethylamino)phenyl]-6-chlorohydroquinolin-2-one |
| 109 | 3-[(2E)-3-(5-fluoro(3-pyridyl))prop-2-enoyl]-4-[4-(dimethylamino)phenyl]-6-chlorohydroquinolin-2-one |
| 110 | 3-[(2Z)-2-bromo-3-(5-fluoro(3-pyridyl))prop-2-enoyl]-6-chloro-4-phenylhydroquinolin-2-one |
| 111 | 3-[(2E)-2-bromo-3-(5-fluoro(3-pyridyl))prop-2-enoyl]-6-chloro-4-phenylhydroquinolin-2-one |
| 112 | 6-Chloro-3-[3-(4-methyl-pyridin-2-yl)-propynoyl]-4-phenyl-1H-quinolin-2-one |

TABLE 1-continued

| Ex. | Name | Structure |
|---|---|---|
| 113 | 6-Chloro-3-[3-(5-chloro-thiophen-2-yl)-acryloyl]-4-phenyl-1H-quinolin-2-one | 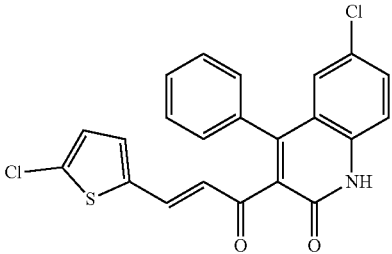 [SMILES: O=C(/C=C/c1ccc(Cl)s1)c1c(-c2ccccc2)c2cc(Cl)ccc2[nH]c1=O] |
| 114 | (E)-6-chloro-3-(3-(5-methyl-1H-benzo[d]imidazol-2-yl)acryloyl)-4-phenyl-1,8-naphthyridin-2(1H)-one | 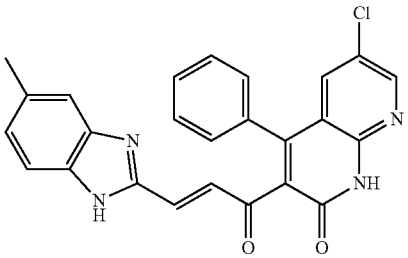 [SMILES: Cc1ccc2[nH]c(/C=C/C(=O)c3c(-c4ccccc4)c4cc(Cl)cnc4[nH]c3=O)nc2c1] |
| 115 | (E)-6-chloro-3-(3-(5-chloropyridin-3-yl)acryloyl)-4-phenylquinolin-2(1H)-one | 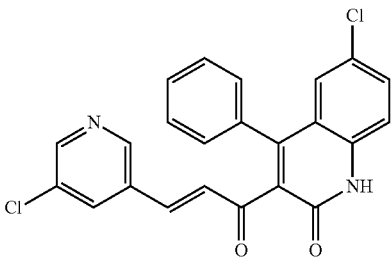 [SMILES: O=C(/C=C/c1cncc(Cl)c1)c1c(-c2ccccc2)c2cc(Cl)ccc2[nH]c1=O] |

Preparation of the Compounds

The compounds used in the reactions described herein are made according to known organic synthesis techniques, starting from commercially available chemicals and/or from compounds described in the chemical literature. "Commercially available chemicals" are obtained from standard commercial sources including Acros Organics (Geel, Belgium), Aldrich Chemical (Milwaukee, Wis., including Sigma Chemical and Fluka), Apin Chemicals Ltd. (Milton Park, UK), Ark Pharm, Inc. (Libertyville, Ill.), Avocado Research (Lancashire, U.K.), BDH Inc. (Toronto, Canada), Bionet (Cornwall, U.K.), Chemservice Inc. (West Chester, Pa.), Combi-blocks (San Diego, Calif.), Crescent Chemical Co. (Hauppauge, N.Y.), eMolecules (San Diego, Calif.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Matrix Scientific, (Columbia, S.C.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Ryan Scientific, Inc. (Mount Pleasant, S.C.), Spectrum Chemicals (Gardena, Calif.), Sundia Meditech, (Shanghai, China), TCI America (Portland, Oreg.), Trans World Chemicals, Inc. (Rockville, Md.), and WuXi (Shanghai, China).

Suitable reference books and treatises that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatises that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are also identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein.

In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds of the invention include isotopes of hydrogen, carbon, nitrogen, oxygen, phosphorous, sulfur, fluorine and chloride, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and pharmaceutically acceptable salts, esters, solvate, hydrates or derivatives thereof which contain the aforementioned isotopes and/or other isotopes of other atoms are within the scope of this invention. Certain isotopically-labeled compounds, for example those into which radioactive isotopes such as $^{3}H$ and $^{14}C$ are incorporated, are useful in drug and/or substrate tissue distribution assays. Tritiated, i. e., $^{3}H$ and carbon-14, i. e., $^{14}C$, isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements. In some embodiments, the isotopically labeled compounds, pharmaceutically acceptable salt, ester, solvate, hydrate or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the invention, or by separately reacting a purified compound in its free form with a suitable acid or base, and isolating the salt thus formed.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran or methanol. In addition, the compounds provided herein exist in unsolvated as well as solvated forms. In general, the solvated forms are considered equivalent to the unsolvated forms for the purposes of the compounds and methods provided herein.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical compositions may also be formulated in rectal compositions such as suppositories or retention enemas, e.g., containing conventional suppository bases such as cocoa butter, polyethylene glycol, or other glycerides.

Pharmaceutical compositions may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical compositions suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation.

Pharmaceutical compositions for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

Methods of Dosing and Treatment Regimens

In some embodiments, described herein are methods for the treatment of cancer, comprising administering a therapeutically effective amount of a compound described herein, or a pharmaceutically acceptable salt, solvate, tautomer, or N-oxide thereof to a subject in need thereof. In some embodiments, the cancer is melanoma. In some embodiments, the cancer is prostate cancer, pancreatic cancer or colorectal cancer.

In some embodiments, described herein are methods for the treatment of a disease mediated by altered translation initiation via targeting of eIF4G, comprising administering a therapeutically effective amount of a compound described herein, or a pharmaceutically acceptable salt, solvate, tautomer, or N-oxide thereof to a subject in need thereof. In some embodiments, the disease mediated by altered translation initiation via targeting of eIF4G is cancer. In some embodiments, the disease mediated by altered translation initiation via targeting of eIF4G is melanoma. In some embodiments, the disease mediated by altered translation initiation via targeting of eIF4G is prostate cancer, pancreatic cancer or colorectal cancer.

In some embodiments, described herein are methods for the treatment of a disease mediated by inhibiting the eIF4F complex assembly, comprising administering a therapeutically effective amount of a compound described herein, or a pharmaceutically acceptable salt, solvate, tautomer, or N-oxide thereof to a subject in need thereof. In some embodiments, the disease mediated by inhibiting the eIF4F complex assembly is cancer. In some embodiments, disease mediated by inhibiting the eIF4F complex assembly is melanoma. In some embodiments, disease mediated by inhibiting the eIF4F complex assembly is prostate cancer, pancreatic cancer or colorectal cancer.

In some embodiments, described herein are methods for the treatment of a drug resistant cancer, comprising administering a therapeutically effective amount of a compound described herein, or a pharmaceutically acceptable salt, solvate, tautomer, or N-oxide thereof to a subject in need thereof. In some embodiments, the drug resistant cancer is melanoma. In some embodiments, the drug resistant cancer is resistant to one or more BRAF inhibitor. In some embodiments, the drug resistant cancer is resistant to one or more MEK inhibitor.

In some embodiments, described herein are methods for the treatment of cancer mediated by inhibition of AKT, NFκB, or mTOR components, comprising administering a therapeutically effective amount of a compound described herein, or a pharmaceutically acceptable salt, solvate, tautomer, or N-oxide thereof to a subject in need thereof.

In some embodiments, described herein are methods for the treatment of cancer mediated by inhibiting DNA damage response and DNA repair activities, comprising administering a therapeutically effective amount of a compound described herein, or a pharmaceutically acceptable salt, solvate, tautomer, or N-oxide thereof to a subject in need thereof.

In some embodiments, described herein are methods for the treatment of cancer mediated by inhibition of cell growth and induction of cell death, comprising administering a therapeutically effective amount of a compound described herein, or a pharmaceutically acceptable salt, solvate, tautomer, or N-oxide thereof to a subject in need thereof.

The disclosed methods are useful in the prevention and treatment of solid tumors, soft tissue tumors, and metastases thereof. Exemplary solid tumors include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small intestine. The disclosed methods are also useful in treating non-solid cancers.

Exemplary cancers include, but are not limited to: Adrenocortical Carcinoma, AIDS-Related Cancers (Kaposi Sarcoma, AIDS-Related Lymphoma, Primary CNS Lymphoma), Anal Cancer, Appendix Cancer, Astrocytomas, Atypical Teratoid/Rhabdoid Tumor, Central Nervous System, Basal Cell Carcinoma, Bile Duct Cancer, Bladder Cancer, Bone Cancer Ewing Sarcoma Family of Tumors, Osteosarcoma and Malignant Fibrous Histiocytoma, Brain Stem Glioma, Brain Tumor (Astrocytomas, Central Nervous System Atypical Teratoid/Rhabdoid Tumor, Central Nervous System Embryonal Tumors, Central Nervous System Germ Cell Tumors, Craniopharyngioma, Ependymoma), Breast Cancer, Bronchial Tumors, Carcinoid Tumor, Gastrointestinal, Carcinoma of Unknown Primary, Cardiac (Heart) Tumors, Atypical Teratoid/Rhabdoid Tumor, Embryonal Tumors, Germ Cell Tumor, Cervical Cancer, Cholangiocarcinoma, Chordoma, Chronic Myeloproliferative Neoplasms, Colon Cancer, Colorectal Cancer, Craniopharyngioma, Cutaneous T-Cell Lymphoma, Ductal Carcinoma In Situ (DCIS), Embryonal Tumors, Endometrial Cancer, Ependymoma, Esophageal Cancer, Esthesioneuroblastoma, Ewing Sarcoma, Extracranial Germ Cell Tumor, Extragonadal Germ Cell Tumor, Eye Cancer, Intraocular Melanoma, Retinoblastoma, Fallopian Tube Cancer, Fibrous Histiocytoma of Bone, Malignant, and Osteosarcoma, Gallbladder Cancer, Gastric (Stomach) Cancer, Gastrointestinal Carcinoid Tumor, Gastrointestinal Stromal Tumors (GIST), Germ Cell Tumor, Ovarian Cancer, Testicular Cancer, Gestational Trophoblastic Disease, Head and Neck Cancer, Heart Cancer, Hepatocellular (Liver) Cancer, Histiocytosis, Langerhans Cell, Hypopharyngeal Cancer, Intraocular Melanoma, Islet Cell Tumors, Pancreatic Neuroendocrine Tumors, Kidney, Renal Cell, Langerhans Cell Histiocytosis, Laryngeal Cancer, Leukemia (Acute Lymphoblastic Leukemia (ALL), Acute Myeloid Leukemia (AML), Chronic Lymphocytic Leukemia (CLL), Chronic Myelogenous Leukemia (CML), Hairy Cell Leukemia), Lip and Oral Cavity Cancer, Liver Cancer (Primary), Lung Cancer (small cell lung cancer, non-small cell lung cancer), Lymphoma (Burkitt Lymphoma, Hodgkin Lymphoma, Non-Hodgkin Lymphoma, Macroglobulinemia, Waldenström), Male Breast Cancer, Malignant Fibrous Histiocytoma of Bone and Osteosarcoma, Melanoma, Intraocular (Eye), Merkel Cell Carcinoma, Mesothelioma, Malignant, Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myeloma, Multiple Myeloma, Myeloproliferative Neoplasms, Chronic, Nasal Cavity and Paranasal Sinus Cancer, Nasopharyngeal Cancer, Neuroblastoma, Oral Cancer, Lip and Oral Cavity Cancer, Oropharyngeal Cancer, Osteosarcoma and Malignant Fibrous Histiocytoma of Bone, Ovarian Cancer, Epithelial, Germ Cell Tumor, Low Malignant Potential Tumor, Pancreatic Cancer, Pancreatic Neuroendocrine Tumors (Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Plasma Cell Neoplasm/Multiple Myeloma, Pleuropulmonary Blastoma, Primary Peritoneal Cancer, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Sarcoma, Osteosarcoma (Bone Cancer), Rhabdomyosarcoma, Soft Tissue, Uterine, Sezary Syndrome, Skin Cancer, Melanoma, Merkel Cell Carcinoma, Non-melanoma Cancer, Small Intestine Cancer, Soft Tissue Sarcoma, Squamous Cell Carcinoma, Squamous Neck Cancer with Occult Primary, Stomach (Gastric) Cancer, Testicular Cancer, Throat Cancer, Thymoma and Thymic Carcinoma, Thyroid Cancer, Transitional Cell Cancer of the Renal Pelvis and Ureter, Ureter and Renal Pelvis, Transitional Cell Cancer, Urethral Cancer, Uterine Cancer, Endometrial cancer, Uterine Sarcoma, Vaginal Cancer, Vulvar Cancer, Wilms Tumor. Metastases of the aforementioned cancers can also be treated or prevented in accordance with the methods described herein.

Methods for treating any of the diseases or conditions described herein in a mammal in need of such treatment, involves administration of pharmaceutical compositions that include at least one compound described herein or a pharmaceutically acceptable salt, solvate, tautomer, or N-oxide thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound described herein, or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt thereof, are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

In any case, regardless of the disease, disorder or condition being treated, the overall benefit experienced by the patient may be additive of the two therapeutic agents or the patient may experience a synergistic benefit.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

The compounds described herein, or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

Combination Therapy

Also contemplated herein are combination therapies, for example, co-administering a disclosed compound and an additional active agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration is accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent is effected by any appropriate route including, but not limited to, oral routes, intravenous routes, intramuscular routes, and direct absorption through mucous membrane tissues. The therapeutic agents are administered by the same route or by different routes. For example, a first therapeutic agent of the combination selected is administered by intravenous injection while the other therapeutic agents of the combination are administered orally. Alternatively, for example, all therapeutic agents are administered orally or all therapeutic agents are administered by intravenous injection.

Combination therapy also embraces the administration of the therapeutic agents as described above in further combination with other biologically active ingredients and non-drug therapies. Where the combination therapy further comprises a non-drug treatment, the non-drug treatment is conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination are administered to a patient simultaneously or sequentially. It will be appreciated that the components are present in the same pharmaceutically acceptable carrier and, therefore, are administered simultaneously. Alternatively, the active ingredients are present in separate pharmaceutical carriers, such as, conventional oral dosage forms, that are administered either simultaneously or sequentially.

In some embodiments, a compound described herein, or a pharmaceutically acceptable salt, solvate, tautomer or N-oxide thereof, is administered in combination with a BRAF inhibitor. In some embodiments, a compound described herein, or a pharmaceutically acceptable salt thereof, is administered in combination with a MEK inhibitor. In some embodiments, a compound described herein, or a pharmaceutically acceptable salt thereof, is administered in combination with a BRAF inhibitor and a MEK inhibitor.

BRAF Inhibitors

In some embodiments, a compound described herein, or a pharmaceutically acceptable salt, solvate, tautomer or N-oxide thereof, is administered in combination with a BRAF inhibitor selected from GDC-0879, PLX-4720, sorafenib, dabrafenib (GSK2118436), encorafenib (LGX818), SB590885, RAF265 (CHIR-265), TAK-632, CEP-32496, vemurafenib (PLX4032, RG7204), and AZ628. In some embodiments, a compound described herein, or a pharmaceutically acceptable salt, solvate, tautomer or N-oxide thereof, is administered in combination with PLX-4720. In some embodiments, a compound described herein, or a pharmaceutically acceptable salt, solvate, tautomer or N-oxide thereof, is administered in combination with sorafenib. In some embodiments, a compound described herein, or a pharmaceutically acceptable salt, solvate, tautomer or N-oxide thereof, is administered in combination with dabrafenib. In some embodiments, a compound described herein, or a pharmaceutically acceptable salt, solvate, tautomer or N-oxide thereof, is administered in combination with encorafenib. In some embodiments, a compound described herein, or a pharmaceutically acceptable salt, solvate, tautomer or N-oxide thereof, is administered in combination with vemurafenib.

MEK Inhibitors

In some embodiments, a compound described herein, or a pharmaceutically acceptable salt, solvate, tautomer or N-oxide thereof, is administered in combination with a MEK inhibitor selected from selumetinib (AZD6244), PD0325901, trametinib (GSK1120212), U0126-EtOH, PD184352 (CI-1040), GDC-0623, BI-847325, cobimetinib (GDC-0973, RG7420), PD98059, BIX 02189, binimetinib (MEK162, ARRY-162, ARRY-438162), pimasertib (AS-703026), SL-327, BIX 02188, AZD8330, TAK-733, Honokiol, PD318088, and refametinib (RDEA119, Bay 86-9766). In some embodiments, a compound described herein, or a pharmaceutically acceptable salt, solvate, tautomer or N-oxide thereof, is administered in combination with selumetinib. In some embodiments, a compound described herein, or a pharmaceutically acceptable salt, solvate, tautomer or N-oxide thereof, is administered in combination with trametinib. In some embodiments, a compound described herein, or a pharmaceutically acceptable salt, solvate, tautomer or N-oxide thereof, is administered in combination cobimetinib. In some embodiments, a compound described herein, or a pharmaceutically acceptable salt, solvate, tautomer or N-oxide thereof, is administered in combination with binimetinib. In some embodiments, a compound described herein, or a pharmaceutically acceptable salt, solvate, tautomer or N-oxide thereof, is administered in combination with pimasertib. In some embodiments, a compound described herein, or a pharmaceutically acceptable salt, solvate, tautomer or N-oxide thereof, is administered in combination with refametinib. In some embodiments, a compound described herein, or a pharmaceutically acceptable salt, solvate, tautomer or N-oxide thereof, is administered in combination with PD0325901.

Additional Anti-Cancer Agent

In some embodiments, compounds described herein, or a pharmaceutically acceptable salt, solvate, tautomer, or N-oxide thereof, are administered in combination an additional anti-cancer agent. In some embodiments, the additional anti-cancer agent is chemotherapy, hormone blocking therapy, radiation therapy, monoclonal antibodies, or combinations thereof. In one aspect, compounds described herein, or a pharmaceutically acceptable salt, solvate, tautomer, or N-oxide thereof, are administered or formulated in combination with one or more anti-cancer agents.

1. Chemotherapy

In some embodiments, compounds described herein, or a pharmaceutically acceptable salt, solvate, tautomer, or N-oxide thereof, are administered with chemotherapy. Chemotherapy is the treatment of cancer with drugs that can destroy cancer cells. "Chemotherapy" usually refers to cytotoxic drugs which affect rapidly dividing cells in general, in contrast with targeted therapy. Chemotherapy drugs interfere with cell division in various possible ways, e.g., with the duplication of DNA or the separation of newly formed chromosomes. Most forms of chemotherapy target all rapidly dividing cells and are not specific for cancer cells, although some degree of specificity may come from the inability of many cancer cells to repair DNA damage, while normal cells generally can.

Examples of chemotherapeutic agents used in cancer therapy include, for example, antimetabolites (e.g., folic acid, purine, and pyrimidine derivatives) and alkylating agents (e.g., nitrogen mustards, nitrosoureas, platinum, alkyl sulfonates, hydrazines, triazenes, aziridines, spindle poison, cytotoxic agents, toposimerase inhibitors and others). Exemplary agents include Aclarubicin, Actinomycin, Alitretinon, Altretamine, Aminopterin, Aminolevulinic acid, Amrubicin, Amsacrine, Anagrelide, Arsenic trioxide, Asparaginase. Atrasentan, Belotecan, Bexarotene, endamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Ibrutinib, Idarubicin, Ifosfamide, Irinotecan, Irofulven, Ixabepilone, Larotaxel, Leucovorin, Liposomal doxorubicin, Liposomal daunorubicin. Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Strataplatin, Streptozocin, Talaporfin, Tegafur-uracil, Temoporfin, Temozolomide, Teniposide, Tesetaxel, Testolactone, Tetranitrate, Thiotepa, Tiazofurine, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein. Because some drugs work better together than alone, two or more drugs are often given at the same time. Often, two or more chemotherapy agents are used as combination chemotherapy.

2. Targeted Therapy

In some embodiments, compounds described herein, or a pharmaceutically acceptable salt, solvate, tautomer, or N-oxide thereof, are administered with a targeted therapy. Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as axitinib, bosutinib, cediranib, desatinib, erolotinib, imatinib, gefitinib, lapatinib, lestaurtinib, nilotinib, semaxanib, sorafenib, sunitinib, and vandetanib, and also cyclin-dependent kinase inhibitors such as alvocidib and seliciclib. In some embodiments, the targeted therapy is an IDH1 inhibitor (for example, AGI-5198, AG-120 and AG-881), a Non-Small Cell Lung Cancer SOC agents, an androgen receptor antagonist (for example, bicalutamide, flutamide, nitulamide, apalutamide, enzalutamide, abiraterone acetate, ODM-201, or 4-((1R,2R)-2-Hydroxycyclohexyl)-2(trifluoromethyl)benzonitrile (PF 998425)), or an estrogen receptor antagonist (for example, 7a,17β-[9-[(4,4,5,5,5-pentafluoropentyl)sulfinyl]nonyl]estra-1,3,5(10)-triene-3,17-diol (ICI 182,780), 1,3-Bis(4-hydroxyphenyl)-4-methyl-5-[4-(2-piperidinylethoxy)phenol]-1H-pyrazole dihydrochloride (MPP dihydrochloride), 4-[2-phenyl-5,7-bis(trifluoromethyl)pyrazolo[1,5-a]pyrimidin-3-yl]phenol (PHTPP), 3-[4-(2,4-Bis-trifluoromethylbenzyloxy)-3-methoxyphenyl]-2-cyano-N-(5-trifluoromethyl-1,3,4-thiadiazol-2-yl)acrylamide (XCT 790), or 2-(4-hydroxyphenyl)-3-methyl-1-[10-(pentylsulfonyl)decyl]-1H-indol-5-ol (ZK 164015)). Monoclonal antibody therapy is another strategy in which the therapeutic agent is an antibody which specifically binds to a protein on the surface of the cancer cells. Examples include the anti-HER2/neu antibody trastuzumab typically used in breast cancer, and the anti-CD20 antibody rituximab and tositumomab typically used in a variety of B-cell malignancies. Other exemplary antibodies include ctuximab, panitumumab, trastuzumab, alemtuzumab, bevacizumab, edrecolomab, and gemtuzumab. Exemplary fusion proteins include aflibercept and denileukin diftitox.

Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decays in the vicinity of the cell.

3. Immunotherapy

In some embodiments, compounds described herein, or a pharmaceutically acceptable salt, solvate, tautomer, or N-oxide thereof, are administered with an immunotherapy. Cancer immunotherapy refers to a diverse set of therapeutic strategies designed to induce the patient's own immune system to fight the tumor. Contemporary methods for generating an immune response against tumors include intravesicular BCG immunotherapy for superficial bladder cancer, and use of interferons and other cytokines to induce an immune response in renal cell carcinoma and melanoma patients.

Allogeneic hematopoietic stem cell transplantation can be considered a form of immunotherapy, since the donor's immune cells will often attack the tumor in a graft-versus-tumor effect.

4. Hormonal Therapy

In some embodiments, compounds described herein, or a pharmaceutically acceptable salt, solvate, tautomer, or N-oxide thereof, are administered with a hormonal therapy. The growth of some cancers can be inhibited by providing or blocking certain hormones. Common examples of hormone-sensitive tumors include certain types of breast and prostate cancers. Removing or blocking estrogen or testosterone is often an important additional treatment. In certain cancers, administration of hormone agonists, such as progestogens may be therapeutically beneficial.

Examples

The following examples are provided for illustrative purposes only and not to limit the scope of the claims provided herein.

Example 1: 3-(3-1H-Benzoimidazol-2-yl-acryloyl)-6-chloro-4-(4-trifluoromethyl-phenyl)-1H-quinolin-2-one

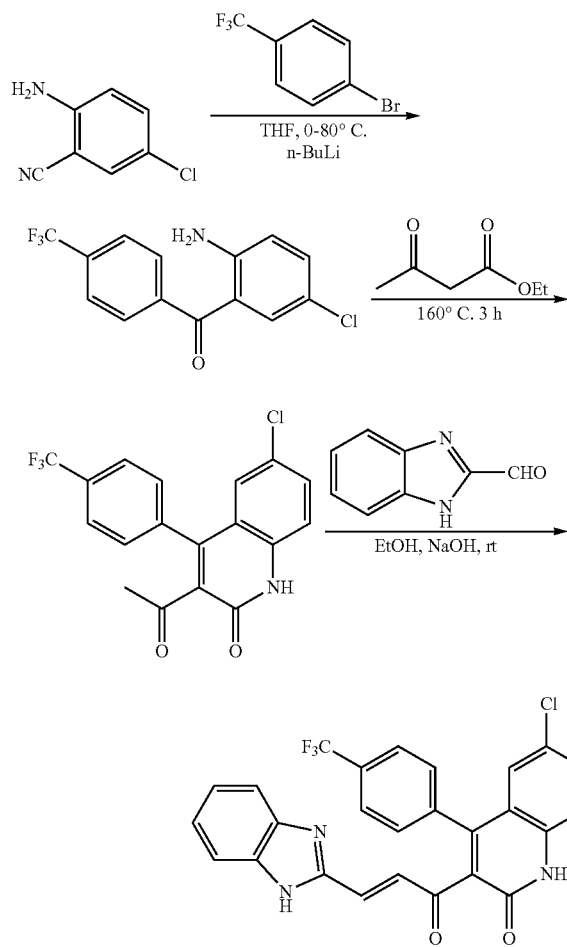

Step 1:
To a solution of 1-bromo-4-trifluoromethyl-benzene (5.0 g, 22.2 mmol) in anhydrous THF (30 mL) was added n-BuLi (8.90 mL, 22.2 mmoL, 2.5 M in hexanes) dropwise at −78° C. After stirring for 10 minutes at 0° C., 2-amino-5-chloro-benzonitrile (0.680 g, 4.50 mmoL) in anhydrous THF (5 mL) was added dropwise. The mixture was stirred for 30 minutes at room temperature, then quenched with water (100 mL). The pH value was adjusted to 8 with 2 M HCl and the mixture was extracted with DCM (100 mL×2). The extracts were washed with brine (50 mL), dried over $Na_2SO_4$ and concentrated to dryness. The residue was purified by silica gel column (PE/EtOAc=10/1) to give (2-amino-5-chloro-phenyl)-(4-trifluoromethyl-phenyl)-methanone (400 mg, yield: 32%) as brown solid.

Step 2:
The mixture of (2-amino-5-chloro-phenyl)-(4-trifluoromethyl-phenyl)-methanone (400 mg, 1.33 mmol) and 3-oxo-butyric acid ethyl ester (173 mg, 1.33 mmol) was heated to 160° C. with stirring for 1 h. After cooled to room temperature, the mixture was filtered. The filtrate cake was recrystallized from EtOH to afford 3-acetyl-6-chloro-4-(4-trifluoromethyl-phenyl)-1H-quinolin-2-one (350 mg, yield: 72%) as yellow solid.

Step 3:
The mixture of 3-acetyl-6-chloro-4-(4-trifluoromethyl-phenyl)-1H-quinolin-2-one (60.0 mg, 0.160 mmol), 1H-benzoimidazole-2-carbaldehyde (28.0 mg, 0.190 mmol) and NaOH (8.0 mg, 0.190 mmol) in EtOH (3 mL) was stirred at 40° C. for 1 hr. After cooled to room temperature, the mixture was diluted with water (2 mL), and the pH value was adjusted to 8 with 1 M HCl. The precipitate was filtered to afford yellow solid, which was dissolved in DMSO and purified by pre-HPLC to afford 3-(3-1H-benzoimidazol-2-yl-acryloyl)-6-chloro-4-(4-trifluoromethyl-phenyl)-1H-quinolin-2-one (29 mg, yield: 37%) as yellow solid.

$^1$HNMR (300 MHz, DMSO-d6): δ=12.88 (s, 1H), 12.55 (s, 1H), 7.86 (d, J=7.5 Hz, 2H), 7.72-7.64 (m, 2H), 7.59-7.40 (m, 5H), 7.28-7.22 (m, 2H), 7.13 (d, J=16.5 Hz, 1H), 6.95 (s, 1H). MS: m/z 494.1 (M+H$^+$).

Example 2: 3-(3-1H-Benzoimidazol-2-yl-acryloyl)-6-chloro-4-(4-trifluoromethoxy-phenyl)-1H-quinolin-2-one

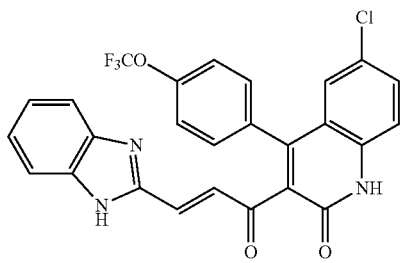

This compound was prepared as described in Example 1.
$^1$HNMR (300 MHz, DMSO-d6): δ=12.88 (s, 1H), 12.52 (s, 1H), 7.72-7.51 (m, 8H), 7.38 (d, J=16.5 Hz, 1H), 7.30-7.25 (m, 2H), 7.09 (d, J=16.5 Hz, 1H), 6.98 (d, J=2.4 Hz, 1H). MS: m/z 510.0 (M+H$^+$).

Example 3: 3-(3-1H-Benzoimidazol-2-yl-acryloyl)-6-chloro-4-(4-methoxy-phenyl)-1H-quinolin-2-one

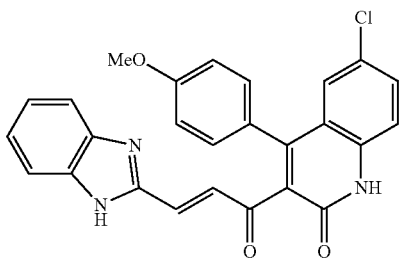

This compound was prepared as described in Example 1.
$^1$H NMR (300 MHz, DMSO-d6): δ=12.88 (s, 1H), 12.43 (s, 1H), 7.69-7.64 (m, 2H), 7.54-7.46 (m, 2H), 7.37-7.24 (m, 5H), 7.10-7.00 (m, 4H), 3.76 (s, 3H). MS: m/z 456.1 (M+H$^+$).

Example 4: 3-(3-1H-Benzoimidazol-2-yl-acryloyl)-6-chloro-4-p-tolyl-1H-quinolin-2-one

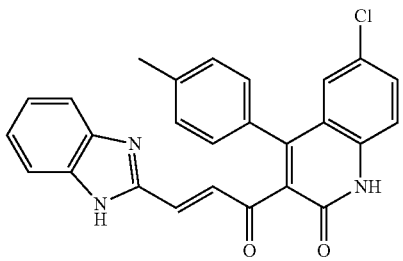 [SMILES: Cc1ccc(-c2c(C(=O)/C=C/c3nc4ccccc4[nH]3)c(=O)[nH]c3ccc(Cl)cc23)cc1]

This compound was prepared as described in Example 1.
$^1$H NMR (300 MHz, CDCl3): δ=12.88 (s, 1H), 12.43 (s, 1H), 7.65-7.54 (m, 3H), 7.47-6.80 (m, 10H), 2.63 (s, 3H). MS: m/z 440. 1 (M+H$^+$).

Example 5: 3-(3-1H-Benzoimidazol-2-yl-acryloyl)-6-chloro-4-(4-chloro-phenyl)-1H-quinolin-2-one

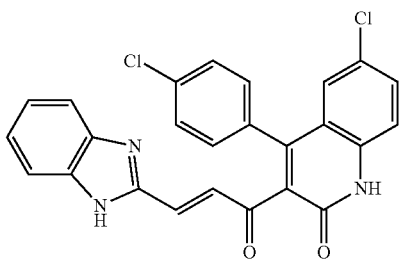

This compound was prepared as described in Example 1.
1HNMR (400 MHz, DMSO-d6): δ=12.88 (s, 1H), 12.50 (s, 1H), 7.68 (dd, J=8.8, 2.0 Hz, 2H), 7.56-7.48 (m, 4H), 7.41-7.36 (m, 2H), 7.28-7.24 (m, 3H), 7.12-7.08 (d, J=1.6 Hz, 1H), 7.01 (s, 1H). MS: m/z 460.0 (M+H$^+$).

Example 6: 3-(3-1H-Benzoimidazol-2-yl-acryloyl)-6-chloro-4-pyridin-3-yl-1H-quinolin-2-one

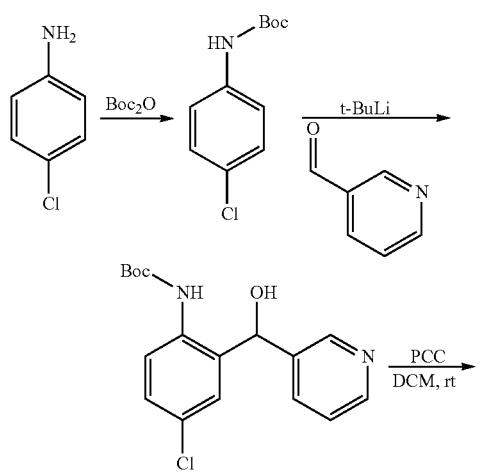

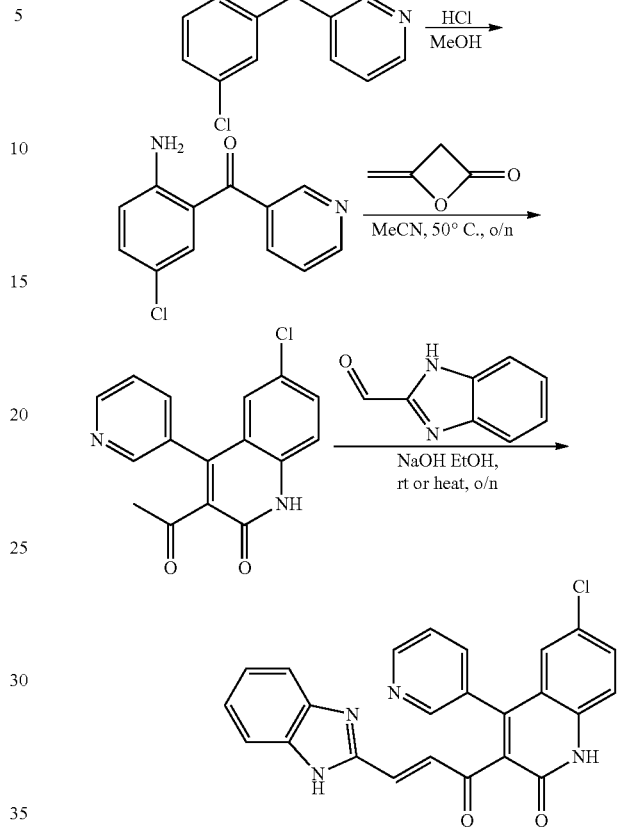

Step 1:
The solution of 4-chloro-phenylamine (12.0 g, 94.1 mmol), Boc$_2$O (30.5 g, 141 mmol) in toluene (100 mL) was stirred at reflux overnight. After cooled to room temperature, the solution was concentrated to dryness in vacuum. The residue was purified by silica gel column (PE) to afford (4-chloro-phenyl)-carbamic acid tert-butyl ester (21.0 g, yield: 48%) as white solid.
$^1$H NMR (400 MHz, DMSO-d6): δ=7.29 (d, J=8.8 Hz, 2H), 7.22 (d, J=8.4 Hz, 2H), 6.47 (s, 1H), 1.51 (9H, s).

Step 2:
To a solution of (4-chloro-phenyl)-carbamic acid tert-butyl ester (3.0 g, 13.2 mmol) in THF (40 mL) was added dropwise n-BuLi (21.9 mL, 1.5 M in pentanes) at −78° C. under N$_2$. After half an hour, pyridine-3-carbaldehyde (1.50 g, 14.5 mmol) in THF (10 mL) was added to the mixture dropwise at this temperature. The mixture was warmed to room temperature and stirred overnight. The mixture was quenched with aqueous NH$_4$Cl (50 mL) and extracted with EA (50 mL×3). The organic layers were concentrated an purified by silica gel column (PE/EA=5/1) to afford [4-chloro-2-(hydroxy-pyridin-3-yl-methyl)-phenyl]-carbamic acid tert-butyl ester (1.10 g, yield: 25%) as yellow solid. $^1$HNMR (400 MHz, DMSO-d6): δ=8.54 (s, 1H), 8.46 (d, J=4.0 Hz, 1H), 7.43 (d, J=8.4 Hz, 1H), 7.65-7.58 (m, 2H), 7.29-7.25 (m, 2H), 7.06 (d, J=2.4 Hz, 1H), 5.89 (s, 1H), 4.11 (brs, 1H), 1.43 (s, 9H).

Step 3:
To a stirred solution of [4-chloro-2-(hydroxy-pyridin-3-yl-methyl)-phenyl]-carbamic acid tert-butyl ester (750 mg, 2.25 mmol) in DCM (10 mL) was added PCC (579 mg, 2.70 mmol). The mixture was stirred at room temperature overnight followed by filtration. The filtrate was concentrated to dryness in vacuum and the residue was purified by silica gel column (PE/EA=5/1) to afford [4-chloro-2-(pyridine-3-carbonyl)-phenyl]-carbamic acid tert-butyl ester (1.20 g, yield: 70%) as a yellow solid.

Step 4:

The solution of [4-chloro-2-(pyridine-3-carbonyl)-phenyl]-carbamic acid tert-butyl ester. (1.20 g, 3.61 mmol) in HCl/methanol (4 M, 20 mL) was stirred at room temperature for 2 hrs. After removal of the solvent, the residue was diluted with EA (20 mL). The pH value was adjusted to 8 with aqueous $K_2CO_3$. The organic layer was washed with brine, dried over anhydrous $Na_2SO_4$, filtered. The filtrate was concentrated in vacuum to afford (2-amino-5-chloro-phenyl)-pyridin-3-yl-methanone (690 mg, yield: 82%) as a yellow solid.

Step 5:

The solution of (2-amino-5-chloro-phenyl)-pyridin-3-yl-methanone (300 mg, 1.29 mmol) and diketene (168 mg, 1.29 mmol) in acronitrile (2 mL) was stirred at 50° C. overnight. The reaction was cooled to room temperature, filtered to afford 3-acetyl-6-chloro-4-pyridin-3-yl-1H-quinolin-2-one (250 mg, yield: 65%) as yellow solid. $^1$HNMR (400 MHz, DMSO-d6): δ=12.48 (s, 1H), 8.70 (dd, J=4.8, 1.6 Hz, 1H), 8.54 (d, J=1.6 Hz, 1H), 7.85-7.82 (m, 1H), 7.67 (dd, J=8.4 Hz, 2.0 Hz, 1H), 7.56 (dd, J=7.2 Hz, 4.4 Hz, 1H), 7.45 (d, J=8.8 Hz, 1H), 6.92 (d, J=2.4 Hz, 1H), 2.30 (s, 3H).

Step 6:

The procedure is similar to Example 1. $^1$HNMR (300 MHz, DMSO-$d_6$): δ=12.70 (s, 1H), 12.56 (s, 1H), 8.66-8.64 (m, 1H), 8.53 (s, 1H), 7.83 (d, J=6.3 Hz, 1H), 7.73-7.64 (m, 2H), 7.54-7.50 (m, 3H), 7.41 (s, 1H), 7.28-7.22 (m, 3H), 6.99 (s, 1H). MS: m/z=427.0 (M+H$^+$)

Example 7: 6-Chloro-3-(3-phenyl-acryloyl)-4-pyridin-3-yl-1H-quinolin-2-one

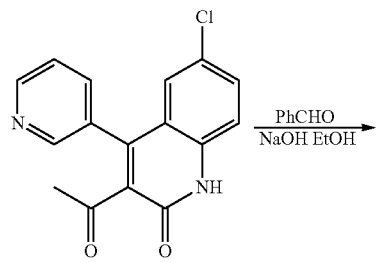

This compound was prepared as described in Example 6. $^1$HNMR (300 MHz, DMSO-d6): δ=12.44 (s, 1H), 8.63 (d, J=4.8 Hz, 1H), 8.52 (s, 1H), 7.93 (s, 1H), 7.81 (d, J=6.3 Hz, 1H), 7.70-7.67 (m, 2H), 7.51-7.47 (m, 3H), 7.42-7.39 (m, 3H), 6.96 (s, 1H), 6.84-6.78 (m, 1H). MS: m/z 387.0 (M+H$^+$)

Example 8: 3-(3-1H-Benzoimidazol-2-yl-acryloyl)-6-chloro-4-pyridin-2-yl-1H-quinolin-2-one

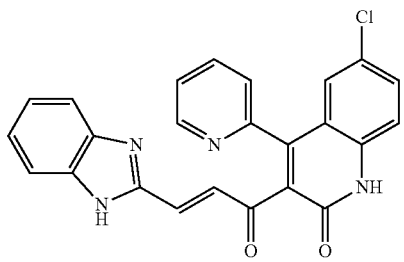

This compound was prepared as described in Example 6. $^1$HNMR (300 MHz, DMSO-d6): δ=8.66 (d, J=3.9 Hz, 1H), 7.96-7.90 (m, 1H), 7.69-7.43 (m, 6H), 7.33-7.12 (m, 5H). MS: m/z 427.0 (M+H$^+$).

Example 9: 3-(3-1H-Benzoimidazol-2-yl-acryloyl)-6-chloro-4-thiophen-2-yl-1H-quinolin-2-one

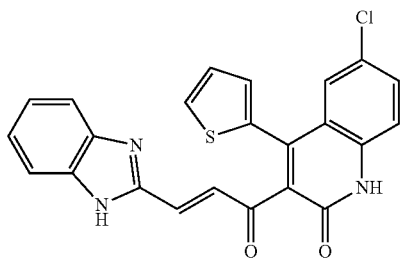 [SMILES: O=C(/C=C/c1nc2ccccc2[nH]1)c1c(-c2cccs2)c2cc(Cl)ccc2[nH]c1=O]

This compound was prepared as described in Example 6. $^1$HNMR (300 MHz, DMSO-d6): δ=12.51 (s, 1H), 7.78 (d, J=2.4 Hz, 1H), 7.70 (d, J=2.4 Hz, 1H), 7.62-7.59 (m, 2H), 7.49 (d, J=8.7 Hz, 1H), 7.38 (d, J=6.0 Hz, 2H), 7.29-7.21 (m, 2H), 7.20-7.17 (m, 2H), 7.12-7.07 (m, 1H). MS: m/z 432.0 (M+H$^+$)

Example 10: 3-(3-1H-Benzoimidazol-2-yl-acryloyl)-6-chloro-4-thiophen-2-yl-1H-quinolin-2-one

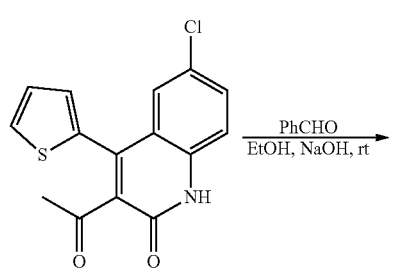

-continued

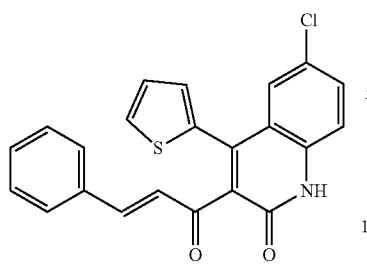

This compound was prepared as described in Example 6.
1HNMR (400 MHz, DMSO-d6): δ=12.38 (s, 1H), 7.75-7.47 (m, 1H), 7.74-7.66 (m, 3H), 7.47 (m, 2H), 7.41-7.38 (m, 3H), 7.33 (d, J=2.4 Hz, 1H), 7.12-7.14 (m, 2H), 6.80 (d, J=16.4 Hz, 1H). MS: m/z 392.0 (M+H$^+$)

Example 11: (E)-3-(3-(1H-benzo[d]imidazol-2-yl)acryloyl)-6-chloro-4-cyclohexylquinolin-2(1H)-one

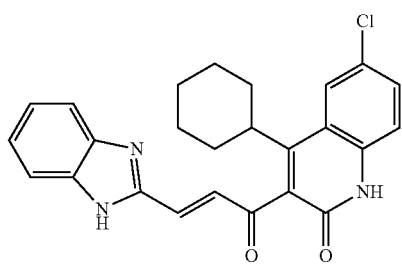 [SMILES: O=C(/C=C/c1nc2ccccc2[nH]1)c1c(C2CCCCC2)c2cc(Cl)ccc2[nH]c1=O]

This compound was prepared as described in Example 6.
$^1$HNMR (300 MHz, DMSO-d6): δ=12.26 (s, 1H), 8.04 (s, 1H), 7.67-7.61 (m, 4H), 7.42 (d, J=9.0 Hz, 1H), 7.35-7.33 (s, 2H), 7.28-7.27 (m, 2H), 2.52-2.48 (m, 1H), 1.76-1.62 (m, 10H). MS: m/z 432.1 (M+H$^+$).

Example 12: 6-chloro-3-cinnamoyl-4-cyclohexylquinolin-2(1H)-one

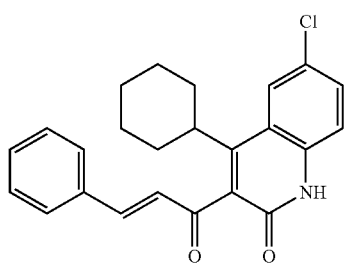 [SMILES: O=C(/C=C/c1ccccc1)c1c(C2CCCCC2)c2cc(Cl)ccc2[nH]c1=O]

This compound was prepared as described in Example 6.
$^1$HNMR (300 MHz, DMSO-d6): δ=12.14 (s, 1H), 8.01 (s, 1H), 7.78-7.70 (m, 2H), 7.64-7.60 (m, 1H), 7.52-7.36 (s, 5H), 7.07 (d, J=16.2 Hz, 1H), 2.52-2.48 (m, 1H), 1.76-1.62 (m, 10H). MS: m/z 392.0 (M+H$^+$).

Example 13: 3-(3-1H-Benzoimidazol-2-yl-acryloyl)-6-nitro-4-phenyl-1H-quinolin-2-one

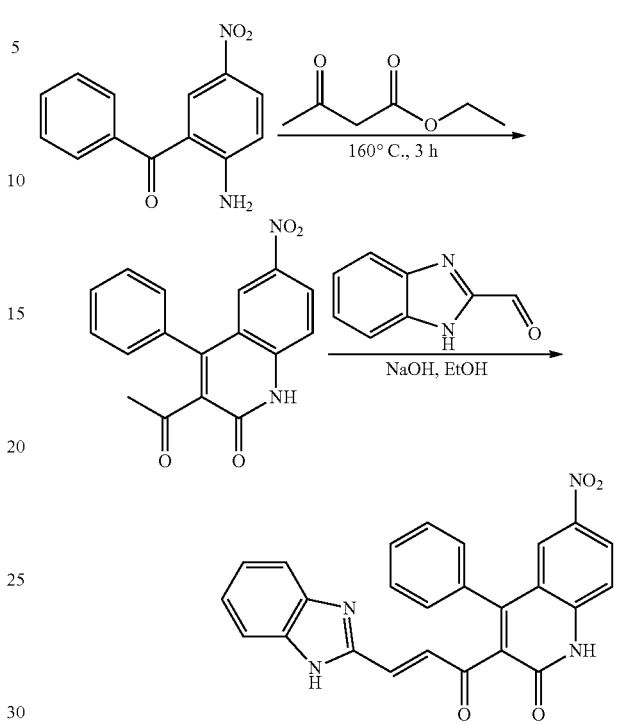

Step 1:
The solution of (2-amino-5-nitro-phenyl)-phenyl-methanone (500 mg, 4.33 mmol) and 3-oxo-butyric acid ethyl ester (0.261 mL) was stirred at 160° C. for 3 hrs. After cooled to room temperature, the reaction was filtered to give 3-acetyl-6-nitro-4-phenyl-1H-quinolin-2-one (300 mg, yield: 47%) as yellow solid.
Step 2:
The mixture of NaOH (15.6 mg, 0.390 mmol), 3-acetyl-6-nitro-4-phenyl-1H-quinolin-2-one (100 mg, 0.325 mmol), 1H-benzoimidazole-2-carbaldehyde (52.1 mg, 0.357 mmol) in ethanol (1 mL) was stirred at room temperature overnight. The reaction was diluted with DCM (10 mL) and washed with water (10 mL). The organic layer was evaporated to dryness and the residue was purified by pre-HPLC to afford 3-(3-1H-benzoimidazol-2-yl-acryloyl)-6-nitro-4-phenyl-1H-quinolin-2-one (36 mg, yield: 26%) as yellow solid.
$^1$HNMR (400 MHz, DMSO-d6): δ=12.88 (s, 1H), 8.45 (dd, J=9.2, 2.4 Hz, 1H), 7.93 (d, J=2.4 Hz, 1H), 7.64 (m, 2H), 7.53-7.49 (m, 5H), 7.39-7.37 (m, 3H), 7.27-7.22 (m, 2H), 7.06 (d, J=16.4 Hz, 1H). MS: m/z 437.1 (M+H$^+$).

Example 14: 6-Amino-3-(3-1H-benzoimidazol-2-yl-propionyl)-4-phenyl-1H-quinolin-2-one

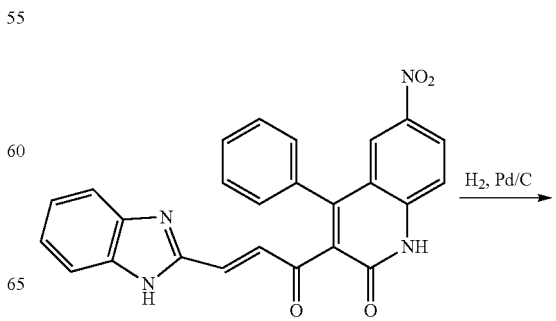

155
-continued

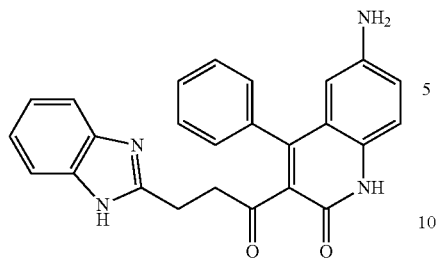

The mixture of 3-(3-1H-benzoimidazol-2-yl-acryloyl)-6-nitro-4-phenyl-1H-quinolin-2-one (20.0 mg, 0.0491 mmol), Pd/C (2.0 mg, 10%, wet) in methanol (2 mL) was stirred at room temperature under $H_2$ balloon overnight. The mixture was filtered through celite pad. The filtrate was evaporated in vacuum to afford 6-amino-3-(3-1H-benzoimidazol-2-yl-propionyl)-4-phenyl-1H-quinolin-2-one (8.0 mg, yield: 44%) as yellow solid.

$^1$HNMR (400 MHz, DMSO-d6+CD$_3$OD): δ=7.44-7.40 (m, 2H), 7.38-7.35 (m, 3H), 7.25-7.22 (m, 2H), 7.18 (d, J=8.8 Hz, 1H), 7.12-7.09 (m, 2H), 6.94 (d, J=2.8 Hz, 1H), 6.23 (s, 1H), 3.15 (t, J=7.6 Hz, 2H), 2.87 (t, J=7.6 Hz, 2H). MS: m/z 409.1 (M+H$^+$).

Example 15: 6-Amino-3-(3-1H-benzoimidazol-2-yl-acryloyl)-4-phenyl-1H-quinolin-2-one

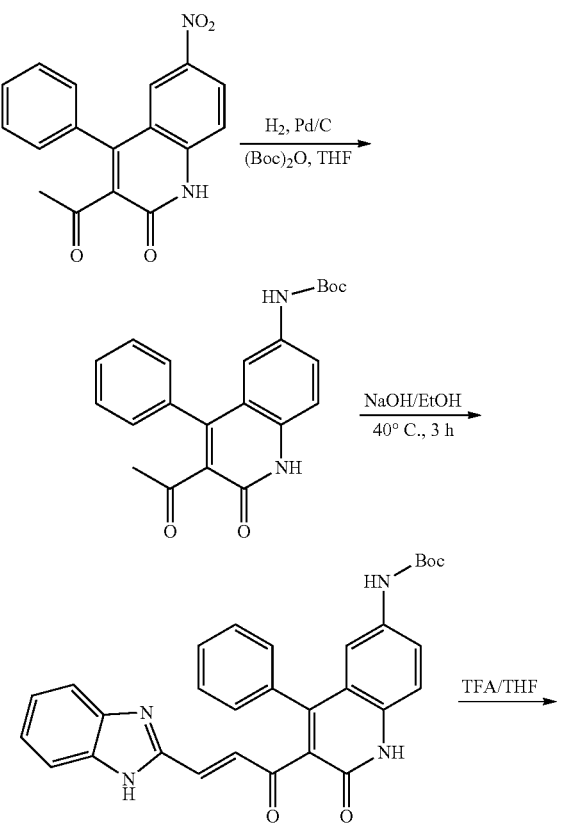

156
-continued

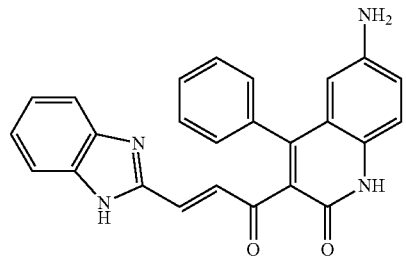

Step 1:

The mixture of 3-acetyl-6-nitro-4-phenyl-1H-quinolin-2-one (450 mg, 0.461 mmol), Pd/C (45.0 mg, 10%, wet) and (Boc)$_2$O (631 mg, 2.92 mmol) in THF (20 mL) was stirred at room temperature under $H_2$ balloon overnight. The mixture was filtered. The filtrate was evaporated in vacuum to afford 6-amino-3-(3-1H-benzoimidazol-2-yl-acryloyl)-4-phenyl-1H-quinolin-2-one (300 mg, yield: 54%) as a yellow solid.

Step 2:

This step was prepared as described in Example 13.

Step 3:

The mixture of [3-(3-1H-benzoimidazol-2-yl-acryloyl)-2-oxo-4-phenyl-1,2-dihydro-quinolin-6-yl]-carbamic acid tert-butyl ester (60.0 mg, 0.118 mmol) and TFA (5.0 mL) in THF (20 mL) was stirred at room temperature overnight. The reaction solution was concentrated and the residue was diluted with EA (30 mL). The mixture was neutralized with saturated NaHCO$_3$ solution. The organic layer was evaporated to dryness. The residue was purified by pre-HPLC to afford 6-amino-3-(3-1H-benzoimidazol-2-yl-acryloyl)-4-phenyl-1H-quinolin-2-one (10.0 mg, yield: 21%) as yellow solid. $^1$HNMR (400 MHz, DMSO-d$_6$): δ=12.84 (s, 1H), 11.95 (s, 1H), 7.64 (d, J=6.4 Hz, 1H), 7.52 (d, J=8.0 Hz, 1H), 7.45-7.36 (m, 3H), 7.27-7.19 (m, 6H), 7.04 (d, J=16.4 Hz, 1H), 6.94 (dd, J=8.4, 2.4 Hz, 1H), 6.27 (d, J=2.0 Hz, 1H), 5.08 (s, 2H). MS: m/z 407.1 (M+H$^+$).

Example 16: 6-Nitro-4-phenyl-3-(3-phenyl-acryloyl)-1H-quinolin-2-one

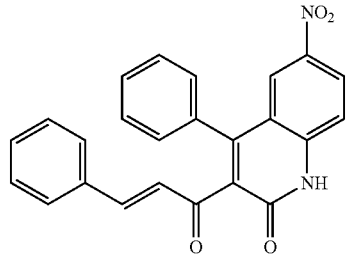 [SMILES: O=C(/C=C/c1ccccc1)c1c(-c2ccccc2)c2cc([N+](=O)[O-])ccc2[nH]c1=O]

This compound was prepared as described in Example 13. $^1$HNMR (400 MHz, DMSO-d6): δ=12.79 (s, 1H), 8.44 (dd, J=8.8, 2.4 Hz, 1H), 7.91 (d, J=2.8 Hz, 1H), 7.65 (dd, J=8.0, 1.6 Hz, 2H), 7.63-7.60 (m, 1H), 7.58-7.54 (m, 1H), 7.50-7.45 (m, 3H), 7.42-7.36 (m, 5H), 6.77 (d, J=16.4 Hz, 1H). MS: m/z 397.1 (M+H$^+$)

Example 17: 3-[3-(4-Dimethylamino-phenyl)-acryloyl]-6-nitro-4-phenyl-1H-quinolin-2-one

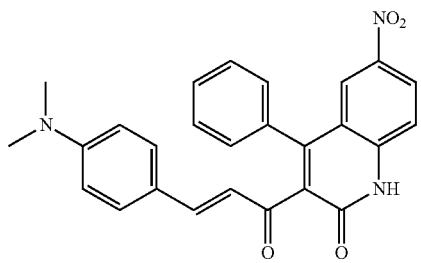 [SMILES: CN(C)c1ccc(/C=C/C(=O)c2c(-c3ccccc3)c3cc([N+](=O)[O-])ccc3[nH]c2=O)cc1]

This compound was prepared as described in Example 13. ¹HNMR (400 MHz, DMSO-d6): δ=12.72 (s, 1H), 8.42 (dd, J=9.2, 2.4 Hz, 1H), 7.89 (d, J=2.8 Hz, 1H), 7.59 (d, J=9.2 Hz, 1H), 7.47-7.45 (m, 5H), 7.36-7.34 (m, 3H), 6.66 (d, J=9.2 Hz, 2H), 6.45 (d, J=16.4 Hz, 1H), 2.97 (s, 6H). MS: m/z 440.1 (M+H⁺).

Example 18: 3-[3-(4-Dimethylamino-phenyl)-acryloyl]-6-nitro-4-phenyl-1H-quinolin-2-one

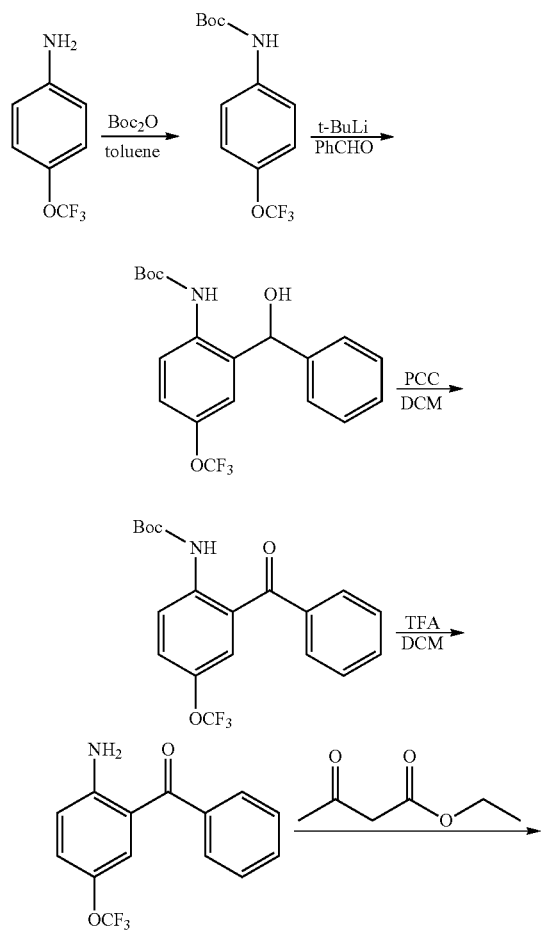

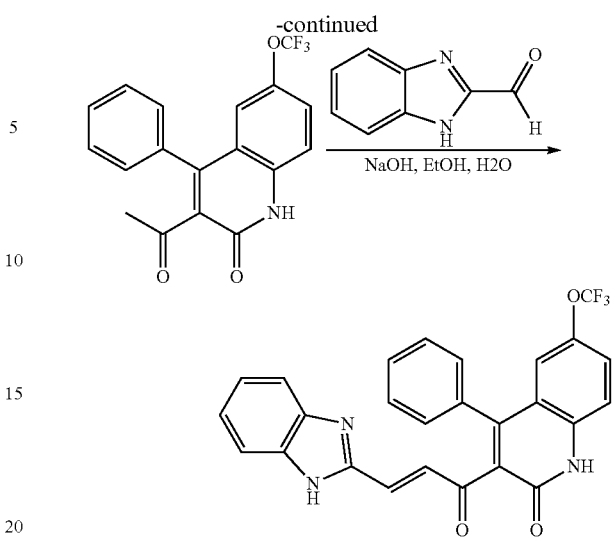

Step 1:

A mixture of 4-trifluoromethoxy-phenylamine (2.0 g, 12.42 mmol) and (Boc)₂ (2.70 g, 12.42 mmol) in toluene (30 mL) was stirred at reflux for 2 hrs. After cooled to room temperature, the solution was concentrated to dryness in vacuum. The residue was purified by silica gel column (PE) to afford (4-trifluoromethoxy-phenyl)-carbamic acid tert-butyl ester (3.0 g, yield: 99%) as a white solid. ¹HNMR (300 MHz, CDCl₃): δ=7.38 (d, J=7.5 Hz, 2H), 7.15 (d, J=7.5 Hz, 2H), 6.53 (brs, 1H), 1.51 (s, 9H). MS: m/z 278.1 (M+H⁺).

Step 2:

To a solution of (4-trifluoromethoxy-phenyl)-carbamic acid tert-butyl ester (3.0 g, 10.87 mmol) in dry THF (30 mL) was added t-BuLi in pentanes (18.0 mL, 1.5 mol/L) dropwise at −78° C. After the addition, the reaction was stirred at −50° C. for 1 hr. Then benzaldehyde (1.15 g, 10.9 mmol) was added at −78° C., and the mixture was stirred at room temperature overnight. The mixture was quenched with chilly saturated NH₄Cl (50 mL) and extracted with EA (50 mL×3). The organic layers were washed with brine (100 mL), dried over anhydrous Na₂SO₄ and concentrated to give crude product, which was purified by silica gel column (PE) to afford [2-(hydroxy-phenyl-methyl)-4-trifluoromethoxy-phenyl]-carbamic acid tert-butyl ester (1.80 g, yield: 44%) as white solid.

Step 3:

To a solution of [2-(hydroxy-phenyl-methyl)-4-trifluoromethoxy-phenyl]-carbamic acid tert-butyl ester (1.80 g, 4.71 mmol) in DCM (30 mL) was added PCC (1.20 g, 5.65 mmol). The mixture was stirred at room temperature for 18 hrs. The reactant was filtered. The filtrate was washed with water, dried over anhydrous Na₂SO₄ and concentrated to give (2-benzoyl-4-trifluoromethoxy-phenyl)-carbamic acid tert-butyl ester (1.70 g, yield: 99%) as a yellow solid. ¹HNMR (300 MHz, CDCl₃): δ=8.95 (brs, 1H), 7.93 (d, J=7.5 Hz, 1H), 7.76 (d, J=7.5 Hz, 1H), 7.68-7.63 (m, 4H), 7.53-7.49 (2H, m), 1.26 (s, 9H).

Step 4:

To a solution of (2-benzoyl-4-trifluoromethoxy-phenyl)-carbamic acid tert-butyl ester (1.70 g, 4.45 mmol) in DCM (20 mL) was added TFA (5.0 mL), and the reaction mixture was stirred at room temperature for 30 mins. The resultant was concentrated directly to remove DCM and TFA and the residue was diluted with DCM. The pH value was adjusted to 7-8 with saturated NaHCO₃. The organic layer was wash with brine, dried over anhydrous Na₂SO₄ and concentrated to give (2-amino-5-trifluoromethoxy-phenyl)-phenyl-methanone (1.10 g, yield: 88%) as a yellow solid.

Step 5:

A mixture of (2-amino-5-trifluoromethoxy-phenyl)-phenyl-methanone (400 mg, 0.45 mmol) and 3-oxo-butyric acid ethyl ester (186 mg, 0.45 mmol) was stirred at 160° C. for 2 hrs. After cooled to room temperature, the resulting solid was washed with PE to give 3-acetyl-4-phenyl-6-trifluoromethoxy-1H-quinolin-2-one (200 mg, yield: 16%) as a yellow solid. $^1$HNMR (400 MHz, CDCl$_3$): δ=7.77 (s, 1H), 7.55-7.53 (m, 5H), 7.33 (d, J=7.5 Hz, 2H), 2.27 (s, 3H).

Step 6:

To a solution of 3-acetyl-4-phenyl-6-trifluoromethoxy-1H-quinolin-2-one (100 mg, 0.30 mmol) in H$_2$O (1 mL) and EtOH (5 mL) was added NaOH (18.0 mg, 0.440 mmol). After stirred at room temperature for 30 mins, 1H-benzoimidazole-2-carbaldehyde (53.0 mg, 0.330 mmol) was added to the mixture and the mixture was stirred at 35° C. overnight. The mixture was concentrated to dryness in vacuum and the residue was diluted with EA (20 mL), washed with with water (10 mL), brine (10 mL) and dried over Na$_2$SO$_4$. The solution was concentrated to dryness and the residue was purified by prep-HPLC to give 3-(3-1H-Benzoimidazol-2-yl-acryloyl)-4-phenyl-6-trifluoromethoxy-1H-quinolin-2-one (30.0 mg, 21%) as a yellow solid. $^1$HNMR (400 MHz, DMSO-d6): δ=12.75 (brs, 2H), 7.65 (dd, J=7.6, 1.6 Hz, 1H), 7.61-7.55 (m, 3H), 7.50-7.42 (m, 3H), 7.38 (d, J=16.4 Hz, 1H), 7.33 (dd, J=7.6, 1.6 Hz, 2H), 7.25-7.21 (m, 2H), 7.04 (d, J=16.4 Hz, 1H), 6.94 (d, J=2.0 Hz, 1H). MS: m/z 476.1 (M+H$^+$).

Example 19: 3-(3-1H-Benzoimidazol-2-yl-acryloyl)-4-phenyl-6-trifluoromethyl-1H-quinolin-2-one

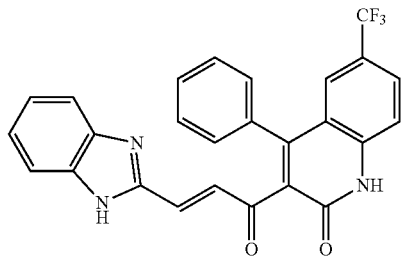 [SMILES: O=C(/C=C/c1nc2ccccc2[nH]1)c1c(-c2ccccc2)c2cc(C(F)(F)F)ccc2[nH]c1=O]

This compound was prepared as described in Example 18. $^1$HNMR (400 MHz, DMSO-d6): δ=12.75 (brs, 2H), 7.66 (dd, J=7.6, 1.6 Hz, 1H), 7.63-7.56 (m, 3H), 7.48-7.32 (m, 7H), 7.22 (d, J=7.5 Hz, 2H), 7.06 (d, J=2.4 Hz, 1H). MS: m/z 460.1 (M+H$^+$).

Example 20: 3-(3-1H-Benzoimidazol-2-yl-acryloyl)-6-fluoro-4-phenyl-1H-quinolin-2-one

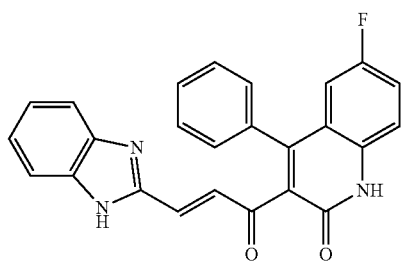 [SMILES: O=C(/C=C/c1nc2ccccc2[nH]1)c1c(-c2ccccc2)c2cc(F)ccc2[nH]c1=O]

This compound was prepared as described in Example 18. $^1$H NMR (400 MHz, DMSO-d6): δ=12.90 (brs, 1H), 12.42 (brs, 1H), 7.65 (d, J=7.2 Hz, 1H), 7.56-7.43 (m, 6H), 7.33-7.20 (m, 5H), 7.06 (d, J=16.4 Hz, 1H), 6.77 (d, J=9.6 Hz, 1H). MS: m/z 410.1 (M+H$^+$).

Example 21: 3-(3-1H-Benzoimidazol-2-yl-acryloyl)-6-methoxy-4-phenyl-1H-quinolin-2-one

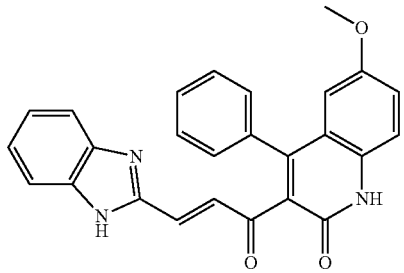 [SMILES: COc1ccc2[nH]c(=O)c(C(=O)/C=C/c3nc4ccccc4[nH]3)c(-c3ccccc3)c2c1]

This compound was prepared as described in Example 18. 1HNMR (300 MHz, DMSO-d6): δ=12.86 (brs, 1H), 12.23 (brs, 1H), 7.65 (d, J=8.1 Hz, 1H), 7.52 (d, J=7.8 Hz, 1H), 7.45-7.42 (m, 4H), 7.33-7.21 (m, 6H), 7.06 (d, J=16.2 Hz, 1H), 6.53 (d, J=2.1 Hz, 1H), 3.61 (s, 3H). MS: m/z 422.1 (M+H$^+$).

Example 22: 3-(3-1H-Benzoimidazol-2-yl-acryloyl)-4-phenyl-1H-[1,7]naphthyridin-2-one

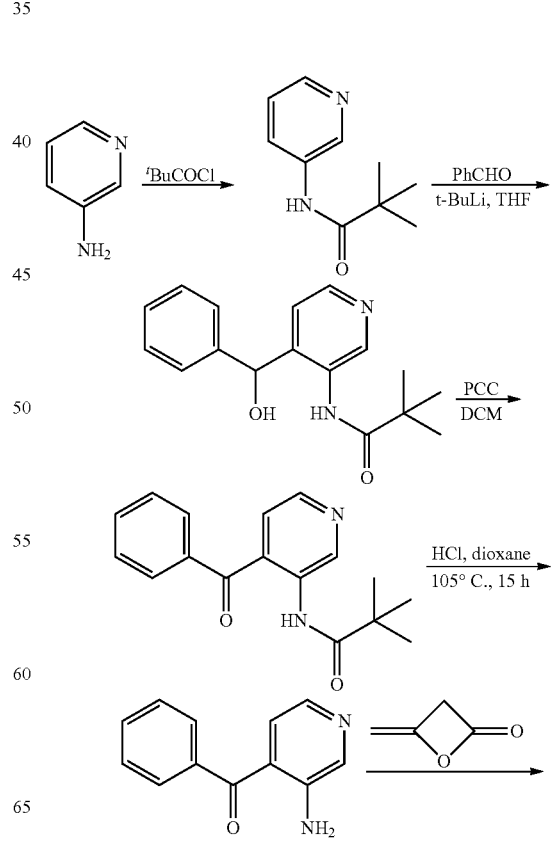

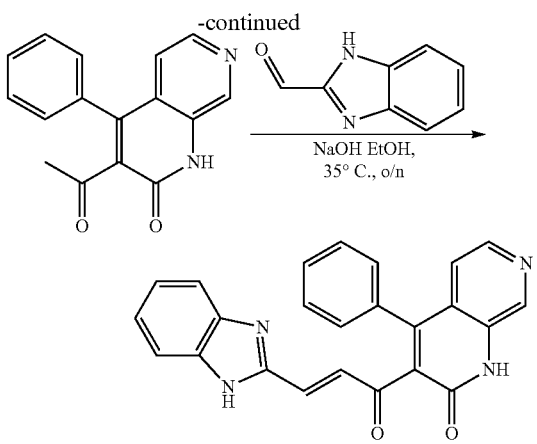

Step 1:

To a solution of pyridin-3-ylamine (4.0 g, 42.0 mmol) in dry DCM (30 mL) was added 2,2-dimethyl-propionyl chloride (6.12 g, 52.0 mmol) and Et$_3$N (ml) dropwise at 0° C. After the addition, the reaction mixture was stirred at room temperature overnight. The reactant was concentrated to dryness in vacuum. The residue was purified by silica gel column to give 2,2-dimethyl-N-pyridin-3-yl-propionamide (6.0 g, yield: 81%) as a white solid. $^1$HNMR (400 MHz, CDCl$_3$): δ=8.55 (d, J=2.4 Hz, 1H), 8.34 (d, J=5.6 Hz, 1H), 8.19 (d, J=1.2 Hz, 1H), 7.50 (brs, 1H), 7.28-7.24 (m, 1H), 1.33 (s, 9H).

To a solution of (4-trifluoromethoxy-phenyl)-carbamic acid tert-butyl ester (3.0 g, 10.87 mmol) in dry THF (30 mL) was added t-BuLi in pentanes (18.0 mL, 1.5 mol/L) dropwise at −78° C. After the addition, the reaction was stirred at −50° C. for 1 hr. Then benzaldehyde (1.15 g, 10.9 mmol) was added at −78° C., and the mixture was stirred at room temperature overnight. The mixture was quenched with chilly saturated NH$_4$Cl (50 mL) and extracted with EA (50 mL×3). The organic layers were washed with brine (100 mL), dried over anhydrous Na$_2$SO$_4$ and concentrated to give crude product, which was purified by silica gel column (PE) to afford [2-(hydroxy-phenyl-methyl)-4-trifluoromethoxy-phenyl]-carbamic acid tert-butyl ester (1.80 g, yield: 44%) as a white solid.

Step 2:

To a solution of 2,2-dimethyl-N-pyridin-3-yl-propionamide (3.0 g, 17.0 mmol) in dry THF (50 mL) was added t-BuLi in pentanes (28.0 mL, 1.5 M in pentanes) dropwise at −78° C. After the addition, the reaction was stirred at −50° C. for 1 hr. Then benzaldehyde (2.17 g, 20.5 mmol) was added at −78° C. The mixture was allowed to warm to room temperature and stirred overnight. The mixture was quenched with chilly saturated NH$_4$Cl (60 mL) and extracted with EA (60 mL×3). The organic layers were washed with brine (100 mL), dried over anhydrous Na$_2$SO$_4$ and concentrated to give crude product, which was purified by silica gel column (PE) to afford N-[4-(hydroxy-phenyl-methyl)-pyridin-3-yl]-2,2-dimethyl-propionamide (1.60 g, yield: 33%) as a yellow solid. $^1$H NMR (300 MHz, CDCl$_3$): δ=9.34 (s, 1H), 8.73 (brs, 1H), 8.25 (d, J=4.8 Hz, 1H), 7.36-7.28 (m, 5H), 7.05 (d, J=5.2 Hz, 1H), 5.89 (s, 1H), 1.31 (s, 9H).

Step 3:

To a solution of N-[4-(hydroxy-phenyl-methyl)-pyridin-3-yl]-2,2-dimethyl-propionamide (1.40 g, 4.90 mmol) in DCM (20 mL) was added PCC (1.20 g, 5.65 mmol). The mixture was stirred at room temperature for 18 hrs. The reactant was filtered. The filtrate was washed with water, dried over anhydrous Na$_2$SO$_4$ and concentrated to give N-(4-benzoyl-pyridin-3-yl)-2,2-dimethyl-propionamide (500 mg, yield: 36%) of as yellow oil. $^1$HNMR (300 MHz, DMSO-d$_6$): δ=9.70 (brs, 1H), 8.64 (brs, 1H), 8.54 (d, J=7.5 Hz, 1H), 7.83-7.81 (m, 3H), 7.51-7.47 (2H, m), 7.41 (m, 1H), 0.97 (s, 9H).

Step 4:

To a solution of N-(4-benzoyl-pyridin-3-yl)-2,2-dimethyl-propionamide (500 mg, 1.77 mmol) in dioxane (20 mL) was added 1 N HCl (8 mL). Then the mixture was stirred at 105° C. for 15 hrs. After cooled to room temperature, the pH value was adjust to 7-8 with saturated NaHCO$_3$. The mixture was extracted with EA (30 mL×3). The extracts were washed with brine (60 mL), dried over Na$_2$SO$_4$ and concentrated in vacuum to give (3-amino-pyridin-4-yl)-phenyl-methanone (300 mg, yield: 36%) as yellow oil. $^1$HNMR (300 MHz, DMSO-d6): δ=12.01 (s, 1H), 8.32 (s, 1H), 7.75 (d, J=5.1 Hz, 1H), 7.70-7.52 (m, 5H), 7.09 (d, J=5.1 Hz, 2H), 6.86 (brs, 2H).

Step 5:

To a solution of (3-amino-pyridin-4-yl)-phenyl-methanone (120 mg, 0.605 mmol) in CH$_3$CN (3 mL) was added a solution of diketene (50.0 mg, 0.0595 mmol) in CH$_3$CN (0.5 mL). Then the mixture was stirred at 50° C. for 15 hrs. The reaction was cooled to room temperature and filtered to afford 3-acetyl-4-phenyl-1H-[1,7]naphthyridin-2-one (50.0 mg, yield: 31%) as a white solid. $^1$HNMR (400 MHz, DMSO-d6): δ=12.52 (brs, 1H), 8.75 (s, 1H), 8.29 (d, J=5.4 Hz, 1H), 7.54-7.52 (m, 3H), 7.36-7.34 (m, 2H), 6.98 (d, J=5.1 Hz, 1H), 2.22 (s, 3H).

Step 6:

The procedure is similar to Example 13. $^1$HNMR (400 MHz, DMSO-d6): δ=12.60 (brs, 1H), 8.81 (s, 1H), 8.33 (d, J=5.1 Hz, 1H), 7.59-7.45 (m, 5H), 7.38-7.33 (m, 3H), 7.26-7.22 (m, 2H), 7.05-7.02 (m, 2H). MS: m/z 393.1 (M+H$^+$).

Example 23: 4-Phenyl-3-(3-pyridin-4-yl-acryloyl)-1H-[1,7]naphthyridin-2-one

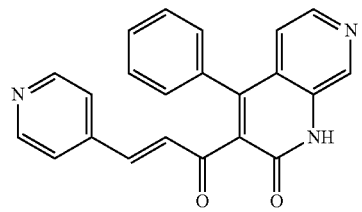 [SMILES: O=C(/C=C/c1ccncc1)c1c(-c2ccccc2)c2ccncc2[nH]c1=O]

This compound was prepared as described in Example 22. $^1$HNMR (400 MHz, DMSO-d6): δ=8.81 (s, 1H), 8.60 (d, J=7.5 Hz, 2H), 8.32 (d, J=7.5 Hz, 1H), 7.61 (d, J=7.5 Hz, 2H), 7.53 (d, J=16.4 Hz, 1H), 7.48-7.43 (m, 3H), 7.34-7.32 (m, 2H), 7.03-6.98 (m, 2H). MS: m/z 354.1 (M+H$^+$).

Example 24: 3-(3-1H-Benzoimidazol-2-yl-acryloyl)-4-phenyl-1H-[1,6]naphthyridin-2-one

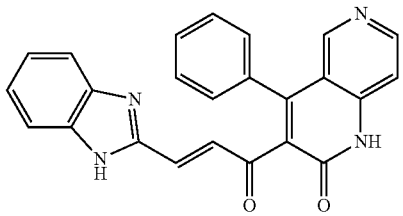 [SMILES: O=C(/C=C/c1nc2ccccc2[nH]1)c1c(-c2ccccc2)c2cnccc2[nH]c1=O]

This compound was prepared as described in Example 22. ¹HNMR (400 MHz, DMSO-d6): δ=12.86 (brs, 1H), 12.58 (brs, 1H), 8.57 (d, J=5.6 Hz, 1H), 8.26 (s, 1H), 7.64 (d, J=5.6 Hz, 1H), 7.53-7.36 (m, 8H), 7.26-7.22 (m, 2H), 7.03 (d, J=16.4 Hz, 1H). MS: m/z 393.1 (M+H⁺).

Example 25: 3-(3-1H-Benzoimidazol-2-yl-acryloyl)-4-phenyl-1H-[1,8]naphthyridin-2-one

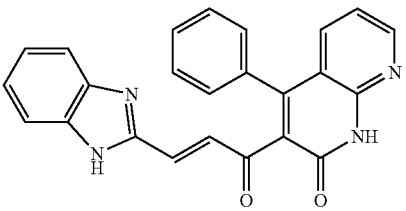 [SMILES: O=C(/C=C/c1nc2ccccc2[nH]1)c1c(-c2ccccc2)c2cccnc2[nH]c1=O]

This compound was prepared as described in Example 22. 1HNMR (400 MHz, DMSO-d6): δ=12.91 (brs, 1H), 12.70 (brs, 1H), 8.63 (dd, J=4.4, 1.6 Hz, 1H), 7.64 (d, J=8.0 Hz, 1H), 7.54-7.21 (m, 11H), 7.05 (d, J=16.4 Hz, 1H). MS: m/z 393.1 (M+H⁺).

Example 26: 4-Phenyl-3-(3-phenyl-acryloyl)-1H-[1,7]naphthyridin-2-one

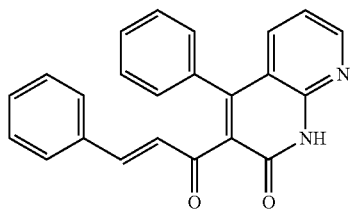 [SMILES: O=C(/C=C/c1ccccc1)c1c(-c2ccccc2)c2cccnc2[nH]c1=O]

This compound was prepared as described in Example 22. ¹HNMR (400 MHz, DMSO-d6): δ=12.58 (brs, 1H), 8.60 (dd, J=4.8, 2.0 Hz, 1H), 7.66-7.64 (m, 1H), 7.53-7.25 (m, 11H), 6.74 (d, J=16.4 Hz, 1H). MS: m/z 353.1 (M+H⁺).

Example 27: 6-Chloro-4-phenyl-3-(3-thiophen-3-yl-acryloyl)-1H-quinolin-2-one

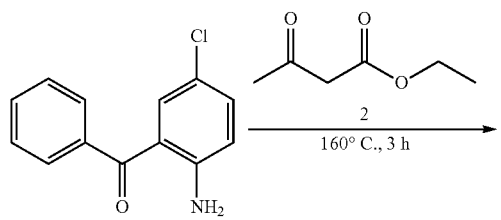

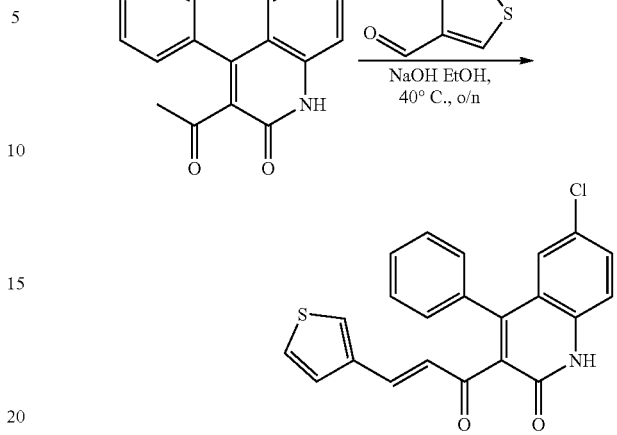

Step 1:

The mixture of (2-amino-5-chloro-phenyl)-phenyl-methanone (2.0 g, 8.70 mmol) and 3-oxo-butyric acid ethyl ester (1.13 g, 8.70 mmol) was heated to 160° C. with stirring for 3 hrs. The reaction was cooled to room temperature. The yellow solid was recrystallized from EtOH to afford 3-acetyl-6-chloro-4-phenyl-1H-quinolin-2-one (1.30 g, yield: 50%) as a yellow solid.

Step 2:

3-Acetyl-6-chloro-4-phenyl-1H-quinolin-2-one (60.0 mg, 0.20 mmol), thiophene-3-carbaldehyde (23.0 mg, 0.220 mmol) and NaOH (9.0 mg 0.220 mmol) was dissolved in EtOH (3 mL). The mixture was stirred for at 40° C. for 1 hr. After cooled to room temperature, the mixture was diluted with water (2 mL). The pH value was adjusted to 8. The resulting solid was collected by filtration and purified by prep-TLC to afford 6-chloro-4-phenyl-3-(3-thiophen-3-yl-acryloyl)-1H-quinolin-2-one (42 mg, yield: 53%) as a yellow solid. ¹HNMR (400 MHz, DMSO-d6): δ=12.31 (brs, 1H), 7.97 (d, J=2.8 Hz, 1H), 7.65 (dd, J=8.8, 2.0 Hz, 1H), 7.59-7.57 (m, 1H), 7.51-7.41 (m, 6H), 7.31-7.29 (m, 2H), 6.96 (d, J=2.4 Hz, 1H), 6.56 (d, J=16.4 Hz, 1H). MS: m/z 392.0 (M+H⁺).

Example 28: 6-Chloro-4-phenyl-3-(3-pyridin-4-yl-acryloyl)-1H-quinolin-2-one

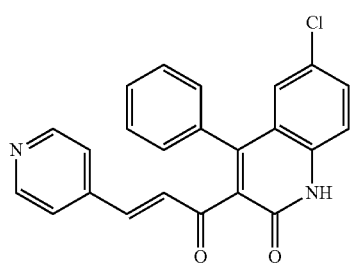 [SMILES: O=C(/C=C/c1ccncc1)c1c(-c2ccccc2)c2cc(Cl)ccc2[nH]c1=O]

This compound was prepared as described in Example 27. ¹HNMR (400 MHz, DMSO-d6): δ=12.39 (s, 1H), 8.59 (d, J=5.6 Hz, 2H), 7.68 (dd, J=8.8, 2.0 Hz, 1H), 7.61 (d, J=5.6 Hz, 2H), 7.51-7.41 (m, 5H), 7.32 (d, J=6.4 Hz, 2H), 7.01-6.97 (m, 2H). MS: m/z 387.1 (M+H⁺).

Example 29: 6-Chloro-3-[3-(1-methyl-1H-indol-2-yl)-acryloyl]-4-phenyl-1H-quinolin-2-one

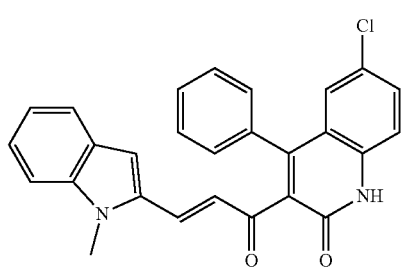 [SMILES: Cn1c(/C=C/C(=O)c2c(-c3ccccc3)c3cc(Cl)ccc3[nH]c2=O)cc2ccccc21]

This compound was prepared as described in Example 27.
¹HNMR (400 MHz, DMSO-d6): δ=12.34 (s, 1H), 7.67-7.64 (dd, J=8.8, 2.0 Hz, 1H), 7.56-7.42 (m, 7H), 7.37-7.35 (m, 2H), 7.24-7.19 (m, 1H), 7.10 (s, 1H), 7.05 (t, J=7.6 Hz, 1H), 7.00 (d, J=2.4 Hz, 1H), 6.80 (d, J=16.4 Hz, 1H), 3.76 (s, 3H). MS: m/z 439.1 (M+H⁺).

Example 30: 6-Chloro-3-[3-(1-methyl-1H-indol-5-yl)-acryloyl]-4-phenyl-1H-quinolin-2-one

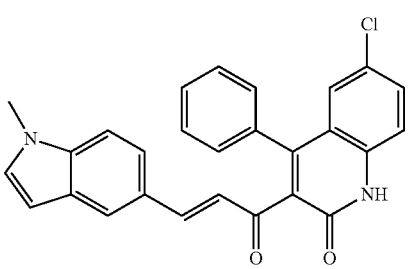 [SMILES: Cn1ccc2cc(/C=C/C(=O)c3c(-c4ccccc4)c4cc(Cl)ccc4[nH]c3=O)ccc21]

This compound was prepared as described in Example 27.
¹HNMR (400 MHz, DMSO-d6): δ=12.30 (s, 1H), 7.86 (s, 1H), 7.65 (dd, J=8.8, 2.0 Hz, 1H), 7.57 (d, J=16.4 Hz, 1H), 7.50-7.32 (m, 9H), 6.97 (d, J=2.4 Hz, 1H), 6.65 (d, J=16.4 Hz, 1H), 6.44 (d, J=3.2 Hz, 1H), 3.79 (s, 3H). MS: m/z 439.1 (M+H⁺).

Example 31: 6-Chloro-4-phenyl-3-(3-phenyl-acryloyl)-1H-quinolin-2-one

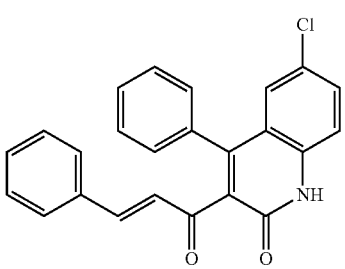 [SMILES: O=C(/C=C/c1ccccc1)c1c(-c2ccccc2)c2cc(Cl)ccc2[nH]c1=O]

This compound was prepared as described in Example 27.
¹HNMR (400 MHz, DMSO-d6): δ=12.35 (s, 1H), 7.67-7.64 (m, 3H), 7.51-7.32 (m, 10H), 6.98 (d, J=2.0 Hz, 1H), 6.75 (d, J=16.4 Hz, 1H). MS: m/z 386.1 (M+H⁺).

Example 32: 6-Chloro-4-phenyl-3-(3-pyridin-3-yl-acryloyl)-1H-quinolin-2-one

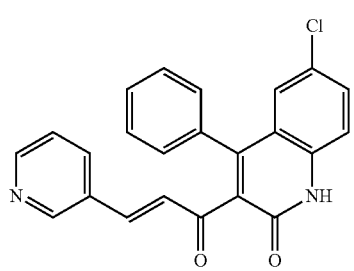 [SMILES: O=C(/C=C/c1cccnc1)c1c(-c2ccccc2)c2cc(Cl)ccc2[nH]c1=O]

This compound was prepared as described in Example 27.
¹HNMR (300 MHz, CDCl₃): δ=12.99 (s, 1H), 8.63-8.58 (m, 2H), 7.74 (d, J=8.1 Hz, 1H), 7.45-7.27 (m, 10H), 6.80 (d, J=16.2 Hz, 1H). MS: m/z 387.1 (M+H⁺).

Example 33: 6-Chloro-3-[3-(4-chloro-phenyl)-acryloyl]-4-phenyl-1H-quinolin-2-one

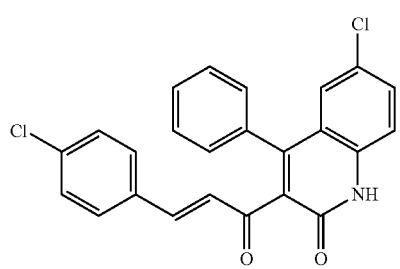 [SMILES: O=C(/C=C/c1ccc(Cl)cc1)c1c(-c2ccccc2)c2cc(Cl)ccc2[nH]c1=O]

This compound was prepared as described in Example 27.
¹HNMR (400 MHz, DMSO-d6): δ=12.34 (s, 1H), 7.71-7.64 (m, 3H), 7.51-7.27 (m, 9H), 6.97 (d, J=2.0 Hz, 1H), 6.77 (d, J=16.4 Hz, 1H). MS: m/z 420.0 (M+H⁺).

Example 34: 6-Chloro-4-phenyl-3-(3-p-tolyl-acryloyl)-1H-quinolin-2-one

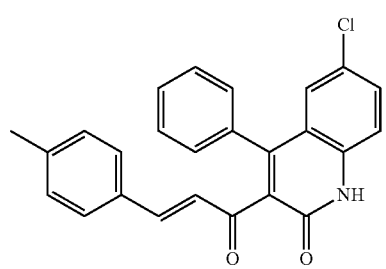

This compound was prepared as described in Example 27.
1HNMR (400 MHz, DMSO-d6): δ=12.33 (s, 1H), 7.64 (d, J=9.2 Hz, 1H), 7.54 (d, J=8.0 Hz, 2H), 7.47-7.40 (m, 5H), 7.31 (d, J=8.0 Hz, 2H), 7.20 (d, J=8.0 Hz, 2H), 6.97 (s, 1H), 6.68 (d, J=16.4 Hz, 1H), 2.31 (s, 3H). MS: m/z 400.1 (M+H⁺).

Example 35: 6-Chloro-3-[3-(4-dimethylamino-phenyl)-acryloyl]-4-phenyl-1H-quinolin-2-one

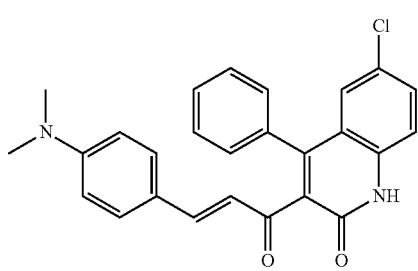 [SMILES: CN(C)c1ccc(/C=C/C(=O)c2c(-c3ccccc3)c3cc(Cl)ccc3[nH]c2=O)cc1]

This compound was prepared as described in Example 27. ¹HNMR (400 MHz, DMSO-d6): δ=12.28 (s, 1H), 7.64 (dd, J=8.8, 2.4 Hz, 1H), 7.47-7.29 (m, 9H), 6.95 (d, J=2.0 Hz, 1H), 6.66 (d, J=8.8 Hz, 2H), 6.43 (d, J=16.0 Hz, 1H), 2.97 (s, 6H). MS: m/z 429.1 (M+H⁺).

Example 36: 3-(3-Benzo[b]thiophen-2-yl-acryloyl)-6-chloro-4-phenyl-1H-quinolin-2-one

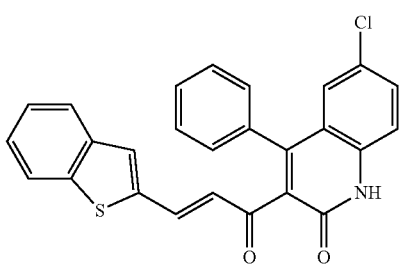

This compound was prepared as described in Example 27. ¹HNMR (400 MHz, DMSO-d6): δ=12.35 (s, 1H), 8.40 (s, 1H), 8.11-8.04 (m, 2H), 7.74 (d, J=16.4 Hz, 1H), 7.66 (dd, J=8.8, 2.4 Hz, 1H), 7.45-7.36 (m, 8H), 7.00 (d, J=2.4 Hz, 1H), 6.86 (d, J=16.8 Hz, 1H). MS: m/z 442.0 (M+H⁺).

Example 37: 6-Chloro-4-phenyl-3-(3-pyrimidin-5-yl-acryloyl)-1H-quinolin-2-one

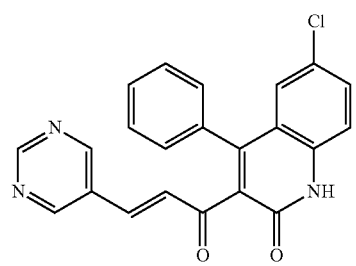 [SMILES: O=C(/C=C/c1cncnc1)c1c(-c2ccccc2)c2cc(Cl)ccc2[nH]c1=O]

This compound was prepared as described in Example 27. ¹HNMR (300 MHz, DMSO-d6): δ=12.38 (s, 1H), 9.15 (s, 1H), 9.08 (s, 2H), 7.68 (dd, J=8.7, 2.1 Hz, 1H), 7.55-7.32 (m, 7H), 7.05 (d, J=16.8 Hz, 1H), 6.99 (d, J=2.1 Hz, 1H). MS: m/z 388.0 (M+H⁺).

Example 38: 6-Chloro-3-[3-(5-fluoro-pyridin-3-yl)-acryloyl]-4-phenyl-1H-quinolin-2-one

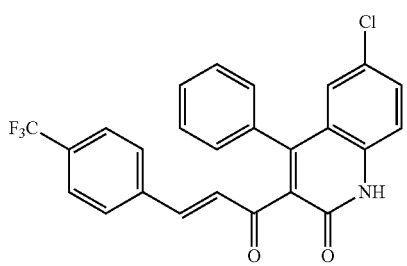 [SMILES: O=C(/C=C/c1ccc(C(F)(F)F)cc1)c1c(-c2ccccc2)c2cc(Cl)ccc2[nH]c1=O]

This compound was prepared as described in Example 27. ¹HNMR (300 MHz, DMSO-d6): δ=12.39 (s, 1H), 8.71 (s, 1H), 8.59 (s, 1H), 8.12 (d, J=9.0 Hz, 1H), 7.69-7.43 (m, 6H), 7.34-7.31 (m, 2H), 6.99 (t, J=8.2 Hz, 2H). MS: m/z 405.1 (M+H⁺).

Example 39: 6-Chloro-4-phenyl-3-[3-(4-trifluoromethyl-phenyl)-acryloyl]-1H-quinolin-2-one

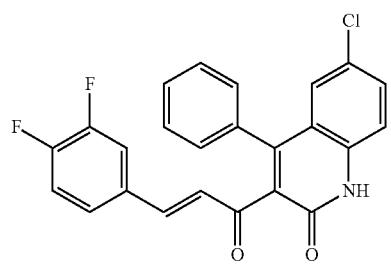 [SMILES: O=C(/C=C/c1ccc(F)c(F)c1)c1c(-c2ccccc2)c2cc(Cl)ccc2[nH]c1=O]

This compound was prepared as described in Example 27. ¹HNMR (300 MHz, DMSO-d6): δ=12.38 (s, 1H), 7.89 (d, J=8.1 Hz, 2H), 7.75-7.56 (m, 4H), 7.49-7.41 (m, 4H), 7.34-7.31 (m, 2H), 6.98 (d, J=2.4 Hz, 1H), 6.90 (d, J=16.5 Hz, 1H). MS: m/z 454.1 (M+H⁺).

Example 40: 6-Chloro-3-[3-(3,4-difluoro-phenyl)-acryloyl]-4-phenyl-1H-quinolin-2-one This compound was prepared as described in Example 27. ¹HNMR (300 MHz, DMSO-d6): δ=12.36 (s, 1H), 7.88-7.82 (m, 1H), 7.66 (dd, J=8.7, 2.4 Hz, 1H), 7.58-7.30 (m, 9H), 6.97 (d, J=2.4 Hz, 1H), 6.80 (d, J=16.2 Hz, 1H). MS: m/z 422.0 (M+H⁺).

Example 41: 6-Chloro-3-[3-(2,4-difluoro-phenyl)-acryloyl]-4-phenyl-1H-quinolin-2-one

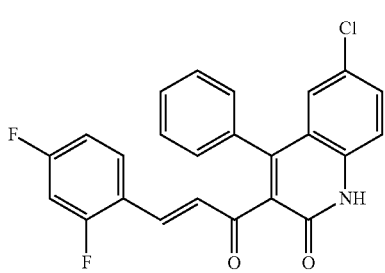 [SMILES: O=C(/C=C/c1ccc(F)cc1F)c1c(-c2ccccc2)c2cc(Cl)ccc2[nH]c1=O]

This compound was prepared as described in Example 27. ¹HNMR (300 MHz, DMSO-d6): δ=12.40 (s, 1H), 7.87 (q, J=7.5 Hz, 1H), 7.67 (d, J=8.7 Hz, 1H), 7.48-7.29 (m, 8H), 7.18-7.12 (m, 1H), 6.98 (s, 1H), 6.83 (d, J=15.9 Hz, 1H). MS: m/z 422.1 (M+H$^+$).

Example 42: 6-Chloro-3-[3-(2,6-difluoro-phenyl)-acryloyl]-4-phenyl-1H-quinolin-2-one

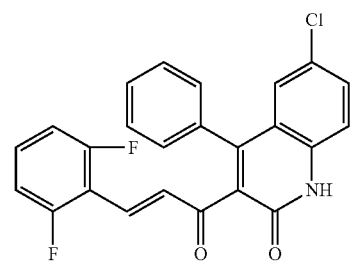 [SMILES: O=C(/C=C/c1c(F)cccc1F)c1c(-c2ccccc2)c2cc(Cl)ccc2[nH]c1=O]

This compound was prepared as described in Example 27. ¹HNMR (300 MHz, DMSO-d6): δ=12.43 (s, 1H), 7.67 (dd, J=8.7, 2.1 Hz, 1H), 7.55-7.45 (m, 5H), 7.35-7.29 (m, 3H), 7.19 (d, J=9.0 Hz, 2H), 7.00 (d, J=2.1 Hz, 1H), 6.86 (d, J=16.5 Hz, 1H). MS: m/z 422.1 (M+H$^+$)

Example 43: 6-Chloro-3-[3-(2-fluoro-4-methoxy-phenyl)-acryloyl]-4-phenyl-1H-quinolin-2-one

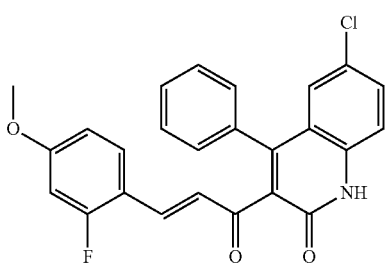 [SMILES: COc1ccc(/C=C/C(=O)c2c(-c3ccccc3)c3cc(Cl)ccc3[nH]c2=O)c(F)c1]

This compound was prepared as described in Example 27. ¹HNMR (300 MHz, DMSO-d6): δ=12.37 (s, 1H), 7.73-7.64 (m, 2H), 7.48-7.28 (m, 7H), 6.97 (d, J=1.5 Hz, 1H), 6.90 (d, J=14.1 Hz, 1H), 6.82 (d, J=9.6 Hz, 1H), 6.70 (d, J=16.5 Hz, 1H), 3.81 (s, 3H). MS: m/z 434.1 (M+H$^+$).

Example 44: 6-Chloro-4-phenyl-3-(3-pyridin-3-yl-acryloyl)-1H-quinolin-2-one

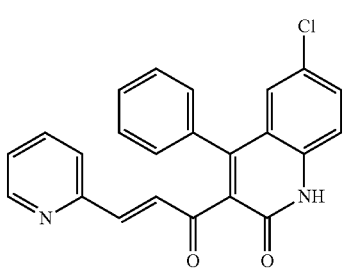 [SMILES: O=C(/C=C/c1ccccn1)c1c(-c2ccccc2)c2cc(Cl)ccc2[nH]c1=O]

This compound was prepared as described in Example 27. 1HNMR (400 MHz, DMSO-d6): δ=12.40 (s, 1H), 8.59 (d, J=4.4 Hz, 1H), 7.79 (t, J=8.0 Hz, 1H), 7.65 (d, J=7.6 Hz, 1H), 7.41-7.33 (m, 4H), 7.26-7.17 (m, 5H), 7.10 (d, J=16.0 Hz, 1H), 6.82 (s, 1H). MS: m/z 387.1 (M+H$^+$).

Example 45: 6-Chloro-3-[3-(1-methyl-1H-imidazol-2-yl)-acryloyl]-4-phenyl-1H-quinolin-2-one

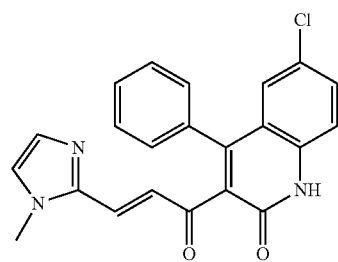 [SMILES: Cn1ccnc1/C=C/C(=O)c1c(-c2ccccc2)c2cc(Cl)ccc2[nH]c1=O]

This compound was prepared as described in Example 27. ¹HNMR (400 MHz, DMSO-d6): δ=12.30 (s, 1H), 7.42-7.34 (m, 3H), 7.28 (s, 1H), 7.25-7.16 (m, 4H), 7.06-7.01 (m, 2H), 6.88 (d, J=15.6 Hz, 1H), 6.81 (d, J=2.0 Hz, 1H), 3.65 (s, 3H). MS: m/z 390.1 (M+H$^+$)

Example 46: 3-[3-(4-Bromo-thiophen-2-yl)-acryloyl]-6-chloro-4-phenyl-1H-quinolin-2-one

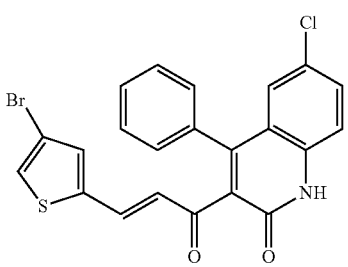 [SMILES: O=C(/C=C/c1cc(Br)cs1)c1c(-c2ccccc2)c2cc(Cl)ccc2[nH]c1=O]

This compound was prepared as described in Example 27. ¹HNMR (400 MHz, DMSO-d6): δ=12.36 (s, 1H), 7.86 (d, J=1.2 Hz, 1H), 7.67-7.62 (m, 2H), 7.58 (s, 1H), 7.48-7.43 (m, 4H), 7.30 (dd, J=7.6, 2.0 Hz, 2H), 6.96 (d, J=2.4 Hz, 1H), 6.49 (d, J=16.4 Hz, 1H). MS: m/z 469.9 (M+H$^+$)

Example 47: 3-[3-(5-Bromo-pyridin-2-yl)-acryloyl]-6-chloro-4-phenyl-1H-quinolin-2-one

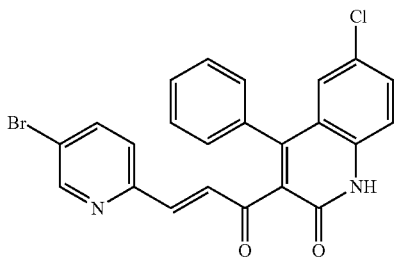

This compound was prepared as described in Example 27. ¹HNMR (400 MHz, DMSO-d6): δ=12.40 (s, 1H), 8.73 (d, J=2.4 Hz, 1H), 8.12 (dd, J=8.4, 2.4 Hz, 1H), 7.69-7.65 (m, 2H), 7.52-7.43 (m, 5H), 7.33-7.30 (m, 2H), 7.05-6.98 (m, 2H). MS: m/z 467.0 (M+H$^+$)

Example 48: 6-Chloro-3-[3-(5-methyl-pyridin-2-yl)-acryloyl]-4-phenyl-1H-quinolin-2-one

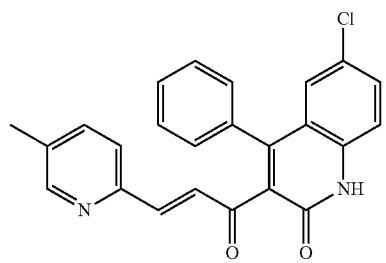 [SMILES: Cc1ccc(/C=C/C(=O)c2c(-c3ccccc3)c3cc(Cl)ccc3[nH]c2=O)nc1]

This compound was prepared as described in Example 27. ¹HNMR (400 MHz, DMSO-d6): δ=12.41 (s, 1H), 8.46 (d, J=3.6 Hz, 1H), 7.71-7.65 (m, 2H), 7.57 (d, J=15.6 Hz, 1H), 7.49-7.46 (m, 4H), 7.37-7.32 (m, 3H), 7.10 (d, J=15.6 Hz, 1H), 7.01 (d, J=2.0 Hz, 1H), 2.34 (s, 3H). MS: m/z 401.1 (M+H$^+$).

Example 49: 6-Chloro-3-[3-(4-fluoro-2-trifluoromethyl-phenyl)-acryloyl]-4-phenyl-1H-quinolin-2-one

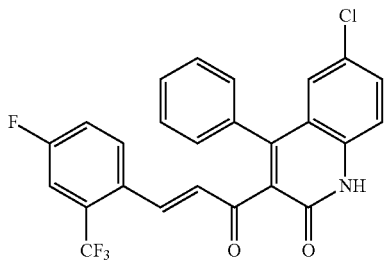 [SMILES: O=C(/C=C/c1ccc(F)cc1C(F)(F)F)c1c(-c2ccccc2)c2cc(Cl)ccc2[nH]c1=O]

This compound was prepared as described in Example 27. ¹HNMR (400 MHz, DMSO-d6): δ=12.47 (s, 1H), 8.05-8.01 (m, 1H), 7.74-7.61 (m, 3H), 7.51-7.44 (m, 5H), 7.33-7.27 (m, 2H), 7.04-7.00 (m, 2H). MS: m/z 472.1 (M+H$^+$)

Example 50: 6-Chloro-3-(3-furan-3-yl-acryloyl)-4-phenyl-1H-quinolin-2-one

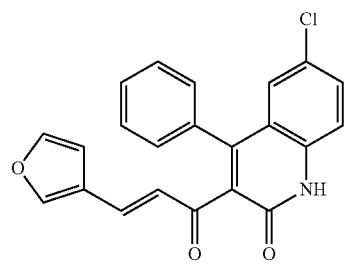 [SMILES: O=C(/C=C/c1ccoc1)c1c(-c2ccccc2)c2cc(Cl)ccc2[nH]c1=O]

This compound was prepared as described in Example 27. ¹HNMR (300 MHz, DMSO-d6): δ=12.35 (s, 1H), 8.04 (s, 1H), 7.71 (s, 1H), 7.65 (dd, J=9.0, 2.4 Hz, 1H), 7.50-7.39 (m, 5H), 7.31-7.27 (m, 2H), 6.95 (d, J=2.1 Hz, 1H), 6.87 (s, 1H), 6.45 (d, J=16.2 Hz, 1H). MS: m/z 376.0 (M+H$^+$)

Example 51: 6-Chloro-4-phenyl-3-(3-thiophen-2-yl-acryloyl)-1H-quinolin-2-one

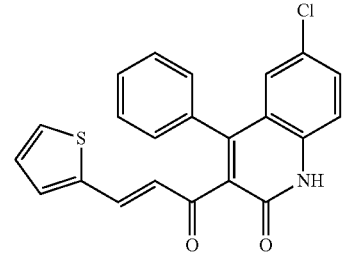 [SMILES: O=C(/C=C/c1cccs1)c1c(-c2ccccc2)c2cc(Cl)ccc2[nH]c1=O]

This compound was prepared as described in Example 27. 1HNMR (400 MHz, DMSO-d6): δ=12.35 (s, 1H), 7.66 (d, J=5.2 Hz, 1H), 7.43 (d, J=3.2 Hz, 1H), 7.41-7.33 (m, 4H), 7.26-7.18 (m, 4H), 7.10 (t, J=4.2 Hz, 1H), 6.80 (d, J=2.4 Hz, 1H), 6.44 (d, J=15.2 Hz, 1H). MS: m/z 392.0 (M+H$^+$).

Example 52: 6-Chloro-4-phenyl-3-(3-pyrazin-2-yl-acryloyl)-1H-quinolin-2-one

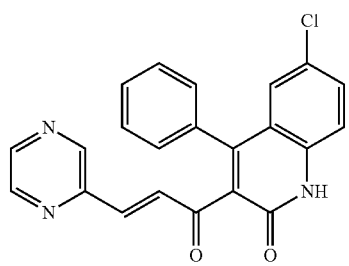 [SMILES: O=C(/C=C/c1cnccn1)c1c(-c2ccccc2)c2cc(Cl)ccc2[nH]c1=O]

This compound was prepared as described in Example 27. ¹HNMR (400 MHz, DMSO-d6): δ=12.42 (s, 1H), 8.90 (s, 1H), 8.69-8.64 (m, 2H), 7.69 (dd, J=8.8, 2.0 Hz, 1H), 7.60 (d, J=16.0 Hz, 1H), 7.50-7.42 (m, 4H), 7.34 (d, J=6.8 Hz, 2H), 7.12 (d, J=16.0 Hz, 1H), 6.99 (d, J=1.6 Hz, 1H). MS: m/z 388.1 (M+H$^+$).

Example 53: 6-Chloro-3-[3-(1-methyl-1H-benzoimidazol-2-yl)-acryloyl]-4-phenyl-1H-quinolin-2-one

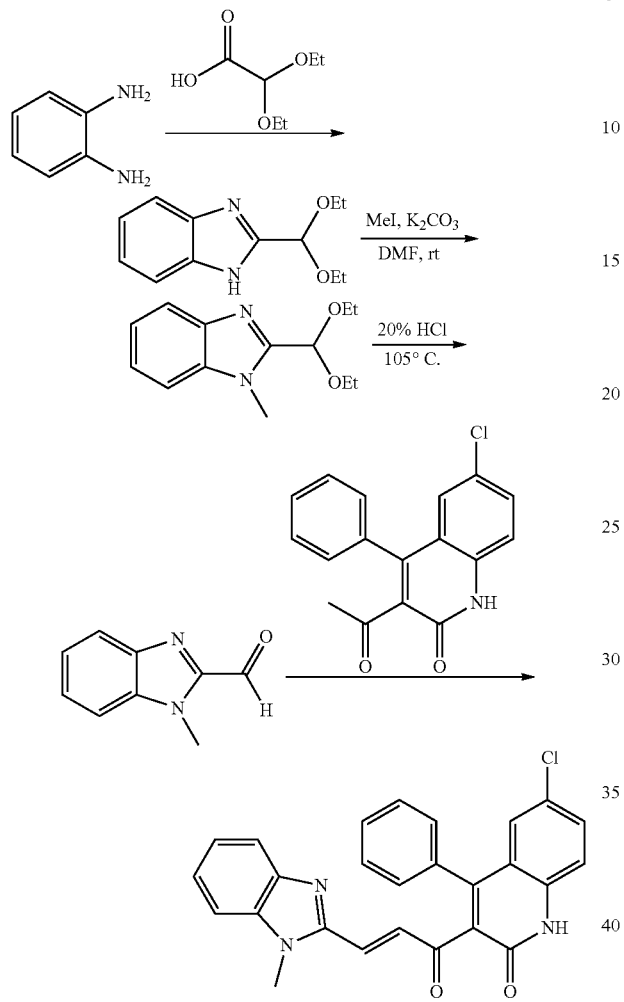

Step 1:

Na (1.65 g, 50 mmol) was dissolved in dry EtOH (30 mL), then 2-diethoxymethyl-1H-benzoimidazole (1.0 g, 9.26 mmol) and diethoxy-acetic acid (1.50 g, 10.2 mmol) was added in sequence. The reaction was stirred at reflux for 24 hrs. The mixture was concentrated as half and the pH value was adjusted to 4-5 with $CH_3CO_2H$. The mixture was extracted with EA (30 mL). The organic layer was washed with brine (20 mL), dried over $Na_2SO_4$ and concentrated to dryness in vacuum. The residue was purified by silica gel column (PE/EA=3/1), then recrystalized from (EA/PE=3/1) to give 2-diethoxymethyl-1H-benzoimidazole (700 mg, yield: 35%) as a yellow solid. $^1$HNMR (400 MHz, $CDCl_3$): δ=9.50 (brs, 1H), 7.81-7.79 (m, 1H), 7.48-7.45 (m, 1H), 7.30-7.25 (m, 2H), 5.76 (s, 1H), 3.79-3.65 (m, 4H), 1.26 (t, J=7.2 Hz, 6H).

Step 2:

To a mixture of 2-diethoxymethyl-1H-benzoimidazole (200 mg, 0.909 mmol) and $K_2CO_3$ (376 mg, 2.73 mmol) in anhydrous DMF (5 mL) was added iodomethane (153 mg, 1.09 mmol) at 0° C. Then the mixture was stirred at room temperature overnight. The reactant was diluted with water (10 mL). The aqueous phase was extracted with EA (10 mL×3). The extracts were washed with brine (10 mL), dried over $Na_2SO_4$. The solution was concentrated to afford 2-diethoxymethyl-1-methyl-1H-benzoimidazole (200 mg, yield: 94%) as a yellow solid.

Step 3:

A solution of 2-diethoxymethyl-1-methyl-1H-benzoimidazole (170 mg, 0.73 mmol) in aqueous HCl (2 mL, 20%) was stirred at 105° C. for 1 hr. After cooled to room temperature, the pH value was adjusted to 7-8 with aqueous $NaHCO_3$. The aqueous phase was extracted with EA (5 mL×2). The organic layers were washed with brine (20 mL), dried over $Na_2SO_4$. The solution was concentrated to afford 2-diethoxymethyl-1-methyl-1H-benzoimidazole (135 mg, yield: 99%) as a white solid.

Step 4:

3-Acetyl-6-chloro-4-phenylquinolin-2(1H)-one (100 mg, 0.31 mmol) was added to a solution of NaOH (18 mg, 0.44 mmol) in EtOH (20 mL) and $H_2O$ (1 mL). The mixture was stirred at room temperature for 30 mins. Then 1-methyl-1H-benzo[d]imidazole-2-carbaldehyde (60 mg, 0.37 mmol) was added and the mixture was stirred at 35° C. overnight. The mixture was concentrated to dryness and the residue was diluted with EA (10 mL). The mixture was washed with water (10 mL), brine (10 mL) and dried over anhydrous $Na_2SO_4$. The mixture was concentrated to give a crude solid, which was purified by prep-HPLC to give 6-chloro-3-[3-(1-methyl-1H-benzoimidazol-2-yl)-acryloyl]-4-phenyl-1H-quinolin-2-one (50 mg, yield: 37%) as a yellow solid. $^1$HNMR (400 MHz, DMSO-$d_6$): δ=12.41 (brs, 1H), 7.69-7.02 (m, 13H), 7.01 (d, J=3.2 Hz, 1H), 3.88 (s, 3H). MS: m/z 440.1 (M+H$^+$).

Example 54: (E)-6-chloro-3-(3-(5-chloro-1-(4-methoxybenzyl)-1H-benzo[d]imidazol-2-yl)acryloyl)-4-phenylquinolin-2(1H)-one

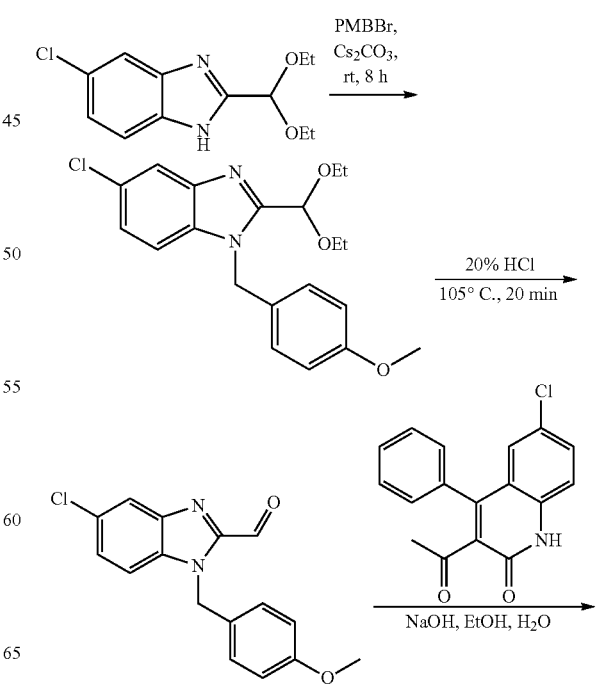

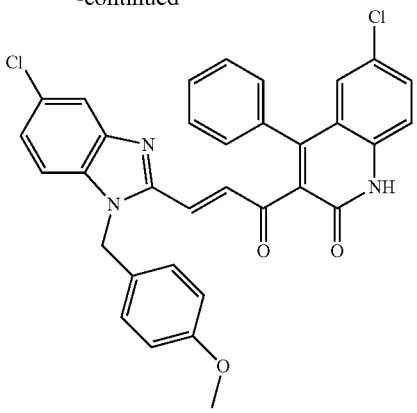

This compound was prepared as described in Example 53. ¹HNMR (400 MHz, DMSO-d$_6$): δ=12.44 (brs, 1H), 7.76-7.30 (m, 9H), 7.20-7.14 (m, 2H), 7.00-6.94 (m, 3H), 6.79 (d, J=8.4 Hz, 2H), 5.81 (s, 2H), 3.69 (s, 3H). MS: m/z 580.1 (M+H$^+$).

Example 55 and 56: 3-[3-(1-Benzyl-1H-benzoimidazol-2-yl)-acryloyl]-6-chloro-4-phenyl-1H-quinolin-2-one and 1-benzyl-3-[3-(1-benzyl-1H-benzoimidazol-2-yl)-acryloyl]-6-chloro-4-phenyl-1H-quinolin-2-one

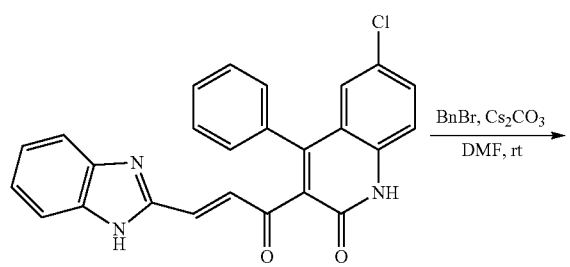

To a mixture of (E)-3-(3-(1H-benzo[d]imidazol-2-yl)acryloyl)-6-chloro-4-phenylquinolin-2(1H)-one (100 mg, 0.24 mmol) in dry DMF (1 mL) was added Cs$_2$CO$_3$ (115 mg, 0.35 mmol) and benzyl bromide (40 mg, 0.24 mmol), and the mixture was stirred at room temperature for 50 mins. The reaction was quenched with water (2 mL) and the aqueous phase was extracted with EtOAc (10 mL×2). The extracts were washed with brine (10 mL) and dried over Na$_2$SO$_4$. The solution was concentrated to dryness in vacuum and the residue was purified by prep-TLC to give 3-[3-(1-benzyl-1H-benzoimidazol-2-yl)-acryloyl]-6-chloro-4-phenyl-1H-quinolin-2-one (Example 55, 10 mg, yield: 8.0%) and 1-benzyl-3-[3-(1-benzyl-1H-benzoimidazol-2-yl)-acryloyl]-6-chloro-4-phenyl-1H-quinolin-2-one (Example 56, 11 mg, yield: 7.7%) as a yellow solid for both of them.

Example 55

¹HNMR (400 MHz, DMSO-d$_6$): δ=12.87 (brs, 1H), 7.71-22 (m, 17H), 7.12-7.08 (m, 2H), 5.64 (s, 2H). MS: m/z 516.2 (M+H$^+$).

Example 56

¹HNMR (400 MHz, DMSO-d$_6$): δ=7.70-7.59 (m, 5H), 7.43-7.19 (m, 16H), 7.03-7.01 (m, 3H), 5.71 (s, 2H), 5.63 (s, 2H). MS: m/z 606.2 (M+H$^+$).

Example 57: 6-Chloro-3-{3-[1-(2-methoxy-ethyl)-1H-benzoimidazol-2-yl]-acryloyl}-4-phenyl-1H-quinolin-2-one

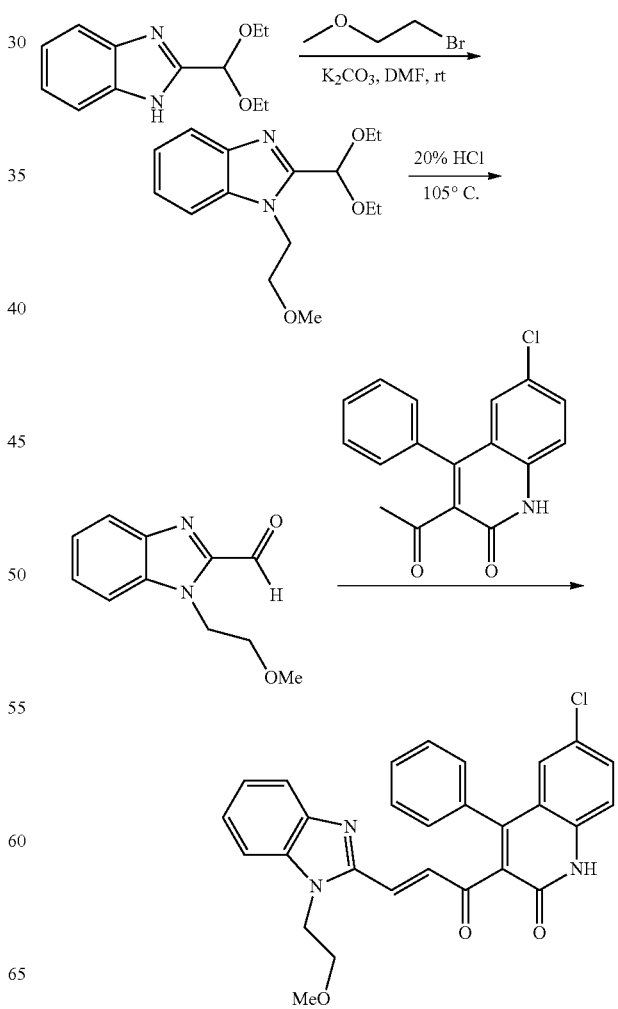

This compound was prepared as described in Example 53.
¹HNMR (400 MHz, DMSO-d₆): δ=12.44 (brs, 1H), 7.67-7.60 (m, 4H), 7.54-7.46 (m, 4H), 7.36-7.00 (m, 5H), 7.99 (d, J=3.2 Hz, 1H), 4.54 (t, J=6.4 Hz, 2H), 3.54 (t, J=6.4 Hz, 2H), 3.11 (s, 3H). MS: m/z 484 (M+H⁺).

Example 58: 6-Chloro-3-[3-(1-ethyl-1H-benzoimidazol-2-yl)-acryloyl]-4-phenyl-1H-quinolin-2-one

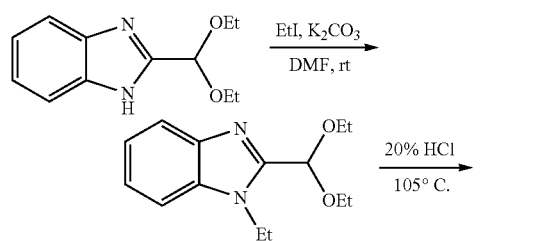

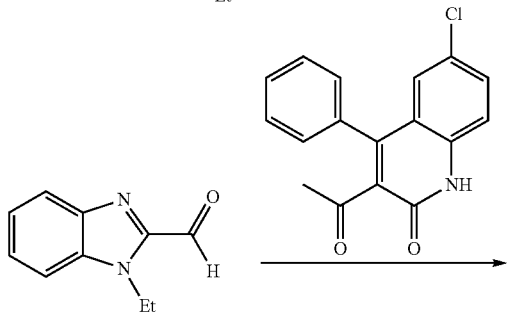

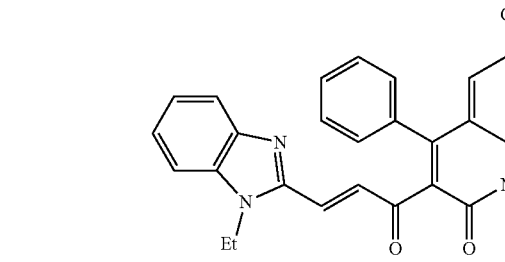

This compound was prepared as described in Example 53.
¹HNMR (400 MHz, DMSO-d₆): δ=12.44 (brs, 1H), 7.69-7.62 (m, 3H), 7.55 (d, J=15.6 Hz, 1H), 7.49-7.45 (m, 4H), 7.37-7.18 (m, 5H), 7.01 (d, J=2.4 Hz, 1H), 4.44 (q, J=7.2 Hz, 2H), 1.24 (t, J=7.2 Hz, 3H). MS: m/z 454 (M+H⁺).

Example 59: 6-Chloro-1-methyl-3-[3-(1-methyl-1H-benzoimidazol-2-yl)-acryloyl]-4-phenyl-1H-quinolin-2-one

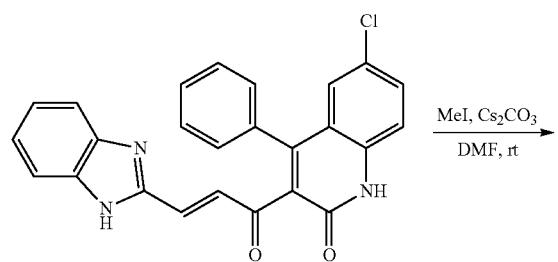

-continued

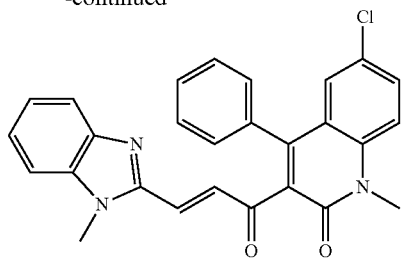

This compound was prepared as described in Example 55.
¹HNMR (400 MHz, DMSO-d₆): δ=7.78-7.76 (m, 2H), 7.65-7.54 (m, 3H), 7.48-7.45 (m, 3H), 7.37-7.16 (m, 5H), 7.08 (s, 1H), 3.88-3.85 (m, 3H), 3.76-3.73 (m, 3H). MS: m/z 454.1 (M+H⁺).

Example 60: (E)-6-chloro-1-ethyl-3-(3-(1-ethyl-1H-benzo[d]imidazol-2-yl)acryloyl)-4-phenylquinolin-2(1H)-one

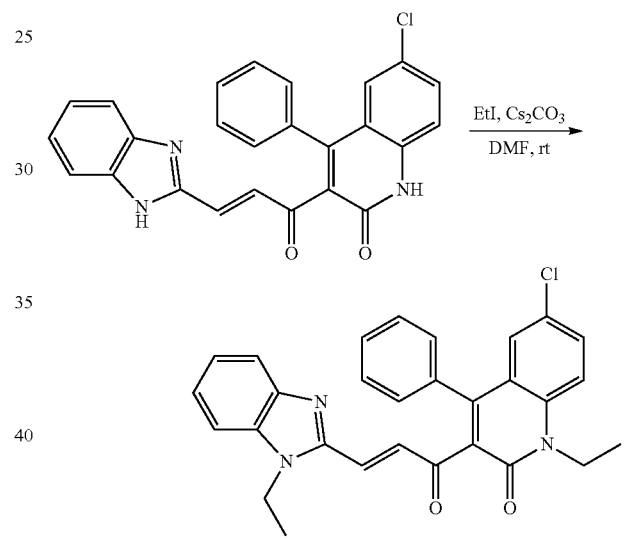

This compound was prepared as described in Example 55.
¹HNMR (400 MHz, DMSO-d₆): δ=7.84-7.76 (m, 2H), 7.65-7.55 (m, 3H), 7.50-7.44 (m, 3H), 7.387.17 (m, 5H), 7.09 (d, J=2.0 Hz, 1H), 3.87 (s, 3H), 3.74 (s, 3H). MS: m/z 482.1 (M+H⁺).

Example 61-1: 6-Chloro-3-[3-(5-methyl-1H-benzoimidazol-2-yl)-acryloyl]-4-phenyl-1H-quinolin-2-one

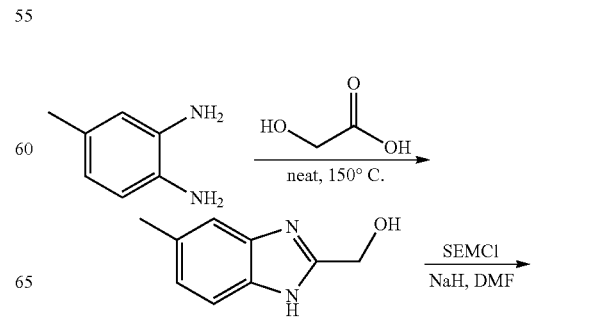

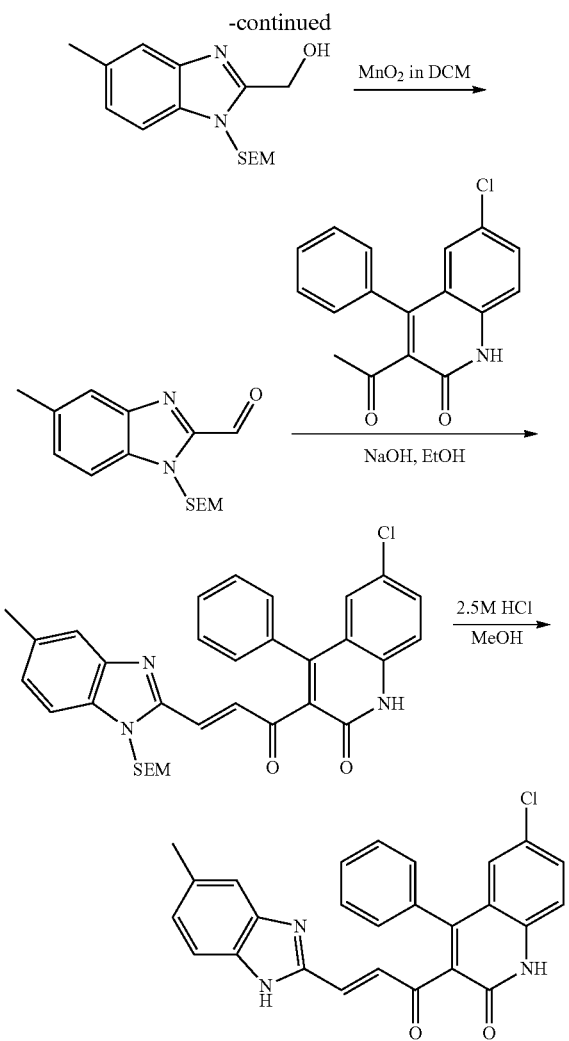

Step 1:

The mixture of 4-methyl-benzene-1,2-diamine (500 mg, 4.10 mmol) and hydroxy-acetic acid (374 mg, 4.92 mmol) was heated to 150° C. with stirring for 3 hrs. After cooled to room temperature, the reactant was purified by silica gel column (DCM/MeOH=30/1) to afford (5-methyl-1H-benzoimidazol-2-yl)-methanol (400 mg, yield: 70%) as a yellow solid.

Step 2:

To a solution of (5-methyl-1H-benzoimidazol-2-yl)-methanol (300 mg, 1.85 mmol) in dry DMF (5 mL) was added NaH (81 mg, 2.03 mmol, 60% dispersion in mineral oil). After stirred for 30 mines at room temperature, SEMCl (308 mg, 1.85 mmol) was added. The mixture was stirred at room temperature for another 4 hrs. The reaction was quenched with water (5 mL). The aqueous phase was extracted with EA (10 mL×3). The organic layer was washed with brine (5 mL), dried over $Na_2SO_4$ and concentrated to dryness. The residue was purified by silica gel column (PE/EA=1/1) to give [5-methyl-1-(2-trimethylsilanyl-ethoxymethyl)-1H-benzoimidazol-2-yl]-methanol (400 mg, yield: 74%) as red oil. Note: Based on the HNMR, it gave a mixture of two isomers with SEM protection at different nitrogen.

Step 3:

To a solution of [5-methyl-1-(2-trimethylsilanyl-ethoxymethyl)-1H-benzoimidazol-2-yl]-methanol (400 mg, 1.37 mmol) in dry DCM (20 mL) was added $MnO_2$ (963 mg, 10.9 mmol). The mixture was stirred at rt for 24 h, filtered. The filtrate was evaporated in vacuum to afford 300 mg (yield: 75%) of 5-methyl-1-(2-trimethylsilanyl-ethoxymethyl)-1H-benzoimidazole-2-carbaldehyde as red oil.

Step 4:

5-Methyl-1-(2-trimethylsilanyl-ethoxymethyl)-1H-benzoimidazole-2-carbaldehyde (100 mg, 0.340 mmol) was added to a solution of NaOH (15.0 mg, 0.370 mmol) in dry EtOH (10 mL) and $H_2O$ (1 mL). The mixture was stirred at rt for 30 mines, then 3-acetyl-6-chloro-4-phenyl-1H-quinolin-2-one (90.0 mg, 0.370 mmol) was added and stirred at 35° C. overnight. The mixture was concentrated, diluted with EA (10 mL) and the new suspension was washed with water (10 mL), then brine (10 mL), dried over anhydrous $Na_2SO_4$. The mixture was concentrated to give the solid, which was purified by prep-HPLC to give 100 mg (yield: 73%) of 6-chloro-3-{3-[5-methyl-1-(2-trimethylsilanyl-ethoxymethyl)-1H-benzoimidazol-2-yl]-acryloyl}-4-phenyl-1H-quinolin-2-one as yellow solid. HNMR (400 MHz, $CD_3OD$): δ=7.76 (dd, J=9.2, 2.4 Hz, 1H), 7.69-7.59 (m, 7H), 7.50-7.48 (m, 2H), 7.42-7.33 (m, 3H), 5.78 (s, 2H), 3.69-3.65 (m, 2H), 2.60-2.63 (m, 3H), 0.95 (t, J=8.0 Hz, 2H), 0.01 (s, 9H).

Step 5:

To a solution of 6-chloro-3-{3-[5-methyl-1-(2-trimethylsilanyl-ethoxymethyl)-1H-benzoimidazol-2-yl]-acryloyl}-4-phenyl-1H-quinolin-2-one (100 mg, 0.170 mmol) in EtOH (20 mL) and MeOH (20 mL) was added HCl (20 mL, 2.5 M). Then the mixture was stirred at 65° C. overnight. After cooled to room temperature, the resulting solid was filtered and washed to give 6-chloro-3-[3-(5-methyl-1H-benzoimidazol-2-yl)-acryloyl]-4-phenyl-1H-quinolin-2-one (50.0 mg, yield: 62%) as a yellow solid. $^1$HNMR (400 MHz, DMSO-$d_6$): δ=7.59 (dd, J=9.2, 2.4 Hz, 1H), 7.46-7.41 (m, 5H), 7.32-7.26 (m, 4H), 7.05-7.00 (m, 2H), 6.95 (d, J=2.4 Hz, 1H), 2.39 (s, 3H). MS: m/z 440.0 (M+H$^+$).

Example 62: 6-Chloro-3-[3-(5-chloro-1H-benzoimidazol-2-yl)-acryloyl]-4-phenyl-1H-quinolin-2-one

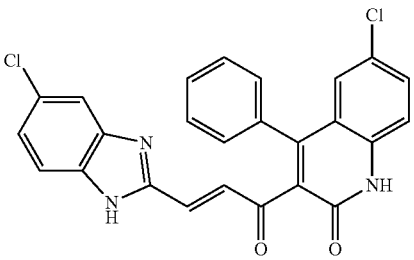 [SMILES: O=C(/C=C/c1nc2cc(Cl)ccc2[nH]1)c1c(-c2ccccc2)c2cc(Cl)ccc2[nH]c1=O]

This compound was prepared as described in Example 61. $^1$HNMR (400 MHz, DMSO-$d_6$): δ=12.50 (brs, 1H), 7.71-7.63 (m, 3H), 7.51-7.30 (9H, m), 7.16 (d, J=16.4 Hz, 1H), 7.00 (d, J=2.0 Hz, 1H). MS: m/z 460.1 (M+H$^+$).

Example 63: 6-Chloro-3-[3-(5,6-dichloro-1H-benzo-imidazol-2-yl)-acryloyl]-4-phenyl-1H-quinolin-2-one

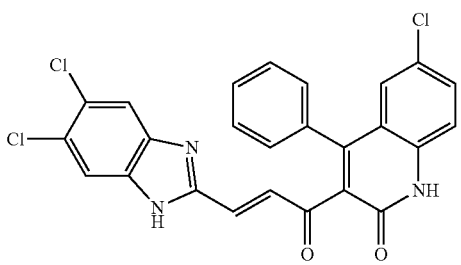 [SMILES: O=C(/C=C/c1nc2cc(Cl)c(Cl)cc2[nH]1)c1c(-c2ccccc2)c2cc(Cl)ccc2[nH]c1=O]

This compound was prepared as described in Example 61. 
¹H NMR (DMSO-d₆, 400 MHz): δ=12.47 (brs, 1H), 7.92-7.89 (m, 2H), 7.68 (d, J=8.8, 2.4 Hz, 1H), 7.50-7.38 (m, 5H), 7.34-7.32 (m, 3H), 7.10 (d, J=16.4 Hz, 1H), 7.00 (d, J=2.0 Hz, 1H). MS: m/z 494.1 (M+H⁺).

Example 64: 6-Chloro-3-[3-(5,6-dichloro-1-ethyl-1H-benzoimidazol-2-yl)-acryloyl]-4-phenyl-1H-quinolin-2-one

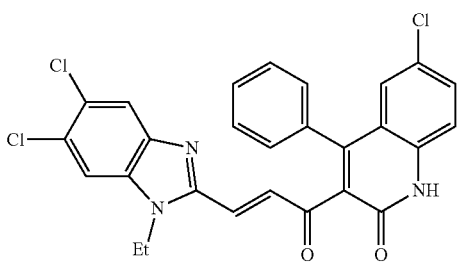 [SMILES: CCn1c(/C=C/C(=O)c2c(-c3ccccc3)c3cc(Cl)ccc3[nH]c2=O)nc2cc(Cl)c(Cl)cc21]

This compound was prepared as described in Example 61. 
¹HNMR (400 MHz, DMSO-d₆): δ=12.45 (brs, 1H), 8.09 (s, 1H), 7.96 (s, 1H), 7.71-7.64 (m, 1H), 7.56-7.45 (m, 5H), 7.37-7.33 (m, 2H), 7.25 (d, J=16.2 Hz, 1H), 7.01 (d, J=2.4 Hz, 1H), 4.45 (q, J=6.9 Hz, 2H), 1.22 (t, J=6.9 Hz, 3H). MS: m/z 522.1 (M+H⁺).

Example 65: 6-Chloro-3-[3-(5-methoxy-1H-benzo-imidazol-2-yl)-acryloyl]-4-phenyl-1H-quinolin-2-one

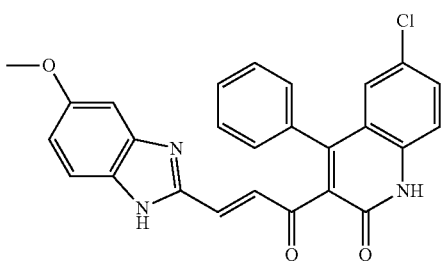 [SMILES: COc1ccc2[nH]c(/C=C/C(=O)c3c(-c4ccccc4)c4cc(Cl)ccc4[nH]c3=O)nc2c1]

This compound was prepared as described in Example 61. 
¹HNMR (400 MHz, DMSO-d₆): δ=12.72 (brs, 1H), 12.45 (brs, 1H), 7.68 (dd, J=6.6, 1.8 Hz, 1H), 7.54-7.44 (m, 5H), 7.40-7.30 (m, 4H), 7.15-6.84 (m, 3H), 3.80 (s, 3H). MS: m/z 456.1 (M+H⁺).

Example 66: 3-[(2E)-3-(5-methoxy(3-pyridyl))prop-2-enoyl]-6-chloro-4-phenylhydroquinolin-2-one

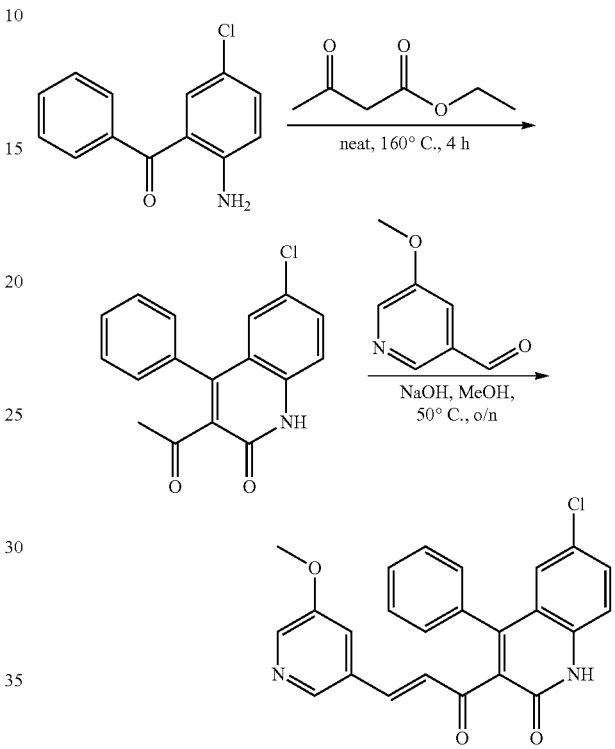

Step 1:

The mixture of (2-amino-5-chloro-phenyl)-phenyl-methanone (9.26 g, 40 mmol) and 3-oxo-butyric acid ethyl ester (20 g, 160 mmol) was heated to 160° C. with stirring for 4 hrs. The reaction was cooled to room temperature. The resulting yellow solid was collected by filtration and recrystallized from EtOH to afford 3-acetyl-6-chloro-4-phenyl-1H-quinolin-2-one (11.05 g, yield: 93%) as a white solid. ¹HNMR (400 MHz, CD₃OD): δ=7.59-7.52 (m, 4H), 7.40 (d, J=9.2 Hz, 1H), 7.37-7.32 (m, 2H), 7.12 (s, 1H), 2.20 (s, 3H).

Step 2:

3-Acetyl-6-chloro-4-phenyl-1H-quinolin-2-one (60.0 mg, 0.20 mmol), 5-methoxynicotinaldehyde (55 mg, 0.40 mmol) and NaOH (16 mg 0.40 mmol) was dissolved in MeOH (20 mL). The mixture was stirred at 50° C. overnight. After cooled to room temperature, the mixture was concentrated and the residue was dissolved in EtOAc (30 mL). The mixture was washed with NH₄Cl solution and brine, and dried over Na₂SO₄. The solution was concentrated to dryness and the residue was purified by prep-TLC (DCM/MeOH=20/1) to afford 3-[(2E)-3-(5-bromo(3-pyridyl))prop-2-enoyl]-6-chloro-4-phenylhydroquinolin-2-one (30 mg, yield: 36%) as a yellow solid. ¹HNMR (400 MHz, DMSO-d₆): δ=12.39 (s, 1H), 8.42 (s, 1H), 8.29 (s, 1H), 7.71-7.65 (m, 2H), 7.57-7.33 (m, 7H), 7.01-6.95 (m, 2H), 3.36 (s, 3H). MS: m/z 417.0 (M+H⁺).

Example 67: 6-Chloro-3-[3-(5-fluoro(3-pyridyl))propanoyl]-4-phenylhydroquinolin-2-one

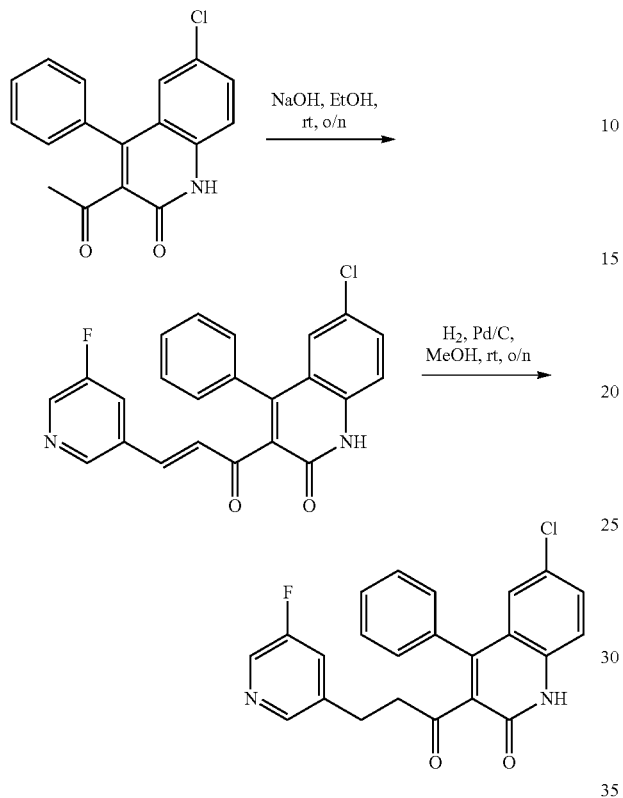

Step 1:

To a solution of 3-acetyl-6-chloro-4-phenyl-1H-quinolin-2-one (100 mg, 0.34 mmol) in EtOH (20 mL) was added 5-fluoro-pyridine-3-carbaldehyde (46 mg, 0.37 mmol) and NaOH (16 mg, 0.40 mmol). Then the mixture was stirred at room temperature overnight. LC/MS monitored the reaction. Resultant was concentrated to dryness and the residue was dissolved in DMF (2 mL), purified by Combi Flash (MeCN in water: 5% to 95%; 30 min) to afford 6-chloro-3-[3-(5-fluoro-pyridin-3-yl)-acryloyl]-4-phenyl-1H-quinolin-2-one (61 mg, yield: 45%) as a yellow solid. $^1$HNMR (400 MHz, DMSO-d6): δ=12.40 (s, 1H), 8.71 (s, 1H), 8.58 (d, J=2.4 Hz, 1H), 8.12 (d, J=9.6 Hz, 1H), 7.68 (dd, J=8.4, 2.0 Hz, 1H), 7.58 (d, J=8.0 Hz, 1H), 7.94-7.42 (m, 4H), 7.34-7.32 (m, 2H), 7.00-6.96 (m, 2H). MS: m/z 405.2 (M+H$^+$).

Step 2:

To a solution of 6-chloro-3-[3-(5-fluoro-pyridin-3-yl)-acryloyl]-4-phenyl-1H-quinolin-2-one (30 mg, 0.07 mmol) in MeOH (10 mL) was added Pd/C (6 mg). Then the mixture was purged with N$_2$, and H$_2$ in succession for three times. It was then stirred under H$_2$ balloon at room temperature overnight. LC/MS monitored the reaction. Resultant was filtered and the filtrate was purified by Pre-HPLC to afford 6-chloro-3-[3-(5-fluoro(3-pyridyl))propanoyl]-4-phenylhydroquinolin-2-one (16 mg, yield: 53%) as a white solid. $^1$HNMR (300 MHz, DMSO-d6): δ=12.41 (s, 1H), 8.34 (d, J=2.7 Hz, 1H), 8.16 (s, 1H), 7.66-7.62 (m, 1H), 7.45-7.27 (m, 7H), 6.93 (d, J=2.1 Hz, 1H), 2.96 (t, J=6.9 Hz, 2H), 2.71 (t, J=6.9 Hz, 2H). MS: m/z 407.2 (M+H$^+$).

Example 68: 3-(3-1H-Benzoimidazol-2-yl-propionyl)-6-chloro-4-phenyl-1H-quinolin-2-one

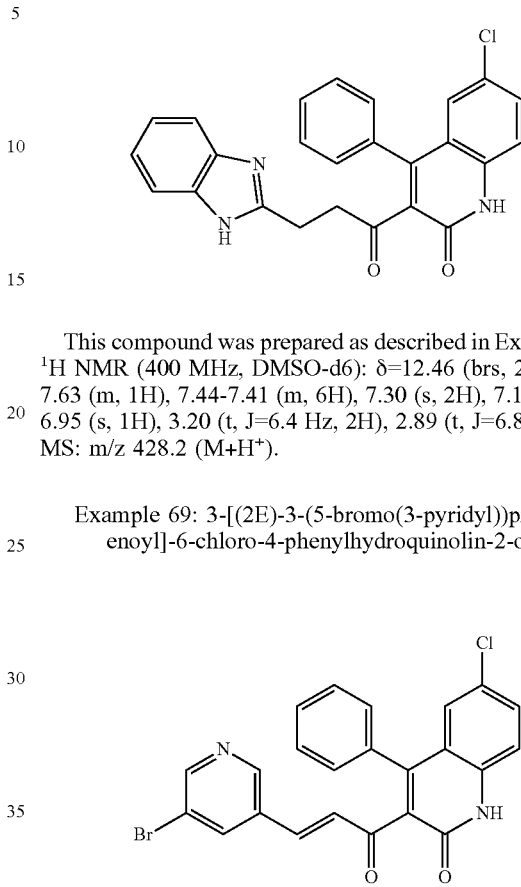

This compound was prepared as described in Example 67. $^1$H NMR (400 MHz, DMSO-d6): δ=12.46 (brs, 2H), 7.65-7.63 (m, 1H), 7.44-7.41 (m, 6H), 7.30 (s, 2H), 7.12 (s, 2H), 6.95 (s, 1H), 3.20 (t, J=6.4 Hz, 2H), 2.89 (t, J=6.8 Hz, 2H). MS: m/z 428.2 (M+H$^+$).

Example 69: 3-[(2E)-3-(5-bromo(3-pyridyl))prop-2-enoyl]-6-chloro-4-phenylhydroquinolin-2-one

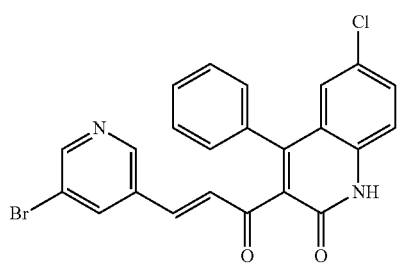

This compound was prepared as described in Example 66. $^1$HNMR (400 MHz, DMSO-d$_6$): δ=12.39 (s, 1H), 8.83 (s, 1H), 8.70 (s, 1H), 8.44 (s, 1H), 7.69-7.66 (m, 1H), 7.54-7.42 (m, 5H), 7.34-7.32 (m, 2H), 7.03-6.98 (m, 2H). MS: m/z 464.9 (M+H$^+$).

Example 69: 3-[(2E)-3-(5-chloro(3-pyridyl))prop-2-enoyl]-6-chloro-4-phenylhydroquinolin-2-one

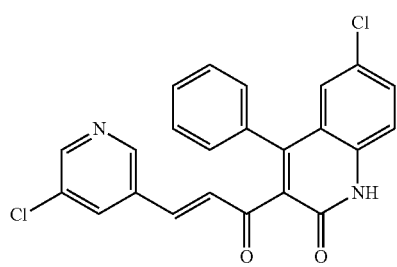

This compound was prepared as described in Example 66. $^1$HNMR (400 MHz, CDCl$_3$): δ=12.40 (s, 1H), 8.83 (s, 1H), 8.80 (s, H), 8.62 (s, 1H), 7.69-7.66 (m, 1H), 7.56-7.44 (m, 5H), 7.34-7.32 (m, 2H), 7.04-6.98 (m, 2H). MS: m/z 421.0 (M+H$^+$).

Example 70: 3-[(2E)-3-(4-methyl(2-pyridyl))prop-2-enoyl]-6-chloro-4-phenylhydroquinolin-2-one

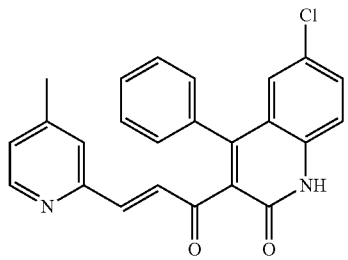

This compound was prepared as described in Example 66. ¹HNMR (400 MHz, CDCl₃): δ=12.41 (s, 1H), 8.46 (d, J=4.8 Hz, 1H), 7.69-7.66 (m, 1H), 7.56 (s, 1H), 7.50-7.44 (m, 6H), 7.33-7.23 (m, 3H), 7.02-6.98 (m, 2H). MS: m/z 401.0 (M+H⁺).

Example 71: 3-[(2E)-3-(4-chloro(2-pyridyl))prop-2-enoyl]-6-chloro-4-phenylhydroquinolin-2-one

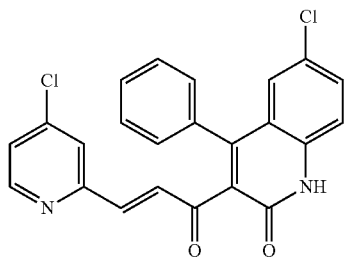

This compound was prepared as described in Example 66. ¹HNMR (400 MHz, CDCl₃): δ=12.59 (s, 1H), 8.64 (s, 1H), 7.97 (s, 1H), 7.74-7.72 (m, 1H), 7.63-7.50 (m, 6H), 7.39-7.38 (m, 2H), 7.14-7.04 (m, 2H). MS: m/z 421.0 (M+H⁺).

Example 72: 5-[(1E)-3-(6-chloro-2-oxo-4-phenyl(3-hydroquinolyl))-3-oxoprop-1-enyl]pyridine-3-carbonitrile

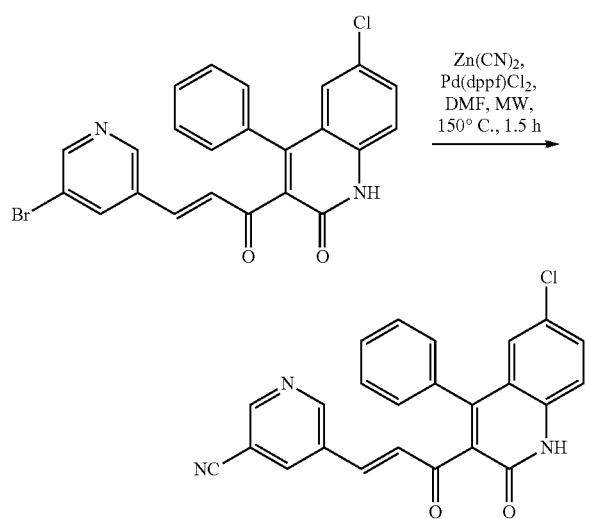

A suspension of 3-[3-(5-bromo-pyridin-3-yl)-acryloyl]-6-chloro-4-phenyl-1H-quinolin-2-one (28 mg, 0.06 mmol), Zinc cyanide (21 mg, 0.18 mmol) and Pd(dppf)Cl₂ (4.4 mg, 0.006 mmol) in DMF (1.5 mL) was purged with N₂ for several minutes. Then the vial was irradiated under microwave at 150° C. for 1.5 hrs. The reaction solution was concentrated to remove the solvent and the residue was dissolved in EtOAc (15 mL). The mixture was washed with water (15 mL), brine (15 mL), and dried over Na₂SO₄. The solution was concentrated to dryness and the residue was purified by prep-TLC (DCM/MeOH=20/1) to afford 5-[(1E)-3-(6-chloro-2-oxo-4-phenyl(3-hydroquinolyl))-3-oxoprop-1-enyl]pyridine-3-carbonitrile (8 mg, yield: 32%) as a yellow solid.

¹HNMR (400 MHz, CD₃OD): δ=8.91 (s, 1H), 8.85 (s, 1H), 8.80 (s, 1H), 840 (s, 1H), 7.62-7.60 (m, 1H), 7.51-7.44 (m, 5H), 7.36-7.33 (m, 2H), 7.19 (s, 1H), 6.98-6.94 (m, 1H). MS: m/z 411.8 (M+H⁺).

Example 73: 3-{(2E)-3-[5-(methoxymethyl)(3-pyridyl)]prop-2-enoyl}-6-chloro-4-phenylhydroquinolin-2-one

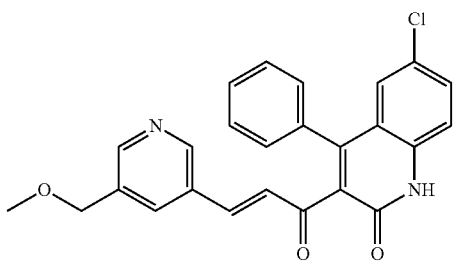 [SMILES: COCc1cncc(/C=C/C(=O)c2c(-c3ccccc3)c3cc(Cl)ccc3[nH]c2=O)c1]

This compound was prepared as described in Example 66. ¹HNMR (400 MHz, DMSO-d₆): δ=12.38 (s, 1H), 8.77 (s, 1H), 8.53 (s, 1H), 8.06 (s, 1H), 7.68-7.35 (m, 8H), 7.00-6.91 (m, 2H), 4.45 (s, 2H), 3.77 (s, 3H). MS: m/z 431.0 (M+H⁺).

Example 74: 3-[(2E)-3-(5-methyl(3-pyridyl))prop-2-enoyl]-6-chloro-4-phenylhydroquinolin-2-one

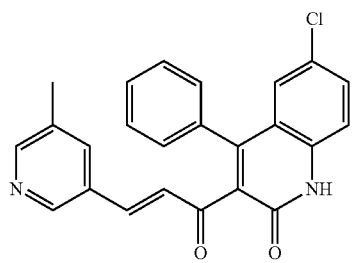 [SMILES: Cc1cncc(/C=C/C(=O)c2c(-c3ccccc3)c3cc(Cl)ccc3[nH]c2=O)c1]

This compound was prepared as described in Example 66. 1HNMR (400 MHz, DMSO-d₆): δ=12.40 (s, 1H), 8.61 (s, 1H), 8.41 (s, 1H), 7.95 (s, 1H), 7.66 (dd, J=8.8, 2.4 Hz, 1H), 7.53-7.30 (m, 7H), 6.98 (d, J=2.0 Hz, 1H), 6.87 (d, J=16.8 Hz, 1H), 2.29 (s, 3H). MS: m/z 401.1 (M+H⁺).

Example 75: 3-[(2E)-3-(4-methoxy(2-pyridyl))prop-2-enoyl]-6-chloro-4-phenylhydroquinolin-2-one

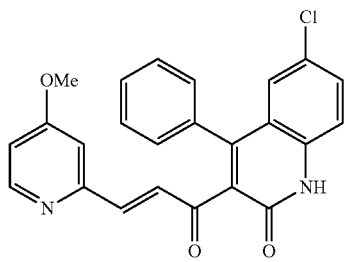 [SMILES: COc1ccnc(/C=C/C(=O)c2c(-c3ccccc3)c3cc(Cl)ccc3[nH]c2=O)c1]

This compound was prepared as described in Example 66. $^1$HNMR (400 MHz, DMSO-d$_6$): δ=12.39 (s, 1H), 8.40 (s, J=6.0 Hz, 1H), 7.66 (dd, J=8.8, 2.4 Hz, 1H), 7.50-7.41 (m, 5H), 7.34-7.30 (m, 3H), 7.04-6.94 (m, 3H), 3.83 (s, 3H). MS: m/z 417.0 (M+H$^+$).

Example 76: 3-{(2E)-3-[5-(trifluoromethyl)(3-pyridyl)]prop-2-enoyl}-6-chloro-4-phenylhydroquinolin-2-one

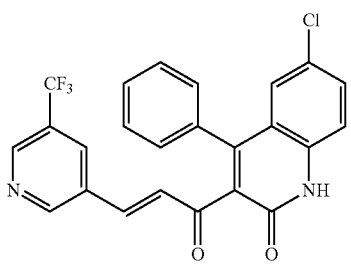

This compound was prepared as described in Example 66. $^1$HNMR (400 MHz, DMSO-d$_6$): δ=12.40 (s, 1H), 9.15 (s, 1H), 8.96 (s, 1H), 8.56 (s, 1H), 7.70-7.61 (m, 2H), 7.51-7.42 (m, 4H), 7.36-7.33 (m, 2H), 7.13 (d, J=16.0 Hz, 1H), 6.99 (m, d, J=2.4 Hz, 1H). MS: m/z 455.0 (M+H$^+$).

Example 77: 3-[(2E)-3-(5-fluoro(3-pyridyl))prop-2-enoyl]-6-chloro-4-(4-fluorophenyl)hydroquinolin-2-one

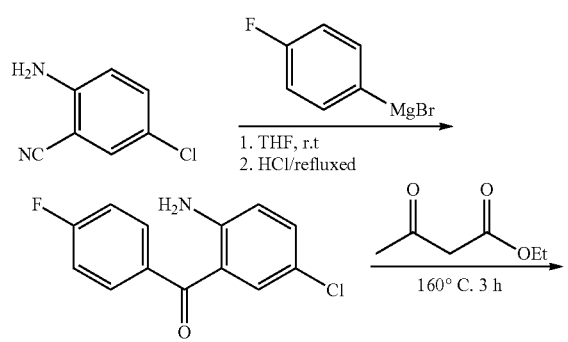

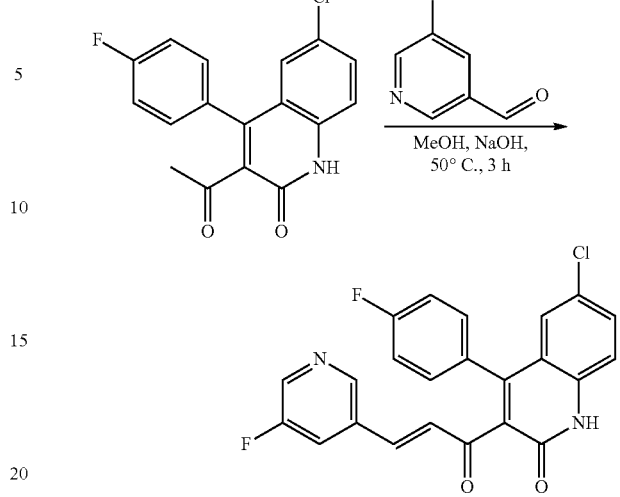

Step 1:

To a solution of (4-fluorophenyl)magnesium bromide (30 mL, 30 mmol) in anhydrous THF (15 mL) was added 2-amino-5-chloro-benzonitrile (1.53 g, 10.0 mmoL) portionwise at 0° C. After the addition, the mixture was stirred at room temperature overnight. The reaction was quenched with 1 N HCl (30 mL) and reflux for 1 hr. The aqueous phase was extracted with DCM (30 mL×2). The extracts were dried over Na$_2$SO$_4$ and concentrated to dryness. The residue was purified by silica gel column (PE/EtOAc=10/1) to give (2-amino-5-chlorophenyl)(4-fluorophenyl)methanone (1.8 g, yield: 72%) as a yellow solid. $^1$HNMR (400 MHz, DMSO-d$_6$): δ=7.67 (dd, J=8.8, 5.2 Hz, 2H), 7.37 (d, J=2.8 Hz, 1H), 7.25 (dd, J=8.0, 2.4 Hz, 1H), 7.17 (d, J=8.4 Hz, 2H), 6.70 (d, J=8.8 Hz, 1H), 5.99 (brs, 2H).

Step 2:

The mixture of (2-amino-5-chlorophenyl)(4-fluorophenyl)methanone (1.8 g, 7.22 mmol) and 3-oxo-butyric acid ethyl ester (3 mL) was heated to 160° C. with stirring for 3 hrs. After cooled to room temperature, the mixture was filtered. The filtrate cake was washed with EtOH (5 mL) to afford 3-acetyl-6-chloro-4-(4-fluorophenyl)quinolin-2(1H)-one (1.06 g, yield: 47%) as a white solid. $^1$HNMR (400 MHz, DMSO-d$_6$): δ=12.41 (s, 1H), 7.64 (dd, J=8.4, 2.0 Hz, 2H), 7.45-7.35 (m, 5H), 6.95 (d, J=2.0 Hz, 1H), 2.24 (s, 3H).

Step 3:

The mixture of 3-acetyl-6-chloro-4-(4-fluorophenyl)quinolin-2(1H)-one (105 mg, 0.33 mmol), 5-fluoronicotinaldehyde (83 mg, 0.67 mmol) and NaOH (27 mg, 0.67 mmol) in mMeOH (25 mL) was stirred at 50° C. for 3 hrs. After cooled to room temperature, the mixture was diluted with water (2 mL), and the pH value was adjusted to 8 with 1 M HCl. The precipitate was filtered to afford yellow solid, which was dissolved in DMSO and purified by pre-HPLC to afford 3-[(2E)-3-(5-fluoro(3-pyridyl))prop-2-enoyl]-6-chloro-4-(4-fluorophenyl)hydroquinolin-2-one (29 mg, yield: 37%) as yellow solid. $^1$HNMR (400 MHz, DMSO-d$_6$): δ=12.40 (s, 1H), 8.72 (s, 1H), 8.59 (s, 1H), 8.14-8.12 (m, 1H), 7.69-7.28 (m, 7H), 7.02-6.98 (m, 2H). MS: m/z 423.0 (M+H$^+$).

Example 78: (E)-6-Chloro-4-(4-fluoro-phenyl)-3-(3-pyridin-2-yl-acryloyl)-1H-quinolin-2-one

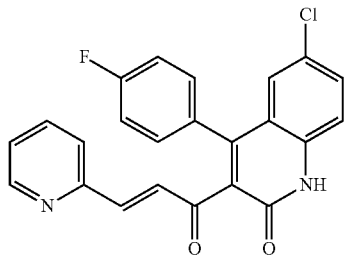 [SMILES: O=C(/C=C/c1ccccn1)c1c(-c2ccc(F)cc2)c2cc(Cl)ccc2[nH]c1=O]

This compound was prepared as described in Example 77. ¹HNMR (400 MHz, DMSO-d$_6$): δ=12.42 (s, 1H), 8.62 (s, 1H), 8.69-7.82 (m, 1H), 7.71-7.66 (m, 2H), 7.53-7.28 (m, 7H), 7.08-7.00 (m, 2H). MS: m/z 405.0 (M+H⁺).

Example 79: 3-[(2E)-3-(5-fluoro(3-pyridyl))prop-2-enoyl]-6-chloro-4-(4-methoxyphenyl)hydroquinolin-2-one

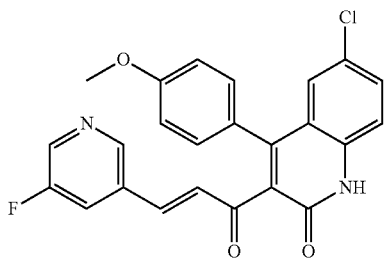 [SMILES: COc1ccc(-c2c(C(=O)/C=C/c3cncc(F)c3)c(=O)[nH]c3ccc(Cl)cc23)cc1]

This compound was prepared as described in Example 77. ¹HNMR (300 MHz, DMSO-d$_6$): δ=12.35 (s, 1H), 8.71 (s, 1H), 8.59 (s, 1H), 8.14-8.11 (m, 1H), 7.67-7.45 (m, 3H), 7.27-7.25 (m, 2H), 7.07-6.97 (m, 4H), 3.76 (s, 3H). MS: m/z 434.7 (M+H⁺).

Example 80: 3-((2E)-3-(2-pyridyl)prop-2-enoyl)-6-chloro-4-(4-methoxyphenyl)hydroquinolin-2-one

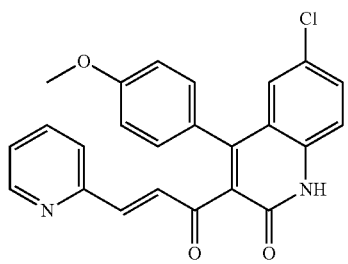

This compound was prepared as described in Example 77. ¹HNMR (300 MHz, DMSO-d$_6$): δ=12.34 (bs, 1H), 8.61 (s, 1H), 7.87-7.81 (m, 1H), 7.71-7.64 (m, 2H), 7.50-7.24 (m, 3H), 7.07-7.05 (m, 2H), 7.02-6.99 (m, 4H), 3.76 (s, 3H). MS: m/z 416.8 (M+H⁺).

Example 81: 3-[(2E)-3-(5-fluoro(3-pyridyl))prop-2-enoyl]-6-chloro-4-(4-chlorophenyl)hydroquinolin-2-one

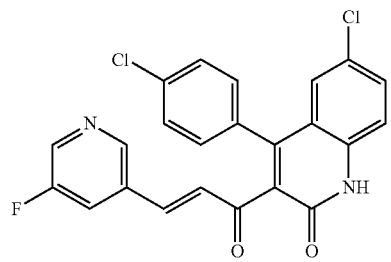

This compound was prepared as described in Example 77. ¹HNMR (400 MHz, DMSO-d$_6$): δ=12.43 (s, 1H), 8.72 (s, 1H), 8.60 (s, 1H), 8.15-8.12 (m, 1H), 7.70-7.48 (m, 5H), 7.38-7.36 (m, 2H), 7.04-7.00 (m, 2H). MS: m/z 439.0 (M+H⁺).

Example 82: 3-((2E)-3-(2-pyridyl)prop-2-enoyl)-6-chloro-4-(4-chlorophenyl)hydroquinolin-2-one

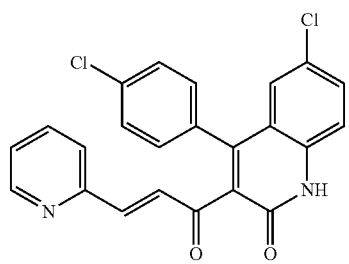

This compound was prepared as described in Example 77. ¹HNMR (400 MHz, DMSO-d$_6$): δ=12.49 (s, 1H), 8.68 (s, 1H), 7.91-7.73 (m, 3H), 7.60-7.14 (m, 7H), 7.15-7.05 (m, 2H). MS: m/z 421.0 (M+H⁺).

Example 83: 3-[(2E)-3-(5-fluoro(3-pyridyl))prop-2-enoyl]-6-chloro-4-[4-(trifluoromethyl)phenyl]hydroquinolin-2-one

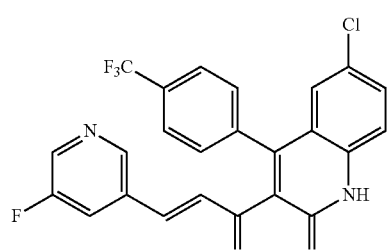

This compound was prepared as described in Example 77. ¹HNMR (400 MHz, DMSO-d$_6$): δ=12.48 (s, 1H), 8.73 (s, 1H), 8.60 (s, 1H), 8.15-8.12 (m, 1H), 7.86-7.50 (m, 7H), 7.07-7.03 (m, 1H), 6.95 (s, 1H). MS: m/z 473.0 (M+H⁺).

Example 84: 3-((2E)-3-(2-pyridyl)prop-2-enoyl)-6-chloro-4-[4-(trifluoromethyl)phenyl]hydroquinolin-2-one

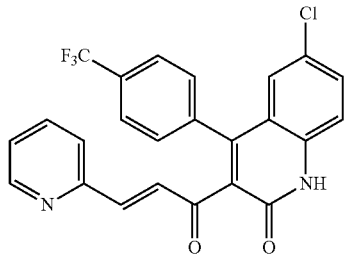

This compound was prepared as described in Example 77. 1HNMR (400 MHz, DMSO-$d_6$): δ=12.47 (s, 1H), 8.62 (d, J=4.0 Hz, 1H), 7.87-7.84 (m, 3H), 7.71-7.39 (m, 7H), 7.10 (d, J=16 Hz, 1H), 6.94 (s, 1H). MS: m/z 455.0 (M+H$^+$).

Example 85: 3-[(2E)-3-(5-fluoro(3-pyridyl))prop-2-enoyl]-6-chloro-4-(4-methylphenyl)hydroquinolin-2-one

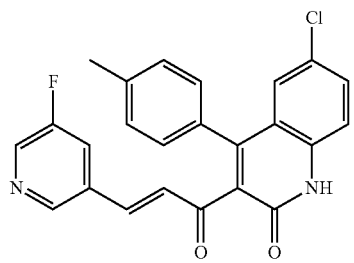

This compound was prepared as described in Example 77. $^1$HNMR (400 MHz, DMSO-d6): δ=12.36 (s, 1H), 8.71 (s, 1H), 8.58 (d, J=2.4 Hz, 1H), 8.13 (dd, J=10.4, 2.0 Hz, 1H), 7.66 (dd, J=8.8, 2.0 Hz, 1H), 7.56 (d, J=16 Hz, 1H), 7.47 (d, J=8.8 Hz, 1H), 7.26-7.20 (m, 4H), 7.01-6.97 (m, 2H), 2.32 (s, 3H). MS: m/z 419.2 (M+H$^+$).

Example 86: 3-((2E)-3-(2-pyridyl)prop-2-enoyl)-6-chloro-4-(4-methylphenyl)hydroquinolin-2-one

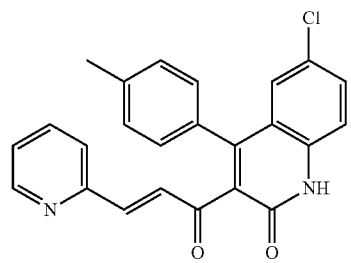 [SMILES: Cc1ccc(-c2c(C(=O)/C=C/c3ccccn3)c(=O)[nH]c3ccc(Cl)cc23)cc1]

This compound was prepared as described in Example 77. $^1$HNMR (400 MHz, DMSO-d6): δ=12.37 (s, 1H), 8.61 (d, J=4.0 Hz, 1H), 7.84-7.83 (m, 1H), 7.82-7.64 (m, 2H), 7.50-7.46 (m, 2H), 7.41-7.38 (m, 1H), 7.39-7.20 (m, 4H), 7.06-7.01 (m, 2H), 2.32 (s, 3H). MS: m/z 401.2 (M+H$^+$).

Example 87: 3-[(2E)-3-(5-fluoro(3-pyridyl))prop-2-enoyl]-6-chloro-4-[4-(trifluoromethoxy)phenyl]hydroquinolin-2-one

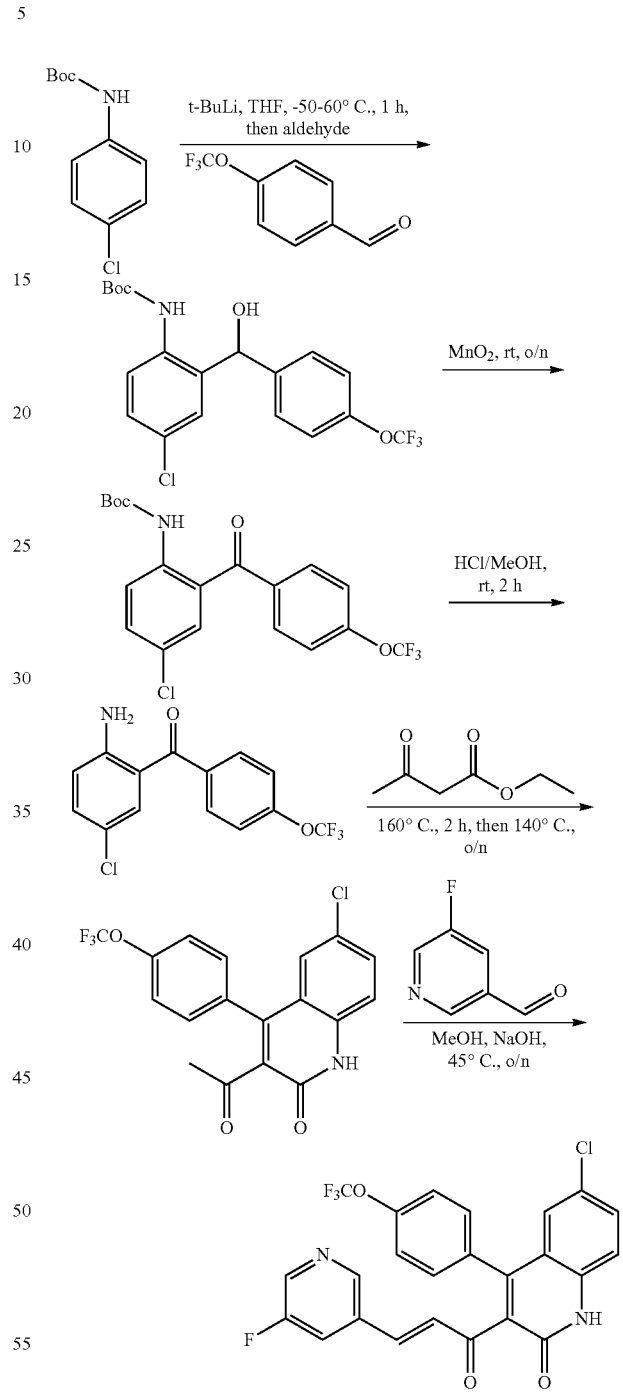

Step 1:

To a solution of (4-chloro-phenyl)-carbamic acid tert-butyl ester (1.0 g, 4.4 mmol) in anhydrous THF (15 mL) was added dropwise t-BuLi (9.1 mL, 1.3 M in pentanes) at −78° C. under N$_2$. The solution was stirred at −50° C.−−60° C. for 1 hour. Then a solution of 4-(trifluoromethoxy)benzaldehyde (0.836 g, 4.4 mmol) in THF (10 mL) was added to the mixture dropwise at −78° C. The mixture was allowed to warm to room temperature and stirred overnight. The mixture was quenched with aqueous NH₄Cl (20 mL) and extracted with EA (50 mL×3). The organic layers were dried over Na₂SO₄ and concentrated to dryness. The residue was purified by silica gel column (PE/EA=5/1) to afford tert-butyl (4-chloro-2-(hydroxy(4-(trifluoromethoxy)phenyl)methyl)phenyl)carbamate (520 mg, yield: 28%) as yellow solid. ¹HNMR (400 MHz, CDCl₃): δ=7.72 (d, J=8.8 Hz, 1H), 7.44 (brs, 1H), 7.35 (d, J=8.8 Hz, 2H), 7.28-7.20 (m, 1H), 7.19 (d, J=8.4 Hz, 2H), 7.07 (d, J=2.4 Hz, 1H), 5.84 (d, J=2.8 Hz, 1H), 3.19 (d, J=3.6 Hz, 1H).

Step 2:

To a solution of tert-butyl (4-chloro-2-(hydroxy(4-(trifluoromethoxy)phenyl)methyl)phenyl)carbamate (520 mg, 1.25 mmol) in DCM (40 mL) was added MnO₂ (435 mg, 5.0 mmol), and the suspension was stirred at room temperature overnight. The mixture was filtered and the filtrate was concentrated to give tert-butyl (4-chloro-2-(4-(trifluoromethoxy)benzoyl)phenyl)carbamate (540 mg, quantitatively) as a yellow solid. ¹HNMR (400 MHz, CDCl₃): δ=9.74 (brs, 1H), 8.39 (d, J=8.8 Hz, 1H), 7.77 (d, J=8.4 Hz, 2H), 7.50 (dd, J=8.8, 2.4 Hz, 1H), 7.44 (d, J=2.4 Hz, 1H), 7.34 (d, J=8.4 Hz, 2H).

Step 3:

The mixture of tert-butyl (4-chloro-2-(4-(trifluoromethoxy)benzoyl)phenyl)carbamate (540 mg, 1.25 mmol) and HCl/MeOH (40 mL) was stirred at room temperature for 2 hrs. The solvent was removed and the residue was dissolved in EtOAc (30 mL). The pH value was adjusted with 1N aqueous NaOH to 7-8. The organic layer was washed with brine (30 mL×2) and dried over Na₂SO₄. The solution was concentrated to give (2-amino-5-chlorophenyl)(4-(trifluoromethoxy)phenyl)methanone (386 mg, yield: 97%) as a yellow solid. MS: m/z 316.1 (M+H⁺).

Step 4:

The mixture of (2-amino-5-chlorophenyl)(4-(trifluoromethoxy)phenyl)methanone (386 mg, 1.23 mmol) and ethyl 3-oxobutanoate (2 mL) was stirred at 160° C. for 2 hrs, then at 140° C. overnight. The resulting solid was collected by filtration and air dried to afford 3-acetyl-6-chloro-4-(4-(trifluoromethoxy)phenyl)quinolin-2(1H)-one (207 mg, 54%) as a yellow solid. MS: m/z 381.5 (M+H⁺).

Step 5:

To a solution of 3-acetyl-6-chloro-4-(4-(trifluoromethoxy)phenyl)quinolin-2(1H)-one (100 mg, 0.26 mmol) in MeOH (20 mL) was added 5-fluoronicotinaldehyde (65 mg, 0.520 mmol) and NaOH (21 mg 0.52 mmol), and the mixture was stirred at 45° C. overnight. After cooled to room temperature, the mixture was concentrated and the residue was dissolved in EtOAc (30 mL). The mixture was washed with NH₄Cl solution (20 mL) and brine (20 mL), and dried over Na₂SO₄. The solution was concentrated to dryness and the residue was purified by prep-TLC (DCM/MeOH=20/1) to afford 3-[(2E)-3-(5-fluoro(3-pyridyl))prop-2-enoyl]-6-chloro-4-[4-(trifluoromethoxy)phenyl]hydroquinolin-2-one (28 mg, yield: 22%) as a yellow solid. ¹HNMR (400 MHz, DMSO-d₆): δ=12.44 (s, 1H), 8.71 (s, 1H), 8.60 (s, 1H), 8.13-8.11 (m, 1H), 7.70-7.45 (m, 7H), 7.04 (d, 1H), 7.00-6.98 (m, 1H). MS: m/z 489.0 (M+H⁺).

Example 88: 3-((2E)-3-(2-pyridyl)prop-2-enoyl)-6-chloro-4-[4-(trifluoromethoxy)phenyl]hydroquinolin-2-one

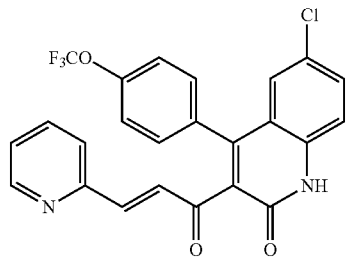

This compound was prepared as described in Example 87. ¹HNMR (400 MHz, DMSO-d₆): δ=12.44 (s, 1H), 8.61 (s, 1H), 7.87-7.83 (m, 1H), 7.70-7.67 (m, 2H), 7.55-7.39 (m, 7H), 7.07 (d, J=16 Hz, 1H), 6.97 (s, 1H). MS: m/z 471.0 (M+H⁺).

Example 89: 4-[3-((2E)-3-(2-pyridyl)prop-2-enoyl)-6-chloro-2-oxo-4-hydroquinolyl]benzenecarbonitrile

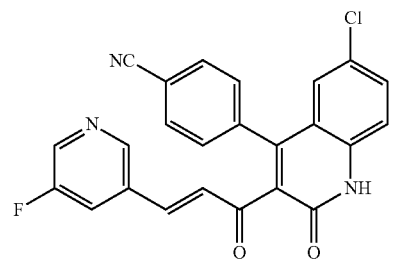

This compound was prepared as described in Example 87. ¹HNMR (300 MHz, DMSO-d₆): δ=12.49 (s, 1H), 8.72 (s, 1H), 8.60 (s, 1H), 8.15-8.12 (m, 1H), 7.96-7.94 (m, 2H), 7.71-7.48 (m, 5H), 7.08 (d, J=16.8 Hz, 1H), 6.94 (s, 1H). MS: m/z 430.0 (M+H⁺).

Example 90: 4-[3-((2E)-3-(2-pyridyl)prop-2-enoyl)-6-chloro-2-oxo-4-hydroquinolyl]benzenecarbonitrile

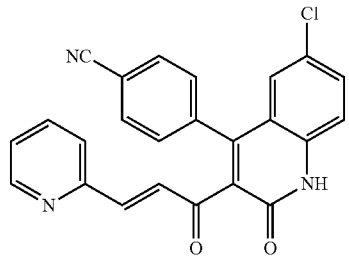

This compound was prepared as described in Example 87. ¹HNMR (400 MHz, DMSO-d₆): δ=12.50 (s, 1H), 8.62 (d, J=3.6 Hz, 1H), 7.96-7.86 (m, 3H), 7.71-7.42 (m, 7H), 7.10 (d, J=15.6 Hz, 1H), 6.94 (s, 1H). MS: m/z 412.0 (M+H⁺).

Example 91: 3-[(2E)-3-(5-fluoro(3-pyridyl))prop-2-enoyl]-4-(4-bromophenyl)-6-chlorohydroquinolin-2-one

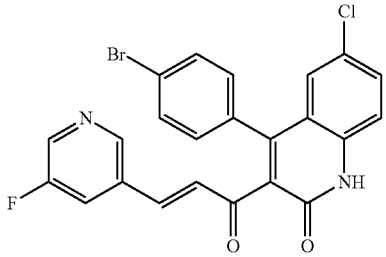 [SMILES: O=C(/C=C/c1cncc(F)c1)c1c(-c2ccc(Br)cc2)c2cc(Cl)ccc2[nH]c1=O]

This compound was prepared as described in Example 87. ¹HNMR (400 MHz, CDCl₃): δ=12.16 (s, 1H), 8.47 (s, 2H), 7.62-7.60 (m, 2H), 7.51-7.48 (m, 2H), 7.38-7.36 (m, 2H), 7.26-7.17 (m, 3H), 6.87 (d, J=16 Hz, 1H). MS: m/z 482.9 (M+H⁺).

Example 92: 3-((2E)-3-(2-pyridyl)prop-2-enoyl)-4-(4-bromophenyl)-6-chlorohydroquinolin-2-one

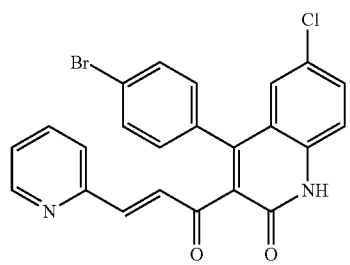

This compound was prepared as described in Example 87. ¹HNMR (400 MHz, DMSO-d₆): δ=12.43 (s, 1H), 8.63 (s, 1H), 7.85-7.83 (m, 1H), 7.71-7.66 (m, 4H), 7.54-7.28 (m, 5H), 7.08 (d, J=16 Hz, 1H), 6.99 (s, 1H). MS: m/z 464.9 (M+H⁺).

Example 93: 3-[(2E)-3-(5-fluoro(3-pyridyl))prop-2-enoyl]-6-chloro-4-(4-methyl(2-pyridyl))hydroquinolin-2-one

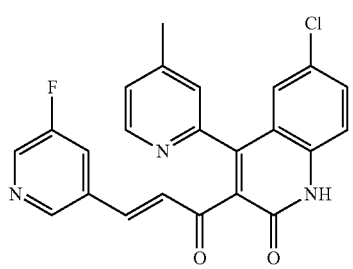 [SMILES: Cc1ccnc(-c2c(C(=O)/C=C/c3cncc(F)c3)c(=O)[nH]c3ccc(Cl)cc23)c1]

This compound was prepared as described in Example 87. ¹HNMR (400 MHz, DMSO-d₆): δ=12.46 (s, 1H), 8.69 (s, 1H), 8.59 (d, J=2.8 Hz, 1H), 8.49 (d, J=4.8 Hz, 1H), 8.12 (d, J=10.8 Hz, 1H), 7.67 (dd, J=8.8, 1.6 Hz, 1H), 7.50-7.45 (m, 2H), 7.34 (s, 1H), 7.26 (d, J=4.8 Hz, 1H), 7.11-7.04 (m, 2H), 2.31 (s, 3H). MS: m/z 419.8 (M+H⁺).

Example 94: 3-((2E)-3-(2-pyridyl)prop-2-enoyl)-6-chloro-4-(4-methyl(2-pyridyl))hydroquinolin-2-one

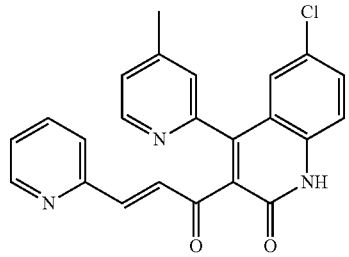 [SMILES: Cc1ccnc(-c2c(C(=O)/C=C/c3ccccn3)c(=O)[nH]c3ccc(Cl)cc23)c1]

This compound was prepared as described in Example 87. ¹HNMR (400 MHz, DMSO-d₆): δ=12.45 (s, 1H), 8.62 (d, J=4.4 Hz, 1H), 8.49 (d, J=4.8 Hz, 1H), 7.84 (t, J=7.8 Hz, 1H), 7.70-7.65 (m, 2H), 7.48 (d, J=8.8 Hz, 1H), 7.42-7.25 (m, 4H), 7.15-7.10 (m, 2H), 2.29 (s, 3H). MS: m/z 402.0 (M+H⁺).

Example 95: 3-[(2E)-3-(5-fluoro(3-pyridyl))prop-2-enoyl]-6-chloro-4-(5-methyl(3-pyridyl))hydroquinolin-2-one

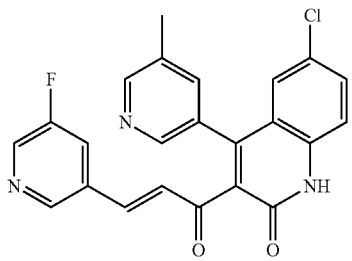 [SMILES: Cc1cncc(-c2c(C(=O)/C=C/c3cncc(F)c3)c(=O)[nH]c3ccc(Cl)cc23)c1]

This compound was prepared as described in Example 87. 1HNMR (400 MHz, DMSO-d₆): δ=12.47 (s, 1H), 8.73 (s, 1H), 8.61 (d, J=2.0 Hz, 1H), 8.47 (s, 1H), 8.32 (s, 1H), 8.13 (d, J=11.6 Hz, 1H), 7.72-7.68 (m, 1H), 7.64-7.57 (m, 2H), 7.49 (d, J=8.4 Hz, 1H), 7.06-6.98 (m, 2H), 2.29 (s, 3H). MS: m/z 420.0 (M+H⁺).

Example 96: 3-((2E)-3-(2-pyridyl)prop-2-enoyl)-6-chloro-4-(5-methyl(3-pyridyl))hydroquinolin-2-one

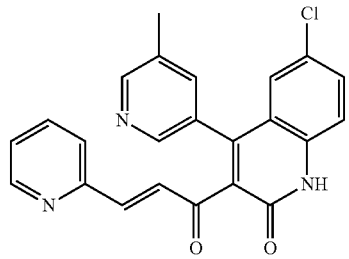 [SMILES: Cc1cncc(-c2c(C(=O)/C=C/c3ccccn3)c(=O)[nH]c3ccc(Cl)cc23)c1]

This compound was prepared as described in Example 87. ¹HNMR (400 MHz, DMSO-d₆): δ=12.49 (s, 1H), 8.63 (d, J=3.6 Hz, 1H), 8.47 (s, 1H), 8.32 (s, 1H), 7.86 (t, J=12.8 Hz, 1H), 7.72-7.67 (m, 2H), 7.63 (s, 1H), 7.56-7.39 (m, 3H), 7.07 (d, J=16.4 Hz, 1H), 6.98 (d, J=2.4 Hz, 1H), 2.29 (s, 3H). MS: m/z 401.8 (M+H$^+$).

Example 97: 3-[(2E)-3-(5-fluoro(3-pyridyl))prop-2-enoyl]-6-chloro-4-(5-methoxy(3-pyridyl))hydroquinolin-2-one

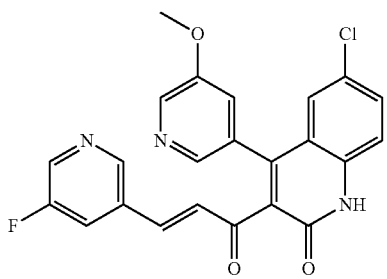 [SMILES: COc1cncc(-c2c(C(=O)/C=C/c3cncc(F)c3)c(=O)[nH]c3ccc(Cl)cc23)c1]

This compound was prepared as described in Example 87. $^1$HNMR (400 MHz, DMSO-d$_6$): δ=12.48 (s, 1H), 8.74 (s, 1H), 8.61 (s, 1H), 8.36 (s, 1H), 8.16-8.11 (m, 2H), 7.71-7.45 (m, 4H), 7.07-7.04 (m, 2H), 3.77 (s, 3H). MS: m/z 436.0 (M+H$^+$).

Example 98: 3-((2E)-3-(2-pyridyl)prop-2-enoyl)-6-chloro-4-(5-methoxy(3-pyridyl))hydroquinolin-2-one

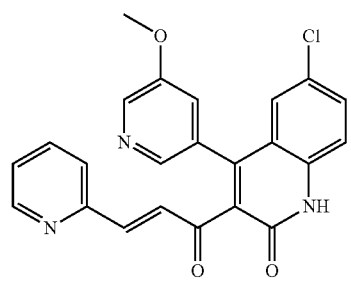 [SMILES: COc1cncc(-c2c(C(=O)/C=C/c3ccccn3)c(=O)[nH]c3ccc(Cl)cc23)c1]

This compound was prepared as described in Example 87. 1HNMR (400 MHz, DMSO-d$_6$): δ=12.47 (s, 1H), 8.63 (s, 1H), 8.35 (s, 1H), 8.10 (s, 1H), 7.86-7.85 (m, 1H), 7.72-7.68 (m, 2H), 7.58-7.41 (m, 4H), 7.12 (s, 1H), 7.05 (d, J=10.4 Hz, 1H), 3.77 (s, 3H). MS: m/z 418.0 (M+H$^+$).

Example 99: 3-[(2E)-3-(5-fluoro(3-pyridyl))prop-2-enoyl]-6-chloro-4-(5-fluoro(3-pyridyl))hydroquinolin-2-one

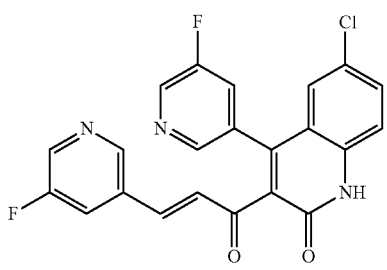 [SMILES: O=C(/C=C/c1cncc(F)c1)c1c(-c2cncc(F)c2)c2cc(Cl)ccc2[nH]c1=O]

This compound was prepared as described in Example 87. $^1$HNMR (400 MHz, DMSO-d$_6$): δ=12.53 (s, 1H), 8.73 (s, 1H), 8.67 (s, 1H), 8.61 (s, 1H), 8.41 (s, 1H), 8.15-8.13 (m, 1H), 7.88-7.86 (m, 1H), 7.72-7.50 (m, 3H), 7.09 (s, 1H), 7.05 (s, 1H). MS: m/z 424.0 (M+H$^+$).

Example 100: 3-((2E)-3-(2-pyridyl)prop-2-enoyl)-6-chloro-4-(5-fluoro(3-pyridyl))hydroquinolin-2-one

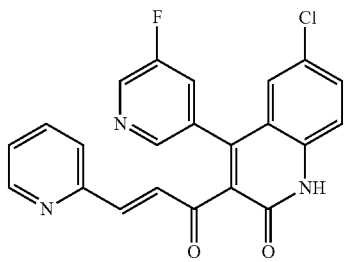 [SMILES: O=C(/C=C/c1ccccn1)c1c(-c2cncc(F)c2)c2cc(Cl)ccc2[nH]c1=O]

This compound was prepared as described in Example 87. $^1$HNMR (400 MHz, DMSO-d$_6$): δ=12.54 (s, 1H), 8.66-8.64 (m, 2H), 8.42 (s, 1H), 7.89-7.85 (m, 2H), 7.72-7.70 (m, 2H), 7.59-7.42 (m, 3H), 7.12-7.08 (m, 2H). MS: m/z 406.0 (M+H$^+$).

Example 101: 3-[(2E)-3-(5-fluoro(3-pyridyl))prop-2-enoyl]-6-chloro-4-(5-chloro(3-pyridyl))hydroquinolin-2-one

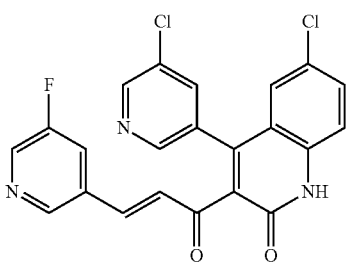 [SMILES: O=C(/C=C/c1cncc(F)c1)c1c(-c2cncc(Cl)c2)c2cc(Cl)ccc2[nH]c1=O]

This compound was prepared as described in Example 87. $^1$HNMR (400 MHz, CD$_3$OD): δ=8.66 (d, J=2.4 Hz, 1H), 8.59 (s, 1H), 8.48-8.46 (m, 2H), 7.98-7.92 (m, 2H), 7.66 (dd, J=8.8, 2.4 Hz, 1H), 7.56 (d, J=16.8 Hz, 1H), 7.48 (d, J=8.8 Hz, 1H), 7.13 (d, J=2.4 Hz, 1H), 7.06 (d, J=16.0 Hz, 1H). MS: m/z 439.7 (M+H$^+$).

Example 102: 3-((2E)-3-(2-pyridyl)prop-2-enoyl)-6-chloro-4-(5-chloro(3-pyridyl))hydroquinolin-2-one

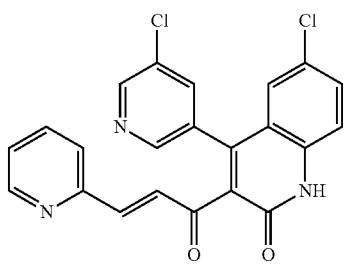 [SMILES: O=C(/C=C/c1ccccn1)c1c(-c2cncc(Cl)c2)c2cc(Cl)ccc2[nH]c1=O]

This compound was prepared as described in Example 87. $^1$HNMR (400 MHz, DMSO-d$_6$): δ=12.52 (s, 1H), 8.70 (d, J=2.0 Hz, 1H), 8.62 (d, J=9.2 Hz, 1H), 8.49 (d, J=2.0 Hz, 1H), 8.04 (t, J=2.4 Hz, 1H), 7.89-7.84 (m, 1H), 7.73-7.68 (m, 2H), 7.55 (d, J=16.0 Hz, 1H), 7.49 (d, J=8.8 Hz, 1H), 7.40 (d, J=4.8 Hz, 1H), 7.13 (d, J=16.0 Hz, 1H), 7.06 (d, J=2.4 Hz, 1H). MS: m/z 422.0 (M+H$^+$).

Example 103: (E)-4-(5-Bromo-pyridin-3-yl)-6-chloro-3-[3-(5-fluoro-pyridin-3-yl)-acryloyl]-1H-quinolin-2-one

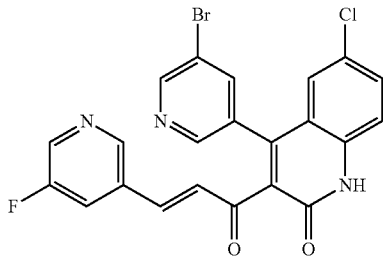

This compound was prepared as described in Example 87. $^1$HNMR (400 MHz, CDCl$_3$): δ=12.38 (s, 1H), 8.73 (s, 1H), 8.46-8.39 (m, 3H), 7.77 (s, 1H), 7.41-7.31 (m, 4H), 7.06 (s, 1H), 6.96 (d, J=16.4 Hz, 1H). MS: m/z 483.9 (M+H$^+$).

Example 104: 3-((2E)-3-(2-pyridyl)prop-2-enoyl)-4-(5-bromo(3-pyridyl))-6-chlorohydroquinolin-2-one

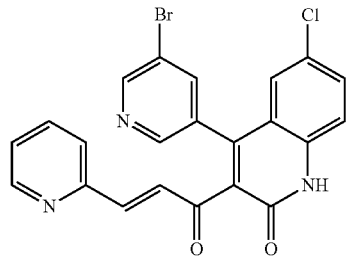

This compound was prepared as described in Example 87. 1HNMR (400 MHz, DMSO-d$_6$): δ=12.52 (s, 1H), 8.77 (s, 1H), 8.64 (s, 1H), 8.53 (s, 1H), 8.16 (s, 1H), 7.86-7.84 (m, 1H), 7.71-7.70 (m, 2H), 7.58-7.40 (m, 3H), 7.09 (d, J=15.6 Hz, 1H), 7.06 (s, 1H). MS: m/z 465.9 (M+H$^+$).

Example 105: 5-{3-[(2E)-3-(5-fluoro(3-pyridyl))prop-2-enoyl]-6-chloro-2-oxo-4-hydroquinolyl}pyridine-3-carbonitrile

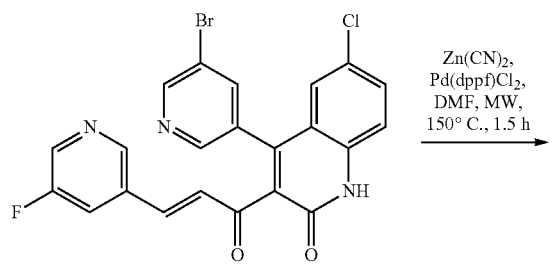

Zn(CN)$_2$, Pd(dppf)Cl$_2$, DMF, MW, 150° C., 1.5 h

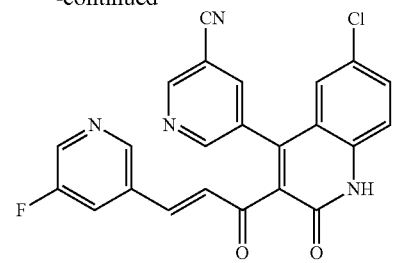

This compound was prepared as described in Example 72. $^1$HNMR (400 MHz, CDCl$_3$): δ=12.25 (s, 1H), 9.00 (s, 1H), 8.74 (s, 1H), 8.56 (s, 1H), 8.51 (s, 1H), 7.96 (s, 1H), 7.56-7.38 (m, 4H), 7.14 (d, J=16.4 Hz, 1H), 7.01 (s, 1H). MS: m/z 431.0 (M+H$^+$).

Example 106: 5-[3-((2E)-3-(2-pyridyl)prop-2-enoyl)-6-chloro-2-oxo-4-hydroquinolyl]pyridine-3-carbonitrile

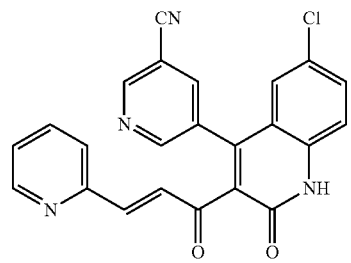 [SMILES: N#Cc1cncc(-c2c(C(=O)/C=C/c3ccccn3)c(=O)[nH]c3ccc(Cl)cc23)c1]

This compound was prepared as described in Example 72. $^1$HNMR (400 MHz, CDCl$_3$): δ=12.54 (s, 1H), 8.97 (s, 1H), 8.75 (s, 1H), 8.63 (s, 1H), 7.96 (s, 1H), 7.75-7.71 (m, 1H), 7.50-7.29 (m, 6H), 6.99 (s, 1H). MS: m/z 412.7 (M+H).

Example 107: Ethyl 5-[3-((2E)-3-(2-pyridyl)prop-2-enoyl)-6-chloro-2-oxo-4-hydroquinolyl]pyridine-3-carboxylate

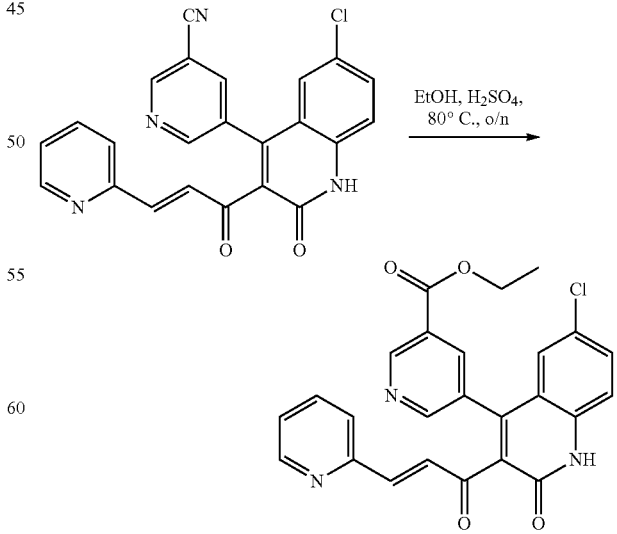

EtOH, H$_2$SO$_4$, 80° C., o/n

To a solution of (E)-5-(6-chloro-2-oxo-3-(3-(pyridin-2-yl)acryloyl)-1,2-dihydroquinolin-4-yl)nicotinonitrile (21 mg, 0.05 mmol) in EtOH (2.5 mL) was added concentrated H2SO4 (0.5 mL), and the mixture was stirred at gentle reflux overnight. The mixture was neutralized with 1N NaOH to pH=6-7 and extracted with EtOAc (20 mL×3). The extracts were dried over Na₂SO₄ and the solution was concentrated to dryness. The residue was purified by prep-HPLC to afford ethyl 5-[3-((2E)-3-(2-pyridyl)prop-2-enoyl)-6-chloro-2-oxo-4-hydroquinolyl]pyridine-3-carboxylate (4.9 mg, yield: 21%) as a yellow solid. ¹HNMR (400 MHz, CDCl₃): δ=11.89 (brs, 1H), 9.23 (s, 1H), 8.64 (s, 1H), 8.55 (d, J=3.6 Hz, 1H), 8.22 (s, 1H), 7.65-7.64 (m, 1H), 7.41-7.19 (m, 6H), 6.98 (s, 1H), 4.32 (q, J=7.2 Hz, 2H), 1.29 (t, J=7.2 Hz, 3H). MS: m/z 459.7 (M+H⁺).

Example 108: 3-((2E)-3-(2-pyridyl)prop-2-enoyl)-4-[4-(dimethylamino)phenyl]-6-chlorohydroquinolin-2-one

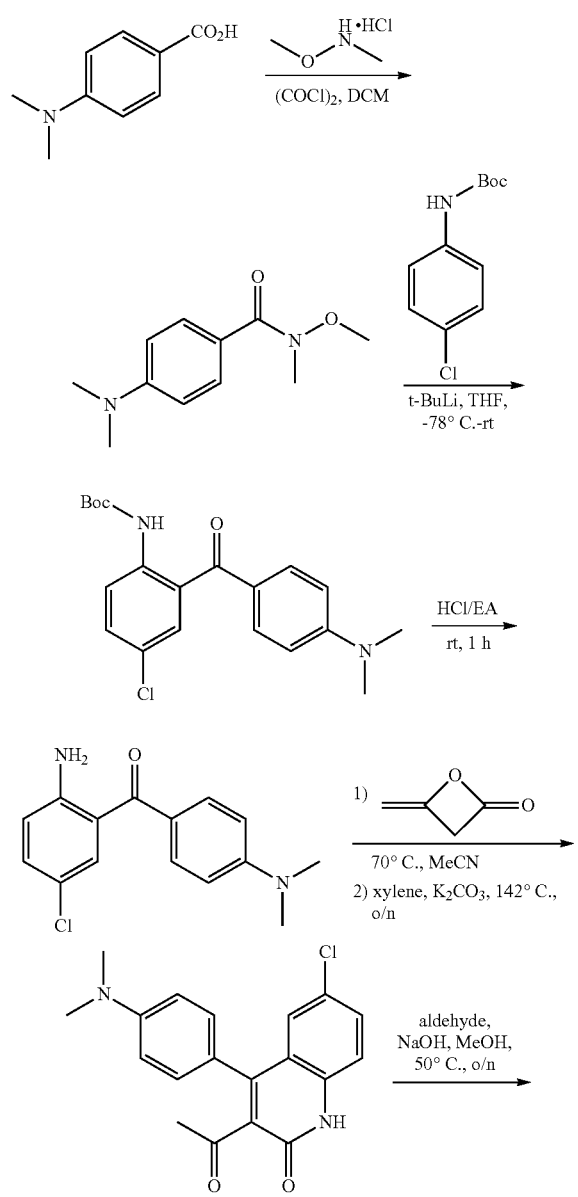

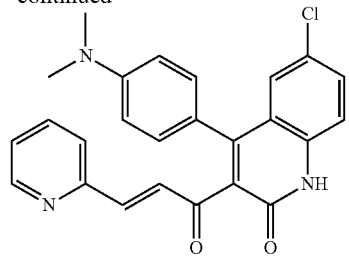

Step 1:
To a mixture of 4-(dimethylamino)benzoic acid (3.3 g, 20 mmol) in DCM (50 mL) was added 2 drops of DMF, followed by dropwise addition of oxalyl chloride (2.7 mL, 30 mmol) at 0° C. for 10 mins. After addition, the mixture was stirred at room temperature overnight. The solvent was concentrated and the remaining chloride was dissolved in DCM (5 mL). To a solution of N,O-dimethylhydroxylamine HCl salt (2.34 g, 24 mmol) and pyridine (10 mL) in DCM (50 mL) was added the above acyl chloride, and the mixture was stirred at room temperature for 4 hrs. The solvent was removed and the residue was dissolved in EtOAc (50 mL). The mixture was washed with aqueous NH₄Cl (30 mL) and brined (30 mL), and dried over Na₂SO₄. The solution was concentrated to afford 4-(dimethylamino)-N-methoxy-N-methylbenzamide (3.07 g, yield: 74%) as a yellow solid. MS: m/z 209.1 (M+H⁺).

Step 2:
To a solution of (4-chloro-phenyl)-carbamic acid tert-butyl ester (1.14 g, 5.0 mmol) in anhydrous THF (15 mL) was added dropwise t-BuLi (10 mL, 1.3 M in pentanes) at −78° C. under N₂. The solution was stirred at −50-−60° C. for 1 hour. Then a solution of 4-(dimethylamino)-N-methoxy-N-methylbenzamide (1.25 g, 6.0 mmol) in THF (10 mL) was added to the mixture dropwise at −78° C. The mixture was allowed to warm to room temperature and stirred overnight. The mixture was quenched with aqueous NH₄Cl (20 mL) and extracted with EA (50 mL×3). The organic layers were washed with brined (20 mL), dried over Na₂SO₄ and concentrated to dryness. The residue was purified by Combi Flash to afford tert-butyl (4-chloro-2-(4-(dimethylamino)benzoyl)phenyl)carbamate (800 mg, yield: 43%) as a yellow solid. MS: m/z 375.1 (M+H⁺).

Step 3:
To a solution of tert-butyl (4-chloro-2-(4-(dimethylamino)benzoyl)phenyl)carbamate (800 mg, 2.1 mmol) in EtOAc (20 mL) was added 1.5 M HCl/EtOAc (20 mL), and the mixture was stirred at room temperature overnight. The mixture was neutralized with 1N NaOH to pH=7-8. The aqueous phase was extracted with EtOAc (20 mL×2). The combined organic layers were dried over Na₂SO₄ and concentrated to afford (2-amino-5-chlorophenyl)(4-(dimethylamino)phenyl)methanone (500 mg, yield: 87%) as a yellow solid. MS: m/z 275.1 (M+H⁺).

Step 4:
The mixture of (2-amino-5-chlorophenyl)(4-(dimethylamino)phenyl)methanone (500 mg, 1.82 mmol) and diketene (2 mL) in MeCN (10 mL) was heated to 70° C. overnight. LCMS [MS: m/z 359.1 (M+H⁺)] showed N-(4-chloro-2-(4-(dimethylamino)benzoyl)phenyl)-3-oxobutanamide was obtained.

The solvent was removed and the residue was diluted with xylene (20 mL), followed by the addition of K₂CO₃ (100 mg, 0.72 mmol). The mixture was heated at 142° C. overnight. The suspension was filtered and the filtrate was concentrated to give 3-acetyl-6-chloro-4-(4-(dimethylamino)phenyl)quinolin-2(1H)-one (507 mg, yield: 81%) as a yellow solid.

Step 5:

To a solution of 3-acetyl-6-chloro-4-(4-(dimethylamino)phenyl)quinolin-2(1H)-one (102 mg, 0.30 mmol) in MeOH (20 mL) was added picolinaldehyde (64 mg, 0.60 mmol) and NaOH (24 mg 0.60 mmol), and the mixture was stirred at room temperature overnight. LCMS showed much 3-acetyl-6-chloro-4-(4-(dimethylamino)phenyl)quinolin-2(1H)-one wasn't consumed. Then the mixture was heated at 80° C. for 2 hrs. The mixture was neutralized with NH$_4$Cl solution (20 mL) to pH=7-8. The aqueous phase was extracted with DCM (20 mL×2). The extracts were dried over Na$_2$SO$_4$ and concentrated to dryness. The residue was purified by prep-HPLC to afford 3-((2E)-3-(2-pyridyl)prop-2-enoyl)-4-[4-(dimethylamino)phenyl]-6-chlorohydroquinolin-2-one (50 mg, yield: 39%) as a yellow solid. $^1$HNMR (400 MHz, DMSO-d$_6$): δ=12.26 (s, 1H), 8.60 (d, J=4.0 Hz, 1H), 7.83 (td, J=7.6, 1.6 Hz, 1H), 7.69 (d, J=8.0 Hz, 1H), 7.63 (d, J=8.8, 2.4 Hz, 1H), 7.47-7.36 (m, 3H), 7.19 (d, J=2.0 Hz, 1H), 7.12 (d, J=8.4 Hz, 2H), 7.01 (d, J=16.0 Hz, 1H), 6.74 (d, J=8.8 Hz, 2H), 2.91 (s, 6H). MS: m/z 430.1 (M+H$^+$).

Example 109: 3-[(2E)-3-(5-fluoro(3-pyridyl))prop-2-enoyl]-4-[4-(dimethylamino)phenyl]-6-chlorohydroquinolin-2-one

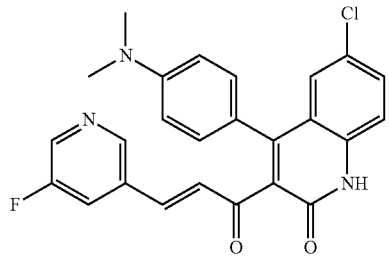

This compound was prepared as described in Example 108. $^1$HNMR (400 MHz, CDCl$_3$): δ=12.47 (s, 1H), 8.43-8.40 (m, 2H), 7.51 (s, 1H), 7.45-7.32 (m, 4H), 7.18-7.16 (m, 2H), 6.73-6.67 (m, 3H), 2.98 (s, 6H). MS: m/z 448.1 (M+H$^+$).

Examples 110 and 111: 3-[(2Z)-2-bromo-3-(5-fluoro(3-pyridyl))prop-2-enoyl]-6-chloro-4-phenyl-hydroquinolin-2-one and 3-[(2E)-2-bromo-3-(5-fluoro(3-pyridyl))prop-2-enoyl]-6-chloro-4-phenylhydroquinolin-2-one

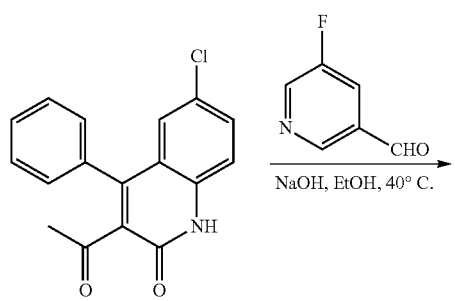

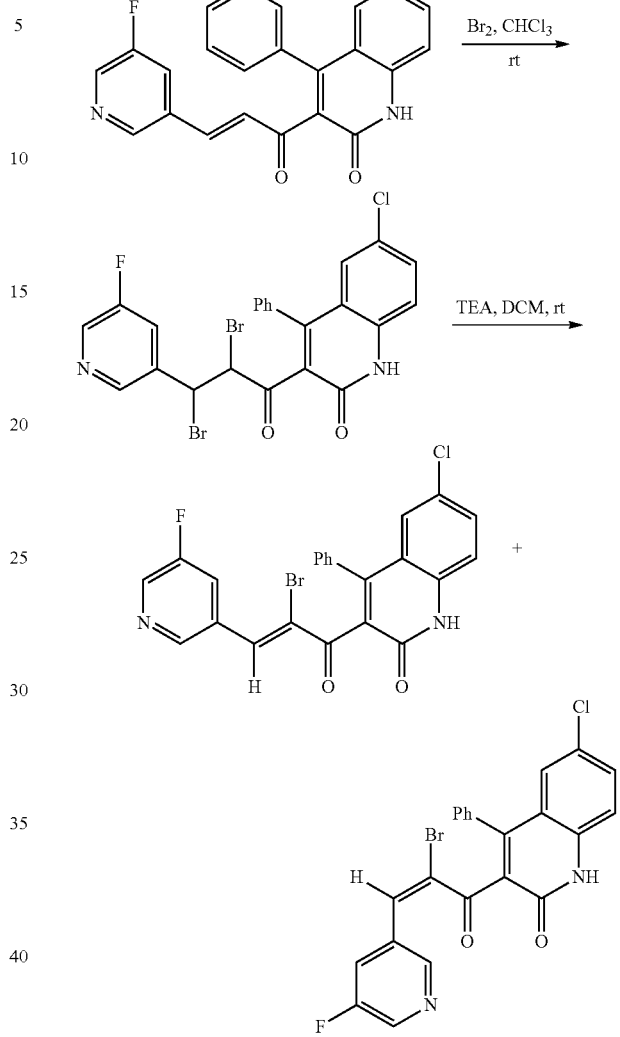

Step 1~2:

To a suspension of 3-acetyl-6-chloro-4-phenyl-1H-quinolin-2-one (297 mg, 1.0 mmol) and 5-fluoro-pyridine-3-carbaldehyde in EtOH (5 mL) was added NaOH (44 mg, 1.1 mmol). The reaction mixture was stirred at 40° C. for 1 hr. After that, the reaction was diluted with water and adjusted with conc. HCl to pH=5. The solid formed was collected by filtration to give crude 6-chloro-3-[3-(5-fluoro-pyridin-3-yl)-acryloyl]-4-phenyl-1H-quinolin-2-one which was dissolved in chloroform (5 mL). To the solution was added Br$_2$ (480 mg, 3.0 mmol). The mixture was stirred at room temperature for 1 hr and partitioned between DCM (50 mL) and saturated Na$_2$SO$_3$ solution (50 mL). The organic layer was washed with saturated NaHCO$_3$ solution (50 mL) and brine (50 mL), dried over Na$_2$SO$_4$ and concentrated. The residue was triturated with EA to give 6-chloro-3-[2,3-dibromo-3-(5-fluoro-pyridin-3-yl)-propionyl]-4-phenyl-1H-quinolin-2-one 1-(4-methoxybenzyl)-3-methyl-1H-pyrazol-5-amine (300 mg, yield: 53% over 2 steps) as a yellow solid. MS: m/z 564.9 (M+H$^+$).

Step 3:

To a solution of 6-chloro-3-[2,3-dibromo-3-(5-fluoro-pyridin-3-yl)-propionyl]-4-phenyl-1H-quinolin-2-one 1-(4- methoxybenzyl)-3-methyl-1H-pyrazol-5-amine (200 mg, 0.35 mmol) in DCM (5 mL) was added TEA (107 mg, 1.06 mmol). The reaction was stirred at room temperature for 1 hr. After concentration, part of the residue was purified by prep. TLC (PE/EA=1/2) to give two isomers.

Isomer 1 was further purified by prep. HPLC to give 3-[(2Z)-2-bromo-3-(5-fluoro(3-pyridyl))prop-2-enoyl]-6-chloro-4-phenylhydroquinolin-2-one (Example 110, 10 mg) as a yellow solid. $^1$HNMR (400 MHz, CDCl$_3$): δ=12.61 (brs, 1H), 8.53 (s, 1H), 8.48 (d, J=3.2 Hz, 1H), 8.05-8.01 (m, 1H), 7.82 (s, 1H), 7.50-7.45 (m, 4H), 7.39 (d, J=8.8 Hz, 1H), 7.32-7.29 (m, 3H). MS: m/z 484.6 (M+H$^+$). 3-[(2E)-2-bromo-3-(5-fluoro(3-pyridyl))prop-2-enoyl]-6-chloro-4-phenylhydroquinolin-2-one was further purified by trituration with EA to give 3-[(2E)-2-bromo-3-(5-fluoro(3-pyridyl))prop-2-enoyl]-6-chloro-4-phenylhydroquinolin-2-one (Example 111, 15 mg) as a yellow solid. $^1$HNMR (400 MHz, CDCl$_3$): δ=12.48 (brs, 1H), 8.53 (s, 1H), 8.48 (d, J=2.4 Hz, 1H), 8.04-8.02 (m, 1H), 7.82 (s, 1H), 7.50-7.47 (m, 4H), 7.39 (d, J=8.8 Hz, 1H), 7.31-7.29 (m, 3H). MS: m/z 484.9 (M+H$^+$).

Example 112: 6-Chloro-3-[3-(4-methyl-pyridin-2-yl)-propynoyl]-4-phenyl-1H-quinolin-2-one

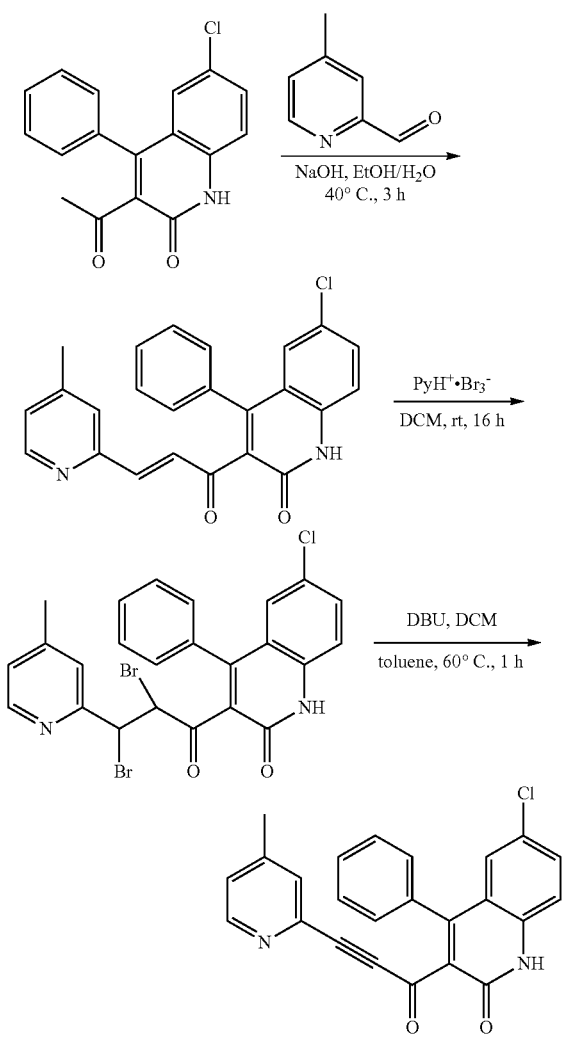

Step 1:
To a suspension of 3-acetyl-6-chloro-4-phenyl-1H-quinolin-2-one (1.7 g, 5.7 mmol) and 4-methyl-pyridine-2-carbaldehyde (0.9 g, 7.4 mmol) in EtOH/H$_2$O (20 mL/20 mL) was added NaOH (1.1 g, 28.6 mmol). The reaction mixture was stirred at 40° C. for 3 hrs. After that, the reaction was diluted with water and adjusted with conc. HCl to pH=7. The solid formed was collected by filtration and purified by silica gel column (PE/EA=1/2) to give 6-chloro-3-[3-(4-methyl-pyridin-2-yl)-acryloyl]-4-phenyl-1H-quinolin-2-one (1.8 g, yield: 79%) as a yellow solid. MS: m/z 400.9 (M+H$^+$)

Step 2:
To a solution of 6-chloro-3-[3-(4-methyl-pyridin-2-yl)-acryloyl]-4-phenyl-1H-quinolin-2-one (500 mg, 1.3 mmol) in DCM (30 mL) was added pyridinium tribromide (2.0 g, 6.3 mmol). After stirring at room temperature for 16 hrs, the reaction mixture was diluted with DCM (70 mL). The mixture was washed with Sat.NaHCO$_3$ (50 mL), Sat.Na$_2$SO$_3$ (50 mL), dried over Na$_2$SO$_4$ and concentrated to give crude 6-chloro-3-[2,3-dibromo-3-(4-methyl-pyridin-2-yl)-propionyl]-4-phenyl-1H-quinolin-2-one which was used for next step without further purification. MS: m/z 560.7 (M+H$^+$)

Step 3:
To a solution of 6-chloro-3-[2,3-dibromo-3-(4-methyl-pyridin-2-yl)-propionyl]-4-phenyl-1H-quinolin-2-one (290 mg, crude) in DCM (5 mL) and toluene (5 mL) was added DBU (400 mg, 2.6 mmol). The reaction mixture was stirred at 60° C. for 1 h. After concentration, the residue was purified by silica gel column (PE/EA=4/1) and chiral-HPLC (Chiralpak IE 5 um 4.6*250 mm; Phase:ACN:IPA=90:10; F:1.0 ml/min; W:230 nm; T:30) to give 6-chloro-3-[3-(4-methyl-pyridin-2-yl)-propynoyl]-4-phenyl-1H-quinolin-2-one (35 mg, yield: 7%, two steps) as a yellow solid.

$^1$HNMR (400 MHz, CDCl$_3$): δ=8.60 (d, J=4.8 Hz, 1H), 8.20 (s, 1H), 8.10 (d, J=9.2 Hz, 1H), 7.80 (dd, J=9.2, 2.0 Hz, 1H), 7.59-7.56 (m, 3H), 7.54 (d, J=2.4 Hz, 1H), 7.31 (s, 1H), 7.29-7.26 (m, 3H), 2.51 (s, 3H). MS: m/z 398.8 (M+H$^+$).

Example 113: 6-Chloro-3-[3-(5-chloro-thiophen-2-yl)-acryloyl]-4-phenyl-1H-quinolin-2-one

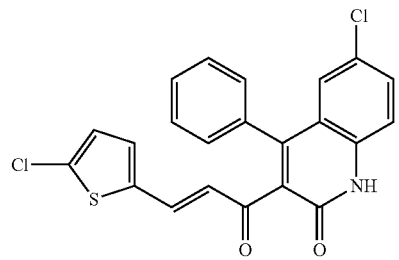 [SMILES: O=C(/C=C/c1ccc(Cl)s1)c1c(-c2ccccc2)c2cc(Cl)ccc2[nH]c1=O]

This compound was prepared as described in Example 27. HNMR (300 MHz, DMSO-d6): δ=12.35 (brs, 1H), 7.66-7.58 (m, 2H), 7.46-7.41 (m, 5H), 7.30 (d, J=7.5 Hz, 2H), 7.17 (d, J=3.3 Hz, 1H), 6.95 (s, 1H), 6.35 (d, J=15.9 Hz, 1H). MS: m/z 426.0 (M+H$^+$).

II. Biological Evaluation
Methods
Cell Culture
Melanoma lines were cultured in high-glucose Dulbecco's modified Eagle's medium (HyClone by Thermo Scientific) with 5% fetal bovine serum and 1% penicillin-streptomycin. All cells were maintained at 37° C. in 5% $CO_2$.

Western Blot Analysis and Antibodies

Cells were rinsed with PBS and lysed in culture plates with lysis buffer (50 mM Tris-HCl, pH 7.4, 150 mM NaCl, 1% NP-40, 1 mM EDTA, 10 μg/ml aprotinin, 1 μg/ml pepstatin A, 10 μg/ml leupeptin, 1 mM phenylmethylsulfonyl fluoride, and 1 mM sodium orthovanadate). Protein concentration was determined using Coomassie Plus Protein Assay Reagent (Thermo Scientific). Equal amounts of cell lysate proteins (50 μg) were resolved by SDS-PAGE and transferred to polyvinylidene difluoride membranes (PerkinElmer Life Sciences). Membranes were blocked with 5% BSA/TBST for 1 h and incubated with primary antibodies for 1 h at room temperate or overnight at 4° C., with shaking. Following three TBST washes, membranes were incubated for 1 h at room temperature with goat anti-rabbit Alexa Fluor 680 F(ab')$_2$ or goat anti-mouse IRDye 800 F(ab')$_2$ diluted 1:10,000. Bound antibodies were detected using the Odyssey Infrared Imaging System (LiCor Biosciences), or by exposing them to X-ray blue film.

Antibodies against p-AKT, p-PRAS40, p-IKK, p-IκB, p-TSC, p-mTOR, p-p70S6K, p-RPS6, p-4E-BP1, pSGK3, AKT, PRAS40, IKK, IB, mTOR, p70S6K, RPS6, 4E-BP1, GSK3, eIF4G1, and eIF4E were purchased from Cell Signaling Technology. Antibodies against p3-actin and α-tubulin were obtained from Santa Cruz Biotechnology. Secondary antibodies were goat anti-rabbit Alexa-680 F(ab')$_2$ (Molecular Probes) and goat anti-mouse IRDye 800 F(ab')$_2$ (Rockland Immunochemicals). All antibodies were used according to the suppliers' recommendations.

m$^7$GTP Pull-Down Assay

As previously described (Dowling R J, et al. mTORC1-mediated cell proliferation, but not cell growth, controlled by the 4E-BPs. Science. 2010; 328:1172-6), cells growing in 100 mm plates were washed (cold PBS), collected, and lysed in 50 mM MOPS/KOH (7.4), 100 mM NaCl, 50 mM NaF, 2 mM EDTA, 2 mM EGTA, 1% NP40, 1% Na-DOC, 7 mM β-mercaptoethanol, protease inhibitors and phosphatase inhibitor cocktail (Roche). Lysates were incubated with m7-GDP-agarose beads (Jena Bioscience) for 20 minutes, washed 4 times with the washing buffer containing 50 mM MOPS/KOH (7.4), 100 mM NaCl, 50 mM NaF, 0.5 mM EDTA, 0.5 mM EGTA, 7 mM (3-mercaptoethanol, 0.5 mM PMSF, 1 mM Na3VO4 and 0.1 mM GTP, and bound proteins were eluted by boiling the beads in loading buffer. m7-GDP-agarose pulled down material was analyzed by Western blot analysis.

In Vitro Translation Assay

The bicistronic dual-reporter constructs that contain the firefly luciferase (FF) sequence, followed by the (encephalomyocarditis virus) EmCV and Hepatitis C virus (HCV) IRES, respectively, and the *Renilla reniformis* (Ren) luciferase sequence, has been previously described (Bordeleau Me., et al. Functional characterization of IRESes by an inhibitor of the RNA helicase eIF4A. Nature chemical biology. 2006; 2:213-20). For measurement of translation from the FF-EmCV-Ren and FF-HCV-Ren constructs, rabbit reticulocyte lysates (RRL) (Life Technologies, Carlsbad, Calif., USA) and the Dual-Glo (Promega, Madison, Wis., USA) read-outs were chosen. Two μl rabbit reticulocyte lysates mixed with Translation Mix 20× (-Met) and Translation Mix 20× (-Leu) in a ratio of 1:1 were pre-incubated with test compounds in 1536-well plates for 1 h at room temperature. Then, translation was started by adding 0.1 μg RNA per well and incubated for 2 h at 30° C. After a short chill phase, 2.5 μl Dual-Glo reagent 1 was added to each well and incubated for 10 min before reading the FF luciferase activity with the ViewLux uHTS Microplate Imager (Perkin Elmer, Waltham, Mass., USA). Directly after, 2.5 μl Dual-Glo reagent 2 was dispensed to each well and incubated at room temperature for 10 min before reading the Ren luciferase activity on the ViewLux. To exclude the possibility that test compounds interfere with any of the luciferase activities, a counter assay was performed in which the compounds were added after the completion of the in vitro translation.

Microarray Expression Profiling of Melanoma Cell Lines

Total RNA from melanoma lines was profiled per manufacturer's protocol on Human Genome U133plus2.0 GeneChips (Affytmetrix), containing ~47,000 probe sets for 38,000 characterized human genes. GeneChips were scanned using the Affymetrix GeneChip Operating Software (GCOS) and the .CEL files were produced for downstream data analysis. The robust multi-array average (GCRMA) method (Bioconductor; bioconductor.org) was used to background-adjust and normalize expression intensity values. Probesets with present calls in less than four of the seven most Compound 38-sensitive and -resistant samples, respectively, were filtered. The limma R software (Bioconductor) package was used to identify the differentially expressed genes (DEGs). The probes with $P<0.05$ and fold change $>1.5$ were used to perform IPA analysis (QIAGEN).

Development of Compound 38-Resistant Cells and Exome Sequencing

UACC903 and UACC3629 cells were treated with increasing Compound 38 concentrations from 0.01-2.5 uM over 12 weeks. Single clones were isolated from 96-well plates, expanded, and genomic DNA was extracted. Exome sequencing of UACC903 Compound 38-sensitive parental and resistant clones was performed by Ion Proton (Life Technologies). The library was made using the Ion AmpliSeq Exome Kit according to the manufacturer's protocol. The exome-seq reads were aligned to the human genome (hg19) in Torrent Suit v4.2 and variants were called with the Torrent Suit Variant Caller v4.2. Exome sequencing of UACC3629 parental and Compound 38 resistant clones was performed using a HiSeq 2000 (lllumina). Exome sequence capture was performed with NimbleGen's Seq Cap EZ Human Exome Library v3.0 (Roche NimbleGen, Inc., Madison, Wis., USA). The generated FASTQ files were preprocessed for high quality reads by Trimmomatic (v0.32), and Novoalign software was used to align high quality reads to human genome (hg19). Deduplication, realignment, and recalibration was performed using GATK, and sequence variants were called using MuTect. We further applied the following criteria to retain high-quality variants specifically appearing in Compound 38-resistant clones (but not their respective parental lines): (1) the sequencing depths for both parent and resistant lines>10, with an alternative allele depth >3; (2) variant quality score in resistant clone >30 (99.9% confidence); (3) variant was not detected in parent cell line; (4) variant is not annotated as observed in the germ line by the 1,000 Genome Project database; (5) variant located within exonic or canonical splicing region with predicted effect on protein coding sequence. After filtering, all mutations were annotated by Ensembl VEP (variant effect predictor) pipeline. Pathway enrichment of mutations was subsequently analyzed using IPA (QIAGEN).

High-Throughput Screen

Melanoma lines WM793, Lu1205, WM1346, and WM1366 were plated in 384-well plates at 1500 cells/well. After incubation at 37° C. overnight, relevant compounds dissolved in DMSO were serially diluted 2-fold from stock solutions and added to wells using an Echo555 acoustic dispenser (Labcyte); the highest drug concentration was 10 μM and that of DMSO was 0.1%. Cell viability was assessed using ATPlite after a 48 h incubation. Cell growth inhibition was calculated as a percentage of DMSO-treated controls. IC$_{50}$ values were calculated using GraphPad Prism.

Proliferation Assay

WM793, Lu1205, WM1346 and WM1366 melanoma cells were seeded at 1500 cells in 50 µL per well in 384-well plates. Cells were allowed to attach overnight. Derivatives were serially diluted 2-fold with media from stock solutions and added to cells. Tests were performed in triplicate, and each microplate included media and DMSO control wells. Cell viability was assessed using ATPlite after 48 or 72 h, according to the manufacturer's protocol. Cell growth inhibition was calculated as a percentage of DMSO-treated controls and plotted against the log drug concentration. IC$_{50}$ values were interpolated from the resulting linear regression curve fit (GraphPad Prism 6).

Colony Formation and Soft Agar Assay

For the colony formation assay, cells were plated in triplicate at 500 cells/well in 6-well plates and grown for 16 h before compounds were added for 1-2 weeks, depending on cell line. Colonies were stained with Accustain Crystal Violet solution (Sigma-Aldrich) for 30 min. Plates were rinsed with water, and colonies (>50 cells per clone) were counted. Colony formation efficiency was calculated relative to the number of colonies in control (DMSO)-treated wells. For soft agar assays, melanoma cells were mixed with agar at a final concentration of 0.35% and layered on top of 0.7% agar in 6-well plates. Media supplemented with different compounds was added to plates and changed once per week. After 4 weeks, colonies were counted in 10 random high-power fields.

LC/MS/MS

UACC903 celllysates (1 mg protein) were first incubated with 10 µM biotin or 10 µM biotinylated-BI-69A11 or 100 µM BI-69A11 for 30 min at room temperature on a rotating wheel. Pierce Monomeric Avidin Agarose beads (100 µL) were then added to each sample, which was incubated another 30 min and then washed five times with PBS. One tenth of the bead mixture was run on SDS PAGE, which was then silver-stained, while the rest of the bead mix was subjected to LC/MS/MS analysis by the SBMRI Proteomics Facility. For tryptic digestion and LC/MS/MS analysis, samples of beads plus protein were re-suspended in 100 µl of 50 mM ammonium bicarbonate, and 2 µl of 0.5M Tris (2-carboxyethyl) phosphine (TCEP) was added to 200 µL of the beads/protein mix at 40° C. for 30 min to reduce proteins. 4 µl of 0.5 M iodoacetamide was added, and proteins were alkylated at room temperature in the dark for 30 min. Mass spectrometry grade trypsin (Promega) was added at a 1:20 ratio to beads for overnight digestion at 37° C. using an EppendorfThermomixer at 800 rpm. Digested peptides were separated from beads by centrifugation and transferred to a new tube. Formic acid was added to the peptide solution (to 2%), followed by desalting using a Micro trap (Thermo) and on-line analysis of peptides by high-resolution, high-accuracy LC-MS/MS, which consisted of an EASY-nLC 1000 HPLC Acclaim Pep Map peptide trap, a 15-cm 3 m Easy-Spray C18 column, an Easy Spray Source, and a Q Exactive Plus mass spectrometer (Thermo Fisher Scientific).

Reverse Phase Protein Array Analysis (RPPA)

UACC903 and WM1346 cells were treated with DMSO (controls) or 1 µM Compound 38 for 24 h in triplicate. Cells were lysed with lysis buffer (1% Triton X-100, 50 mM HEPES, pH 7.4, 150 mM NaCl, 1.5 mM MgCl$_2$, 1 mM EGTA, 100 mM NaF, 10 mM Na pyrophosphate, 1 mM Na$_3$VO$_4$, 10% glycerol, with freshly added protease and phosphatase inhibitors) and centrifuged at 13,000 g for 20 minutes. Denatured protein lysates containing the same amount of protein were then subjected to RPPA analysis at the RPPA Core Facility, Md. Anderson Cancer Center, as previously described (Tibes. R., et al. Reverse phase protein array: validation of a novel proteomic technology and utility for analysis of primary leukemia specimens and hematopoietic stem cells. *Molecular cancer therapeutics* 5, 2512-2521 (2006)), Xenograft All animal studies were conducted in the SBMRI Animal Facility in accordance with the Institutional Animal Care and Use Committee guidelines. Six-week-old female nu/nu mice were purchased Harlan Laboratories (Indianapolis, Ind.) and allowed to acclimatize for 1 week. A375 cells (1×10$^6$, suspended in 200 µL sterile PBS) were injected into subcutaneous flank tissue. When the xenograft size reached ~250 mm$^3$, mice were sorted into different groups. For PLX4720 and Compound 38 combination experiments, mice were either fed PLX4720-containing chow alone (AIN76A Roden Diet with 417 mg PLX4720/kg from Open Source Diets) for the control group or PLX4 720-containing chow plus an IP injection of 1 mg/kg Compound 38 twice a week. For MEKi plus Compound 38 experiments, PD0325901 at 20 mg/kg (formulated in 0.5% hydroxypropyl methylcellulose plus 0.2% Tween-80) was administered by oral gavage twice a week (Monday and Thursday) for the control group, or PD035901 plus IP injection of 1 mg/kg Compound 38 was administered twice a week (Tuesday and Friday). Mice were maintained in a pathogen-free environment with free access to food. Body weight and tumor volume were measured twice a week. Tumor size was measured with linear calipers and calculated using the formula: ([length in millimeters×(width in millimeters)2]/2). Mice were sacrificed after 4 weeks and tumors were fixed in Z-Fix (Anatech, Battle Creek, Mich.) and embedded in paraffin for immunohistochemistry.

Example 1A: Pharmacology Experiment

Quinolinone derivatives were evaluated in a detailed in vitro pharmacology screen (absorption, distribution, metabolism, excretion, toxicity (ADME/T)) as seen in table 2.

TABLE 2

Pharmacological properties of Quinolinone analogs.

| Compound ID | Aqueous Solubility in pION's buffer pH 5.0/6.2/7.4 (ug/mL) | Aqueous Solubility in 1xPBS, pH 7.4 (ug/mL) | PAMPA Permeability, Pe (×10−6 cm/s) Donor pH: 5.0/6.2/7.4 Acceptor pH: 7.4 | Hepatic Microsome Stability (% remaining at 1 Hr) Mouse (no NADPH) | Hepatic Microsome Stability (% Remaining at 1 hr) Human (no NADPH) |
|---|---|---|---|---|---|
| 44 | 5.5/7.2/6.9 | 6.0 | 1481/1549/1187 | 53.71 (39.25) | 26.40 (49.56) |
| 38 | 6.5/6.6/5.5 | 5.6 | 1110/1146/820 | 38.69 (53.97) | 24.12 (57.84) |
| 12 | 1.6/1.4/1.2 | 1.5 | 1012/301/379 | 32.98 (63.69) | 59.85 (57.73) |
| 62 | 0.34/0.42/0.12 | 0.11 | 29/6.2/2.5 | 85.64 (82.96) | 89.89 (54.66) |
| BI-69A11 | 0.16/0.24/0.1 | 0.11 | 13/16/42 | 48.54 (45.01) | 68.24 (61.74) |

Compound 38 PK Study:

Method: Fasted male C57Bl/6J mice were dosed with a 1 mg/mL solution of Compound 38 in 10% DMSO, 10% Tween-80 and 80% water by intravenous injection (2 mg/kg, as a 0.4 mg/mL solution), oral gavage (10 mg/kg as a 1 mg/mL solution) or intraperitoneal injection (10 mg/kg as a 1 mg/mL solution). Plasma was collected at various time points and analyzed by LC/MS/MS to determine compound levels. Curve for the IV, IP, and PO administration are shown in FIG. 1. Compound 38 exhibited a clearance of 67 mL/min/kg, a $t_{1/2}$ of 2.95 h in mouse, and a % F of 20.

Example 2A: Antiproliferative Properties

Quinolinone derivatives were examined in four human melanoma lines as shown in FIG. 2A-FIG. 2D. Mutant BRAF (Lu1205), mutant BRAF (WM793), mutant NRAS (WM1346), or mutant NRAS (WM1366) melanoma lines were plated in 384-well plates at 1500 cells per well and grown overnight. DMSO or the quinolinone derivatives were then added at indicated concentrations. Cell viability was assessed 48 h later using ATPlite. Cell growth inhibition was calculated as a percentage of DMSO-treated controls and plotted against the log drug concentration. Experiments were performed in triplicate.

Figure 3:
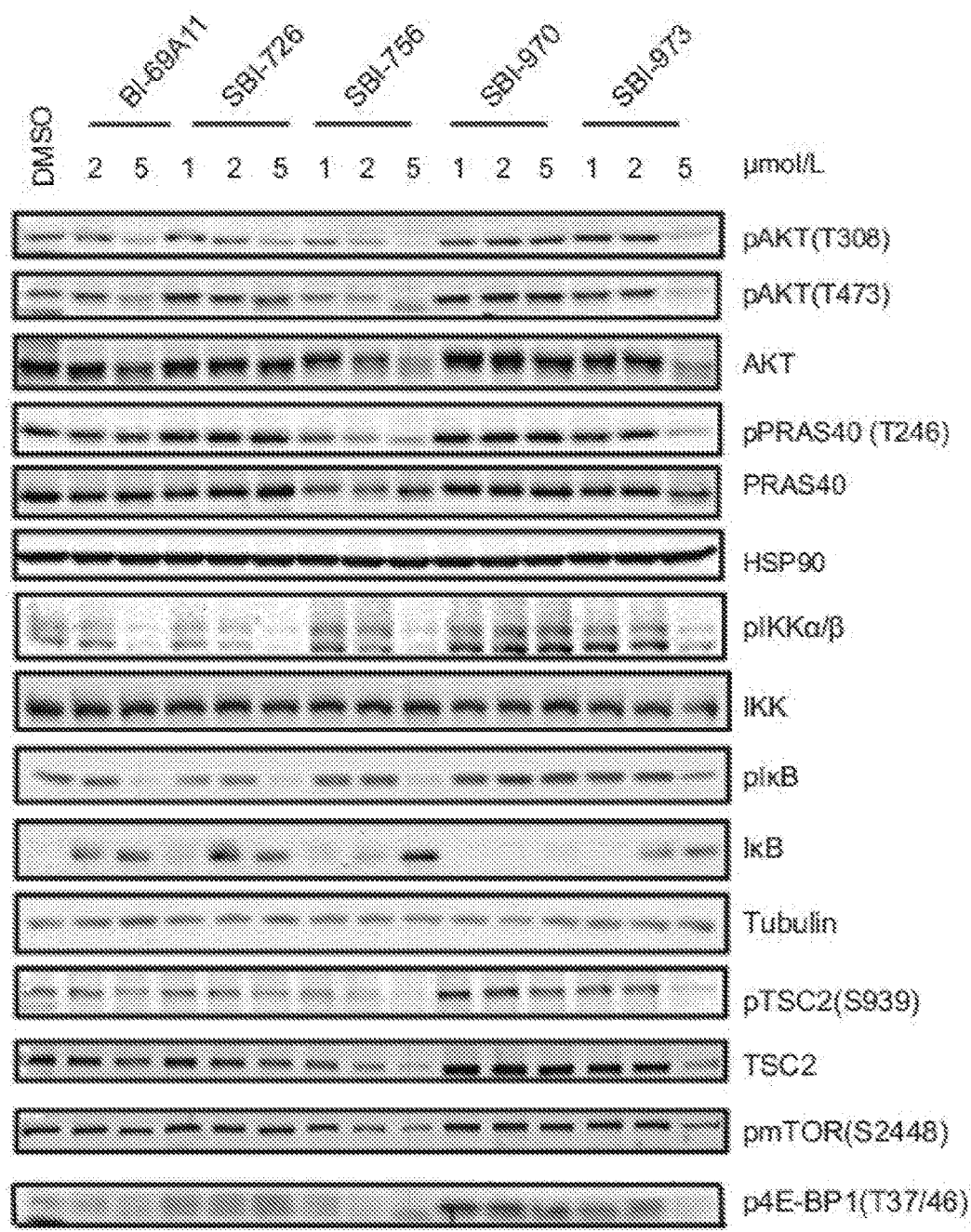
FIG. 3 shows the AKT and NFκB inhibition of SBI-756 (Compound 38), SBI-726 (Compound 44), SBI-970 (Compound 12), SBI-973 (Compound 62), and BI-69A11 (Compound A).
Figure 4A:
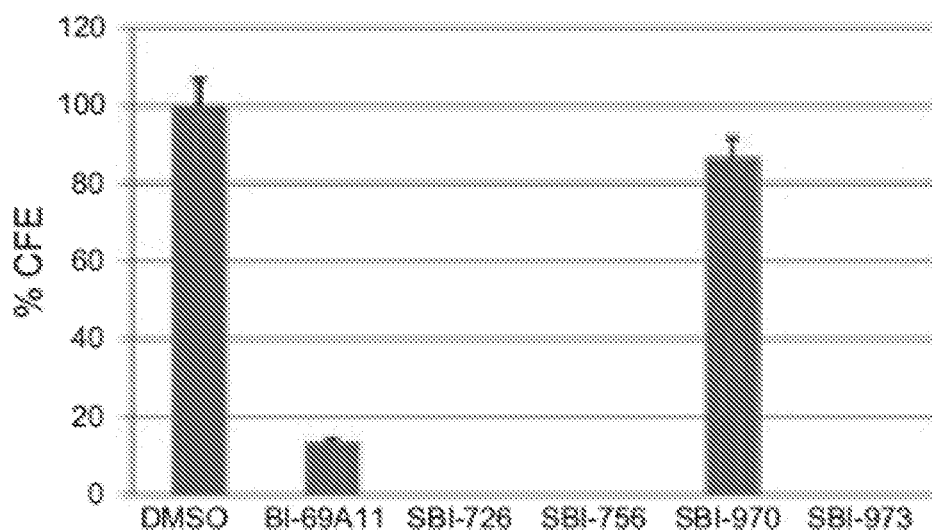
FIG. 4 shows SBI-756 (Compound 38), SBI-726 (Compound 44), SBI-970 (Compound 12), SBI-973 (Compound 62), and BI-69A11 colony forming efficiency (% CFE) in cultured melanoma cells Lu1205 (FIG. 4A) and WM1346 (FIG. 4B).
Figure 4B:
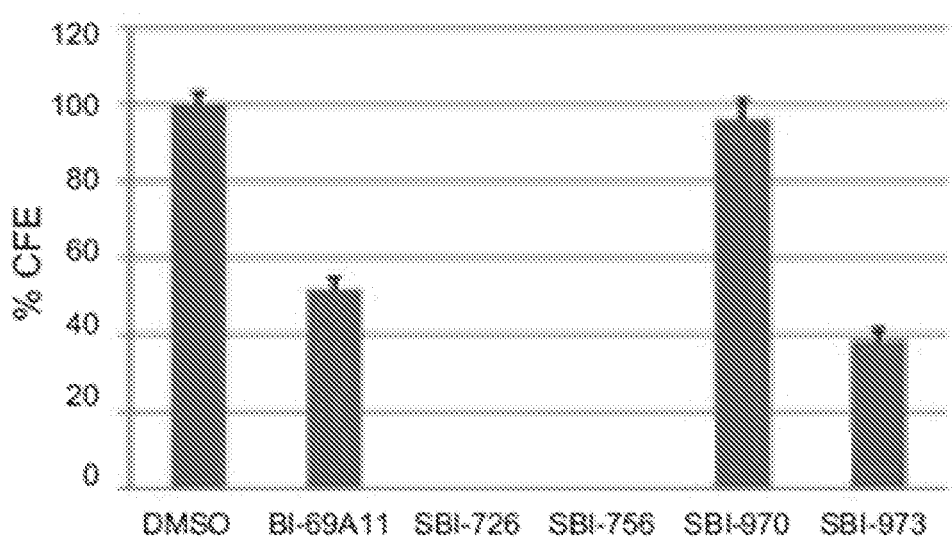
Figure 5A:
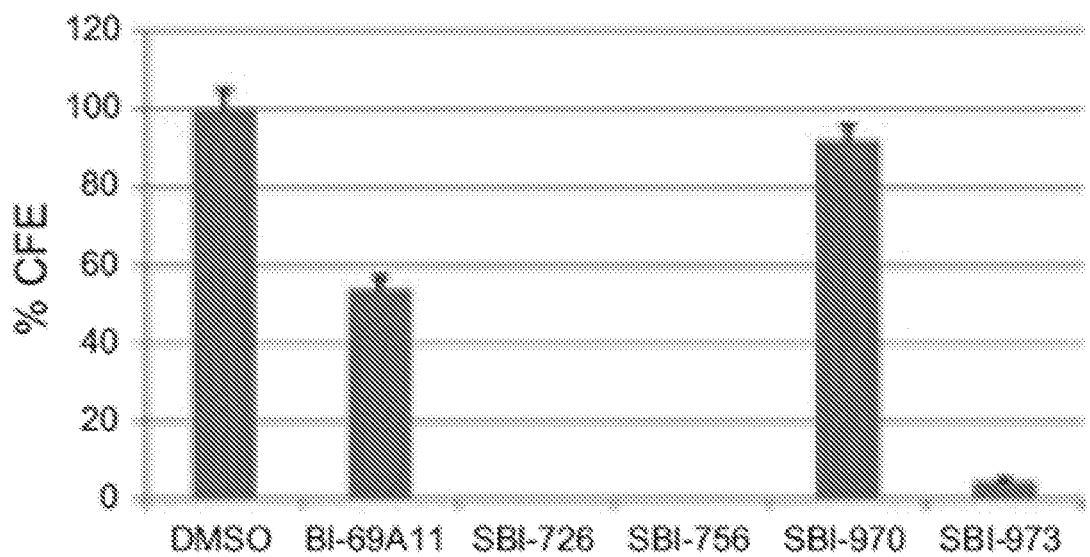
FIG. 5 shows SBI-756 (Compound 38), SBI-726 (Compound 44), SBI-970 (Compound 12), SBI-973 (Compound 62), and BI-69A11 colony forming efficiency (% CFE) in cultured melanoma cells A375 (FIG. 5A), UACC903 (FIG. 5B), and WM3629 (FIG. 5C).
Figure 5B:
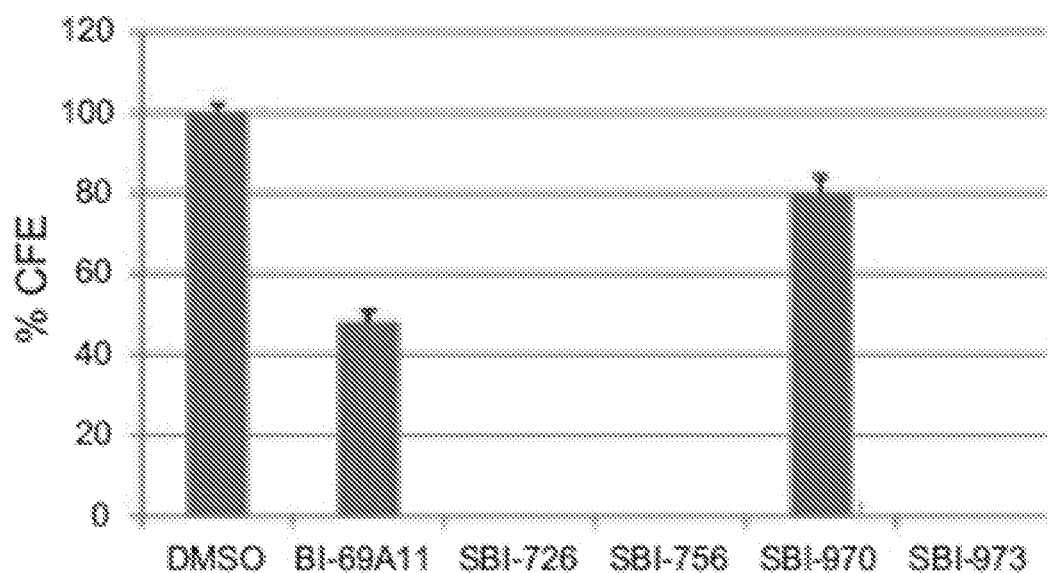
Figure 5C:
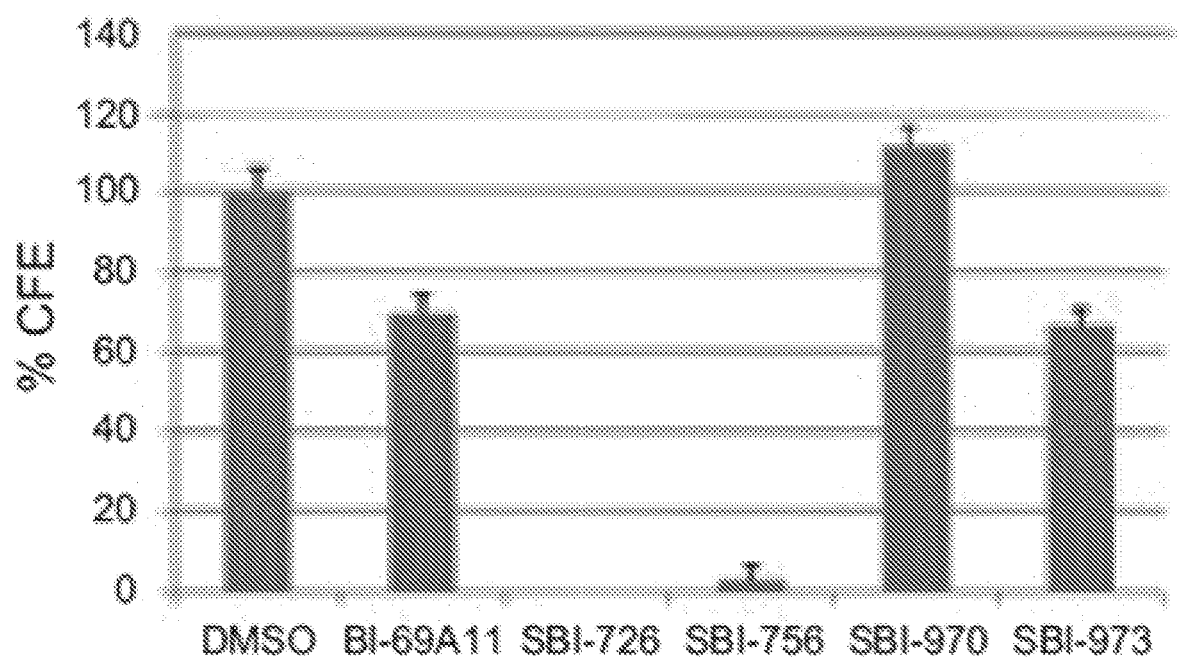

The inhibition of AKT and NF-κB activity of the Quinolinone derivatives was also assessed (as seen in FIG. 3). UACC903 cells were treated with vehicle (DMSO) or indicated concentration of the quinolinone derivatives for 24 h. Whole cells lysates were immunoblotted with indicated antibodies.

The colony formation by BRAF- and NRAS-mutant melanoma cells of the quinolinone derivatives was assessed in Lu1205, WM1346, A375, UACC903, and WM3629 cells. Lu1205, WM1346, A375, UACC903, and WM3629 cells were plated at low density (500 cells/well in 6-well plates) and grown in medium containing indicated compounds. The number of colonies formed after 10 days in culture was determined by crystal violet staining and the % CFE (colony-forming efficiency) were plotted as seen in FIG. 4A, FIG. 4B, FIG. 5A, FIG. 5B and FIG. 5C.

Example 3A: Target Identification

The proteins that interact and may serve as direct targets for Compound 38 were identified using gas chromatography/liquid mass spectrometry (LC/MS-MS) using biotinylated-BI-69A11. Of the 74 proteins that bound specifically (outcompeted using 10× excess of soluble BI-69A11) was eIF4G1 (Table 3), a large scaffolding protein that is a key component of the eIF4F complex.

TABLE 3

List of biotinylated-BI-69A11-bound proteins, identified by LC/MS/MS

| Protein name | Spectral count Replicate #1 | Replicate #2 |
|---|---|---|
| PKM2 Pyruvate kinase | 76 | 84 |
| EIF4G1 Isoform E of Eukaryotic translation initiation factor 4 gamma 1 | 47 | 16 |
| SMC4 Isoform 2 of Structural maintenance of chromosomes protein 4 | 21 | 12 |
| RPSAP58 Similar to Laminin receptor | 19 | 13 |
| RARS Isoform Monomeric of Arginyl-tRNA synthetase, cytoplasmic | 18 | 23 |
| FLNA Putative uncharacterized protein FLNA | 17 | 13 |
| ILK-2; CCT4 T-complex protein 1 subunit delta | 13 | 10 |
| Putative uncharacterized protein ENSP00000393016 | 11 | 10 |
| CHD3; LOC732272 231 kDa protein | 6 | 8 |
| CLINT1 Isoform 2 of Clathrin irnteractor 1 | 6 | 5 |
| FAM21C 147 kDa protein | 6 | 2 |
| FAM21C cDNA FU77522 | 6 | 2 |
| FAM21C Isoform 1 of WASH complex subunit FAM21C | 6 | 2 |
| FAM21C Isoform 2 of WASH complex subunit FAM21C | 6 | 2 |
| FAM21C Isoform 3 of WASH complex subunit FAM21C | 6 | 2 |
| FAM21C Isoform 4 of WASH complex subunit FAM21C | 6 | 2 |
| FAM21C WASH complex subunit FAM21C isoform 2 | 6 | 2 |
| FAM21C WASH complex subunit FAM21C isoform 3 | 6 | 2 |
| HAT1 Histone acetyltransferase 1, isoform CRA_b | 6 | 6 |
| HLTF Isoform 1 of Helicase-like transcription factor | 6 | 5 |
| RPS10 40S ribosomal protein S10 | 6 | 6 |
| UCHL5 cDNA, FU78963, highly similar to Ubiquitin carboxyl-terminal hydrolase isozyme L5 | 6 | 6 |
| UCHL5 Isoform 1 of Ubiquitin carboxyl-terminal hydrolase isozyme L5 | 6 | 6 |
| UCHL5 Isoform 2 of Ubiquitin carboxyl-terminal hydrolase isozyme L5 | 6 | 6 |
| UCHL5 Isoform 3 of Ubiquitin carboxyl-terminal hydrolase isozyme L5 | 6 | 6 |
| UCHL5 Isoform 3 of Ubiquitin carboxyl-terminal hydrolase isozyme L5 | 6 | 6 |
| UCHL5 Isoform 4 of Ubiquitin carboxyl-terminal hydrolase isozyme L5 | 6 | 6 |
| UCHL5 Ubiquitin carboxyl-terminal hydrolase L5 | 6 | 6 |
| UCHL5 Ubiquitin carboxyl-terminal hydrolase L5 18 kDa protein | 6 | 6 |
| H2AFV Histone H2A.V | 5 | 4 |
| HIST1H1E Histone H1.4 | 5 | 5 |
| MRPL21 cDNA FU52689, highly similar to Homo sapiens mitochondrial ribosomal protein L21 (MRPL21), transcript variant 4, mRNA | 5 | 3 |
| NASP Isoform 2 of Nuclear autoantigenic sperm protein | 5 | 5 |

Example 4A: Disruption of the eIF4F Complex

Figure 6:
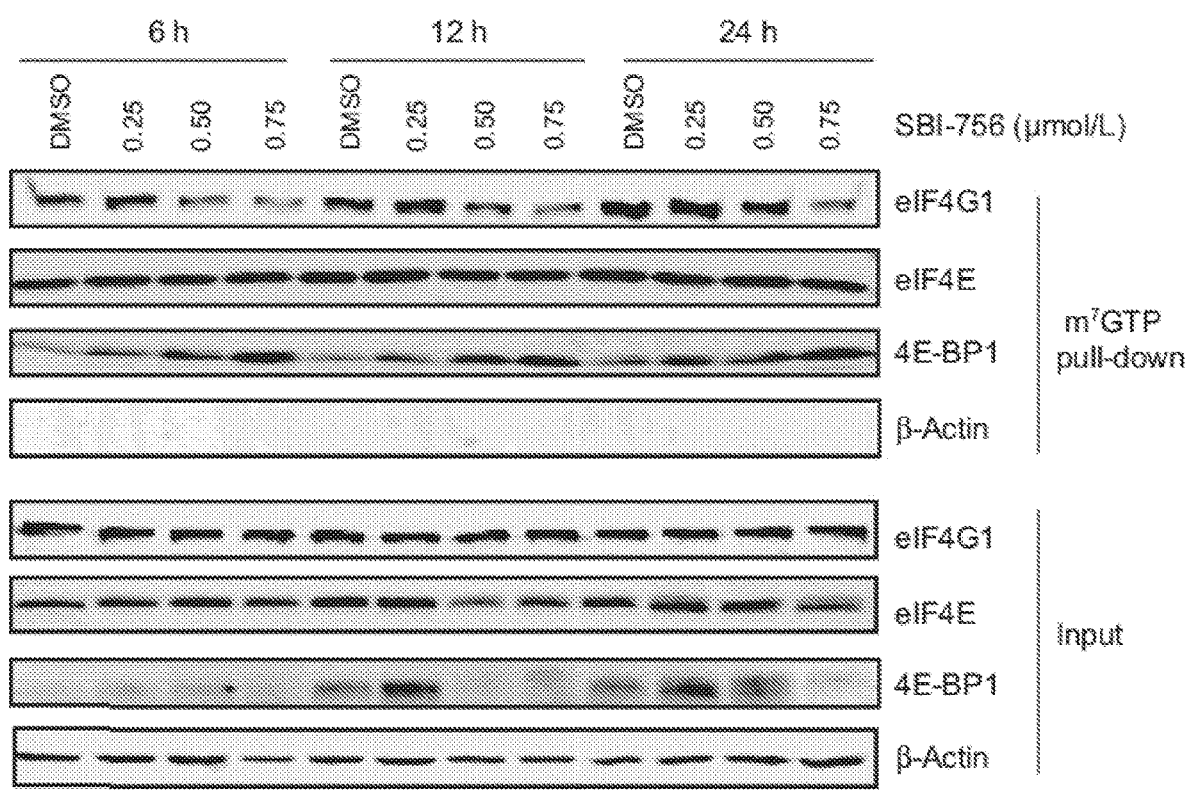
FIG. 6 shows SBI-756 (Compound 38) dose-dependent inhibition of eIF4G1 binding to eIF4E, concomitant with increased binding of inhibitory 4E-BP1 to eIF4E. Western blots show respective protein levels in total cell lysates or following pull-down using $m^7$GTP agarose beads. Bottom plot shows input (5%) and top plot shows $m^7$GTP pull-down (50%).

The dissociation of eIF4G1 from the eIF4F complex was determined using $m^7$GTP-agarose pull-down, which captures the eIF4F complex. Compound 38 dissociated eIF4G1 from the eIF4E in a dose-dependent manner, which was accompanied by a concomitant increase in 4E-BP1:eIF4E binding (as seen in FIG. 6), reflective of impaired eIF4F complex formation. Proteins prepared from UACC903 melanoma cells were treated with indicated Compound 38 concentrations and incubated with $m^7$GTP-agarose beads to capture the eIF4F complex. Shown is dose-dependent inhibition of eIF4G1 binding to eIF4E, concomitant with increased binding of inhibitory 4E-BP1 to eIF4E. Bottom, the total cell lysate.

Figure 7:
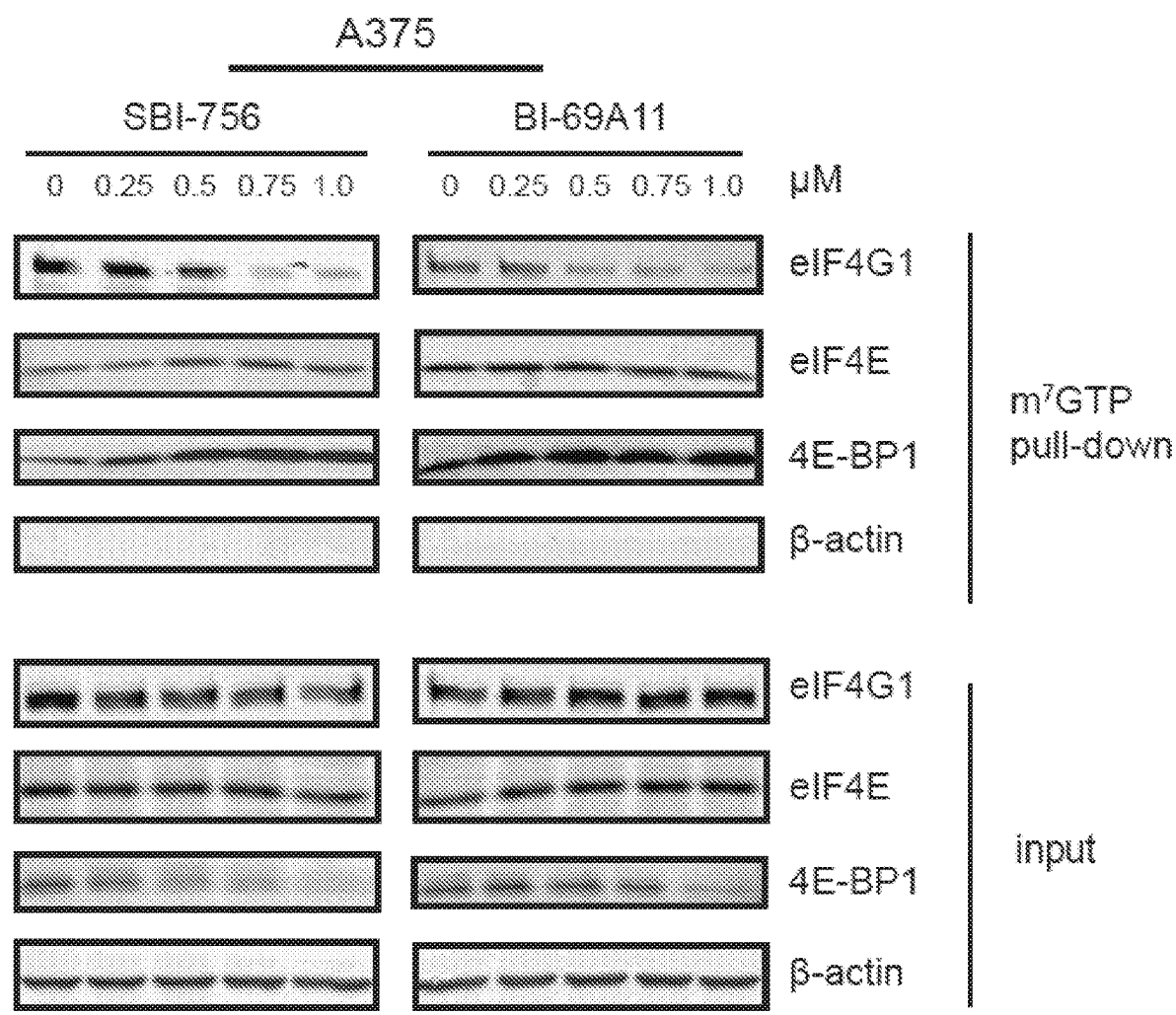
FIG. 7 shows a comparison between SBI-756 (Compound 38) and BI-69A11 effect on the eIF4F complex integrity.

Comparative inhibition of the eIF4F complex between BI-69A11 and Compound 38 is shown in FIG. 7.

Example 5A: Inhibition of the AKT/mTORC1 Signaling Pathway

Figure 8:
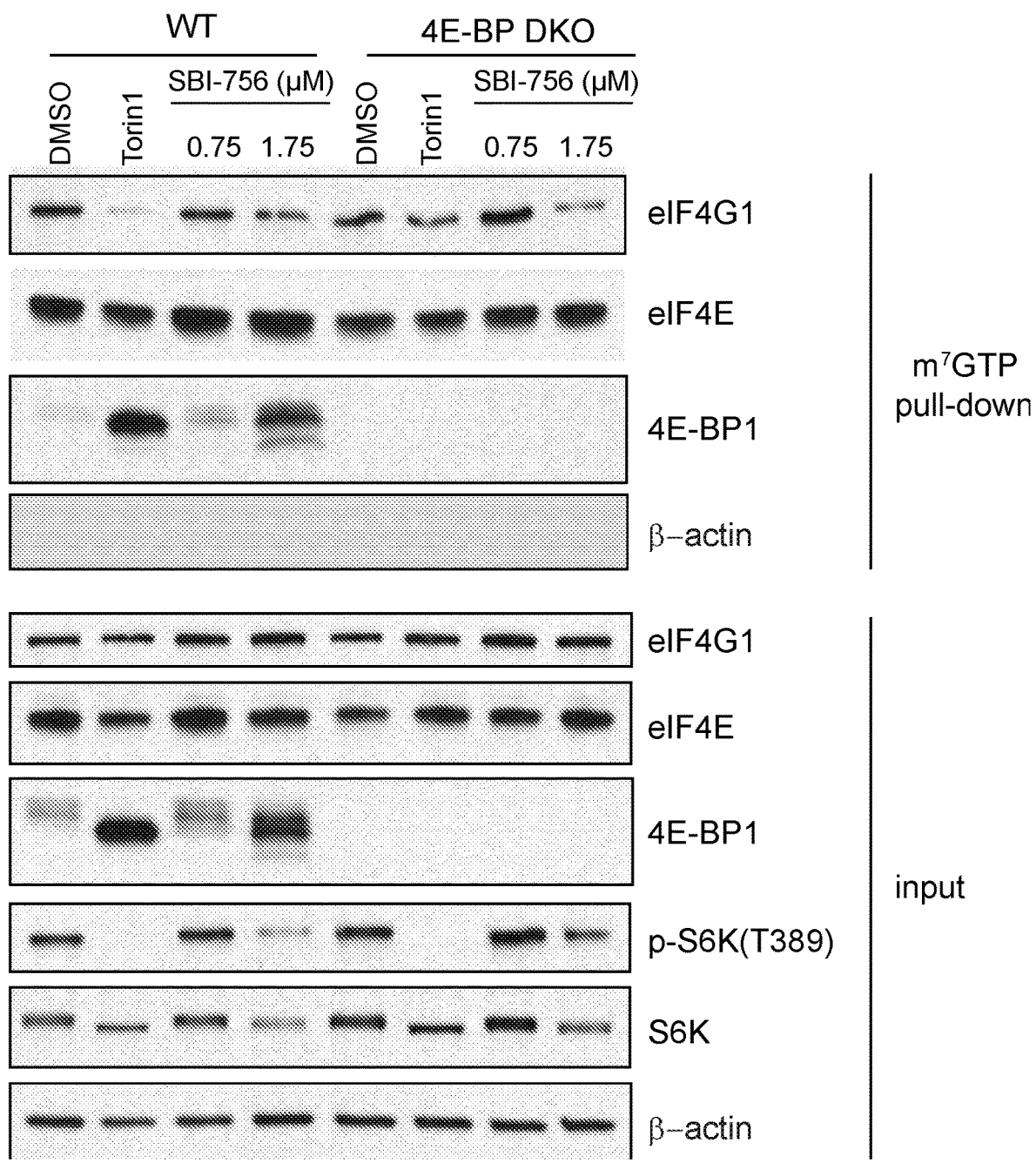
FIG. 8 shows the AKT/mTORC1 inhibition of SBI-756 (Compound 38). Western blots show respective protein levels in total cell lysates or following pull-down using $m^7$GTP agarose beads. Bottom plot shows input (5%) and top plot shows $m^7$GTP pull-down (50%).

Compound 38 also inhibited the AKT/mTORC1 signaling and mTORC1 inhibition disrupted the eIF4F complex via activation of 4E-BPs. To determine whether Compound 38 impeded eIF4F assembly directly or via mTORC1, 4E-BP1/2 DKO MEFs was employed, wherein mTOR inhibition does not impair the eIF4F assembly. Whereas torin1 induced dissociation of eIF4G1 from eIF4E in WT but not in 4E-BPDKOMEFs, Compound 38 reduced eIF4G1:eIF4E association in both WT and 4E-BP DKO MEFs (FIG. 8). Indicated cultures (WT or DKO 4E-BP) were treated with Torin1 (250 nmol/L) or indicated Compound 38 concentrations for 6 hours. Western blots show respective protein levels in total cell lysates or following pull-down using $m^7GTP$ agarose beads. Bottom plot shows input (5%) and top plot shows $m^7GTP$ pull-down (50%). P3-Actin served as a loading control and to exclude contamination in $m^7GTP$ pull-down.

Figure 9:
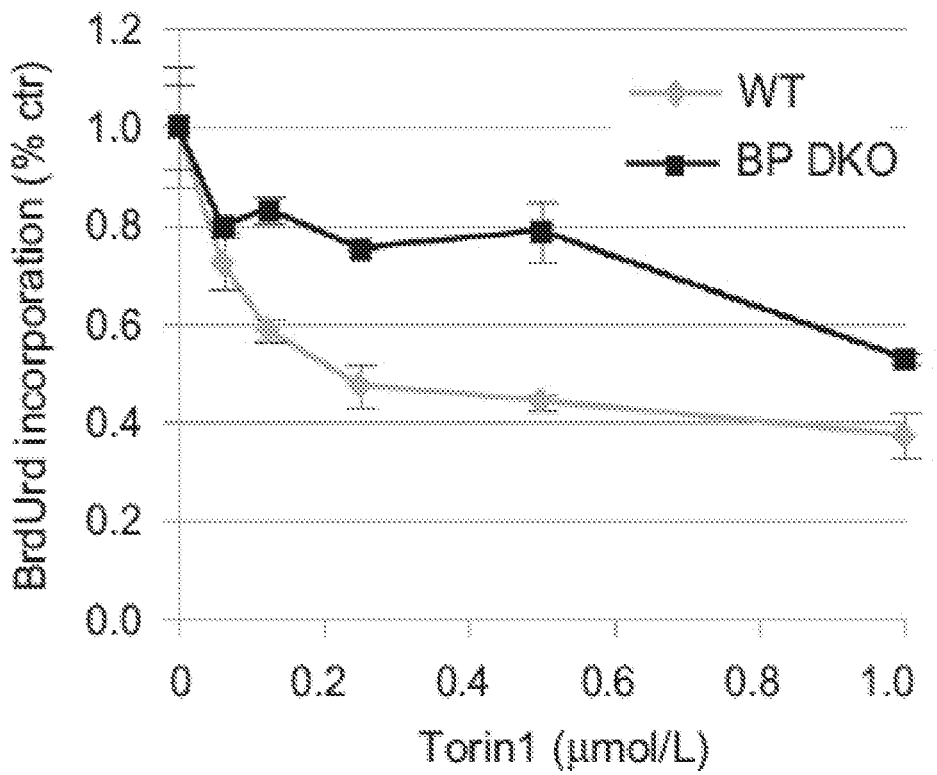
FIG. 9 shows the SBI-756 (Compound 38) and torin1 (mTOR inhibitor) proliferation attenuation of E1A/RAS-transformed 4E-BP DKO MEFs.
Figure 9:
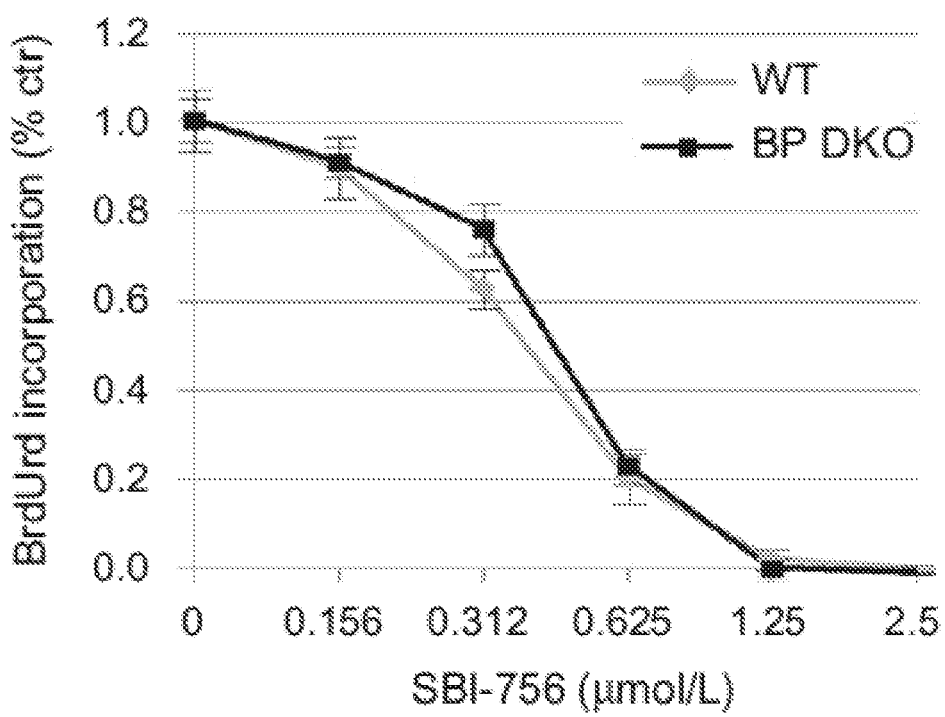

Compound 38, but not torin1, attenuated the proliferation of E1A/RAS-transformed 4E-BP DKO MEFs (FIG. 9). These results substantiate that the effect of Compound 38 on the eIF4F complex assembly is largely mTOR-independent. E1A/Ras-transformed WT or 4e-bp1/4e-bp2 DKO MEFs were treated with either Torin1 or Compound 38 at indicated concentrations and cell proliferation was measured 48 hours later with the aid of BrdUrd incorporation. Values were normalized to DMSO-treated triplicates. Error bars, SD (n=3).

Example 6A: Combination of Compound 38 with Vemurafenib (PLX4032)

Figure 10:
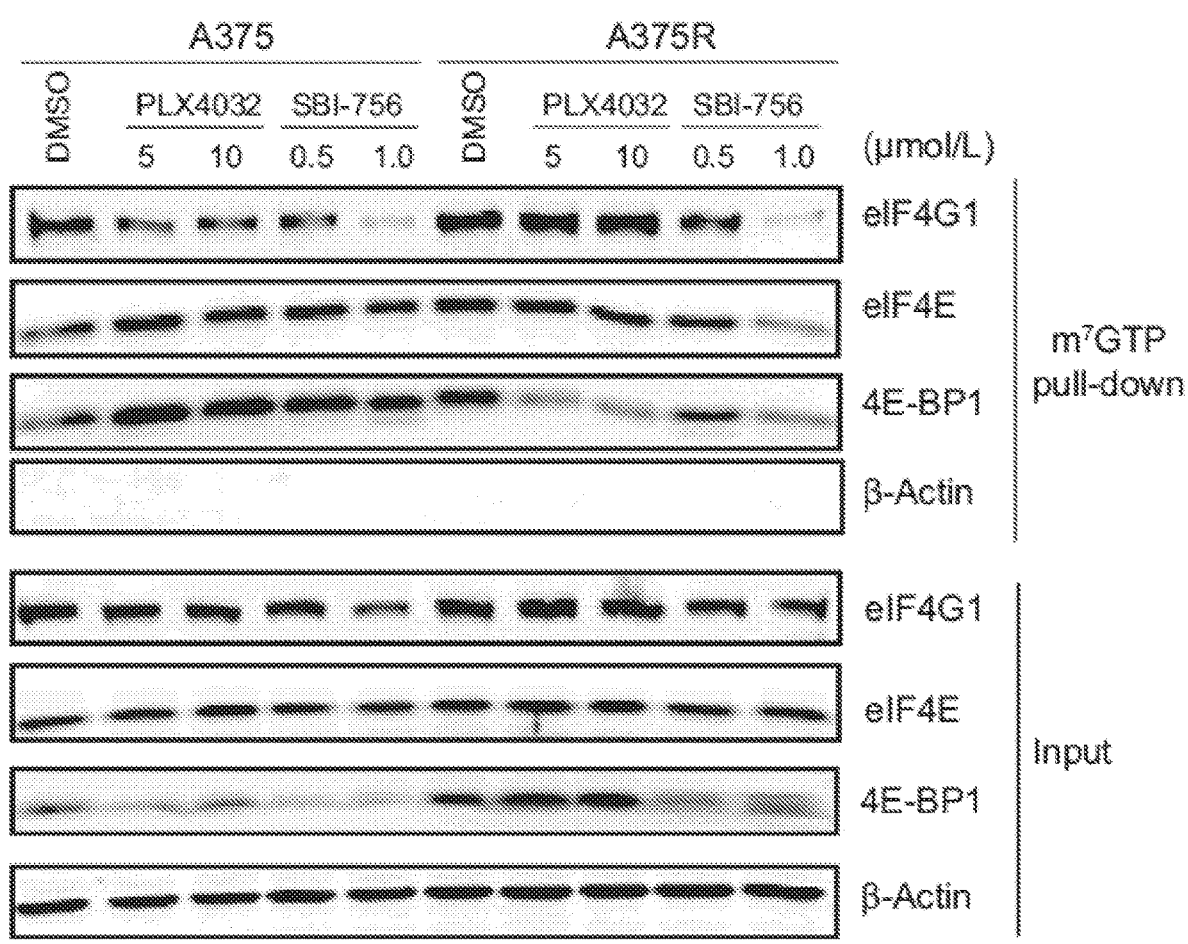
FIG. 10 shows the SBI-756 (Compound 38) dissociation of eIF4G1 from eIF4E in A375R (resistant melanoma cell line) compared to PLX4032 (BRAFi). Western blots show respective protein levels in total cell lysates or following pull-down using $m^7$GTP agarose beads. Bottom plot shows input (5%) and top plot shows $m^7$GTP pull-down (50%).
Figure 11A:
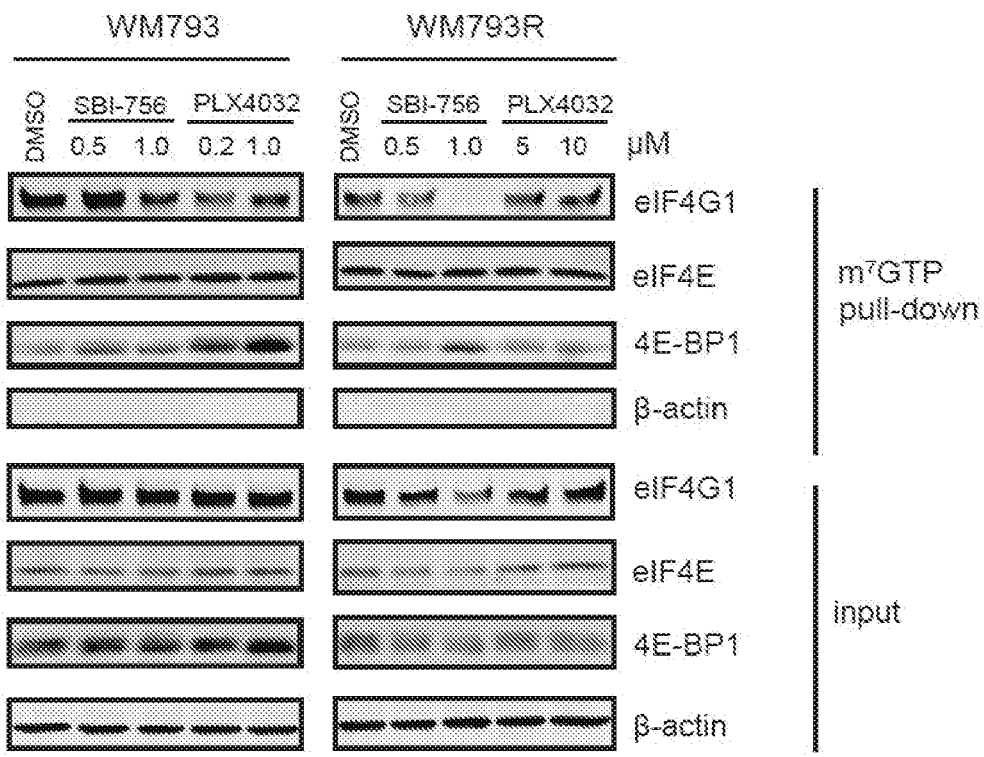
FIG. 11 shows the SBI-756 (Compound 38) dissociation of eIF4G1 from eIF4E in resistant melanoma cell line WM793R (FIG. 11A) and Lu1205R (FIG. 11B) compared to PLX4032 (BRAFi). Western blots show respective protein levels in total cell lysates or following pull-down using $m^7$GTP agarose beads. Bottom plot shows input (5%) and top plot shows $m^7$GTP pull-down (50%).
Figure 11B:
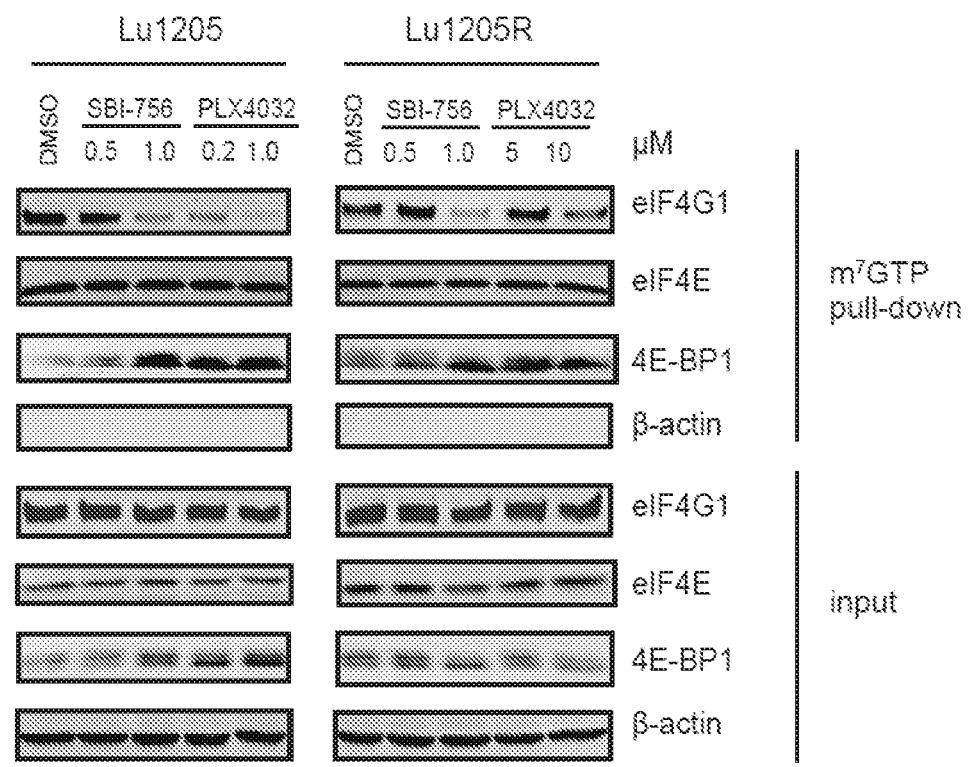
Figure 12A:
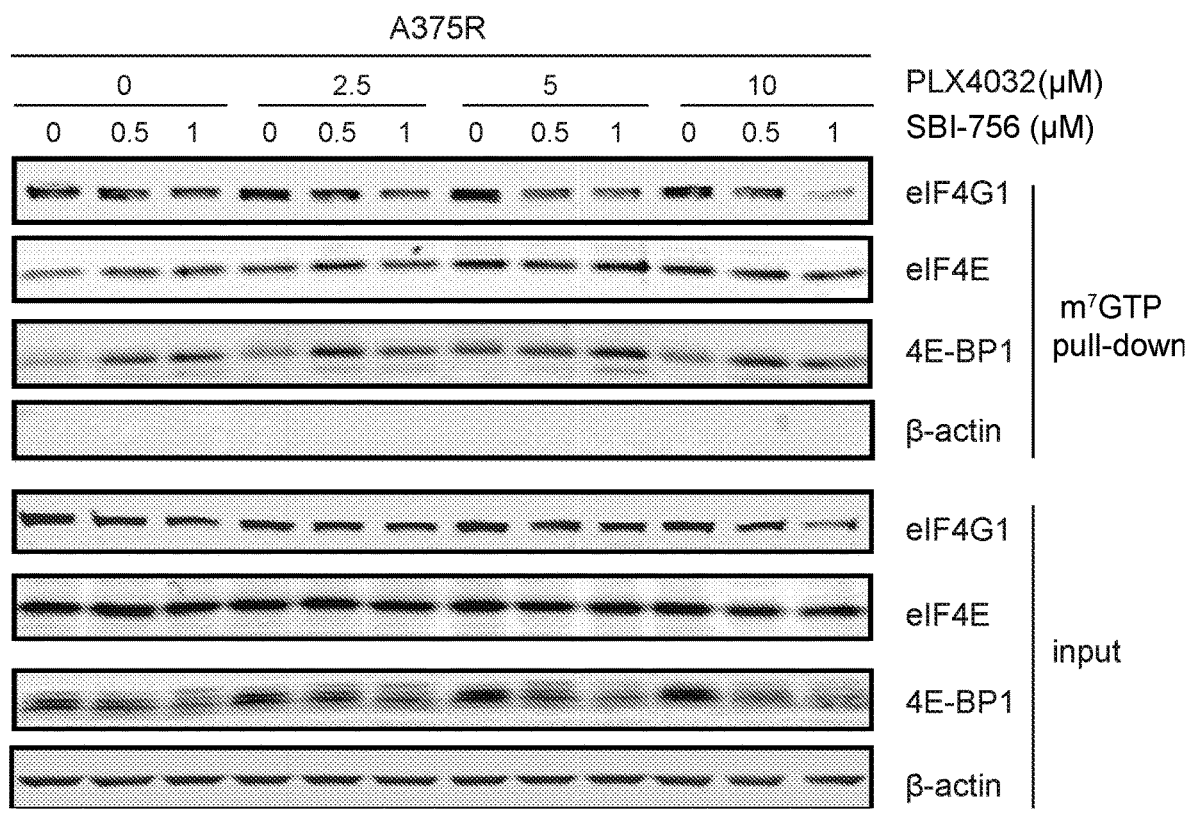
FIG. 12 shows the SBI-756 (Compound 38)/PLX4032 dissociation of eIF4G1 from eIF4E in resistant melanoma resistant cell line A375R (FIG. 12A) and melanoma cell line A375 (FIG. 12B). Western blots show respective protein levels in total cell lysates or following pull-down using $m^7$GTP agarose beads. Bottom plot shows input (5%) and top plot shows $m^7$GTP pull-down (50%).
Figure 12B:
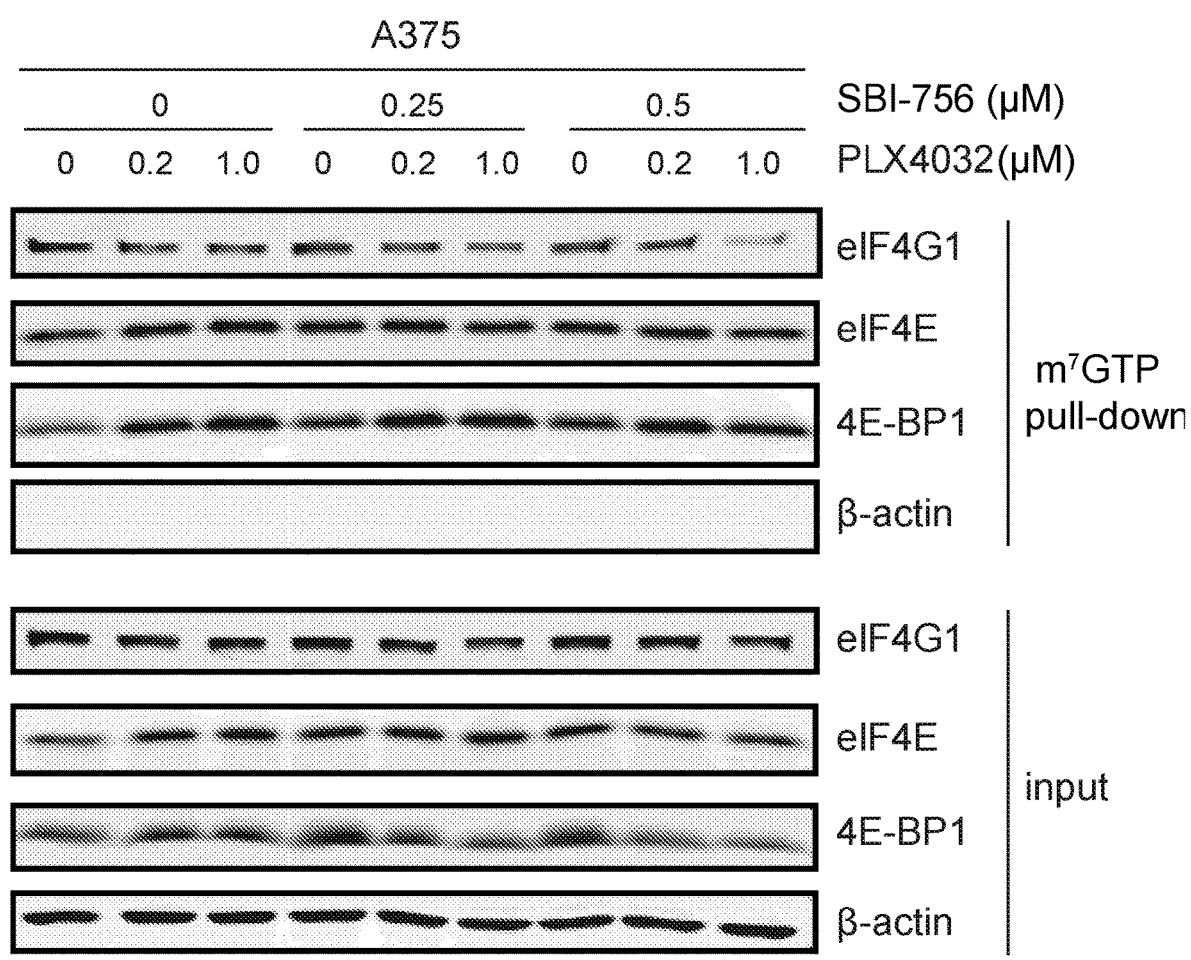
Figure 13A:
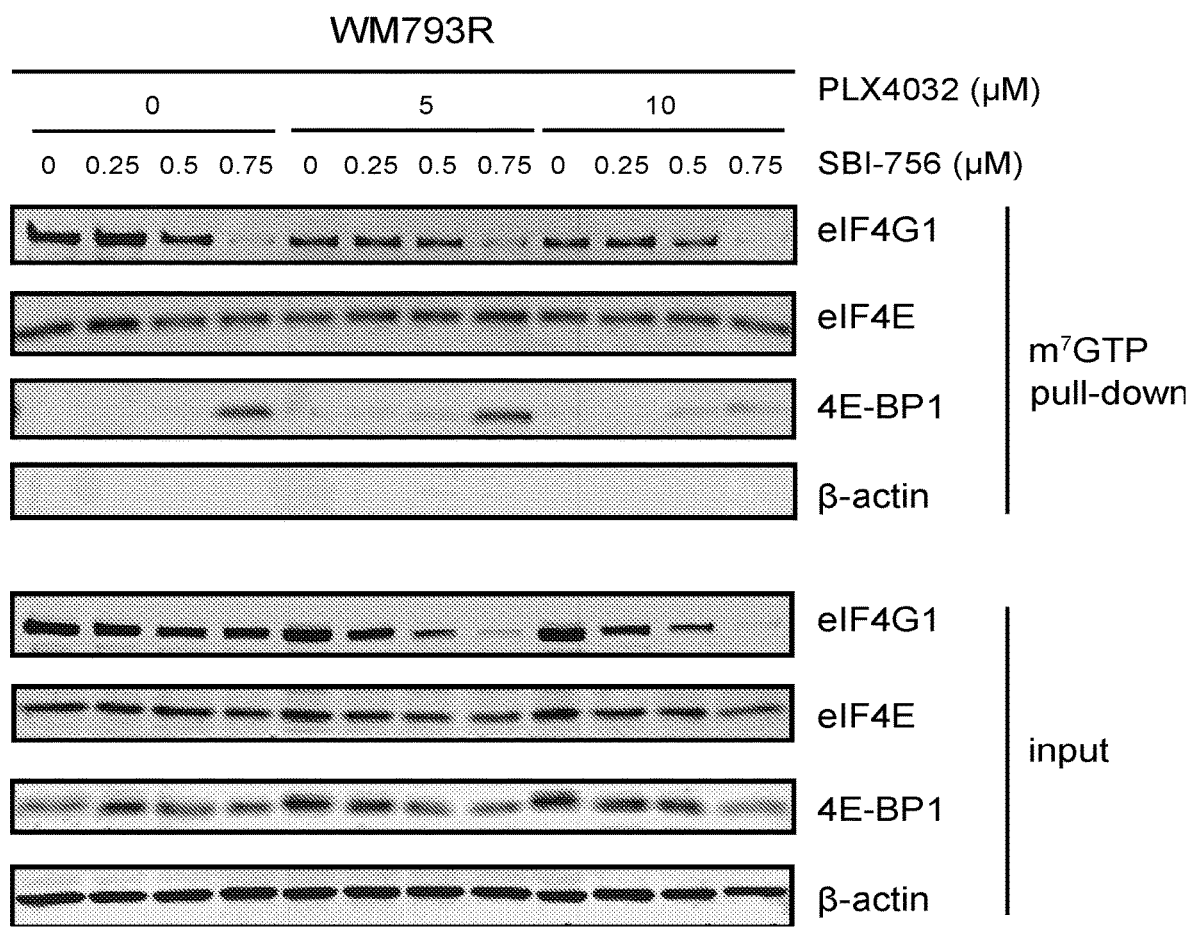
FIG. 13 shows the SBI-756 (Compound 38)/PLX4032 dissociation of eIF4G1 from eIF4E in melanoma resistant cell lines WM793R (FIG. 13A) and Lu1205R (FIG. 13B). Western blots show respective protein levels in total cell lysates or following pull-down using $m^7$GTP agarose beads. Bottom plot shows input (5%) and top plot shows $m^7$GTP pull-down (50%).
Figure 13B:
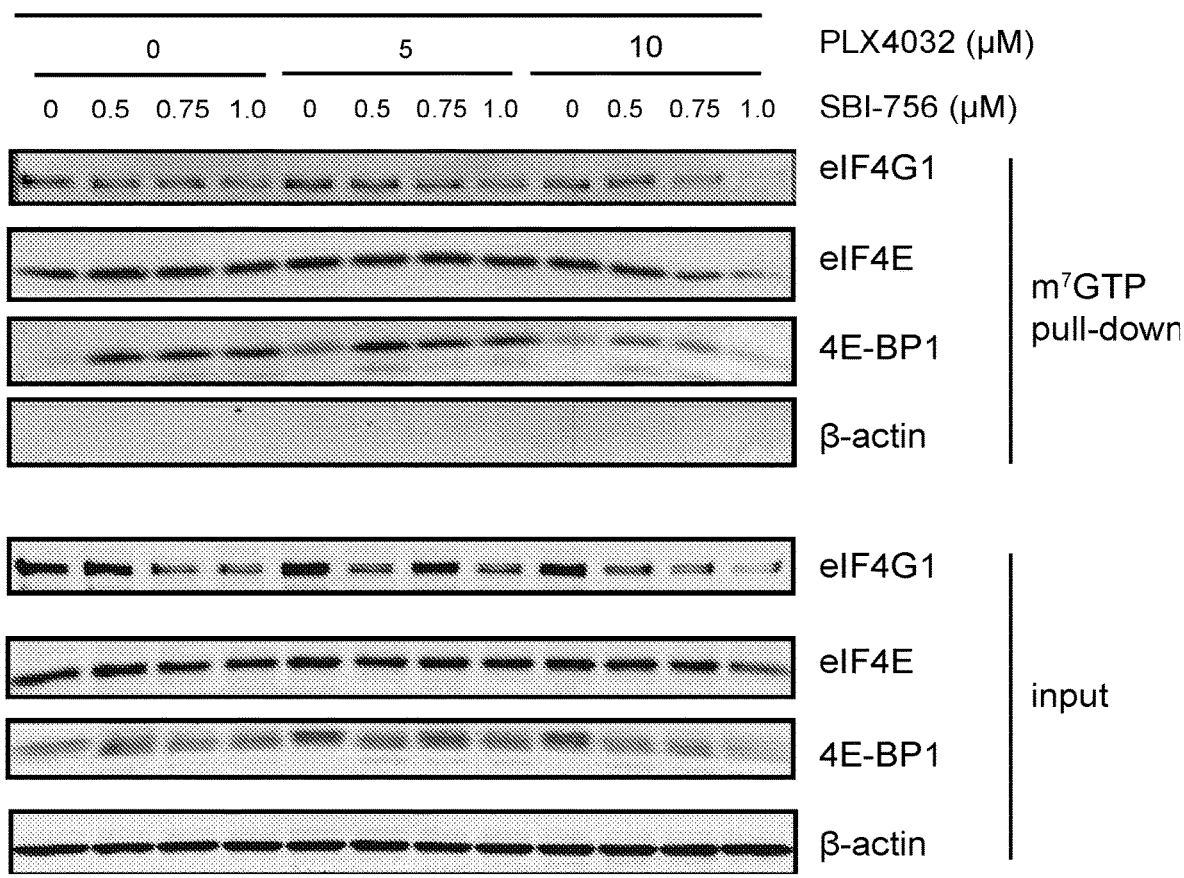

As levels of the eIF4F complex inversely correlate with the effectiveness of various cancer therapies, the integrity of the eIF4F complex after treating melanoma cells with a combination of BRAFi vemurafenib (PLX4032) and Compound 38 was assessed. Comparing A375 melanoma cultures that are sensitive to BRAFi and resistant derivatives (A375R), BRAFi slightly reduced eIF4G1 association with eIF4E, whereas Compound 38 had a more robust effect (FIG. 10). Compound 38, but not the BRAFi PLX4032, significantly promoted a dose dependent dissociation of eIF4G1 from eIF4E in A375R (as seen in FIG. 10), Lu1205R and WM793R cells (as seen in FIG. 11A and FIG. 11B). A375 and A375R (PLX4032-resistant) cells were treated with vehicle (DMSO), a BRAFi (vemurafenib; PLX4032), or Compound 38 at the indicated doses for 24 hours. Cell lysates (200 mg) were subjected to $m^7GTP$ pull-down. Amounts of the indicated proteins in input (5%) or pull-down (50%) samples were determined by Western blotting; 3-actin served as a loading control (input) and to exclude contamination ($m^7GTP$ pull-down). Furthermore, a Compound 38/BRAFi combination decreased the amount of eIF4G1 bound to eIF4E, which was not seen following BRAFi treatment alone (as seen in FIG. 12A, FIG. 12B, FIG. 13A, and FIG. 13B). These findings demonstrate the effectiveness of Compound 38 in disrupting the eIF4F complex by targeting the eIF4G1.

Example 7A: Reverse Phase Protein Array Analysis (RPPA)

Figure 14A:
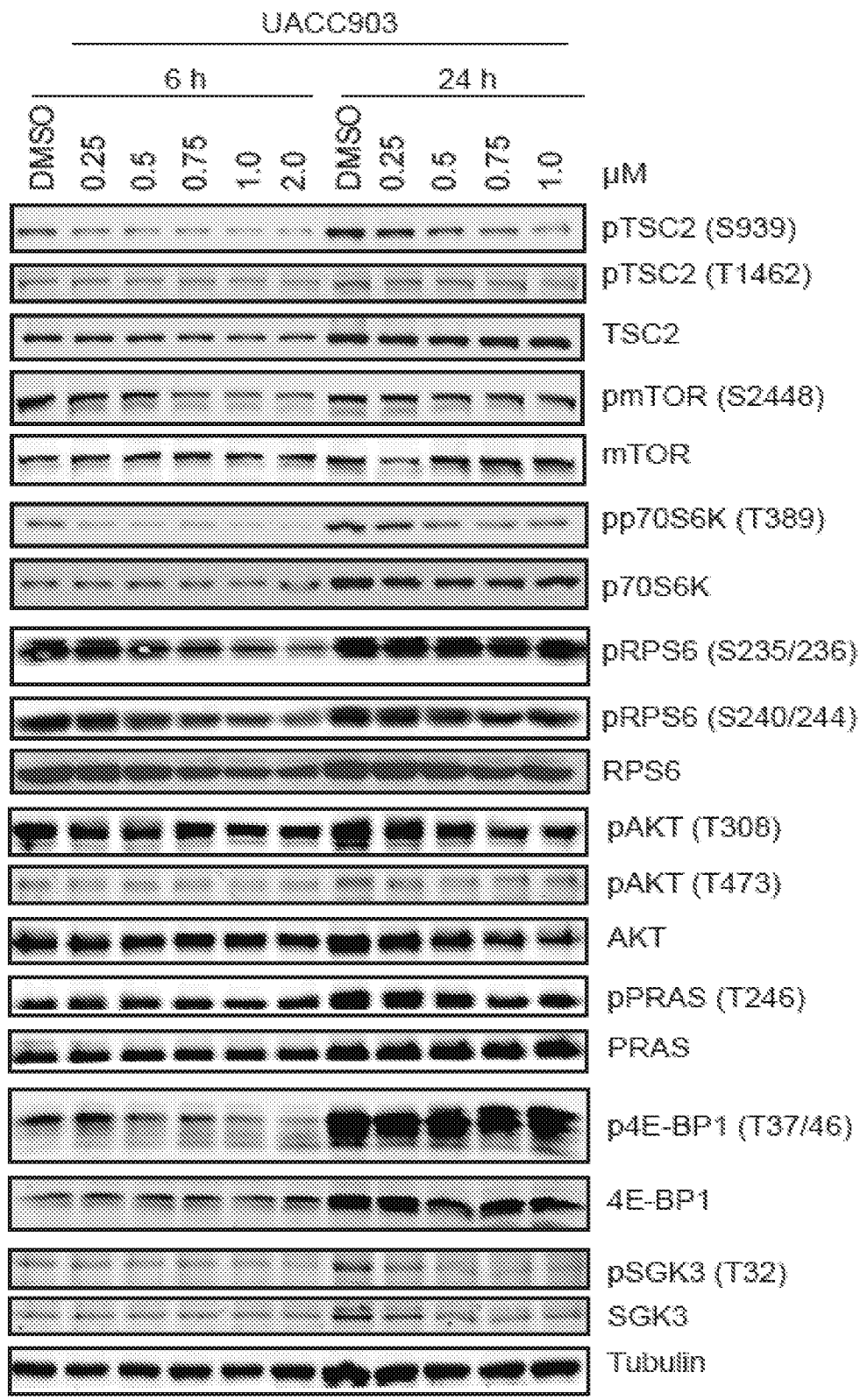
FIG. 14 shows the validation of RPPA data in UACC903 melanoma cells (FIG. 14A) and A375 melanoma cells (FIG. 14B) at the indicated time points performed in Westerns blot with the indicated antibodies.
Figure 14B:
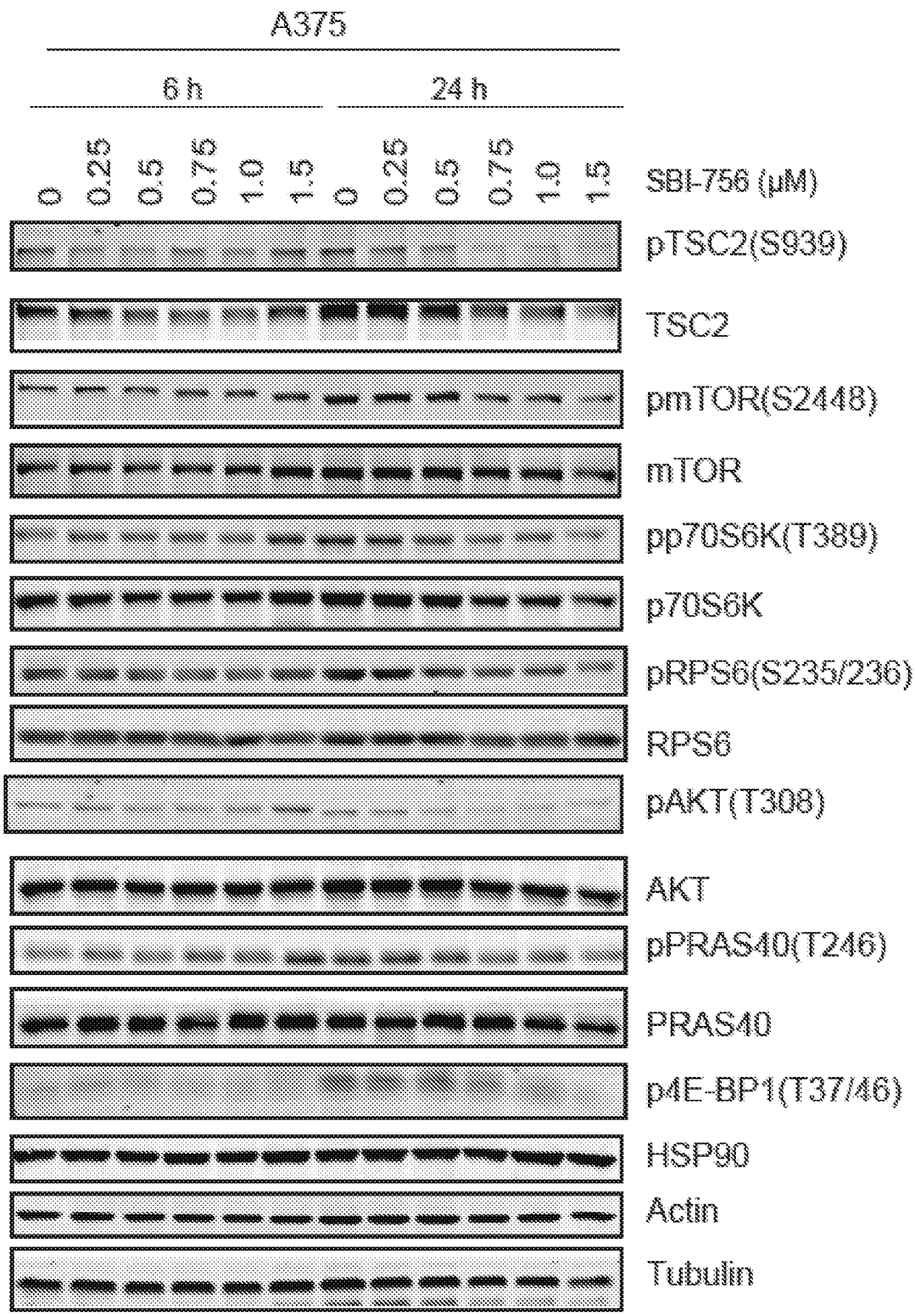

A reverse phase protein array (RPPA) analysis of BRAF- and NRAS-mutant melanomas was performed to identify protein networks affected by Compound 38 (Table 4). Unsupervised clustering of proteins that significantly (P<0.05) changed expression/phosphorylation levels with Compound 38 treatment for 24 hours demonstrated a consistent inhibitory effect in both cell lines on mTOR signaling, and multiple translation initiation regulators, reflected by markedly decreased phosphorylation of S6, mTOR, P70S6K as well as TSC2. Western blot analysis confirmed the dose dependent inhibitory effects of Compound 38 on these proteins and a decrease in 4E-BP1 phosphorylation in UACC903 and A375 cell lines (FIG. 14A and FIG. 14B).

TABLE 4

Proteins significantly inhibited by Compound 38 in UACC903 (BRAF mutant) and WM1346 (NRAS mutant) cell lines.

| | Ratio [Compound 38/DMSO] | | | Unpaired t-test (p) | |
|---|---|---|---|---|---|
| Protein | WM1346 | UACC903 | Average | WM1346 | UACC903 |
| S6_pS240_S244 | 0.65 | 0.61 | 0.63 | 0.0160 | 0.0013 |
| Tuberin | 0.68 | 0.62 | 0.65 | 0.0004 | 0.0031 |
| S6_pS235_S236 | 0.70 | 0.63 | 0.67 | 0.0235 | 0.0013 |
| YB1 | 0.69 | 0.77 | 0.73 | 0.0036 | 0.0017 |
| mTOR_pS2448 | 0.76 | 0.72 | 0.74 | 0.0000 | 0.0003 |
| c-Myc | 0.80 | 0.72 | 0.76 | 0.0027 | 0.0020 |
| Stat5a | 0.67 | 0.85 | 0.76 | 0.0000 | 0.0141 |
| MSH6 | 0.78 | 0.76 | 0.77 | 0.0146 | 0.0001 |
| ATR | 0.76 | 0.84 | 0.80 | 0.0012 | 0.0009 |
| mTOR | 0.71 | 0.90 | 0.80 | 0.0006 | 0.0056 |
| ATM | 0.82 | 0.79 | 0.81 | 0.0024 | 0.0001 |
| p70-S6K_pT389 | 0.81 | 0.82 | 0.81 | 0.0005 | 0.0050 |
| AR | 0.72 | 0.92 | 0.82 | 0.0001 | 0.0032 |
| Rad51 | 0.78 | 0.93 | 0.85 | 0.0005 | 0.0444 |
| Raptor | 0.87 | 0.86 | 0.86 | 0.0077 | 0.0067 |
| GCN5L2 | 0.86 | 0.88 | 0.87 | 0.0119 | 0.0085 |
| Rictor_pT1135 | 0.91 | 0.84 | 0.87 | 0.0437 | 0.0019 |
| c-Kit | 0.94 | 0.86 | 0.90 | 0.0078 | 0.0033 |
| INPP4b | 0.88 | 0.93 | 0.9 | 0.0006 | 0.0325 |
| A-Raf | 0.90 | 0.91 | 0.9 | 0.0094 | 0.023 |
| Chk1 | 0.94 | 0.89 | 0.91 | 0.0279 | 0.0211 |
| Ets-1 | 0.91 | 0.92 | 0.92 | 0.019 | 0.0114 |
| C-Raf | 0.93 | 0.92 | 0.92 | 0.0134 | 0.0047 |
| BRCA2 | 0.90 | 0.96 | 0.93 | 0.0316 | 0.0439 |
| PI3K-p110-alpha | 0.95 | 0.94 | 0.95 | 0.0071 | 0.0312 |
| PI3K-p85 | 0.96 | 0.93 | 0.95 | 0.0342 | 0.0131 |

Example 8A: Identification of -Sensitive and -Resistant Lines

Figure 15:
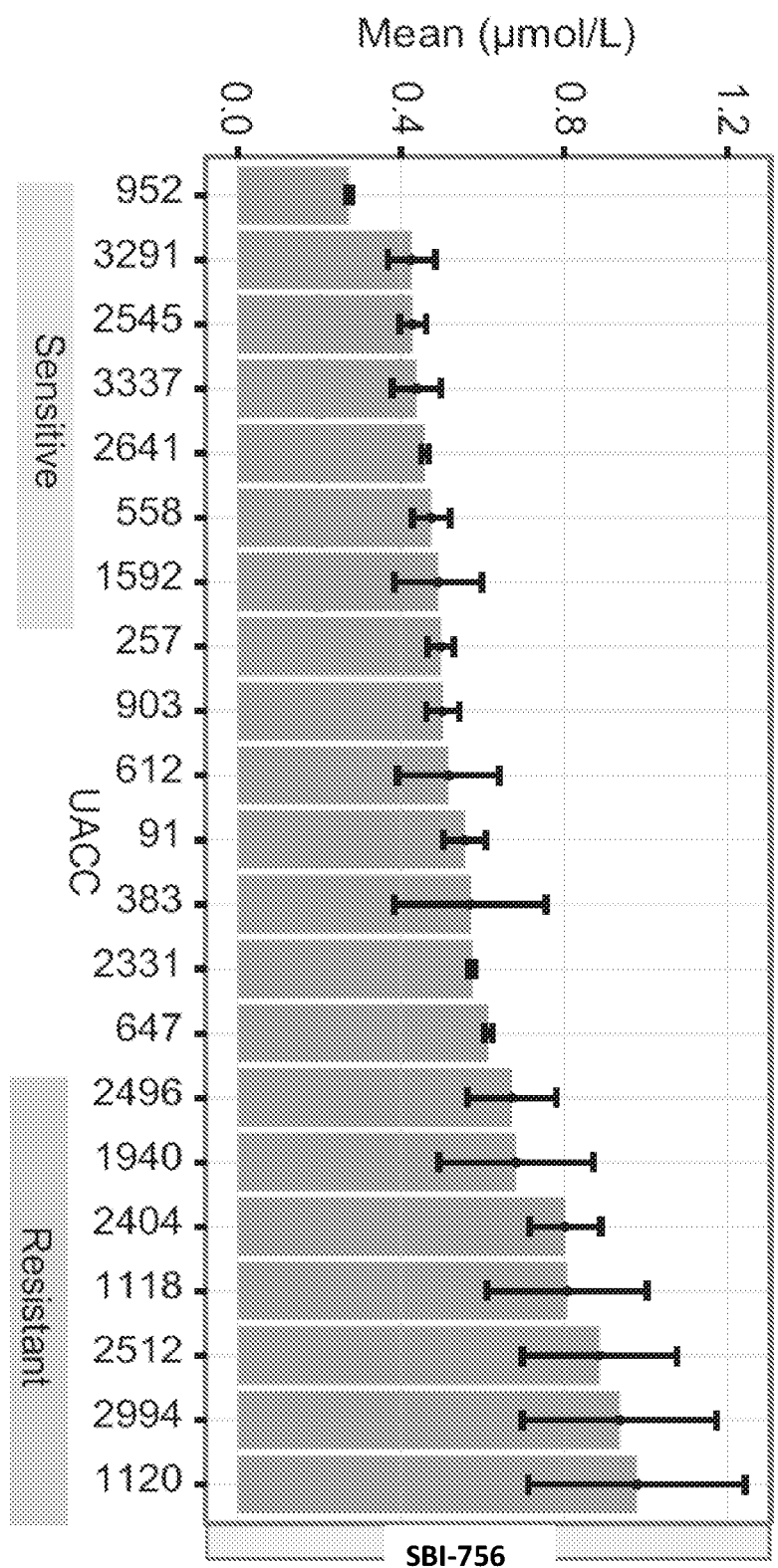
FIG. 15 shows the SBI-756 (Compound 38)-sensitive and -resistant cell lines.

Dose-response analysis of Compound 38 in 21 melanoma lines identified two groups representing respective Compound 38-sensitive and Compound 38-resistant lines (>2-fold expression difference in $IC_{50}$ between groups; FIG. 15). Evaluation of gene expression data from these cell lines enabled mapping differentially expressed genes (DEG) for each group. In total, we detected 1,533 significant DEGs between sensitive and the more resistant cells (P<0.05; fold change >1.5). Analysis of gene enrichment within canonical pathways identified higher expression levels of genes involved in DNA damage response (P=4.1 E×$10^{-9}$), ATM signaling (P=2.8×$10^{-7}$), and CHK-mediated cellcycle checkpoint control (P=6.0×$10^{-7}$) in Compound 38-resistant cells, with concurrently lower expression of G2-M cell-cycle checkpoint control genes (P=1.5×$10^{-8}$). In addition, among genes exhibiting lower expression in resistant lines were key cellcycle regulatory proteins, including, CDKN1A, CDKN2A, and RB1 (P<3.0×$10^{-14}$).

Figure 16A:
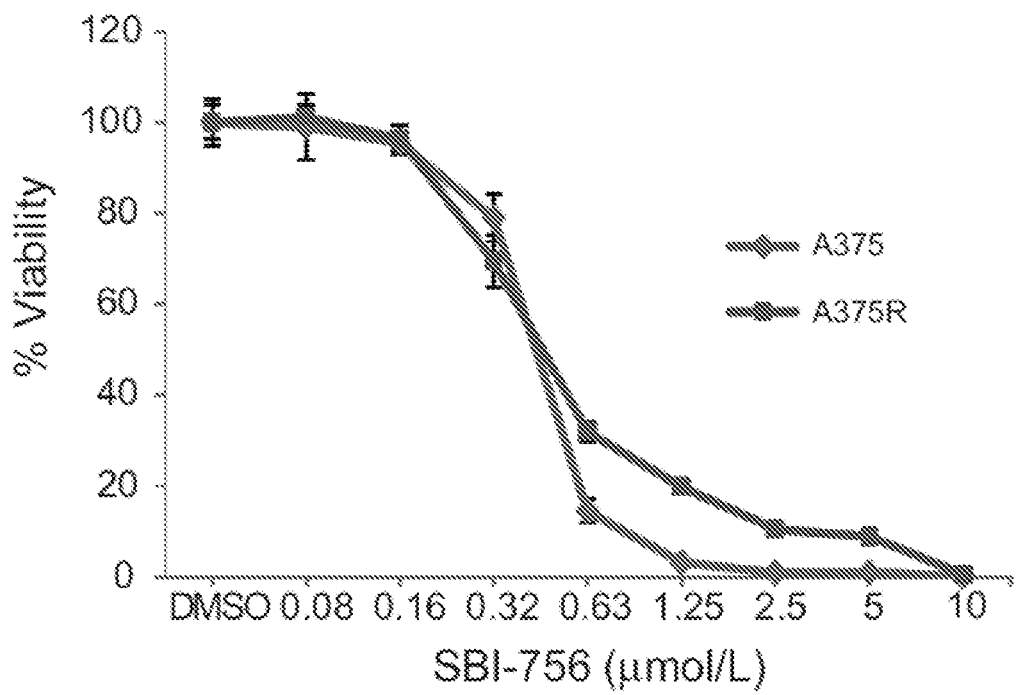
FIG. 16A shows SBI-756 (Compound 38) cell viability in parental (A375) and BRAFi-resistant NF1-mutant melanoma cell lines (A375R).
Figure 16B:
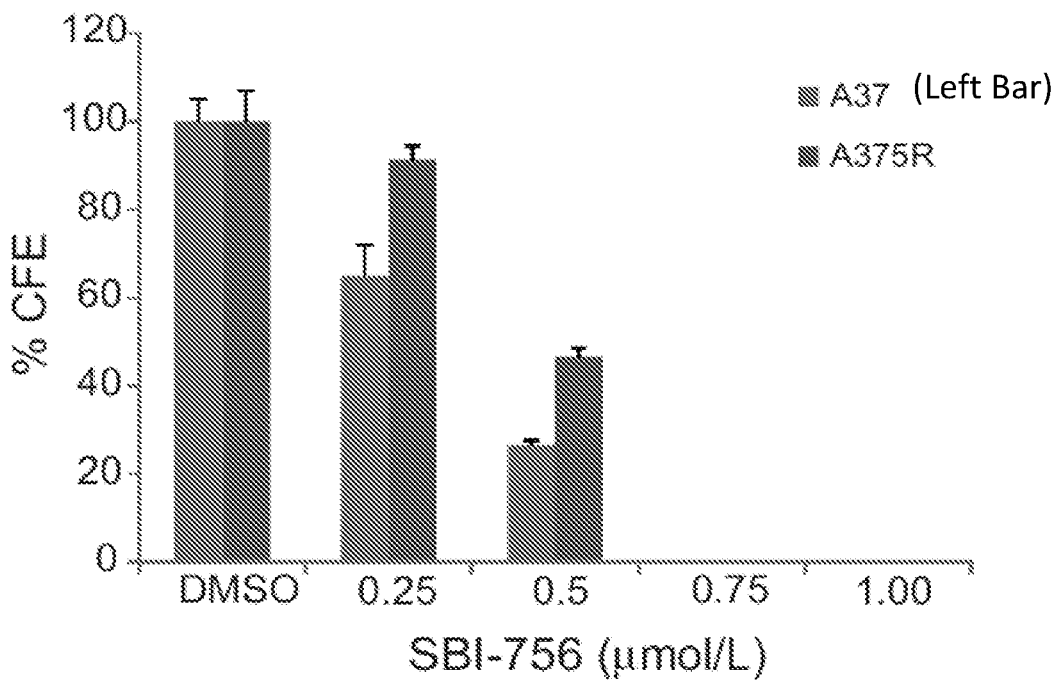
FIG. 16B shows SBI-756 (Compound 38) colony forming efficiency (% CFE) in parental (A375) and BRAFi-resistant NF1-mutant melanoma cell lines (A375R).
Figure 17A:
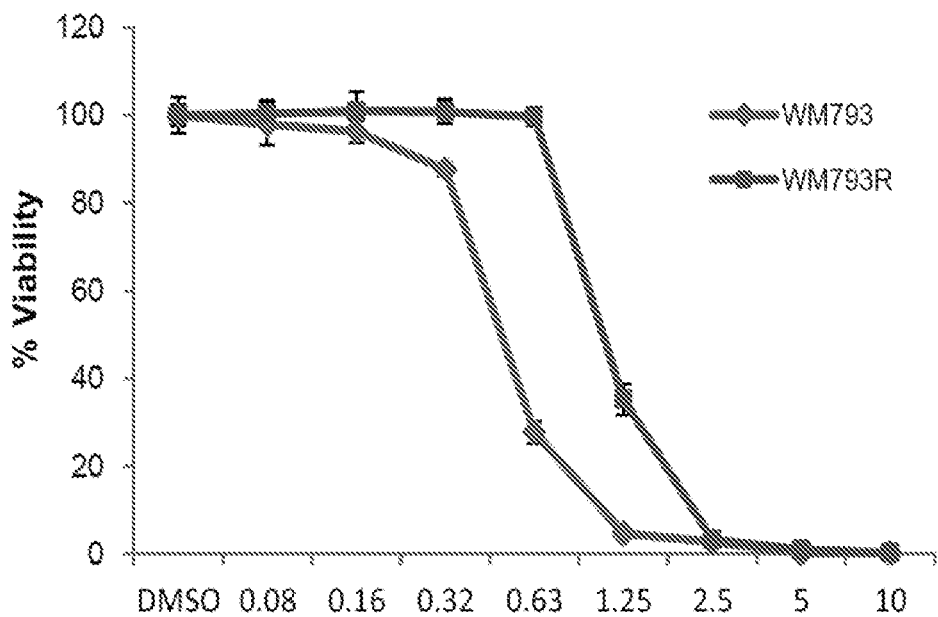
FIG. 17A shows SBI-756 (Compound 38) cell viability in parental (WM793) and BRAFi-resistant NF1-mutant melanoma cell lines (WM793R).
Figure 17B:
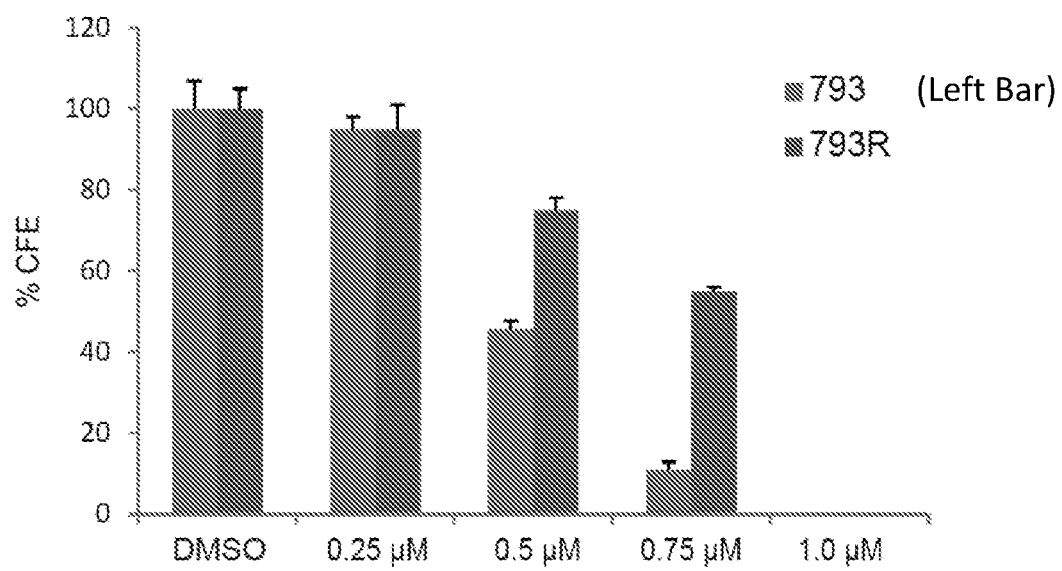
FIG. 17B shows SBI-756 (Compound 38) colony forming efficiency (% CFE) in parental (WM793) and BRAFi-resistant NF1-mutant melanoma cell lines (WM793R).
Figure 18A:
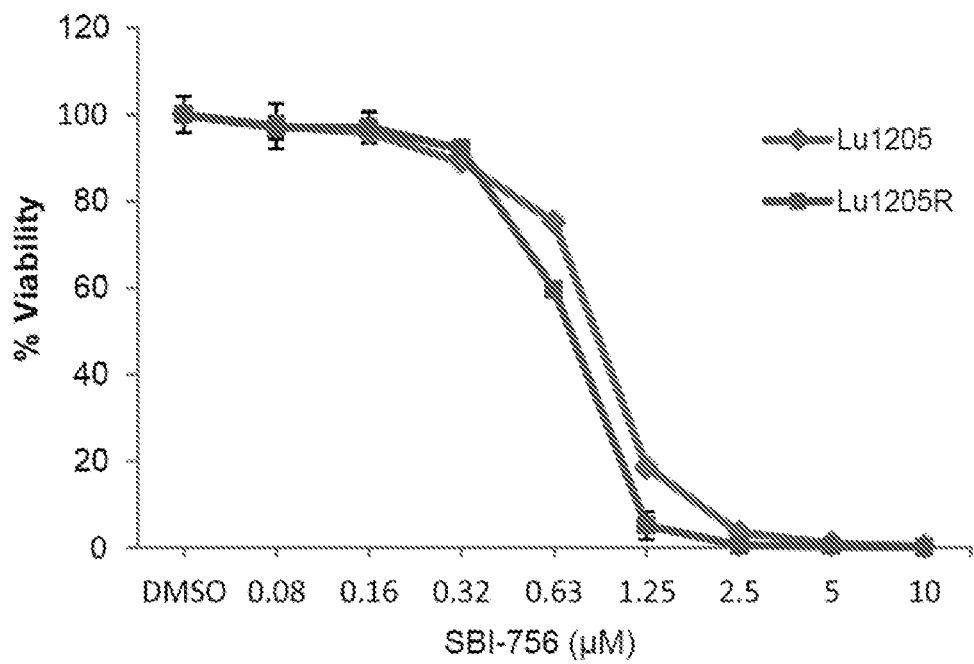
FIG. 18A shows SBI-756 (Compound 38) cell viability in parental (Lu1205) and BRAFi-resistant NF1-mutant melanoma cell lines (Lu1205R).
Figure 18B:
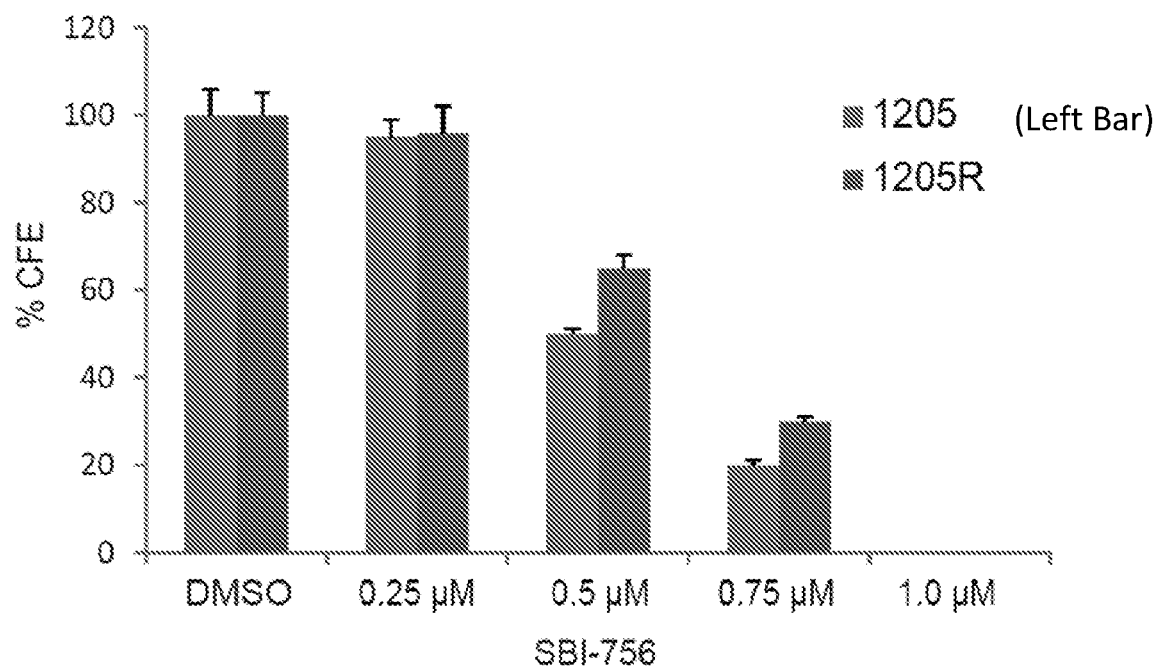
FIG. 18B shows SBI-756 (Compound 38) colony forming efficiency (% CFE) in parental (Lu1205) and BRAFi-resistant NF1-mutant melanoma cell lines (Lu1205R).
Figure 19A:
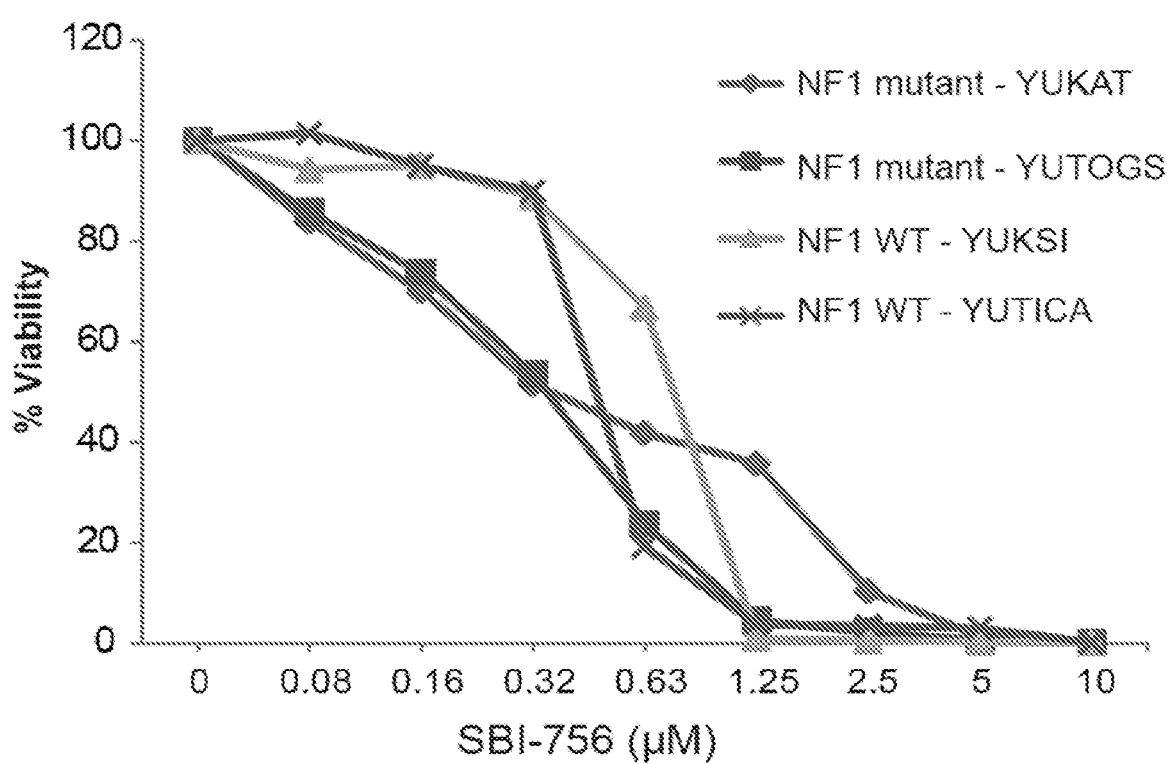
FIG. 19A shows SBI-756 (Compound 38) cell viability in NF1-mutant and NF1-wilt type cell lines.
Figure 19B:
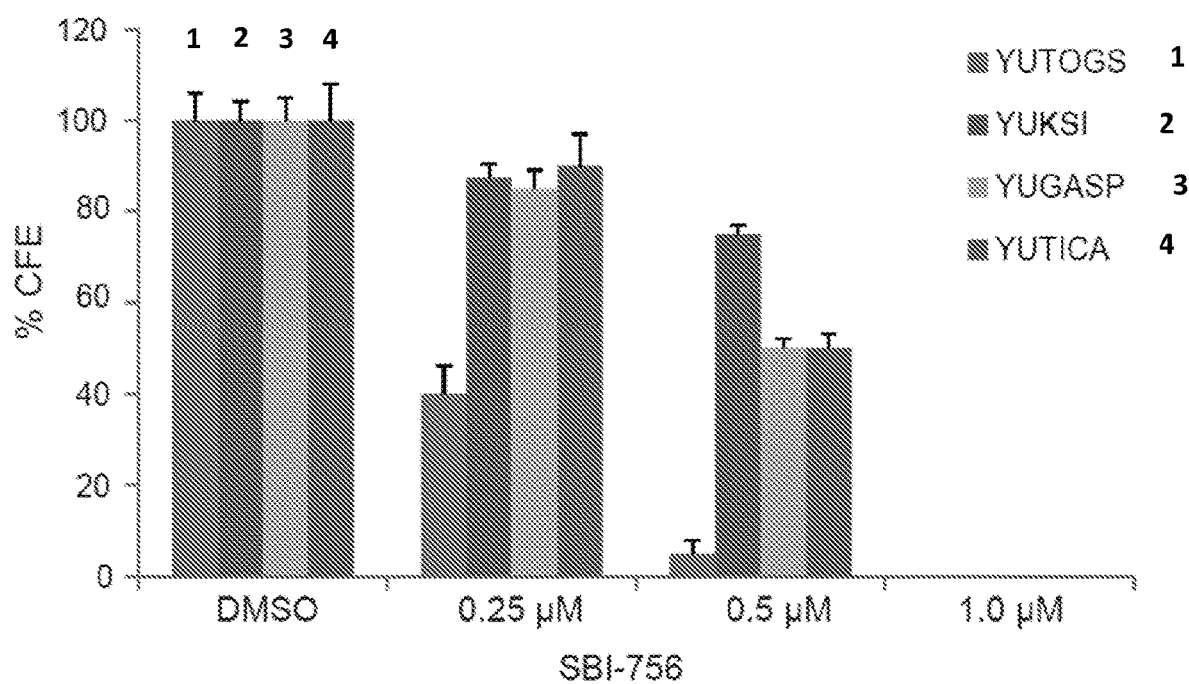
FIG. 19B shows SBI-756 (Compound 38) colony forming efficiency (% CFE) in NF1-mutant and NF1-wilt type cell lines.

To confirm the effect of Compound 38 on the eIF4F complex in BRAFi resistant cultures on neoplastic growth, Compound 38 effectiveness on their two-dimensional (2D) growth in vitro was assessed. Growth in 2D and colony-forming efficiency (CFE) were effectively attenuated in both parental (sensitive) and resistant cultures, with NF1-mutant melanoma lines exhibiting equal or greater sensitivity. Parental and BRAFi-resistant NF1-mutant melanomas (A) were monitored for their response to Compound 38 at the indicated concentrations and for their ability to form CFE (B) (A375: FIG. 16A and FIG. 16B, WM793: FIG. 17A and FIG. 17B, Lu1205: FIG. 18A and FIG. 18B). Effectiveness of Compound 38 in NF1-mutant melanoma was further confirmed in primary cultures (FIG. 19A and FIG. 19B).

Example 9A: In Vivo Experiments

Figure 20:
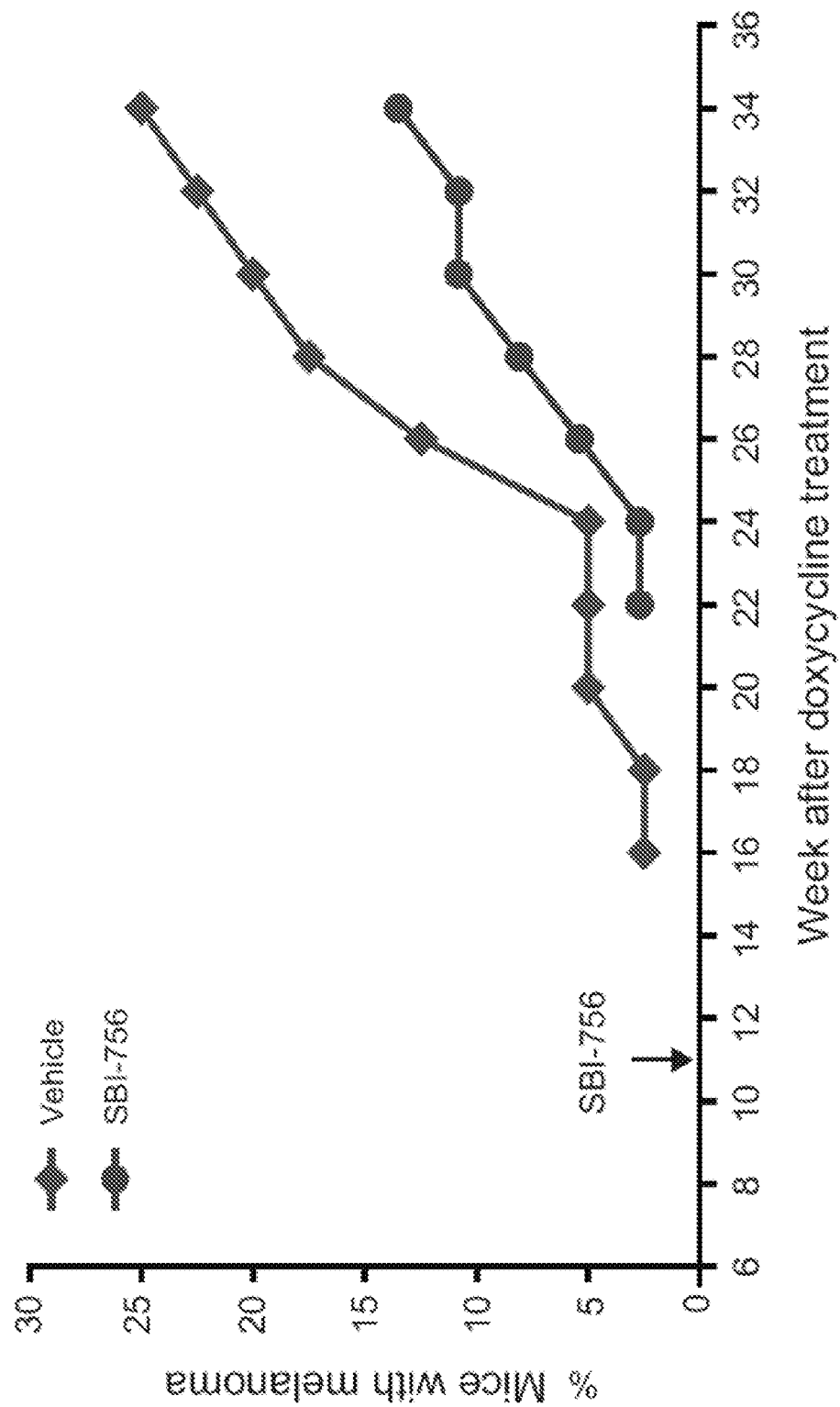
FIG. 20 shows the evaluation of SBI-756 (Compound 38) in an inducible $Nras^{Q61K}/Ink4a^{-/-}$ genetic model in which melanoma tumors emerge within 16 to 20 weeks.

In vivo, Compound 38 was evaluated using an inducible $Nras^{Q61K}/Ink4a^{-/-}$ genetic model in which melanoma tumors emerge within 16 to 20 weeks (FIG. 20). Administration of Compound 38 only, starting 11 weeks after genetic inactivation of Ink4a and induction of $NRas^{Q61E}$ (about 10-14 days prior to tumor appearance), delayed tumor onset (from 20-26 weeks), and reduced tumor incidence, by 50%, compared with the control nontreated group. Mice of the $Nras^{Q61K}$:$Ink4a^{-/-}$ genotype or WT mice (38-40 mice for each genotype) were administered vehicle or Compound 38 at 0.5 mg/kg by intraperitoneal injection twice a week starting at week 11 after $Nras^{Q61K}$ activation and Ink4a inactivation. Tumor development was monitored twice per week. Latency and frequency of melanoma development over the 21-week treatment period (weeks 11-32) are shown.

The growth of A375 tumors in immunodeficient mice subjected to either BRAFi alone or BRAFi combined with Compound 38 was monitored in vivo. Compound 38 toxicity in mice was monitored by liver function (Table 5).

TABLE 5

Blood chemistry following Compound 38 IP administration

| | | Vehicle | | | Compound 38 (1 mg/kg) | | | |
|---|---|---|---|---|---|---|---|---|
| Item | Organ | #1 | #2 | #3 | #4 | #5 | #6 | |
| ALB | Liver | 33 | 37 | 37 | 32 | 34 | 32 | g/L |
| ALP | Liver | 51 | 85 | 100 | 88 | 54 | 24 | μ/L |
| ALT | Liver | 765 | 347 | 167 | 126 | >1000 | 152 | μ/L |
| TBIL | Liver | 3 | 4 | 4 | 5 | 4 | 4 | μmol/L |
| TP | Liver | 41 | 46 | 48 | 42 | 44 | 43 | g/L |
| GLOB | Liver | 7 | 9 | 10 | 10 | 11 | 11 | g/L |
| AMY | Pancreas | 727 | 721 | 789 | 701 | 811 | 1625 | μ/L |
| BUN | Kidney | 13.1 | 9.7 | 11.1 | 7.5 | 9.9 | 7.9 | mmol/L |
| CRE | Kidney | <18 | <18 | <18 | <18 | <18 | <18 | μmol/L |
| CA | Electrolytes | 2.1 | 2.38 | 2.29 | 2.25 | 2.1 | 2.14 | mmol/L |
| PHOS | Electrolytes | 2.89 | 2.57 | 2.82 | 2.4 | 2.27 | 1.64 | mmol/L |
| Na+ | Electrolytes | 140 | 143 | 144 | 137 | 146 | 137 | mmol/L |
| K+ | Electrolytes | 6.2 | 5.5 | 5.8 | 5.5 | 8 | 6.5 | mmol/L |
| GLU | General metabolism | 13.9 | 12.5 | 11.8 | 17.6 | 13.8 | 16.5 | mmol/L |

Figure 21:
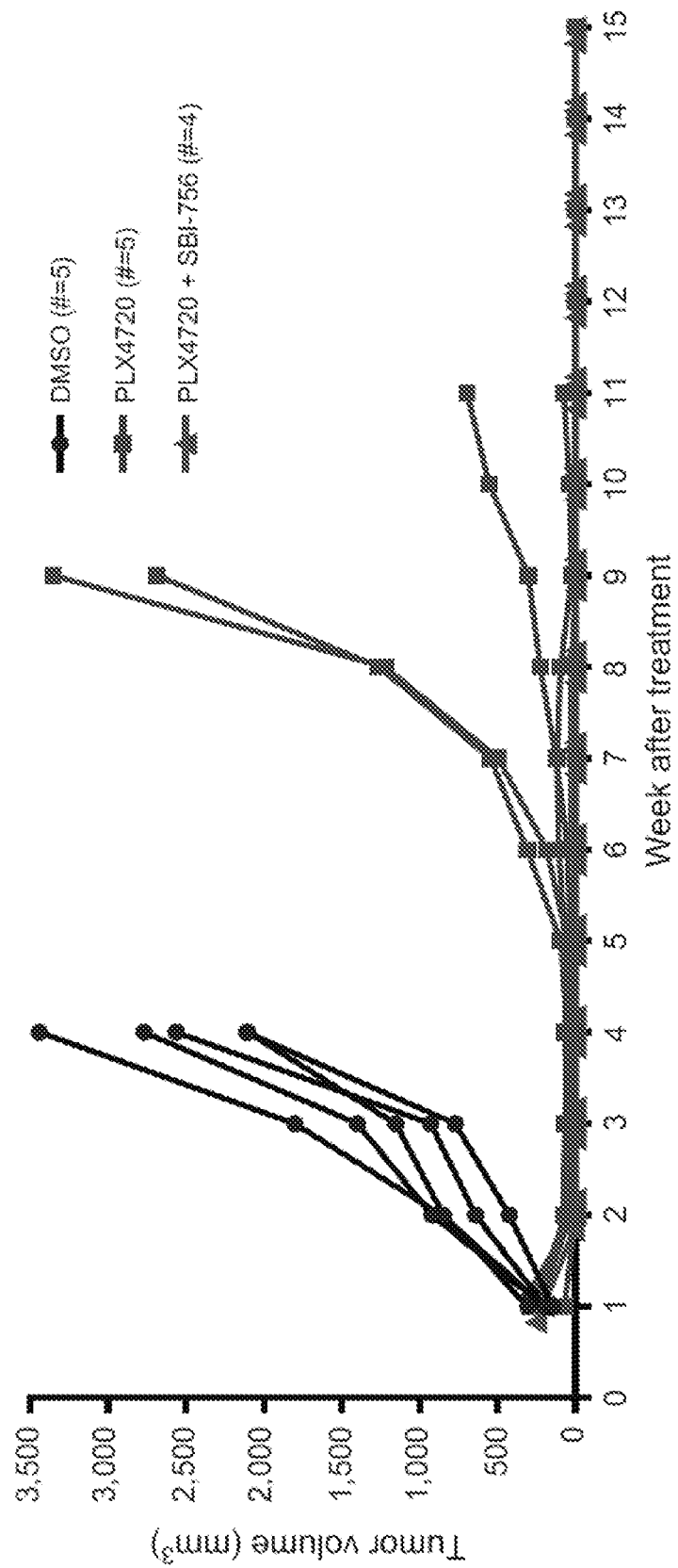
FIG. 21 shows the growth of established tumors (~250 $mm^3$) following treatment with either PLX4720 (BRAFi) alone or a combination of PLX4720/SBI-756 (Compound 38).
Figure 22:
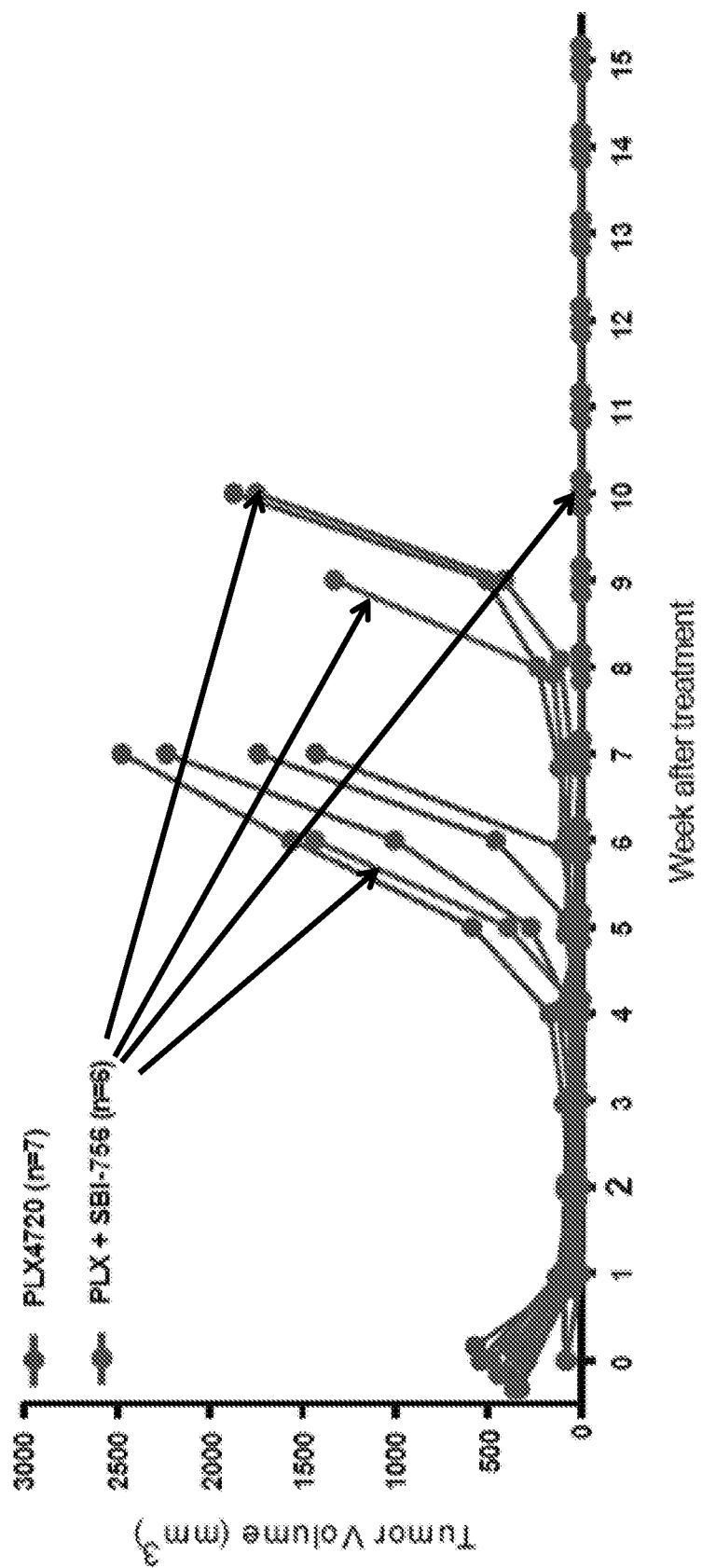
FIG. 22 shows the growth of established tumors (~500 $mm^3$) following treatment with either PLX4720 (BRAFi) alone or a combination of PLX4720/SBI-756 (Compound 38).
Figure 23:
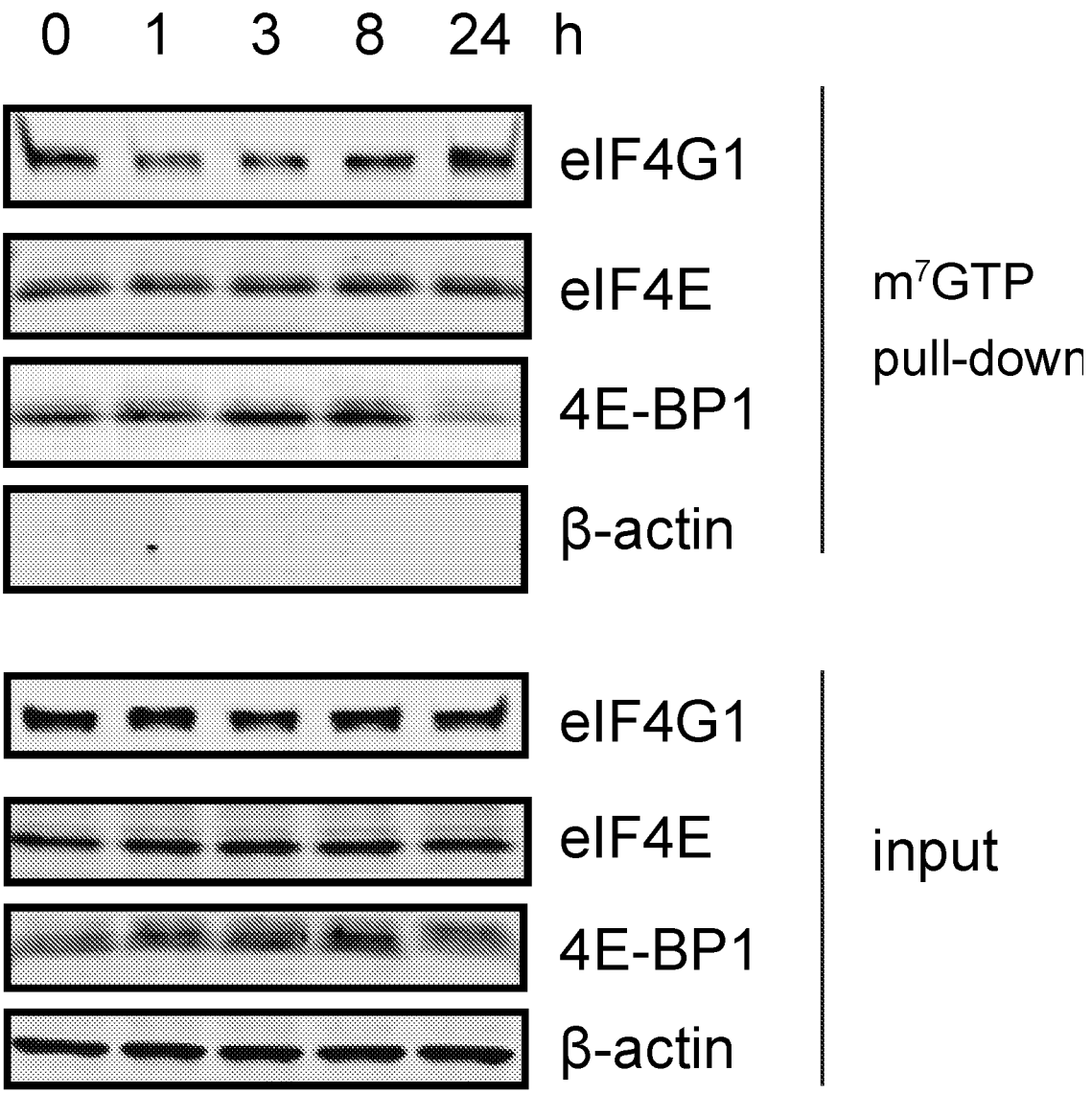
FIG. 23 shows a time-dependent disruption of the eIF4F complex in melanoma tumors grown in animals that were subjected to treatment with both PLX4720 (BRAFi) and SBI-756 (Compound 38). Western blots show respective protein levels in total cell lysates or following pull-down using $m^7$GTP agarose beads. Bottom plot shows input (5%) and top plot shows $m^7$GTP pull-down (50%).

Growth of established tumors (~250 mm³) was largely inhibited by treatment with either BRAFi alone or a combination of BRAFi plus Compound 38 (FIG. 21). A375 human melanomacells were injected subcutaneously (1×10⁶) into the flank of nude mice and allowed to form established tumors. Once tumors reached approximately 250 mm3, mice were randomly grouped and subjected to the indicated treatments [chow containing PLX4720 (417 mg/kg) and/or Compound 38 (1 mg/kg, 2 times per week intraperitoneally)]. Tumor size was measured at the indicated time points. The experiment was repeated twice. Tumors in the BRAFi-treated group (3/5) resumed growth, whereas no tumors were seen in mice (0/4) treated with the drug combination (FIG. 23), suggesting that combining Compound 38 with BRAFi antagonizes BRAFi-resistant melanoma in vivo. When tumors were allowed to reach 500 mm³ before initiating treatment, 5 of 7 (75%) mice subjected to BRAFi treatment alone relapsed as drug-resistant tumors (4/5 within 4-6 weeks), whereas only 3 of 6 (50%) subjected to combination treatment developed resistance, albeit more slowly (2/3 after 8 weeks; FIG. 22). Assessing Compound 38 effect on the eIF4F complex in vivo revealed a time-dependent disruption of the eIF4F complex in melanoma tumors grown in animals that were subjected to treatment with both BRAFi and Compound 38 (up to 8 hours, consistent with the half life of Compound 38; See FIG. 23). Proteins prepared at the indicated times from A375 tumors that were subjected in vivo to treatment with Compound 38 were incubated with m⁷GTP-beads to capture the eIF4F complex. Shown is time-dependent inhibition of eIF4G1 binding to eIF4E in vivo, concomitant with increased binding of inhibitory 4E-BP1 to eIF4E. Bottom plot shows input, total cell lysate. These results demonstrate the disruption of the eIF4F complex in vivo, consistent with the effectiveness of Compound 38 in overcoming BRAFi-resistant phenotype.

The Quinolinone derivatives demonstrated activity in the assay described herein as indicated in the following Table.

TABLE 6

| Ex. | 48 h Cyto-toxicity A375 ($IC_{50}$) | EmCV Cap-dependent translation ($IC_{50}$) | EmCV Cap-independent translation ($IC_{50}$) | HCV cap-dependent translation ($IC_{50}$) | HCV cap-independent translation ($IC_{50}$) |
|---|---|---|---|---|---|
| 1 | B | B | B | B | B |
| 2 | A | B | B | B | B |
| 3 | A | C | D | C | D |
| 4 | B | B | B | B | B |
| 5 | A | B | C | C | C |
| 6 | D | B | B | C | C |

TABLE 6-continued

| Ex. | 48 h Cytotoxicity A375 (IC$_{50}$) | EmCV Cap-dependent translation (IC$_{50}$) | EmCV Cap-independent translation (IC$_{50}$) | HCV cap-dependent translation (IC$_{50}$) | HCV cap-independent translation (IC$_{50}$) |
|---|---|---|---|---|---|
| 7 | C | B | C | C | C |
| 8 | C | D | D | D | D |
| 9 | B | B | B | C | C |
| 10 | D | B | B | C | B |
| 11 | A | B | B | B | B |
| 12 | A | B | C | C | D |
| 13 | B | B | B | C | B |
| 14 | D | D | D | D | D |
| 15 | D | C | C | C | D |
| 16 | B | B | B | C | B |
| 17 | D | D | D | D | D |
| 18 | B | B | B | C | C |
| 19 | B | B | B | C | C |
| 20 | A | C | D | C | D |
| 21 | B | C | C | D | C |
| 22 | D | C | C | C | C |
| 23 | A | D | C | D | D |
| 24 | A | B | B | C | C |
| 25 | C | C | C | C | D |
| 26 | B | B | C | C | C |
| 27 | B | B | B | B | B |
| 28 | A | B | B | B | B |
| 29 | A | D | D | C | D |
| 30 | B | D | D | D | D |
| 31 | B | B | B | B | B |
| 32 | A | B | B | B | B |
| 33 | B | B | B | B | B |
| 34 | B | C | B | B | B |
| 35 | D | D | D | D | D |
| 36 | B | B | C | B | B |
| 37 | B | B | B | B | B |
| 38 | A | B | B | B | B |
| 39 | B | B | B | C | C |
| 40 | A | B | B | B | B |
| 41 | A | B | B | B | B |
| 42 | A | B | B | B | B |
| 43 | A | D | D | B | B |
| 44 | B | B | B | B | B |
| 45 | B | B | B | C | B |
| 46 | B | B | B | B | B |
| 47 | A | B | B | B | B |
| 48 | B | B | B | B | C |
| 49 | A | B | B | B | B |
| 50 | A | B | C | D | D |
| 51 | B | D | D | C | D |
| 52 | B | B | B | C | B |
| 53 | B | B | B | B | B |
| 54 | B | B | B | B | B |
| 55 | B | B | B | B | B |
| 56 | B | B | D | C | B |
| 57 | B | B | B | B | B |
| 58 | B | B | B | B | B |
| 59 | B | B | B | B | B |
| 60 | B | D | D | C | C |
| 62 | A | B | B | B | B |
| 63 | B | B | B | B | B |
| 64 | B | B | C | C | D |
| 65 | A | B | B | B | B |
| 66 | A | B | B | B | B |
| 67 | D | D | D | D | D |
| 68 | D | D | D | D | D |
| 69 | B | B | B | B | B |
| 70 | B | B | B | B | B |
| 71 | B | D | D | C | D |
| 72 | A | B | B | B | B |
| 73 | A | B | B | B | B |
| 74 | A | B | B | B | B |
| 75 | A | B | B | B | B |
| 76 | A | B | B | B | B |
| 77 | A | B | B | B | B |
| 78 | A | B | B | B | B |
| 79 | A | B | B | B | B |
| 80 | B | B | B | C | B |
| 81 | B | B | B | B | B |
| 82 | B | B | B | B | B |
| 83 | B | B | B | B | B |
| 84 | A | B | B | B | B |
| 85 | A | B | B | B | B |
| 86 | B | B | B | B | B |
| 87 | B | B | B | B | B |
| 88 | B | B | B | B | B |
| 89 | B | B | B | B | B |
| 90 | A | B | B | C | B |
| 91 | B | B | B | B | B |
| 92 | A | B | B | B | B |
| 93 | A | D | C | D | D |
| 94 | B | D | D | D | D |
| 96 | B | C | B | D | C |
| 97 | B | B | B | C | B |
| 98 | B | C | C | C | C |
| 99 | B | C | B | C | B |
| 100 | B | C | C | C | C |
| 101 | B | B | C | C | C |
| 102 | B | C | C | C | C |
| 103 | B | B | B | C | B |
| 104 | B | B | B | C | B |
| 105 | B | C | C | C | C |
| 106 | A | D | C | D | C |
| 107 | B | D | C | C | C |
| 108 | B | B | B | C | B |
| 109 | B | B | B | B | B |
| 110 | B | B | B | B | B |
| 111 | B | B | B | B | B |
| 112 | D | D | D | D | D |
| 113 | B | B | B | B | B |
| 114 | B | B | C | D | C |
| 115 | A | B | B | B | B |

A < 2 μM
2 μM ≤ B < 10 μM
10 μM ≤ C < 20 μM
20 μM ≤ D

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

We claim:

1. A compound of Formula (Ia-1') or Formula (Ia-1"), or a pharmaceutically acceptable salt, solvate, tautomer, or N-oxide thereof:

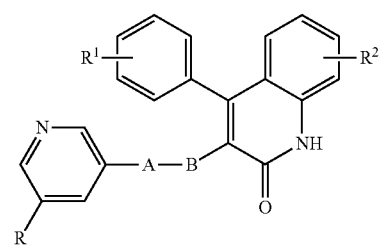

Formula (Ia-1')

Formula (Ia-1″)

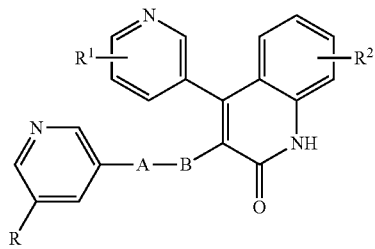

wherein
A is a bond, —CH$_2$—, —CH$_2$CH$_2$—, or —CH=CH;
B is —C(=O)— or —C(=O)NH—;
R is halogen, hydroxyl, C$_1$-C$_6$-alkoxy, cyano, —NR$^a$R$^b$, —C(=O)OR$^c$, C$_1$-C$_6$-alkyl, C$_3$-C$_6$-cycloalkyl, or aryl; wherein the C$_1$-C$_6$-alkyl, C$_1$-C$_6$-alkoxy, C$_3$-C$_6$-cycloalkyl, and aryl are optionally substituted with one or more R$^d$;
R$^1$ is hydrogen, halogen, hydroxyl, C$_1$-C$_6$-alkoxy, cyano, —NR$^a$R$^b$, —C(=O)OR$^c$, C$_1$-C$_6$-alkyl, C$_3$-C$_6$-cycloalkyl, or aryl;
wherein the C$_1$-C$_6$-alkyl, C$_1$-C$_6$-alkoxy, C$_3$-C$_6$-cycloalkyl, and aryl are optionally substituted with one or more R$^d$;
R$^2$ is halogen, hydroxyl, C$_1$-C$_6$-alkoxy, C$_1$-C$_6$-alkyl, or C$_3$-C$_6$-cycloalkyl; wherein the C$_1$-C$_6$-alkyl and C$_3$-C$_6$-cycloalkyl are optionally substituted with one or more R$^d$;
R$^a$ and R$^b$ are independently hydrogen or C$_1$-C$_6$-alkyl; or R$^a$ and R$^b$ taken together with the nitrogen to which they are attached form a C$_3$-C$_6$-heterocycloalkyl optionally substituted with C$_1$-C$_6$-alkyl;
R$^c$ is hydrogen or C$_1$-C$_6$-alkyl; and
each R$^d$ is independently C$_1$-C$_6$-alkyl, halogen, hydroxyl, C$_1$-C$_6$-alkoxy, cyano, or —NR$^a$R$^b$.

2. The compound of claim 1, or a pharmaceutically acceptable salt, solvate, tautomer, or N-oxide thereof, wherein:
B is —C(=O)—.

3. The compound of claim 1, or a pharmaceutically acceptable salt, solvate, tautomer, or N-oxide thereof, wherein:
A is —CH=CH—.

4. The compound of claim 1, or a pharmaceutically acceptable salt, solvate, tautomer, or N-oxide thereof, wherein:
R$^2$ is halogen.

5. The compound of claim 1, or a pharmaceutically acceptable salt, solvate, tautomer, or N-oxide thereof, wherein:
R$^2$ is chloro.

6. The compound of claim 1, or a pharmaceutically acceptable salt, solvate, tautomer, or N-oxide thereof, wherein the compound is:

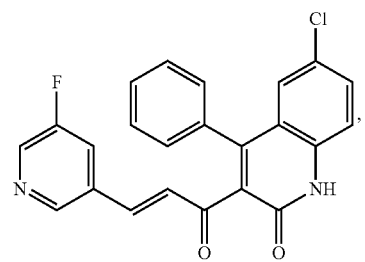

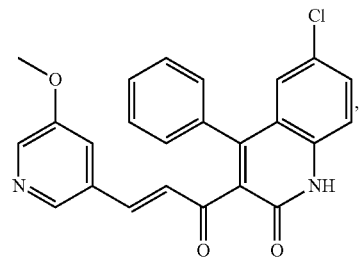

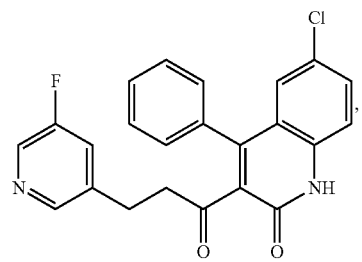

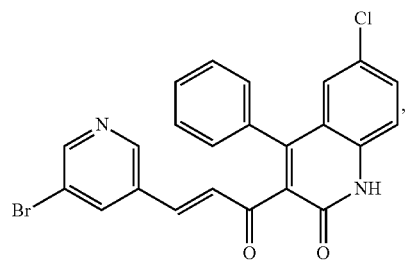

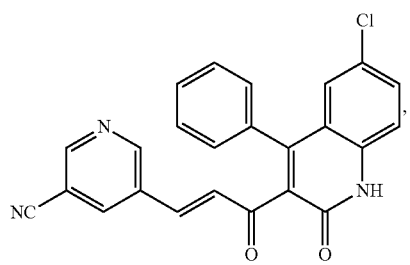

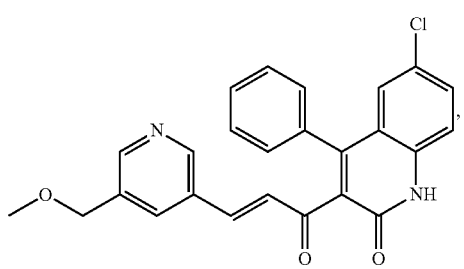

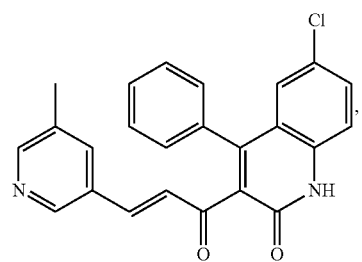

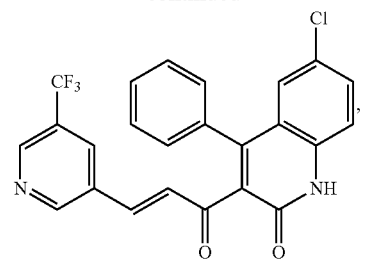 [SMILES: O=C(/C=C/c1cncc(F)c1)c1c(-c2ccccc2)c2cc(Cl)ccc2[nH]c1=O]
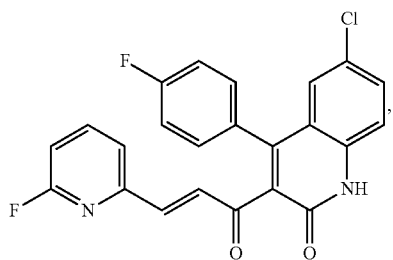
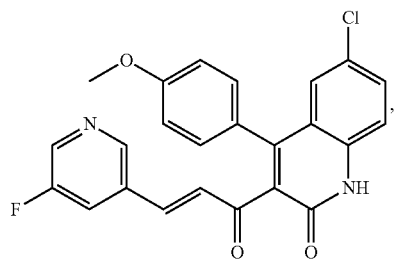
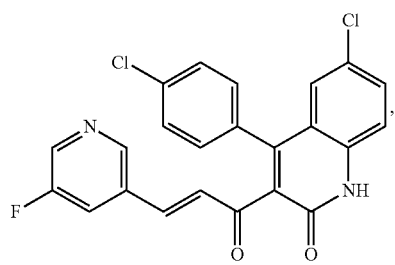
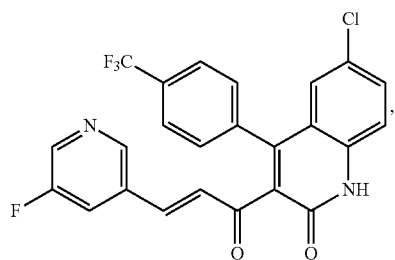
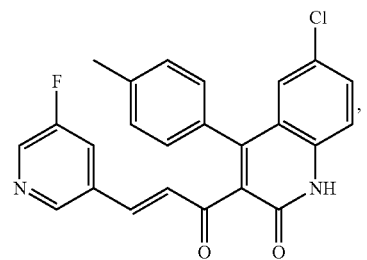
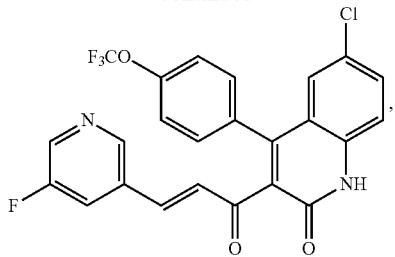
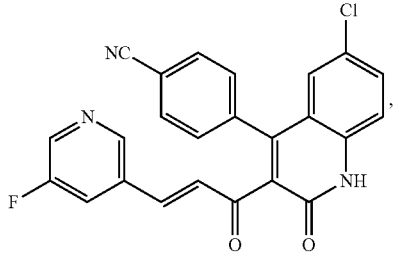
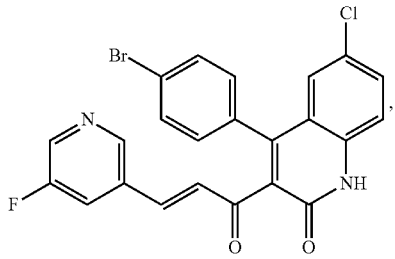
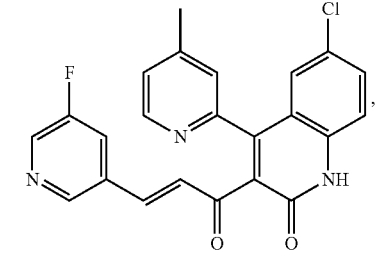
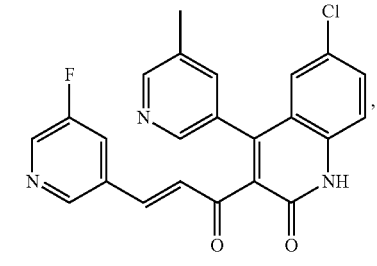
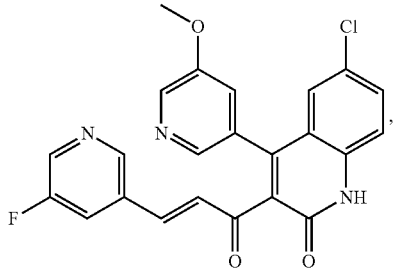

-continued

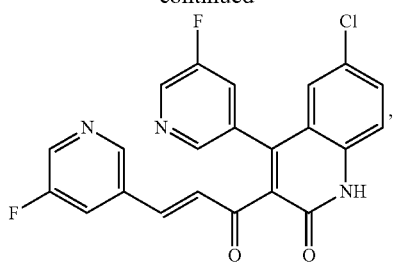

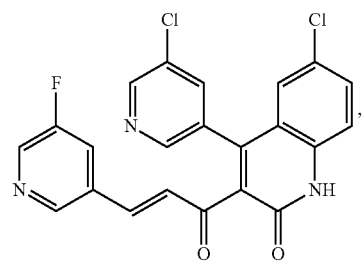

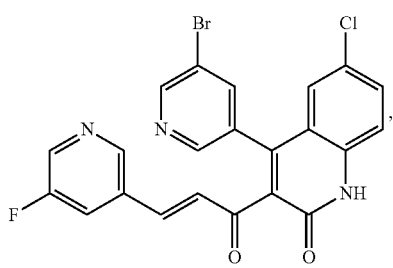

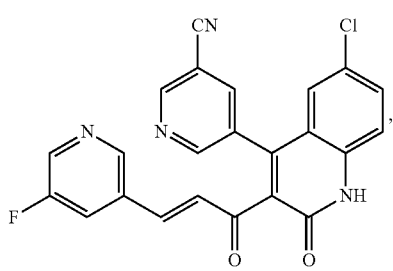

-continued

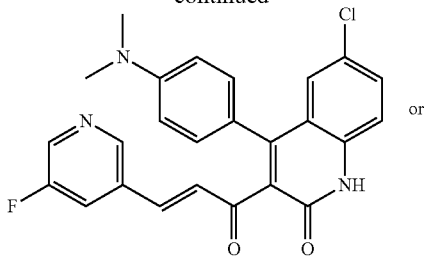

or

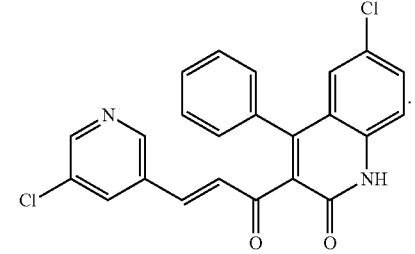

7. The compound of claim 1, or a pharmaceutically acceptable salt, solvate, tautomer, or N-oxide thereof, wherein the compound is:

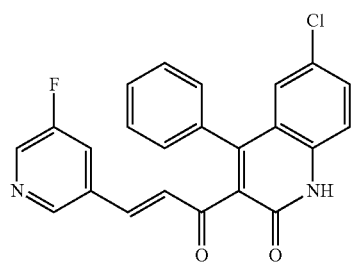

8. A method of treating cancer in a subject in need thereof comprising administering to the subject in need thereof the compound of claim 1, or a pharmaceutically acceptable salt, solvate, tautomer, or N-oxide thereof.

9. The method of claim 8, wherein the cancer is a resistant cancer.

10. The method of claim 8, wherein the cancer is melanoma.

11. The method of claim 8, wherein the cancer is prostate cancer, pancreatic cancer, or colorectal cancer.

* * * * *